US012459957B2

(12) United States Patent
Green et al.

(10) Patent No.: US 12,459,957 B2
(45) **Date of Patent: *Nov. 4, 2025**

(54) THERAPEUTIC COMPOUNDS AND METHODS

(71) Applicant: GENENTECH, INC., South San Francisco, CA (US)

(72) Inventors: Samantha Alyson Green, South San Francisco, CA (US); Jessica Marie Grandner, South San Francisco, CA (US); Steven Thomas Staben, South San Francisco, CA (US); Neri Amara, South San Francisco, CA (US); Vishva M. Dixit, South San Francisco, CA (US); Elisia Villemure, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,963

(22) Filed: May 8, 2024

(65) Prior Publication Data

US 2025/0109142 A1 Apr. 3, 2025

Related U.S. Application Data

(62) Division of application No. 17/862,963, filed on Jul. 12, 2022, now Pat. No. 12,006,331.

(Continued)

(51) Int. Cl.

*C07D 498/04* (2006.01)
*A61K 9/08* (2006.01)

(Continued)

(52) U.S. Cl.

CPC .............. *C07D 498/04* (2013.01); *A61K 9/08* (2013.01); *A61K 9/12* (2013.01); *A61K 9/2013* (2013.01);

(Continued)

(58) Field of Classification Search

CPC ............................ C07D 498/04; C07D 519/00

See application file for complete search history.

(56) References Cited

U.S. PATENT DOCUMENTS

| | | | |
|---|---|---|---|
| 12,006,331 | B2 | 6/2024 | Green et al. |
| 2006/0074064 | A1 | 4/2006 | Venkatesan et al. |
| 2007/0232582 | A1 | 10/2007 | Mansour et al. |

FOREIGN PATENT DOCUMENTS

| | | | |
|---|---|---|---|
| WO | 2020006229 | A1 | 1/2020 |
| WO | 2020030613 | A1 | 2/2020 |

OTHER PUBLICATIONS

Amara, et al., "Selective activation of PFKL suppresses the phagocytic oxidative burst", Cell 184, 4480-4494 (2021).

(Continued)

*Primary Examiner* — Alicia L Otton

(74) *Attorney, Agent, or Firm* — Viksnins Harris Padys Malen LLP

(57) ABSTRACT

The invention provides a compound of formula (I):

(I)

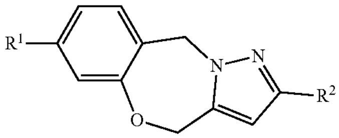

or a prodrug thereof, or a pharmaceutically acceptable salt thereof, wherein $R^1$ and $R^2$ have any of the values described (Continued)

in the specification, as well as compositions comprising a compound of formula (I) or a prodrug thereof, or a pharmaceutically acceptable salt thereof. The compounds are agonists of glycolytic enzyme phosphofructokinase-1 liver type and are useful for treating diseases associated with the activity of glycolytic enzyme phosphofructokinase-1 liver type, such as cancer, diabetes, sepsis, and septic shock.

20 Claims, 1 Drawing Sheet

Related U.S. Application Data

(60) Provisional application No. 63/222,288, filed on Jul. 15, 2021.

(51) Int. Cl.

| | |
|---|---|
| ***A61K 9/12*** | (2006.01) |
| ***A61K 9/20*** | (2006.01) |
| ***A61K 9/48*** | (2006.01) |
| ***A61K 47/02*** | (2006.01) |
| ***A61K 47/06*** | (2006.01) |
| ***A61K 47/10*** | (2017.01) |
| ***A61K 47/12*** | (2006.01) |
| ***C07D 519/00*** | (2006.01) |
| ***C07F 9/6561*** | (2006.01) |

(52) U.S. Cl.

CPC .......... *A61K 9/2018* (2013.01); *A61K 9/2027* (2013.01); *A61K 9/2054* (2013.01); *A61K 9/2059* (2013.01); *A61K 9/485* (2013.01); *A61K 9/4858* (2013.01); *A61K 9/4866* (2013.01); *A61K 47/02* (2013.01); *A61K 47/06* (2013.01); *A61K 47/10* (2013.01); *A61K 47/12* (2013.01); *C07D 519/00* (2013.01); *C07F 9/6561* (2013.01)

(56) References Cited

OTHER PUBLICATIONS

Amulic, B, et al., “Neutrophil function: from mechanisms to disease”, Annu Tev Immunol 30, 459-489 (2012).

Brinkmann, V, “Neutrophil Extracellular Traps in the Second Decade”, J Innate Immun 10, 414-421 (2018).

Brinkmann, V, et al., “Neutrophil extracellular traps kill bacteria”, Science 303, 1532-1535 (2004).

Burgener, S, et al., “Cathepsin G Inhibition by Serpinb1 and Serpinb6 Prevents Programmed Necrosis in Neutrophils and Monocytes and Reduces GSDMD-Driven Inflammation”, Cell Rep 27, 3646-3656, e1-e5 (2019).

Chen, K, et al., “Noncanonical inflammasome signaling elicits gasdermin D-dependent neutrophil extracellular traps”, Sci Immunol 3, eaar6676 (2018).

Diebold, B, et al., “NOX2 as a Target for Drug Development: Indications, Possible Complications, and Progress”, Antioxid Redox Signal 23, 375-405 (2015).

Heyworth, P, et al., “Chronic granulomatous disease”, Curr Opin Immunol 15, 578-584 (2003).

Kambara, H, et al., “Gasdermin D Exerts Anti-inflammatory Effects by Promoting Neutrophil Death”, Cell Rep 22, 2924-2936 (2018).

Kayagaki, N, et al., “Rescue from a fiery death: A therapeutic endeavor”, Science 366, 688-689 (2010).

Kenny, E, et al., “Diverse stimuli engage different neutrophil extracellular trap pathways”, Elife 6, e24437, 21 pages (2017).

Kowalik, M, et al., “Emerging Role of the Pentose Phosphate Pathway in Hepatocellular Carcinoma”, Oncol 7 (87), 11 pages (2017).

Mayadas, T, et al., “The multifaceted functions of neutrophils”, Am Rev Pathol 9, 181-218 (2014).

Neubert, E, et al., “The power from within—understanding the driving forces of neutrophil extracellular trap formation”, J Cell Sci 133, jcs241075, 12 pages (2020).

Patent Cooperation Treaty, International Search Report and Written Opinion for PCT/US2022/036829, 9 pages, dated Oct. 13, 2022.

Roos, D, et al., “Hematologically important mutations: X-linked chronic granulomatous disease (third update)”, Blood Cells Mol Dis 45, 246-265 (2010).

Rosales, C, et al., “Phagocytosis: A Fundamental Process in Immunity”, Biomed Res Int, Article ID 9042851, doi:10.1155/2017/9042851, 18 pages (2017).

Sengelov, H, et al., “Mobilization of granules and secretory vesicles during in vivo exudation of human neutrophils”, J Immunol 154 (8), 4157-4165 (1995).

Sollberger, G, et al., “Gasdermin D plays a vital role in the generation of neutrophil extracellular traps”, Sci Immunol 3, eaar6689, 12 pages (2018).

Thomas, D, “The phagocyte respiratory burst: Historical perspectives and recent advances”, Immunol Lett 192,88-96 (2017).

Zatti, M, et al., “Early changes of hexose monophosphate pathway activity and of NADPH oxidation in phagocytizing leucocytes”, Biochim Biophys Acta 99, 557-561 (1965).

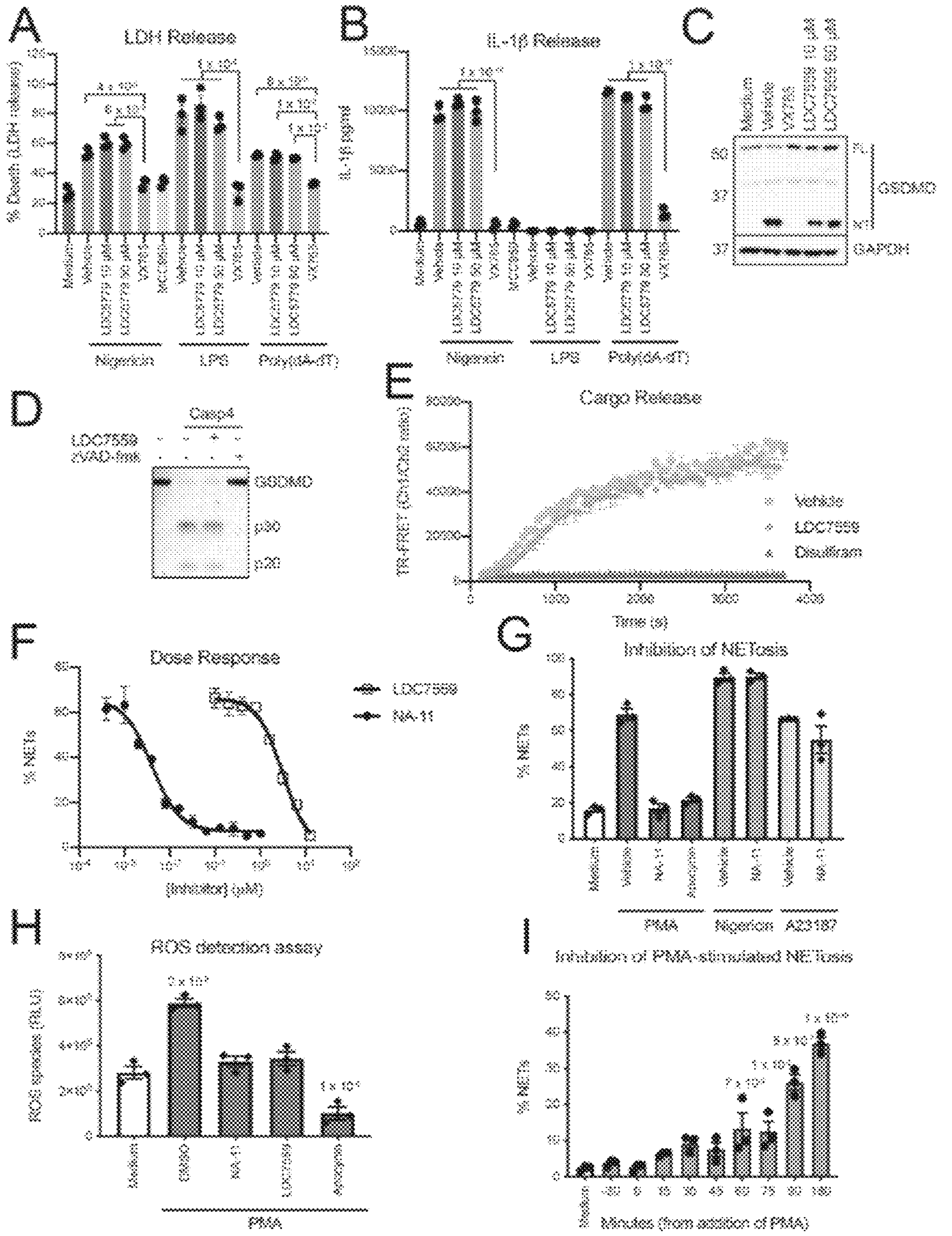
A
LDH Release
Nigericin
LPS
Poly(dA-dT)
B
IL-1β Release
Nigericin
LPS
Poly(dA-dT)
C
GSDMD
GAPDH
D
Casp4
LDC7559
zVAD-fmk
GSDMD
p30
p20
E
Cargo Release
Vehicle
LDC7559
Disulfiram
Time (s)
F
Dose Response
LDC7559
NA-11
% NETs
[Inhibitor] (μM)
G
Inhibition of NETosis
% NETs
PMA
Nigericin
A23187
H
ROS detection assay
PMA
I
Inhibition of PMA-stimulated NETosis
% NETs
Minutes (from addition of PMA)

THERAPEUTIC COMPOUNDS AND METHODS

CROSS-REFERENCE TO RELATED APPLICATIONS

This application is a divisional of U.S. application Ser. No. 17/862,963, filed on 12 Jul. 2022, which claims priority to U.S. Provisional Patent Application No. 63/222,288, filed on 15 Jul. 2021. The entire content of the applications referenced above is hereby incorporated by reference herein.

BACKGROUND OF THE INVENTION

Phagocytes produce bactericidal reactive oxygen species (ROS) within the phagosome in an oxidative burst. The rapid increase in ROS is mediated by NOX2, a nicotinamide adenine dinucleotide phosphate (NADPH)-dependent oxygen reductase (Thomas, D. C., *Immunol. Lett.,* 2017, 192, 88-96). Assembly of the NOX2 complex on phagosome and cellular membranes is accompanied by an increase in oxygen consumption and glucose uptake (Zatti, M., and Rossi, F. *Biochim. Biophys. Acta,* 1965, 99, 557-561). Glucose catabolism through the pentose phosphate pathway increases production of NADPH, which provides NOX2 the reducing equivalents needed to generate superoxide radicals.

Neutrophils are professional phagocytes that are essential for optimal anti-microbial defense, and comprise 50-70% of circulating leukocytes in humans (Mayadas, T. N., et al., *Ann. Rev. Pathol.,* 2014, 9, 181-218). They rely on the oxidative burst for a multitude of functions, including phagocytosis (Rosales, C, and Uribe-Querol, E., *Biomed Res. Int.,* 2017, 9042851. doi: 10.1155/2017/9042851), degranulation (Sengelov, H., et al., J. Immunol., 1995, 154, 4157-4165), ROS production (Amulic, B., et al., *Annu. Rev. Immunol.,* 2012, 30, 459-489), and formation of neutrophil extracellular traps (NETs) (Brinkmann, V., *J. Innate Immun.,* 2018, 10, 414-421; and Brinkmann, V., et al., *Science,* 2004, 303, 1532-1535). Mutations inactivating the NOX2 complex impair the oxidative capacity of neutrophils and cause Chronic Granulomatous Disease (CGD) (Roos, D., et al., *Blood Cells Mol. Dis.,* 2010, 45, 246-265). Patients with CGD are vulnerable to recurrent, chronic, and invasive bacterial and fungal infections (Heyworth, P. G., et al., *Curr. Opin. Immunol.,* 2003, 15, 578-584).

Although neutrophils are crucial for innate immunity, excessive neutrophil activation can be deleterious. Local tissue damage, inflammation, and autoantigens stemming from NETs exacerbate the pathology of chronic conditions such as atherosclerosis, psoriasis, gout, and lupus (Brinkmann, V., *J. Innate Immun.,* 2018, 10, 414-421). Targeting the oxidative burst may have therapeutic potential, but there are safety concerns with inhibitors of NOX2 or enzymes of the pentose phosphate pathway including glucose-6-phosphate dehydrogenase (G6PDH). Barriers to their use include suppression of innate immunity and general toxicity (Diebold, B. A., et al., *Antioxid. Redox Signal,* 2015, 23, 375-405; and Kowalik, M. A., Columbano, A., and Perra, A., *Oncol.,* 2017, 7, 87).

NETosis of neutrophils is crucial for the killing of extracellular bacteria (Brinkmann, V., et al., *Science,* 2004, 303, 1532-1535), but the underlying molecular mechanisms remain largely unknown. Most physiological stimuli, including bacteria, fungi, and crystalline particulates, trigger NOX2-dependent NETosis, but some bacterial toxins acting as potassium and calcium ionophores promote NOX2-independent NETosis (Kenny, E. F., et al., *Elife* 6, 2017, e24437).

NOX2-dependent NETosis is described as a two phased process (Neubert, E., et al., *J Cell Sci.* 133, 2020, jcs241075). During phase 1, active signaling cascades trigger a NOX2-induced oxidative burst and histone modifying enzymes such as neutrophil elastase (NE) and peptidylarginine deaminase 4 (PAD4) enter the nucleus. Phase 2 involves the entropic swelling of chromatin, rupture of the cell membrane, and dissemination of NETs composed of chromatin and granule proteins.

Inhibitors of NETosis may control chronic neutrophil-driven diseases. Recent phenotypic screening of a large chemical library in human neutrophils identified the compound LDC7559 as an inhibitor of NOX2-dependent NETosis (Sollberger, G., et al., *Sci. Immunol.,* 2018, 3, eaar6689). It was proposed to target the pore-forming domain of Gasdermin D (GSDMD), a protein that mediates a lytic form of cell death called pyroptosis. In macrophages, cleavage of GSDMD by human caspases 1, 4, or 5 (mouse caspases 1 or 11) releases an N-terminal fragment that forms pores in membranes (Kayagaki, N. and Dixit, V. M., *Science,* 2010, 366, 688-689). In neutrophils, caspase-4 cleaves GSDMD in response to cytosolic lipopolysaccharide (LPS), leading to the extrusion of NETs (Chen, K. W., et al., *Sci. Immunol.,* 2018, 3, aar6676). GSDMD may also be cleaved by neutrophil-specific proteases such as NE and cathepsin G (Burgener, S. S., et al., *Cell Rep.,* 2019, 27, 3646-3656; and Kambara, H., et al., *Cell Rep.,* 2018, 22, 2924-2936). How LDC7559 inhibited GSDMD to prevent NETosis, and why LDC7559 inhibited NOX2-dependent NETosis, but not NOX2-independent NETosis remained enigmatic.

Currently, there is a need for compounds and methods that are useful to agonize the glycolytic enzyme phosphofructokinase-1 liver type (PFKL). There is also a need for compounds that are useful to suppress NOX2-dependent oxidative burst. Such compounds and methods would be useful for treating diseases that include diabetes and cancer.

SUMMARY

LDC7559 and compounds of formula (I) have been found to agonize PFKL and suppress NOX2-dependent oxidative burst.

In a first embodiment (Embodiment 1; abbreviated as "E1") the invention provides a compound of the invention, which is a compound of formula (I):

(I)

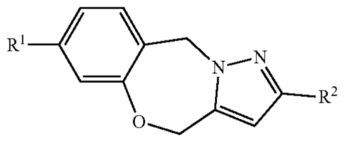

or a prodrug thereof, or a pharmaceutically acceptable salt thereof, wherein:

$R^1$ is —$NR^aR^b$ or a 5-10 membered heteroaryl that is optionally substituted with one or more groups $R^c$;

$R^2$ is a 6-10 membered aryl that is optionally substituted with one or more groups $R^r$; or $R^2$ is a 5-10 membered heteroaryl that is that is optionally substituted with one or more groups $R^s$; or $R^2$ is a 3-10 membered heterocycle that is that is optionally substituted with one or more groups $R^z$;

$R^a$ is $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkanoyl, $(C_3\text{-}C_6)$cycloalkyl ($C_1$-$C_6$)alkyl, ($C_2$-$C_6$)alkynylcarbonyl, 3-6 membered heterocycle, or a 5-6 membered heteroaryl that is optionally substituted with one or more groups $R^f$; wherein each ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkanoyl, ($C_3$-$C_6$)cycloalkyl($C_1$-$C_6$)alkyl, ($C_2$-$C_6$)alkynylcarbonyl, and 3-6 membered heterocycle is optionally substituted with one or more groups independently selected from the group consisting of halo, hydroxy, cyano, ($C_2$-$C_6$)alkenyl, ($C_2$-$C_6$)alkynyl, C(═O)NR$^m$R$^n$, and ($C_1$-$C_6$)alkyl that is optionally substituted with one or more groups independently selected form the group consisting of halo, hydroxy, cyano, —NR$^m$R$^n$, and —C(═O)NR$^m$;

$R^b$ is H or ($C_1$-$C_6$)alkyl;

each $R^c$ is independently selected from the group consisting of cyano, —NR$^d$R$^e$, —C(═O)NR$^d$R$^e$, ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkoxy, and ($C_1$-$C_6$)alkanoyl, wherein each ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkoxy and ($C_1$-$C_6$)alkanoyl is optionally substituted with one or more groups independently selected from the group consisting of halo, hydroxy, carboxy, and cyano;

$R^d$ and $R^e$ are each independently selected from the group consisting of H and ($C_1$-$C_6$)alkyl; or $R^d$ and $R^e$ taken together with the nitrogen to which they are attached form a 3-6 membered heterocyclic ring that is optionally substituted with one or more groups independently selected from the group consisting of halo and ($C_1$-$C_6$)alkyl;

each $R^f$ is independently selected from the group consisting of halo, hydroxy, cyano, —NR$^g$R$^h$, —C(═O)NR$^g$R$^h$, and ($C_1$-$C_6$)alkyl that is optionally substituted with one or more groups independently selected from the group consisting of halo, hydroxy, carboxy, —NR$^g$R$^h$, —C(═O)NR$^g$R$^h$, and cyano;

$R^g$ and $R^h$ are each independently selected from the group consisting of H and ($C_1$-$C_6$)alkyl; or $R^g$ and $R^h$ taken together with the nitrogen to which they are attached form a 3-6 membered heterocyclic ring that is optionally substituted with one or more groups independently selected from the group consisting of halo and ($C_1$-$C_6$)alkyl;

$R^m$ is H or ($C_1$-$C_6$)alkyl that is optionally substituted with one or more groups independently selected from the group consisting of halo, hydroxy, carboxy, cyano, and oxo;

$R^n$ is H or ($C_1$-$C_6$)alkyl that is optionally substituted with one or more groups independently selected from the group consisting of halo, hydroxy, carboxy, cyano, and oxo;

each $R^r$ is independently selected from the group consisting of halo, hydroxy, cyano, —NR$^t$R$^u$, —C(═O)NR$^t$R$^u$, —S(O)$_2$NR$^t$R$^u$, ($C_1$-$C_6$)alkyl, ($C_3$-$C_6$)cycloalkyl, ($C_1$-$C_6$)alkoxy, ($C_1$-$C_6$)alkylthio, —N(H)S(O)$_2$R$^x$, —S(O)$_2$R$^x$, ($C_2$-$C_6$)alkenyl, and ($C_2$-$C_6$)alkynyl, wherein each ($C_1$-$C_6$)alkyl, ($C_3$-$C_6$)cycloalkyl, ($C_1$-$C_6$)alkoxy, ($C_1$-$C_6$)alkylthio, ($C_2$-$C_6$)alkenyl, and ($C_2$-$C_6$)alkynyl is optionally substituted with one or more groups independently selected from the group consisting of halo, hydroxy, carboxy, —NR$^t$R$^u$, —C(═O)NR$^t$R$^u$, —S(O)$_2$NR$^t$R$^u$, —S(O)$_2$R$^x$, and cyano;

each $R^s$ is independently selected from the group consisting of halo, cyano, —NR$^v$R$^u$, —C(═O)NR$^v$R$^w$, —S(O)$_2$NR$^v$R$^w$, ($C_1$-$C_6$)alkyl, ($C_3$-$C_6$)cycloalkyl, ($C_1$-$C_6$)alkoxy, ($C_1$-$C_6$)alkanoyl, ($C_1$-$C_6$)alkylthio, 3-6 membered heterocycle, and —S(O)$_2$R$^y$, wherein each ($C_1$-$C_6$)alkyl, ($C_3$-$C_6$)cycloalkyl, ($C_1$-$C_6$)alkoxy, ($C_1$-$C_6$)alkanoyl, 3-6 membered heterocycle, and ($C_1$-$C_6$)alkylthio, is optionally substituted with one or more groups independently selected from the group consisting of halo, hydroxy, carboxy, —NR$^t$R$^u$, —C(═O)NR$^t$R$^u$, S(O)$_2$NR$^v$R$^w$, —S(O)$_2$R$^y$, and cyano;

$R^t$ and $R^u$ are each independently selected from the group consisting of H, ($C_1$-$C_6$)alkyl, ($C_1$-$C_6$)alkanoyl, and ($C_2$-$C_6$)alkynylcarbonyl; or $R^t$ and $R^u$ taken together with the nitrogen to which they are attached form a 3-6 membered heterocyclic ring that is optionally substituted with one or more groups independently selected from the group consisting of halo and ($C_1$-$C_6$)alkyl;

$R^v$ and $R^w$ are each independently selected from the group consisting of H, ($C_1$-$C_6$)alkyl, and ($C_1$-$C_6$)alkanoyl; or $R^v$ and $R^w$ taken together with the nitrogen to which they are attached form a 3-6 membered heterocyclic ring that is optionally substituted with one or more groups independently selected from the group consisting of halo and ($C_1$-$C_6$)alkyl;

$R^x$ is H or ($C_1$-$C_6$)alkyl that is optionally substituted with one or more groups independently selected from the group consisting of halo, hydroxy, carboxy, cyano, and oxo;

$R^y$ is H or ($C_1$-$C_6$)alkyl that is optionally substituted with one or more groups independently selected from the group consisting of halo, hydroxy, carboxy, cyano, and oxo; and each $R^z$ is independently selected from the group consisting of oxo, halo, hydroxy, and ($C_1$-$C_6$)alkyl that is optionally substituted with one or more groups independently selected from the group consisting of halo, hydroxy, carboxy, —NR$^t$R$^u$, —C(═O)NR$^t$R$^u$, S(O)$_2$NR$^v$R$^w$, —S(O)$_2$R$^y$, cyano, and oxo.

Further embodiments (E2-E81) of the first embodiment of the invention are described below.

E2. The compound of E1, wherein $R^1$ is —NR$^a$R$^b$ or a 5-10 membered heteroaryl that is optionally substituted with one or more groups $R^c$;

$R^2$ is a phenyl that is optionally substituted with one or more groups $R^r$; or $R^2$ is a 5-9 membered heteroaryl that is that is optionally substituted with one or more groups $R^s$; or $R^2$ is a 9-membered heterocycle that is that is optionally substituted with one or more groups $R^z$;

$R^a$ is ($C_1$-$C_6$)alkyl, ($C_3$-$C_6$)cycloalkyl, ($C_2$-$C_6$)alkynyl, ($C_1$-$C_6$)alkanoyl, ($C_2$-$C_6$)alkynylcarbonyl, 3-6 membered heterocycle, or a 5-membered heteroaryl that is optionally substituted with one or more groups $R^f$; wherein each ($C_1$-$C_6$)alkyl and ($C_3$-$C_6$)cycloalkyl is optionally substituted with one or more groups independently selected from the group consisting of halo, cyano, ($C_2$-$C_6$)alkynyl, C(═O)NR$^m$R$^n$, and ($C_1$-$C_6$)alkyl that is optionally substituted with one or more hydroxy;

$R^b$ is H or ($C_1$-$C_6$)alkyl;

each $R^c$ is independently selected from the group consisting of cyano, —NR$^d$R$^e$, and ($C_1$-$C_6$)alkyl that is optionally substituted with one or more cyano;

$R^d$ and $R^e$ are each H;

each $R^f$ is independently selected from the group consisting of halo, hydroxy, cyano, —C(═O)NR$^g$R$^h$, and $(C_1\text{-}C_6)$alkyl that is optionally substituted with one or more groups independently selected from the group consisting of halo, hydroxy and carboxy;

$R^g$ and $R^h$ are each H;

$R'''$ is H;

$R''$ is H;

each $R^r$ is independently selected from the group consisting of halo, hydroxy, cyano, —$NR^tR^u$, —C(=O)$NR^tR^u$, —$S(O)_2NR^tR^u$, $(C_1\text{-}C_6)$alkyl, $(C_3\text{-}C_6)$cycloalkyl, $(C_1\text{-}C_6)$alkoxy, $(C_1\text{-}C_6)$alkylthio, —N(H)$S(O)_2R^x$, —$S(O)_2R^x$, and $(C_2\text{-}C_6)$alkynyl, wherein each $(C_1\text{-}C_6)$alkyl and $(C_2\text{-}C_6)$alkynyl, is optionally substituted with one or more groups independently selected from the group consisting of hydroxy, —$NR^tR^u$, —C(=O)$NR^tR^u$, and cyano;

each $R^s$ is independently selected from the group consisting of halo, cyano, —$NR^vR^w$, —C(=O)$NR^vR^w$, $(C_1\text{-}C_6)$alkyl, $(C_3\text{-}C_6)$cycloalkyl, $(C_1\text{-}C_6)$alkoxy, $(C_1\text{-}C_6)$alkanoyl, $(C_1\text{-}C_6)$alkylthio, 3-6 membered heterocycle, and —$S(O)_2R^y$, wherein each $(C_1\text{-}C_6)$alkyl is optionally substituted with one or more groups independently selected from the group consisting of halo and —$NR^tR^u$;

$R^t$ and $R^u$ are each independently selected from the group consisting of H, $(C_1\text{-}C_6)$alkyl, $(C_1\text{-}C_6)$alkanoyl, and $(C_2\text{-}C_6)$alkynylcarbonyl; or $R^t$ and $R^u$ taken together with the nitrogen to which they are attached form a 3-6 membered heterocyclic ring that is optionally substituted with one or more groups independently selected from the group consisting of halo and $(C_1\text{-}C_6)$alkyl; $R^v$ and $R^w$ are each independently selected from the group consisting of H, $(C_1\text{-}C_6)$alkyl, and $(C_1\text{-}C_6)$alkanoyl;

$R^x$ is $(C_1\text{-}C_6)$alkyl;

$R^y$ is $(C_1\text{-}C_6)$alkyl; and each $R^z$ is independently selected from the group consisting of oxo and $(C_1\text{-}C_6)$alkyl;

or a prodrug thereof, or a pharmaceutically acceptable salt thereof.

E3. The compound or prodrug, or the pharmaceutically acceptable salt thereof of E1 or E2, wherein $R^1$ is —$NR^aR^b$.

E4. The compound or prodrug, or the pharmaceutically acceptable salt thereof of E1, E2, or E3, wherein $R^a$ is $(C_1\text{-}C_6)$alkanoyl that is optionally substituted with one or more groups independently selected form the group consisting of halo and hydroxy.

E5. The compound or prodrug, or the pharmaceutically acceptable salt thereof of E1, E2, or E3, wherein $R^a$ is $(C_1\text{-}C_6)$alkanoyl.

E6. The compound or prodrug, or the pharmaceutically acceptable salt thereof of E1, E2, or E3, wherein $R^a$ is acetyl.

E7. The compound or prodrug, or the pharmaceutically acceptable salt thereof of E1 or E3, wherein $R^a$ is a 3-6 membered heterocycle is optionally substituted with one or more groups independently selected from the group consisting of halo, hydroxy, cyano, $(C_2\text{-}C_6)$alkenyl, $(C_2\text{-}C_6)$alkynyl, C(=O)$NR'''R''$, and $(C_1\text{-}C_6)$alkyl that is optionally substituted with one or more groups independently selected form the group consisting of halo, hydroxy, cyano, —$NR'''R''$, and —C(=O)$NR'''R''$.

E8. The compound or prodrug, or the pharmaceutically acceptable salt thereof of E1 or E3, wherein $R^a$ is $(C_3\text{-}C_6)$cycloalkyl that is optionally substituted with one or more groups independently selected from the group consisting of halo, hydroxy, cyano, $(C_2\text{-}C_6)$alkenyl, $(C_2\text{-}C_6)$alkynyl, C(=O)$NR'''R''$, and $(C_1\text{-}C_6)$alkyl that is optionally substituted with one or more groups independently selected form the group consisting of halo, hydroxy, cyano, —$NR'''R''$, and —C(=O)$NR'''R''$.

E9. The compound or prodrug, or the pharmaceutically acceptable salt thereof of E1 or E3, wherein $R^a$ is $(C_3\text{-}C_6)$cycloalkyl that is optionally substituted with one or more groups independently selected from the group consisting of cyano, $(C_2\text{-}C_6)$alkynyl, C(=O)$NR'''R''$, and $(C_1\text{-}C_6)$alkyl.

E10. The compound or prodrug, or the pharmaceutically acceptable salt thereof of E1, E2, or E3, wherein $R^a$ is a 5-6 membered heteroaryl that is optionally substituted with one or more groups R.

E11. The compound or prodrug, or the pharmaceutically acceptable salt thereof of E1, E2, or E3, wherein $R^a$ is selected from the group consisting of:

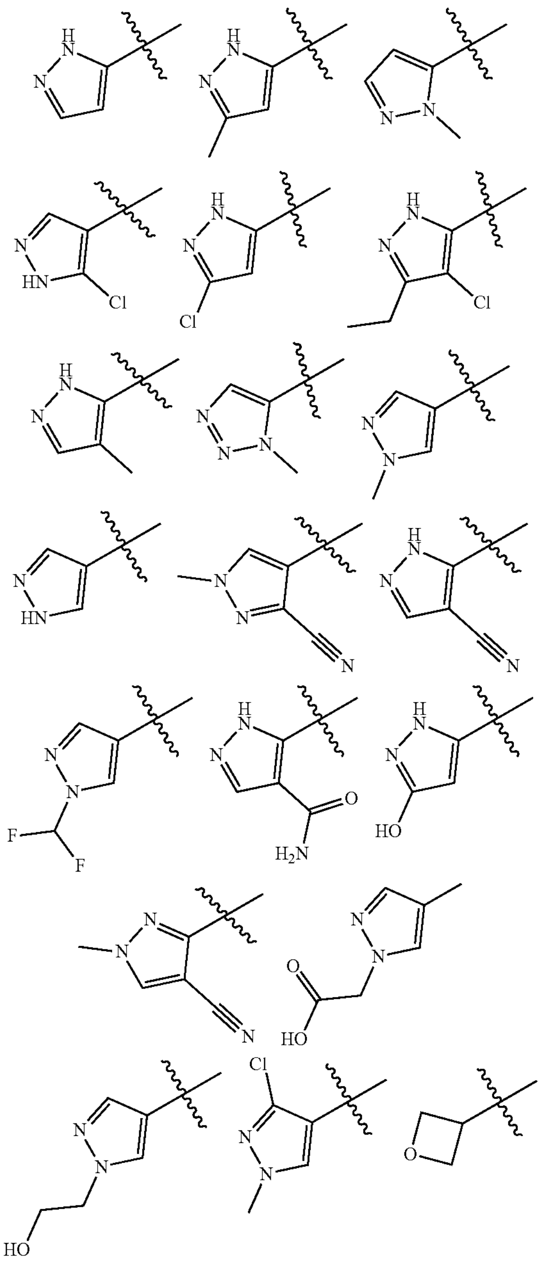

-continued

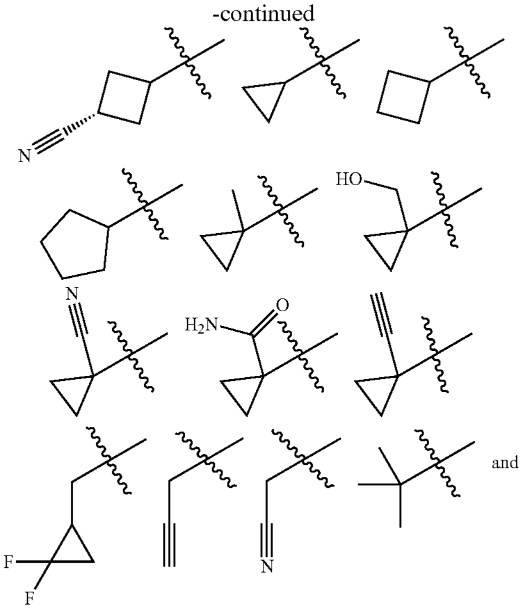

and

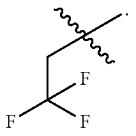

E12. The compound or prodrug, or the pharmaceutically acceptable salt thereof of E1, E2, E3, E4, E5, E6, E7, E8, E9, E10, or E11, wherein $R^b$ is H.

E13. The compound or prodrug, or the pharmaceutically acceptable salt thereof of E1 or E2, wherein $R^1$ is a 5-10 membered heteroaryl that is optionally substituted with one or more groups $R^c$.

E14. The compound or prodrug, or the pharmaceutically acceptable salt thereof of E1 or E2, wherein $R^1$ is a 5-membered heteroaryl that is optionally substituted with one or more groups $R^c$.

E15. The compound or prodrug, or the pharmaceutically acceptable salt thereof of E1, wherein $R^1$ is a 5-membered heteroaryl that is optionally substituted with one or more groups independently selected from the group consisting of cyano, —$NR^dR^e$, and $(C_1-C_6)$alkyl, wherein each $(C_1-C_6)$alkyl is optionally substituted with one or more groups independently selected from the group consisting of halo, and cyano.

E16. The compound or prodrug, or the pharmaceutically acceptable salt thereof of E1 or E2, wherein $R^1$ is selected from the group consisting of:

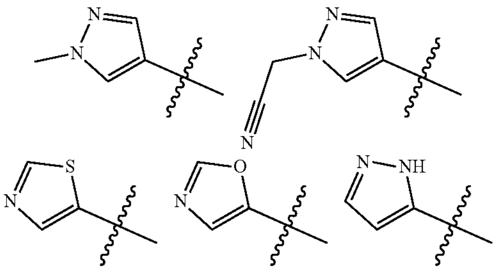

-continued

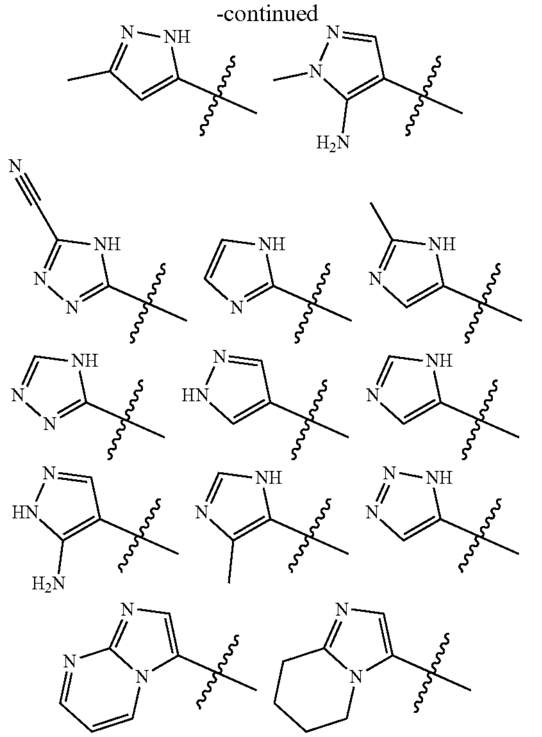

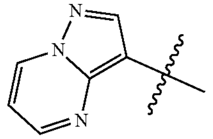

and

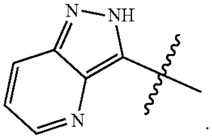

.

E17. The compound or prodrug, or the pharmaceutically acceptable salt thereof of E1, E2, E3, E4, E5, E6, E7, E8, E9, E10, E11, E12, E13, E14, E15, or E16, wherein $R^2$ is a 5-9 membered heteroaryl that is that is optionally substituted with one or more groups $R^s$.

E18. The compound or prodrug, or the pharmaceutically acceptable salt thereof of E1, E2, E3, E4, E5, E6, E7, E8, E9, E10, E11, E12, E13, E14, E15, or E16, wherein $R^2$ is phenyl that is optionally substituted with one or more groups R.

E19. The compound or prodrug, or the pharmaceutically acceptable salt thereof of E1, E2, E3, E4, E5, E6, E7, E8, E9, E10, E11, E12, E13, E14, E15, E16, E17, or E18, wherein each $R^r$ is independently selected from halo, cyano, —$NR^tR^u$, —C(═O)$NR^tR^u$, —$S(O)_2NR^tR^u$, $(C_1-C_6)$alkyl, $(C_3-C_6)$cycloalkyl, $(C_1-C_6)$alkoxy, $(C_1-C_6)$alkylthio, —N(H)$S(O)_2R^x$, and —$S(O)_2R^x$, wherein each $(C_1-C_6)$alkyl is optionally substituted with one or more groups independently selected from the group consisting of hydroxy and —$NR^tR^u$.

E20. The compound or prodrug, or the pharmaceutically acceptable salt thereof of E1, E2, E3, E4, E5, E6, E7, E8, E9, E10, E11, E12, E13, E14, E15, or E16, wherein $R^2$ is selected from the group consisting of:

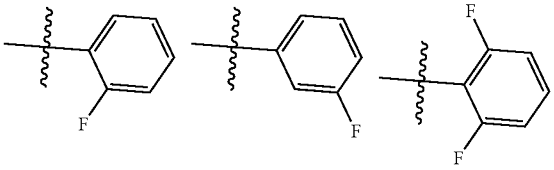

-continued

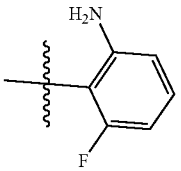
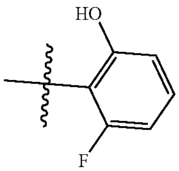
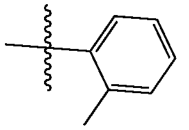
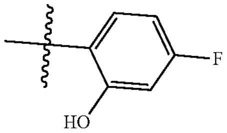
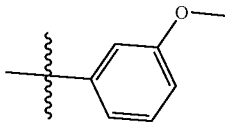
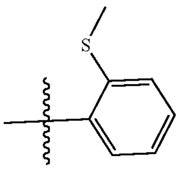
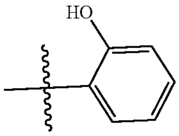
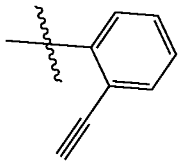
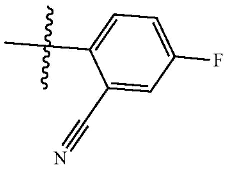
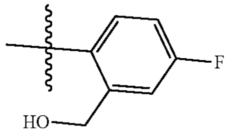
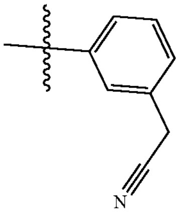
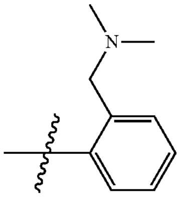
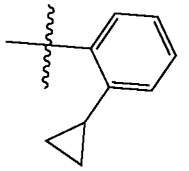
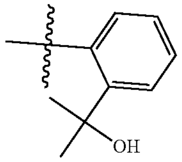
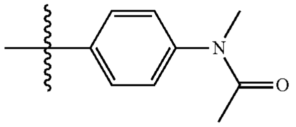
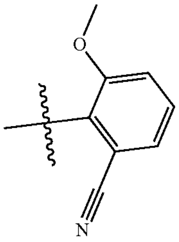
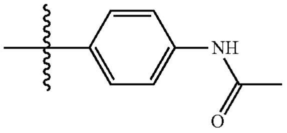
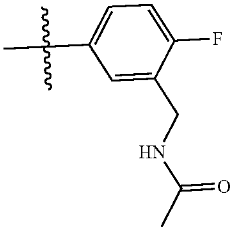
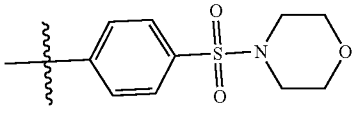

-continued

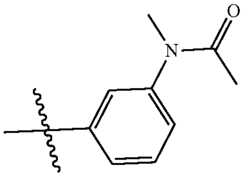
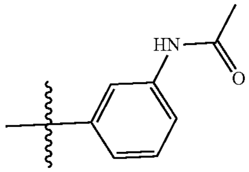
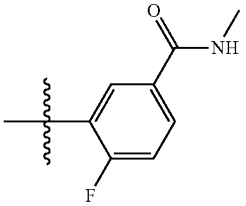
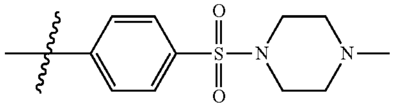
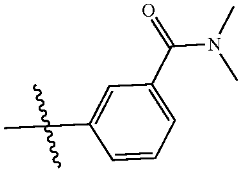
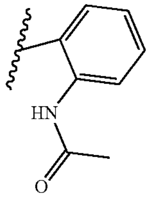
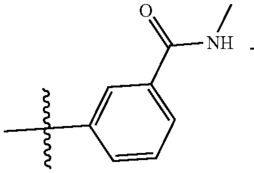
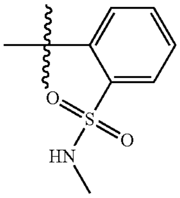
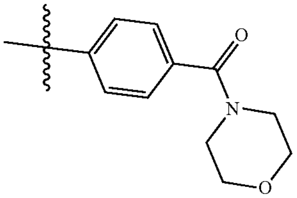

and

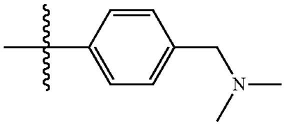

E21. The compound or prodrug, or the pharmaceutically acceptable salt thereof of E1, E2, E3, E4, E5, E6, E7, E8, E9, E10, E11, E12, E13, E14, E15, or E16, wherein $R^2$ is a 5-6 membered heteroaryl that is that is optionally substituted with one or more groups $R^s$.

E22. The compound or prodrug, or the pharmaceutically acceptable salt thereof of E1, E2, E3, E4, E5, E6, E7, E8, E9, E10, E11, E12, E13, E14, E15, E16, or E21, wherein each $R^s$ is independently selected from the group consisting of cyano, —$NR^{Rw}$, —C(═O)$NR^{Rw}$, ($C_1$-$C_6$)alkyl, ($C_3$-$C_6$)cycloalkyl, ($C_1$-$C_6$)alkoxy, ($C_1$-$C_6$)alkylthio, —$S(O)_2R^y$, and ($C_1$-$C_6$)alkanoyl, wherein each ($C_1$-$C_6$)alkyl is optionally substituted with one or more groups independently selected from the group consisting of halo, and —$NR^tR^u$.

E23. The compound or prodrug, or the pharmaceutically acceptable salt thereof of E1, E2, E3, E4, E5, E6, E7, E8, E9, E10, E11, E12, E13, E14, E15, or E16, wherein $R^2$ is selected from the group consisting of:

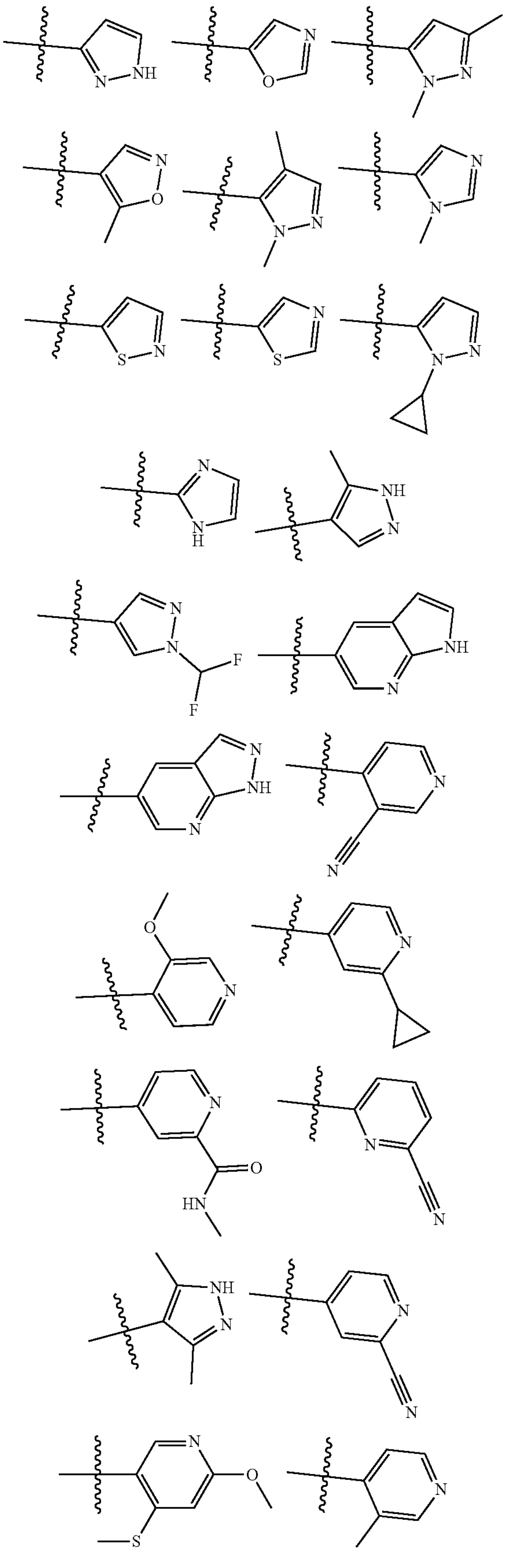

-continued

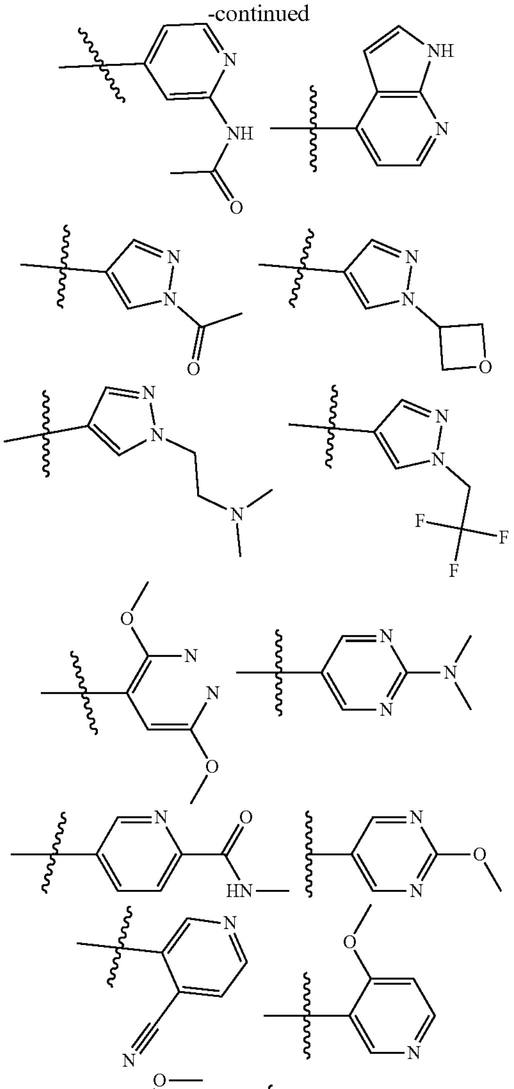

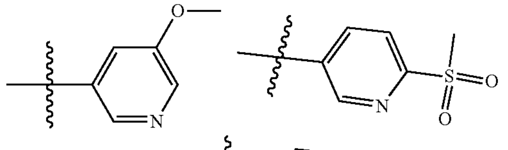

and

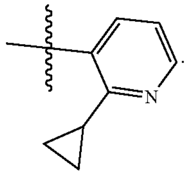

E24. The compound or prodrug, or the pharmaceutically acceptable salt thereof of E1, E3, E4, E5, E6, E7, E8, E9, E10, E11, E12, E13, E14, E15, or E16, wherein $R^2$ is a 3-10 membered heterocycle that is that is optionally substituted with one or more groups $R^z$ E25. The compound or prodrug, or the pharmaceutically acceptable salt thereof of E1, E3, E4, E5, E6, E7, E8, E9, E10, E11, E12, E13, E14, E15, or E16, wherein $R^2$ is a 5-10 membered heterocycle that is that is optionally substituted with one or more groups $R^z$.

E26. The compound or prodrug, or the pharmaceutically acceptable salt thereof of E1, E2, E3, E4, E5, E6, E7, E8, E9, E10, E11, E12, E13, E14, E15, E16, E17, E18, E19, E20, E21, E22, E23, E24, or E25, wherein each $R^z$ is oxo or $(C_1\text{-}C_3)$alkyl.

E27. The compound or prodrug, or the pharmaceutically acceptable salt thereof of E1, E2, E3, E4, E5, E6, E7, E8, E9, E10, E11, E12, E13, E14, E15, or E16, wherein $R^2$ is selected from the group consisting of:

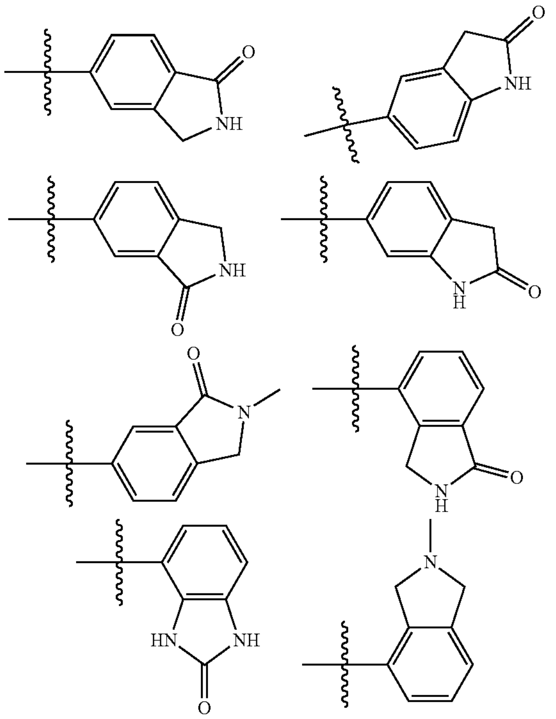

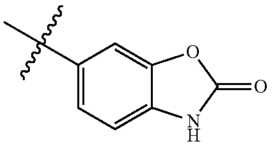 and 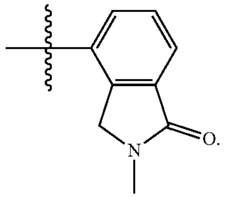

E28. The compound or prodrug, or the pharmaceutically acceptable salt thereof of E1, E3, E4, E5, E6, E7, E8, E9, E10, E11, E12, E13, E14, E15, or E16, wherein $R^2$ is a 6-12 membered aryl that is substituted with one or more groups $R^r$; $R^r$ is —$NR^tR^u$ or ($C_2$-$C_6$)alkynyl that is optionally substituted with one or more groups independently selected from the group consisting of halo, hydroxy, cyano, and oxo; $R^t$ is H; and $R^u$ is ($C_2$-$C_6$)alkynyl-C(═O)— that is optionally substituted with one or more groups independently selected from the group consisting of halo, hydroxy, cyano, and oxo.

E29. The compound or prodrug, or the pharmaceutically acceptable salt thereof of E1, E2, E3, E4, E5, E6, E7, E8, E9, E10, E11, E12, E13, E14, E15, or E16, wherein $R^2$ is a phenyl that is substituted with one or more groups $R^r$; and $R^r$ ($C_2$-$C_6$)alkynyl that is optionally substituted with one or more groups independently selected from the group consisting of hydroxy and cyano.

E30. The compound or prodrug, or the pharmaceutically acceptable salt thereof of E1, E2, E3, E4, E5, E6, E7, E8, E9, E10, E11, E12, E13, E14, E15, or E16, wherein $R^2$ is.

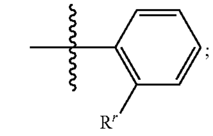

and $R^e$ ($C_2$-$C_6$)alkynyl that is substituted with hydroxy.

E31. The compound or prodrug, or the pharmaceutically acceptable salt thereof of E1, E2, E3, E4, E5, E6, E7, E8, E9, E10, E11, E12, E13, E14, E15, or E16, wherein $R^2$ is selected from the group consisting of:

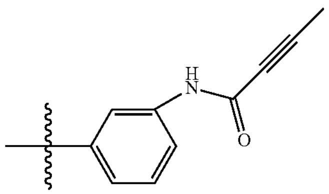 and

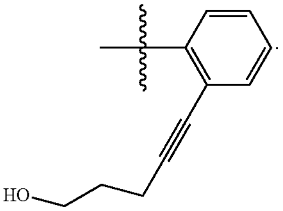

E32. The compound or prodrug, or the pharmaceutically acceptable salt thereof of E1, which is selected from the group consisting of:

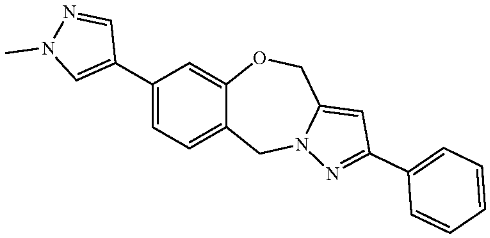

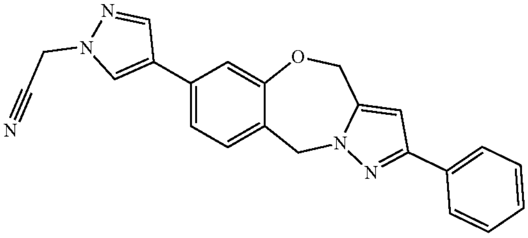

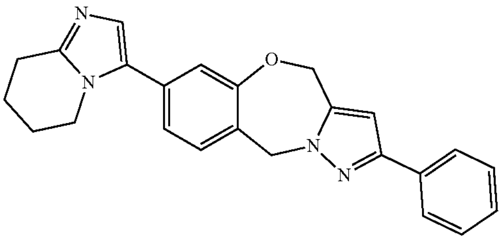

-continued
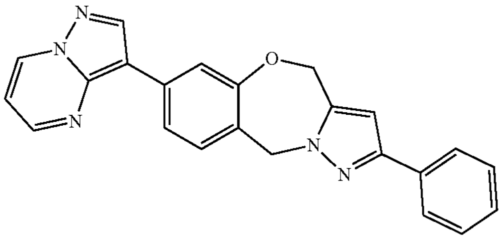
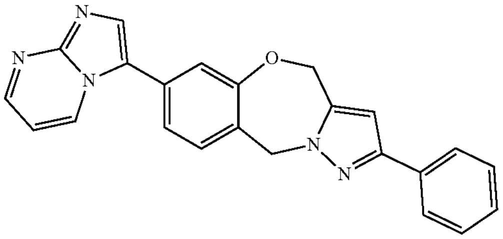
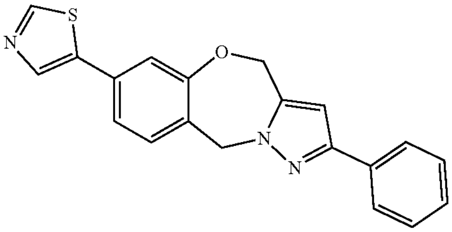
and
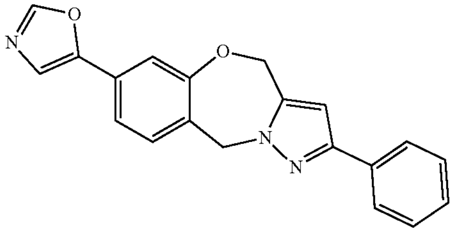 [SMILES: c1ccc(-c2cc3n(n2)Cc2ccc(-c4cnco4)cc2OC3)cc1]
and prodrugs and pharmaceutically acceptable salts thereof.
E33. The compound or prodrug, or the pharmaceutically acceptable salt thereof of E1, which is selected from the group consisting of:
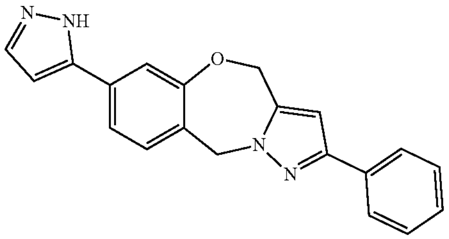
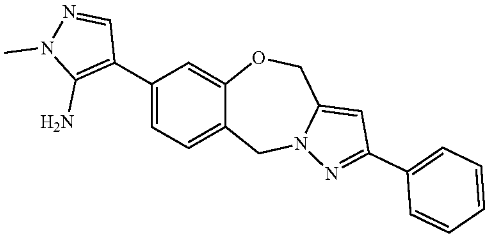
-continued
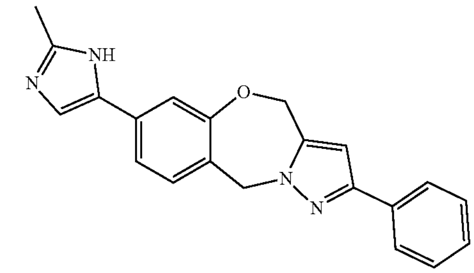
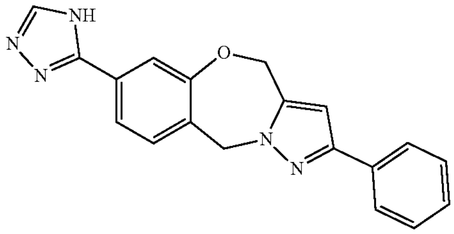
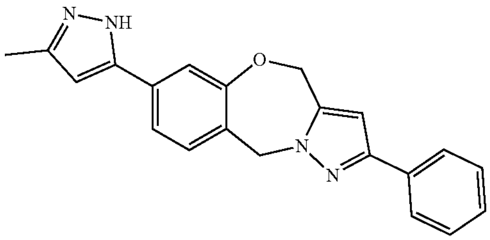
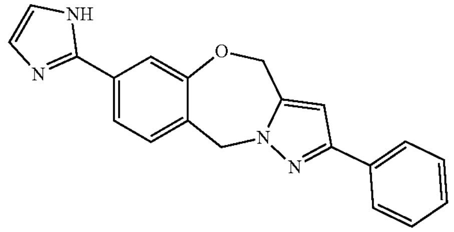
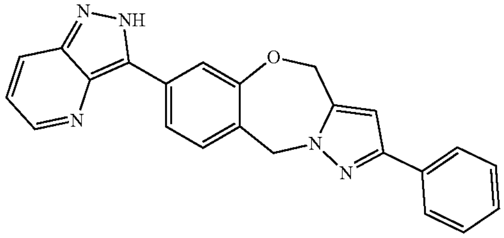
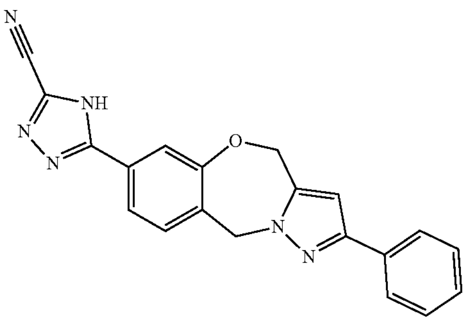

-continued
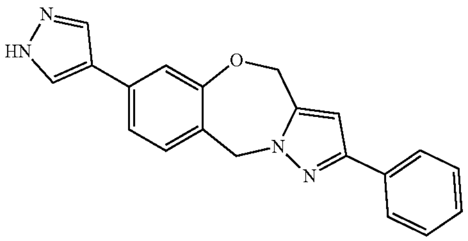
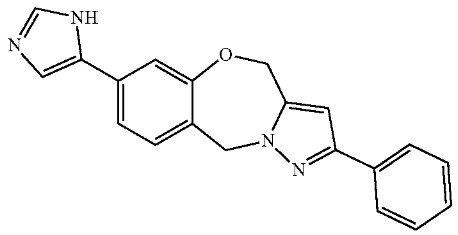
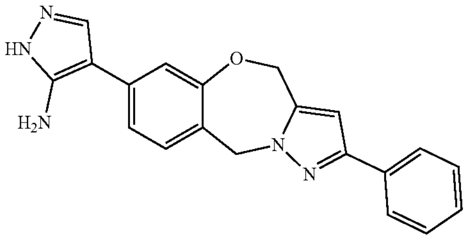
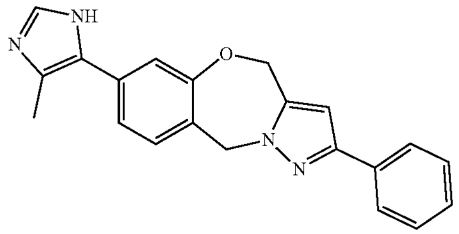
and
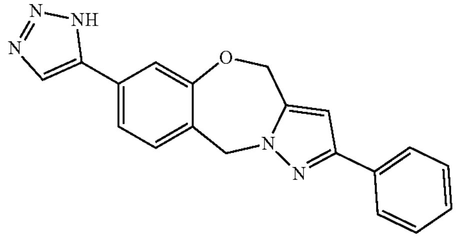
and prodrugs and pharmaceutically acceptable salts thereof.
E34. The compound or prodrug, or the pharmaceutically acceptable salt thereof of E1, which is selected from the group consisting of:
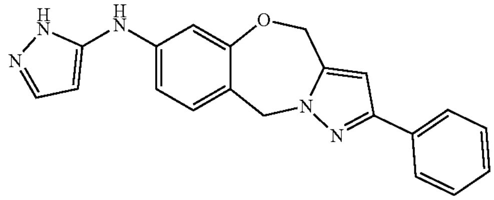
-continued
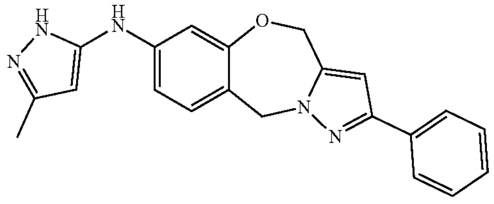
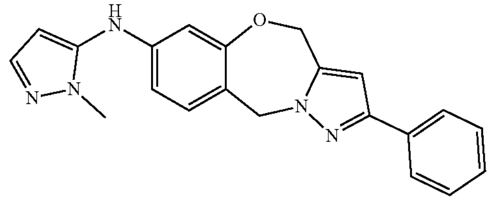
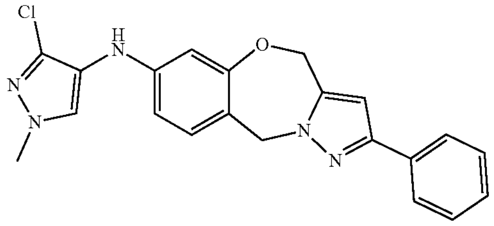
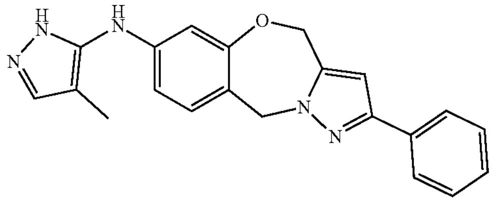
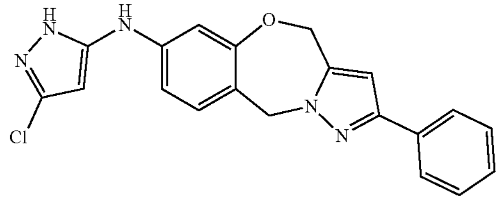
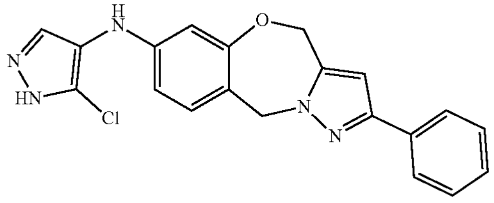
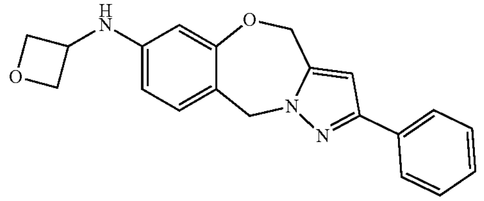
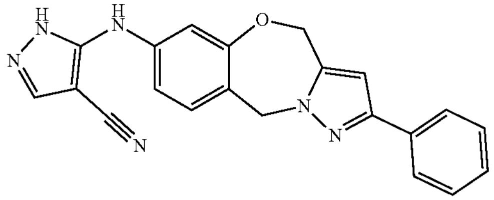

-continued
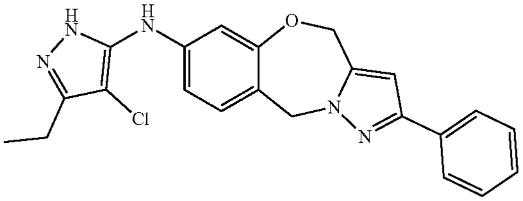
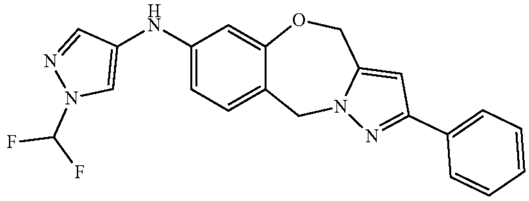
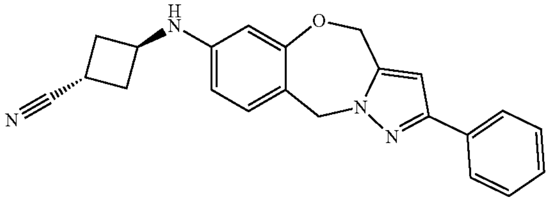
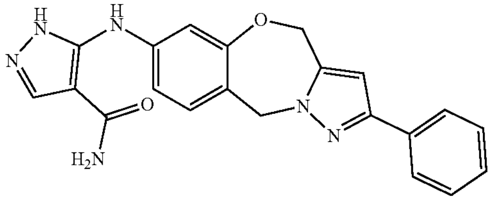
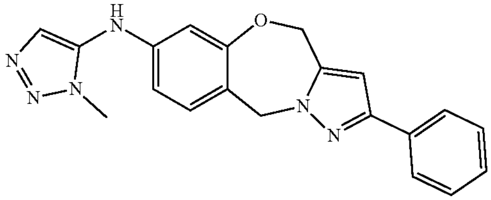
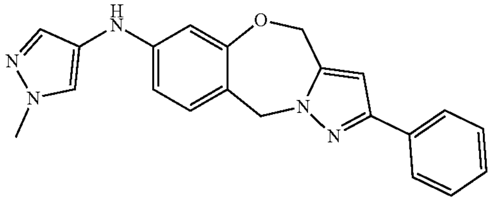
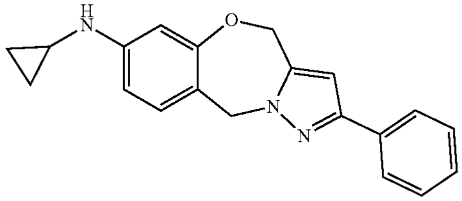
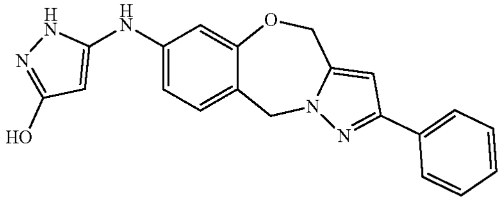
-continued
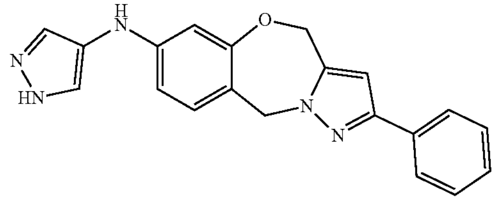
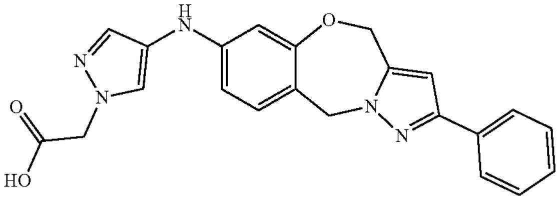
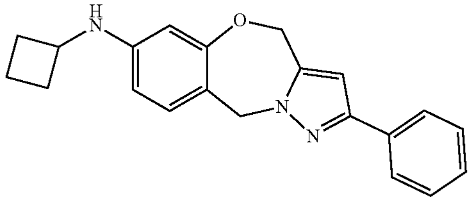
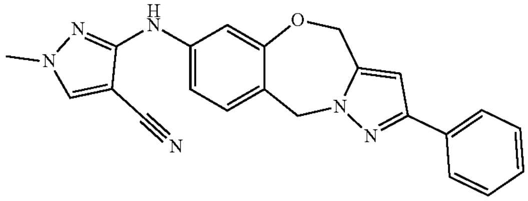
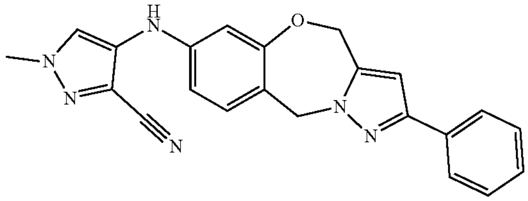
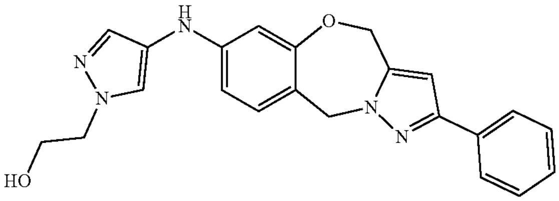
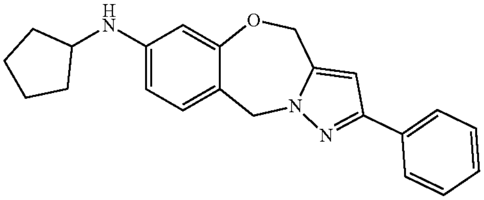
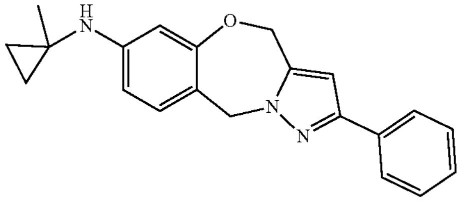

-continued
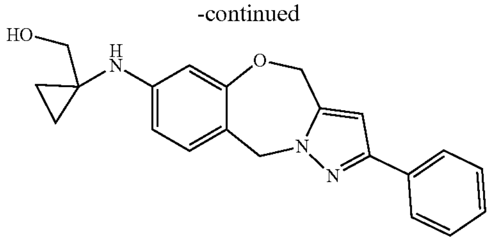
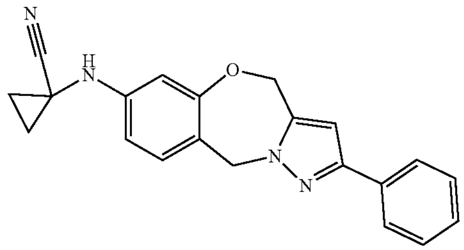
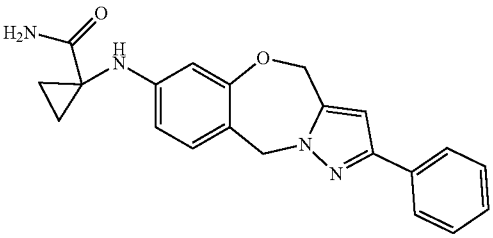
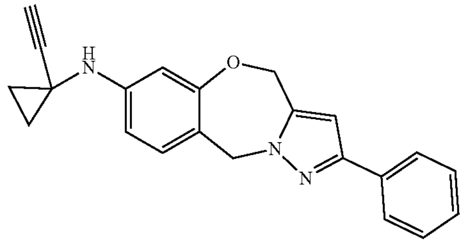
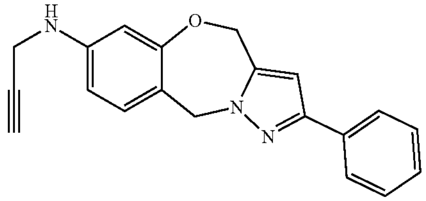
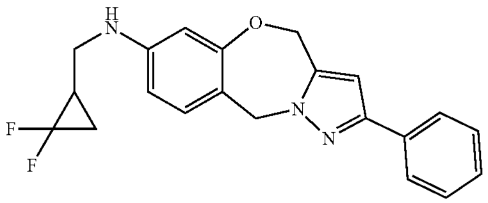
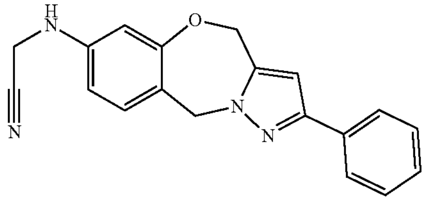
-continued
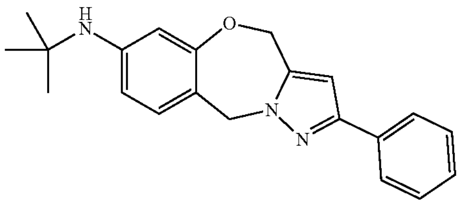
and
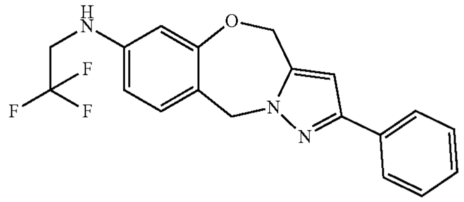
and prodrugs and pharmaceutically acceptable salts thereof.
E35. The compound or prodrug, or the pharmaceutically acceptable salt thereof of E1, which is selected from the group consisting of:
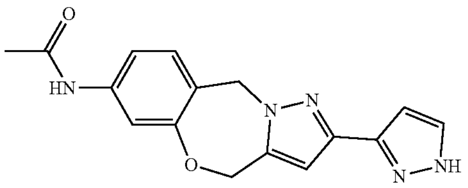
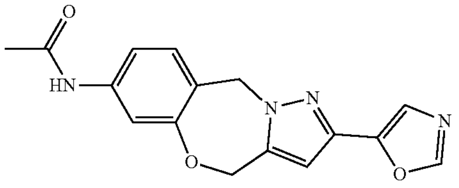
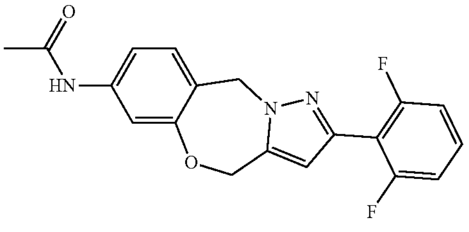
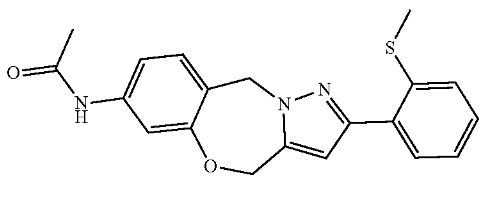
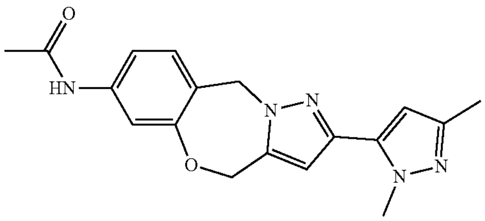

-continued
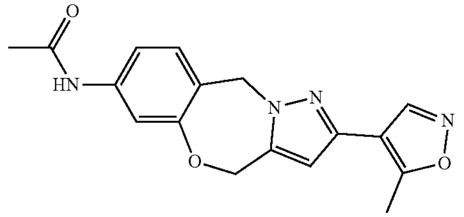
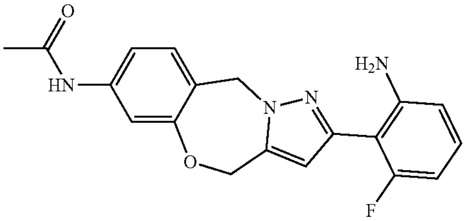
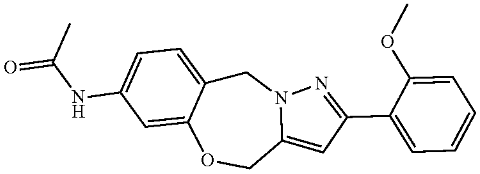
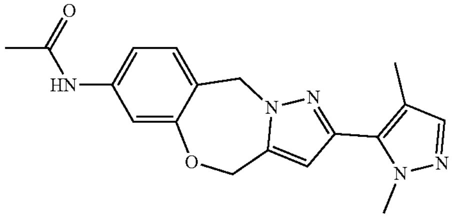
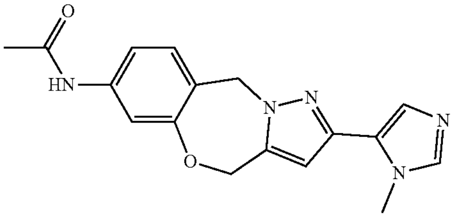
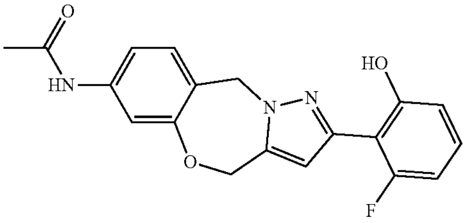
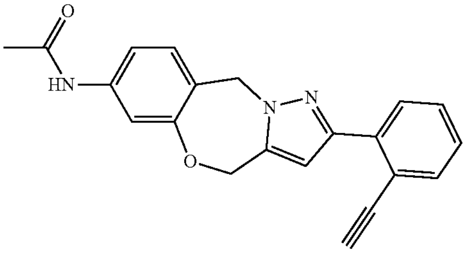
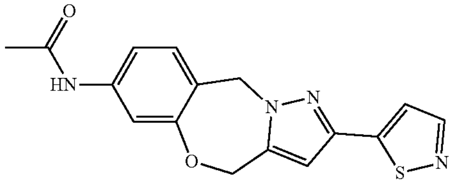
-continued
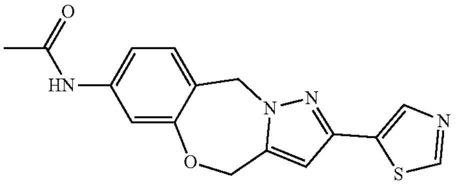
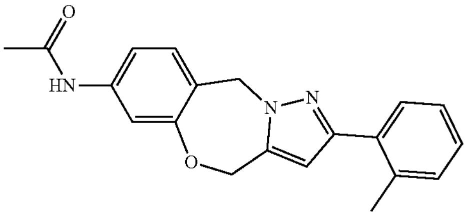
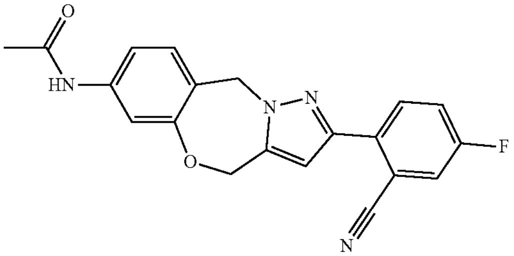
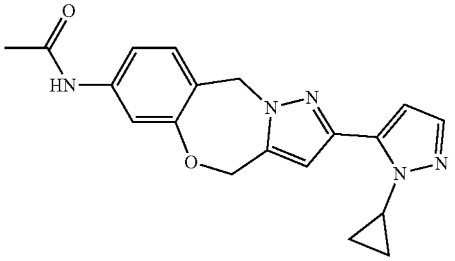
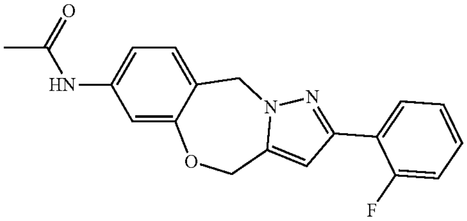
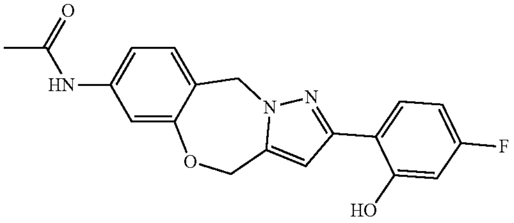
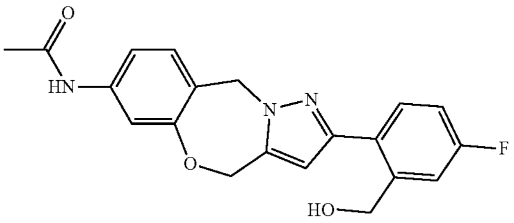

-continued
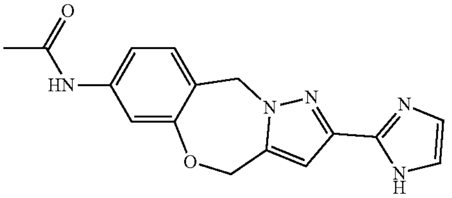
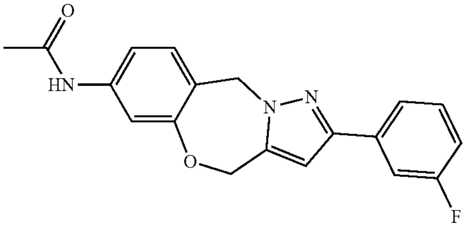
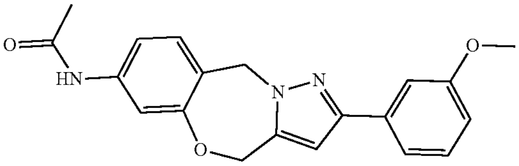
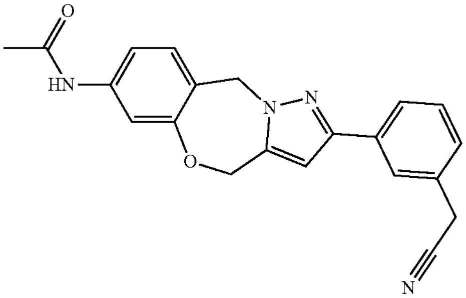
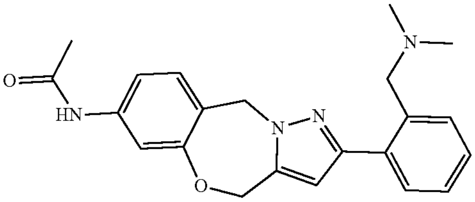
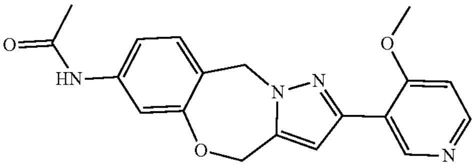
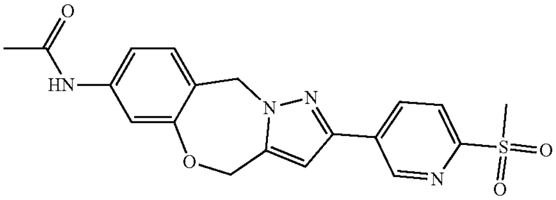
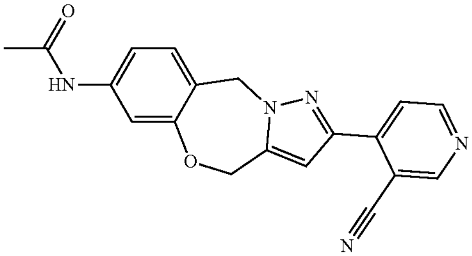
-continued
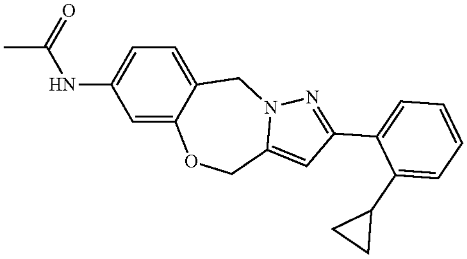
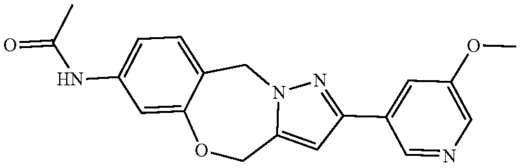
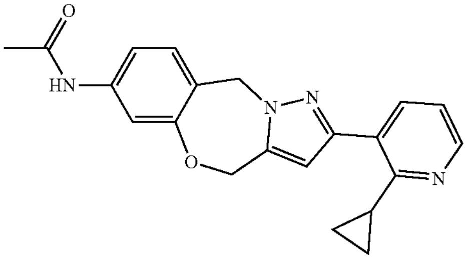
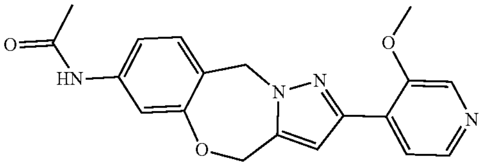
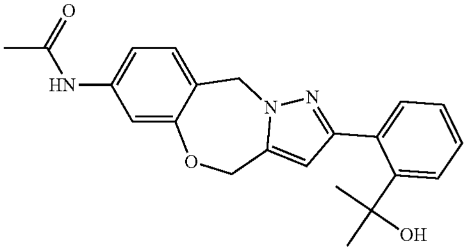
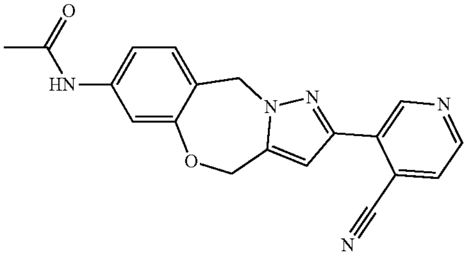
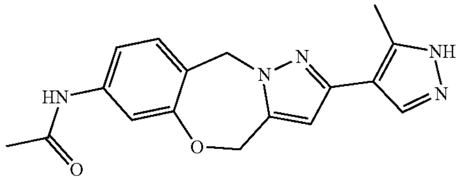

-continued
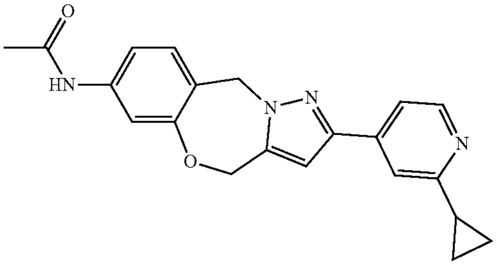
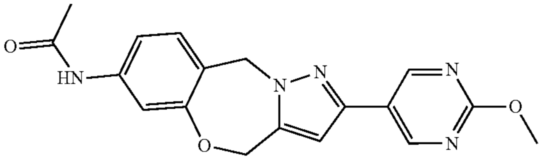
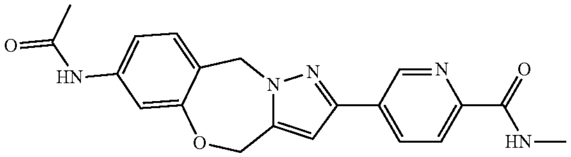
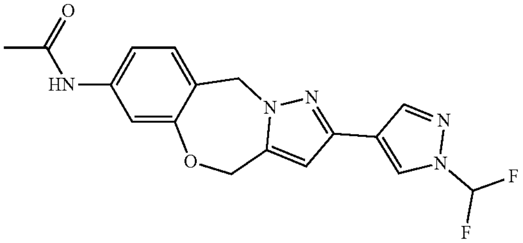
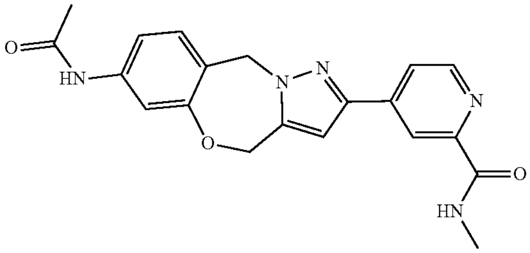
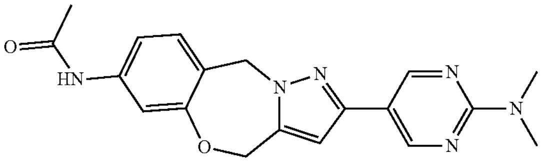
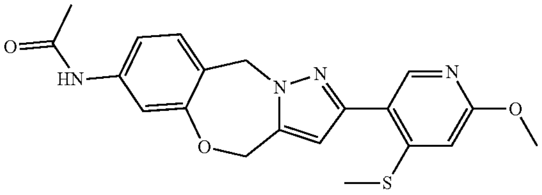
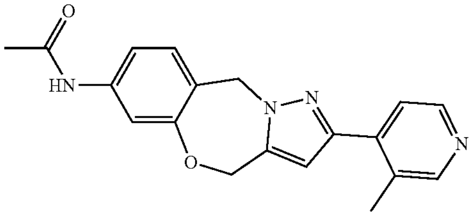
-continued
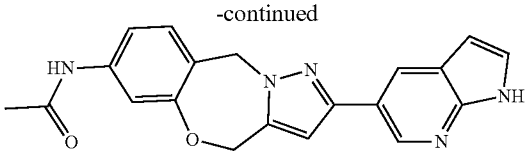
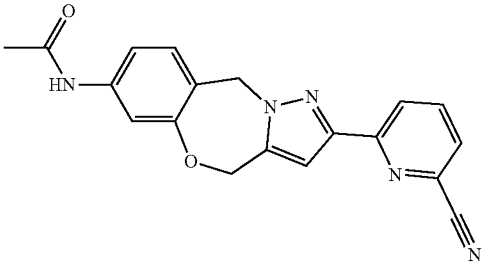
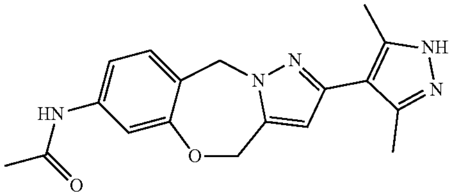
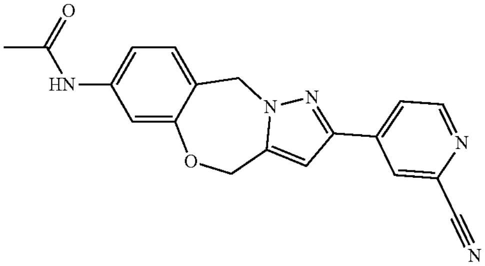
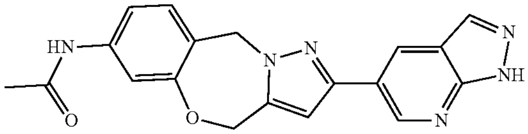
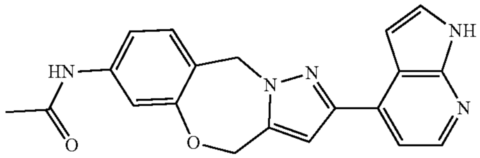
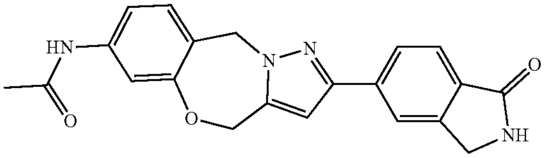
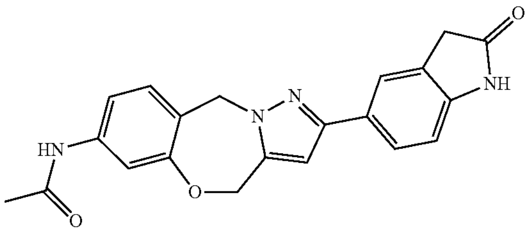
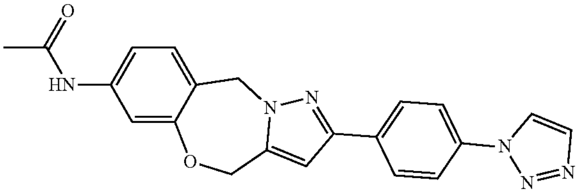

-continued
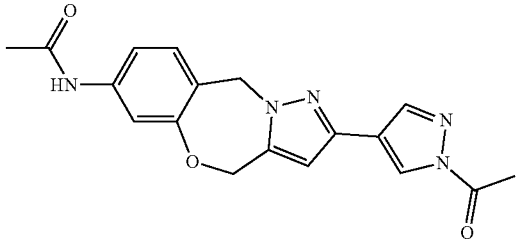
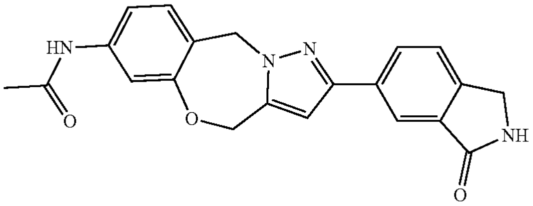
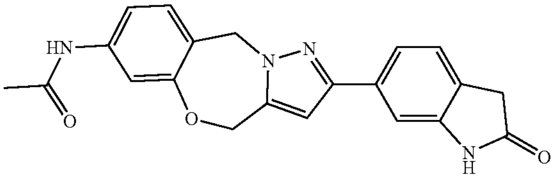
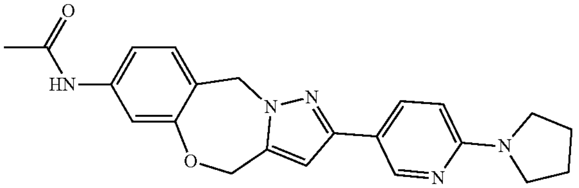
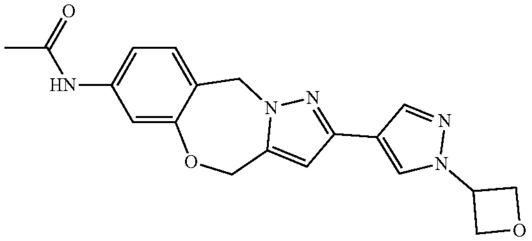
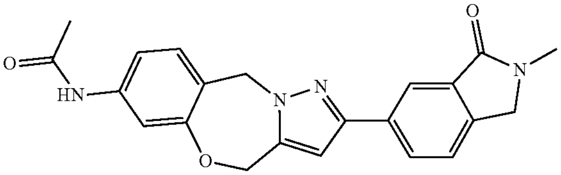
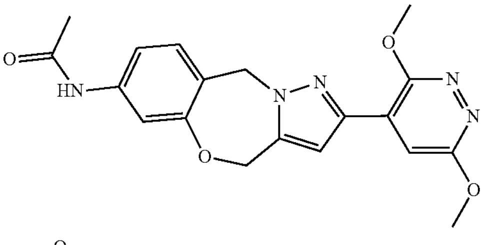
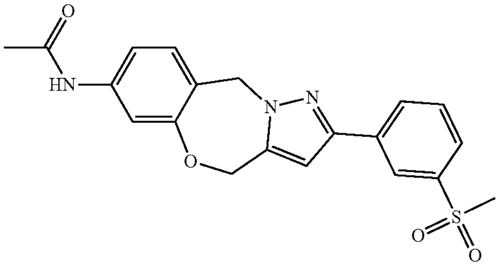
-continued
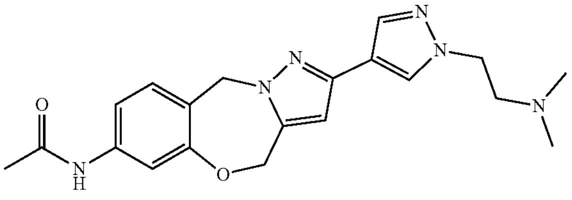
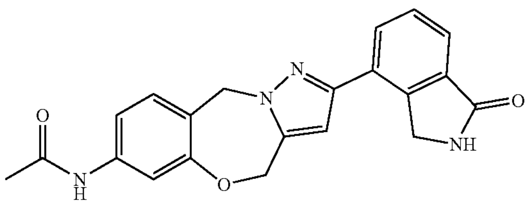
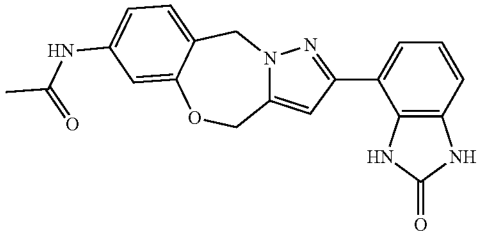
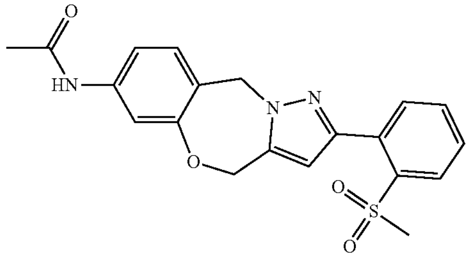
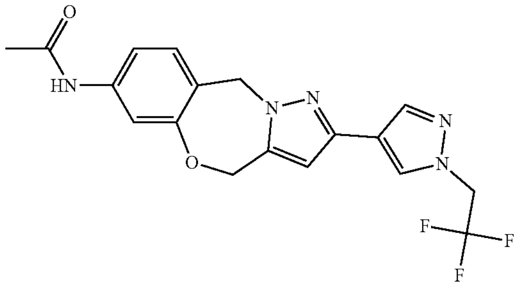
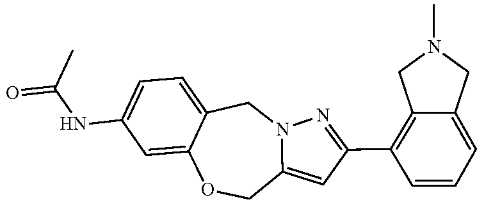
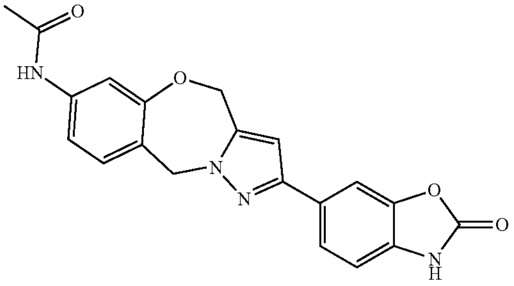

-continued
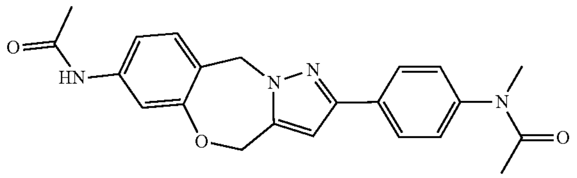
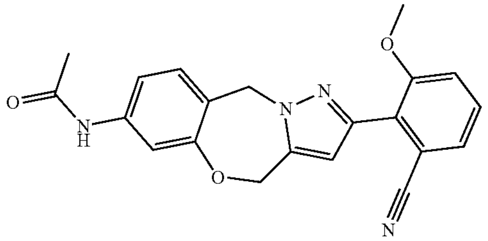
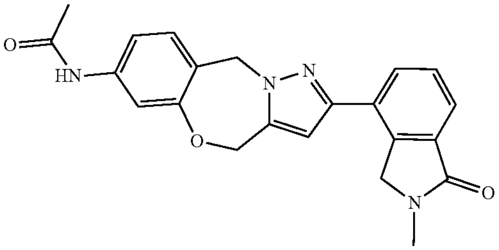
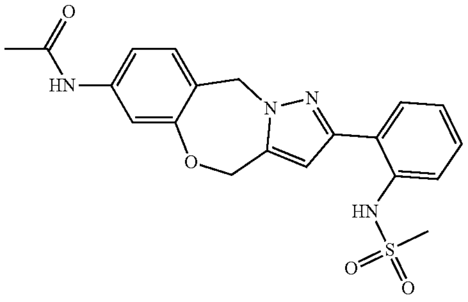
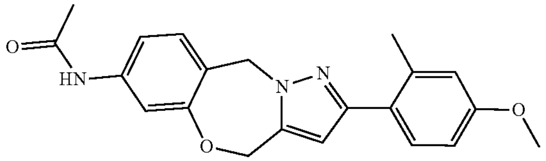
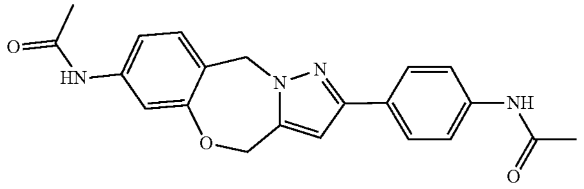
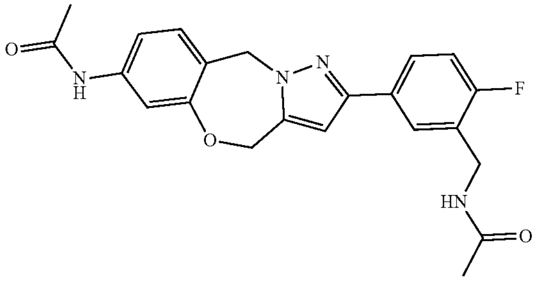
-continued
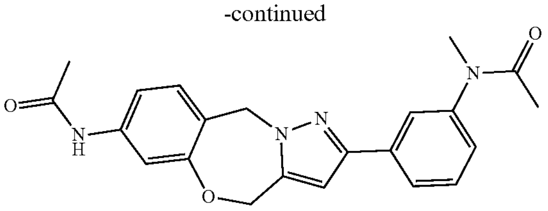
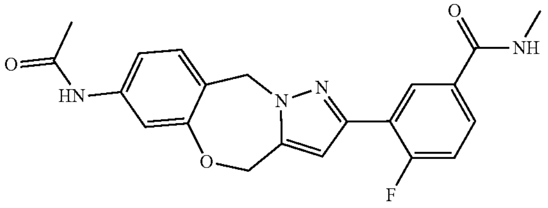
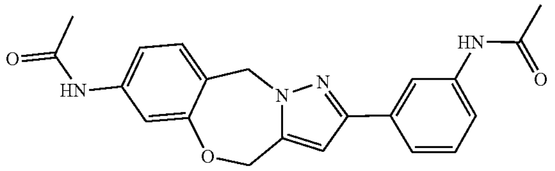
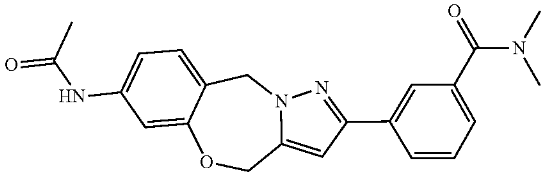
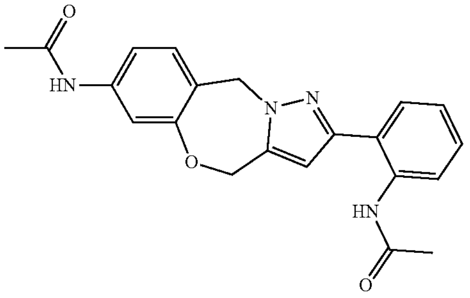
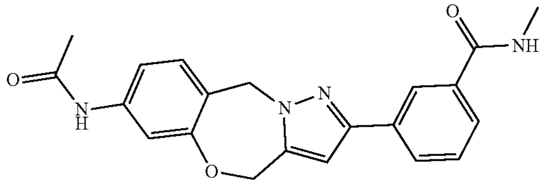
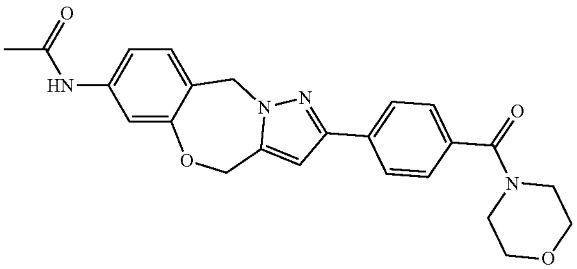
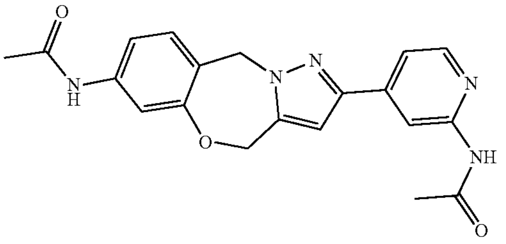

-continued

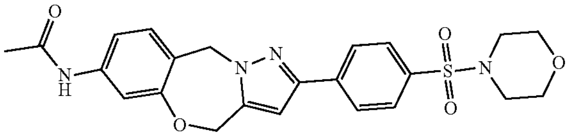

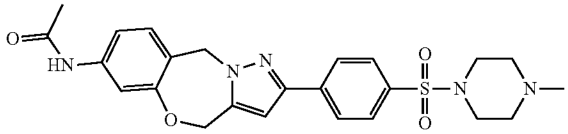

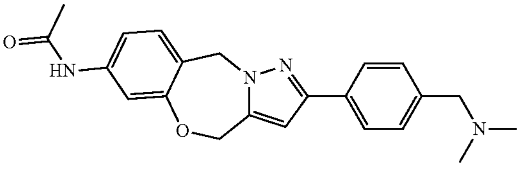

and

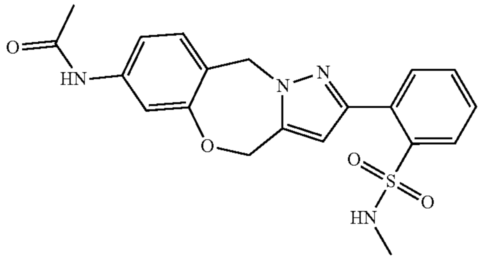

and prodrugs and pharmaceutically acceptable salts thereof.

E36. The compound or prodrug, or the pharmaceutically acceptable salt thereof of E1, which is selected from the group consisting of:

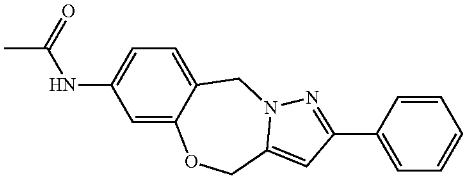

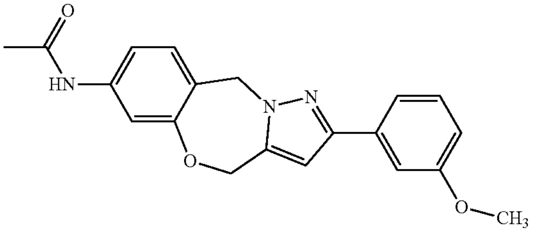

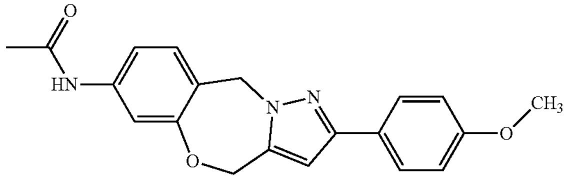

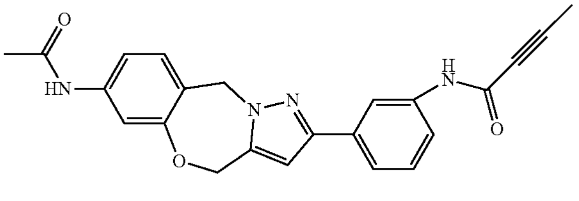

-continued

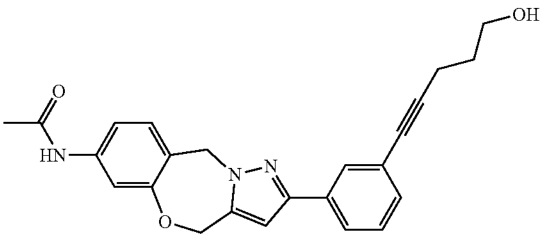

and

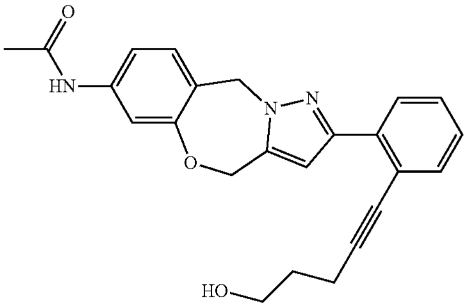

and prodrugs and pharmaceutically acceptable salts thereof.

E37. The compound or prodrug, or the pharmaceutically acceptable salt thereof of E1, which is selected from the group consisting of:

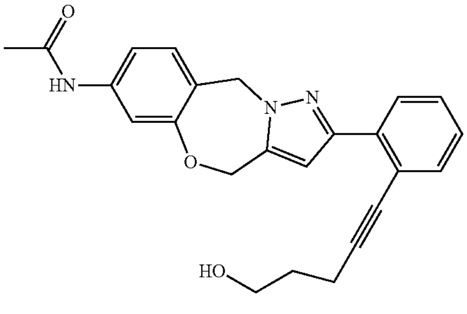 [SMILES: CC(=O)Nc1ccc2c(c1)OCc1cc(-c3ccccc3C#CCCCO)nn1C2]

and prodrugs and pharmaceutically acceptable salts thereof.

E38. The prodrug of E1, which is a compound of formula (I) that comprises a hydroxy group that has been converted to a prodrug group that increases the aqueous solubility of the compound or a pharmaceutically acceptable salt thereof.

E39. The prodrug or pharmaceutically acceptable salt thereof of E38, wherein the hydroxy group has been converted to a prodrug group selected from the group consisting of a phosphate,

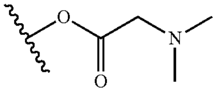

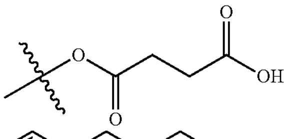

and

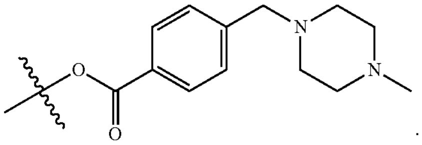

.

E40. The prodrug of E1, which is selected from the group consisting of:
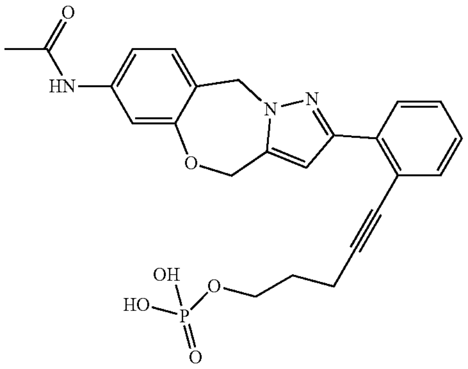
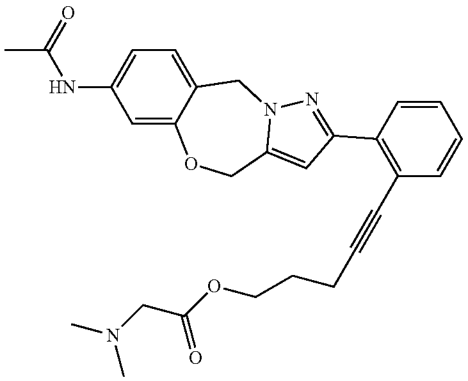
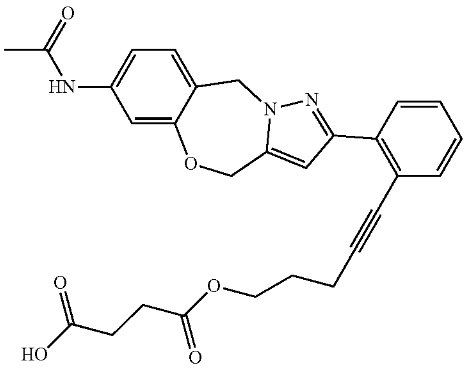
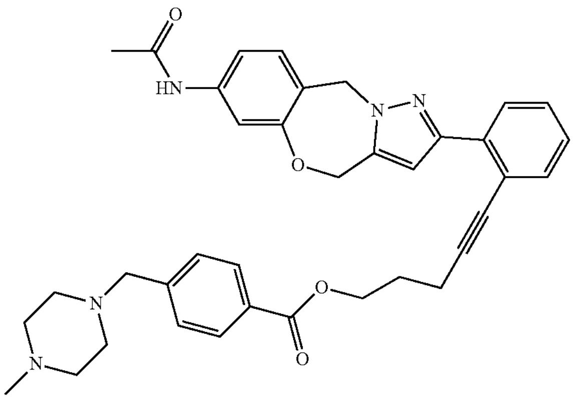
-continued
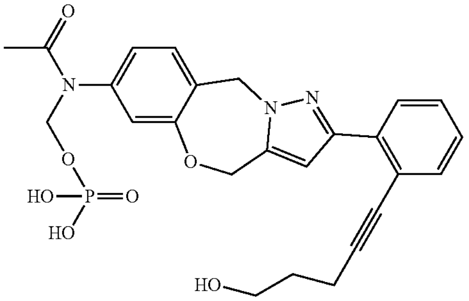
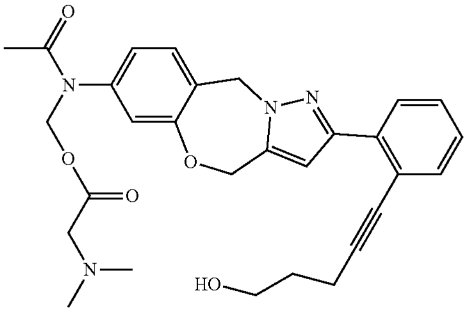
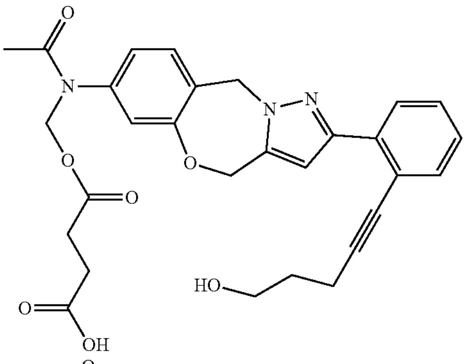
and
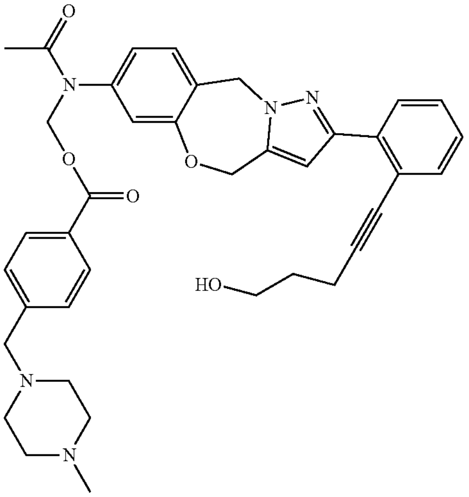
and pharmaceutically acceptable salts thereof.
E41. The compound or prodrug, or the pharmaceutically acceptable salt thereof of E1, E2, E3, E4, E5, E6, E12, E18, or E19, provided the compound is not:

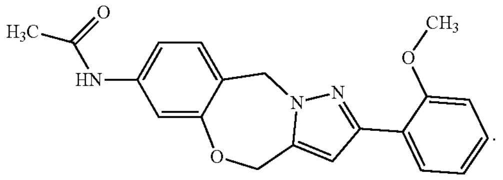 [SMILES: COc1ccccc1-c1cc2n(n1)Cc1ccc(NC(C)=O)cc1OC2]

E42. The compound or prodrug, or the pharmaceutically acceptable salt thereof of E1, E2, E3, E12, E18, or E19, provided $R^1$ in not 3-pentynoylamino or amino, when $R^2$ is 2-methoxyphenyl.

E43. The compound or prodrug, or the pharmaceutically acceptable salt thereof of E1, E2, E3, E4, E5, E6, E7, E8, E9, E10, E11, E12, E13, E14, E15, E16, E18, or E19, provided $R^2$ is not 2-methoxyphenyl.

E44. A compound selected from the group consisting of:

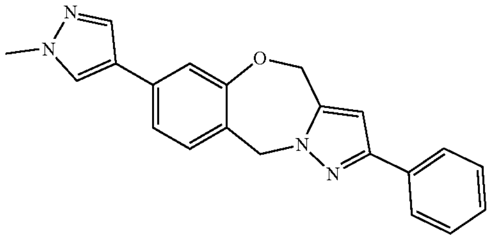

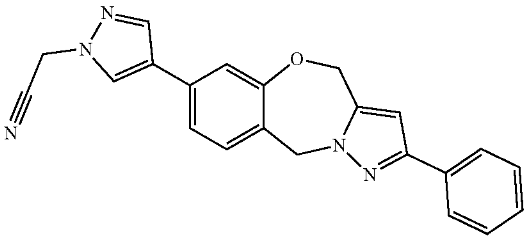

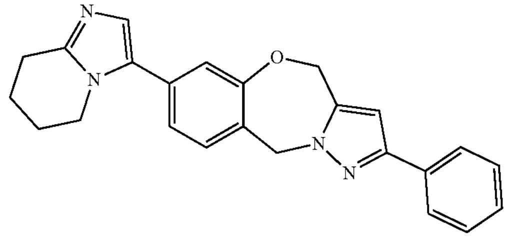

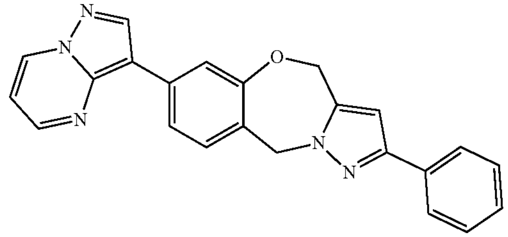

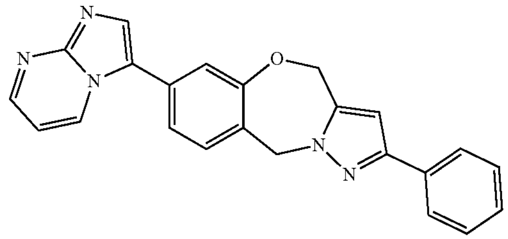

-continued

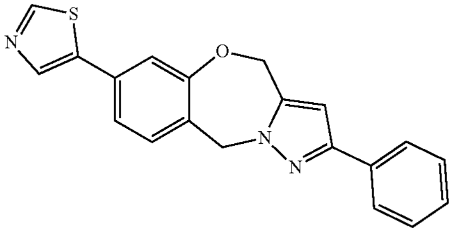

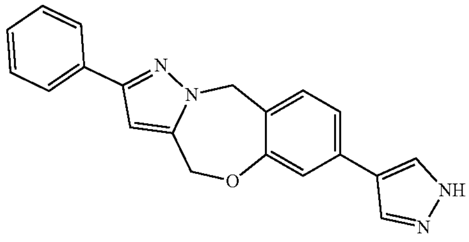

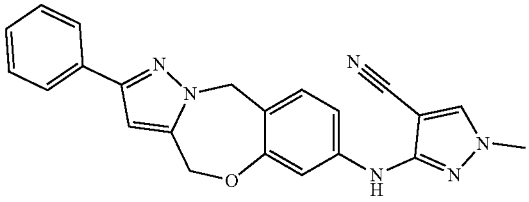

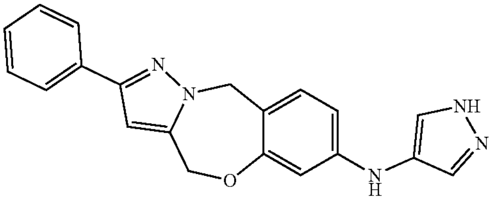

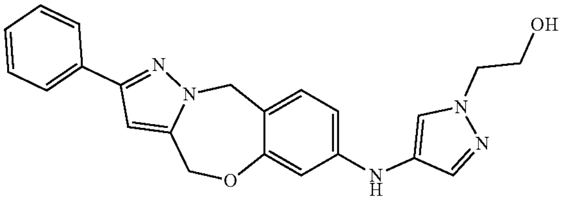

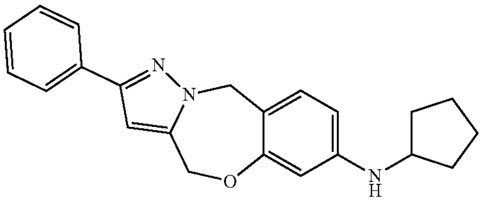

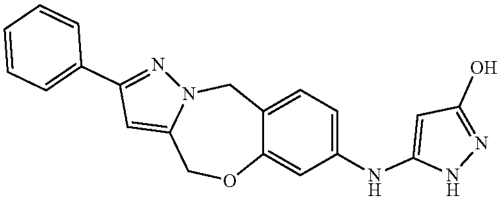

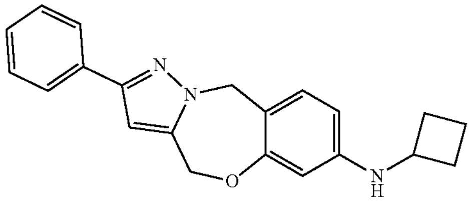

-continued
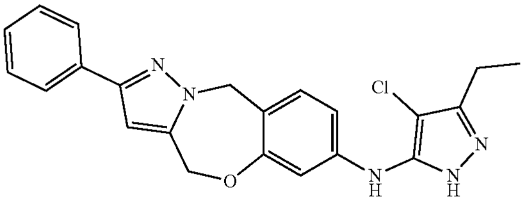
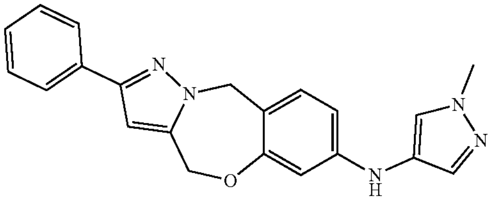
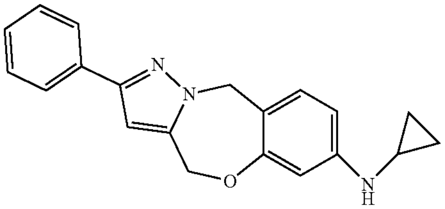
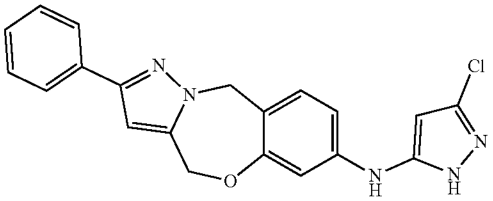
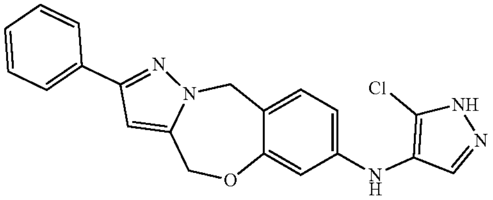
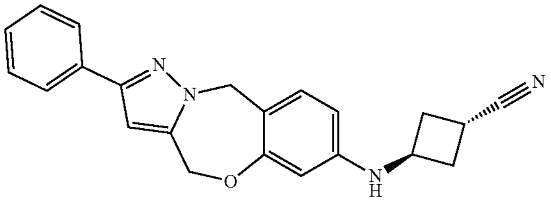
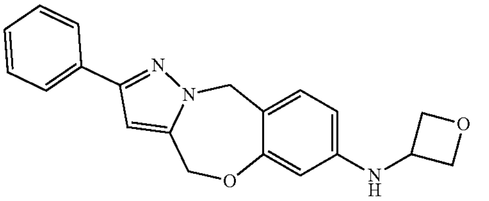
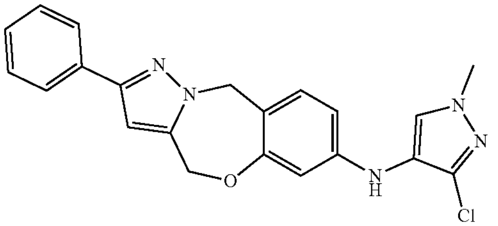
-continued
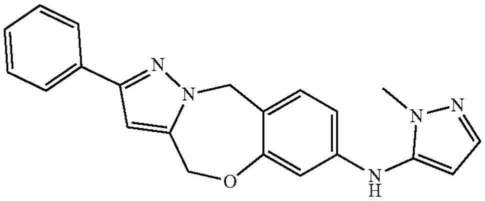
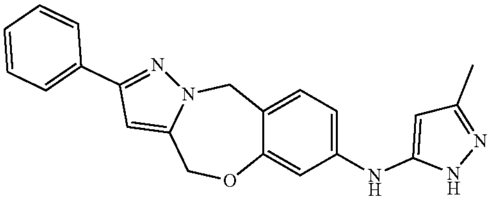
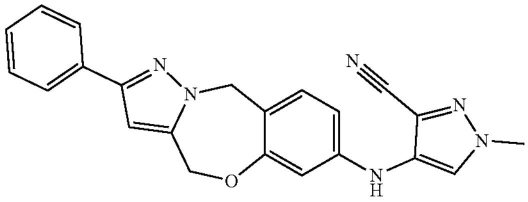
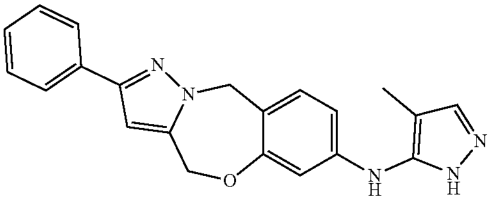
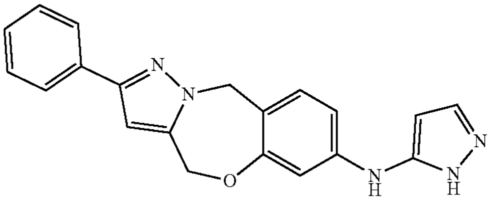
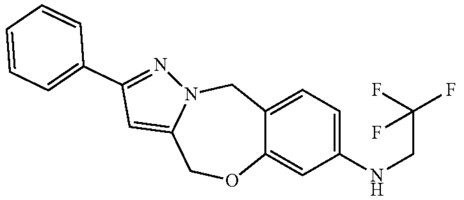
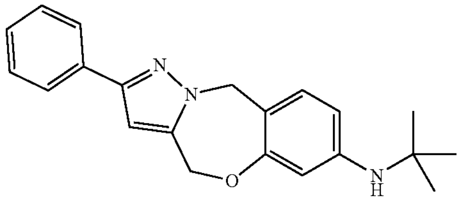
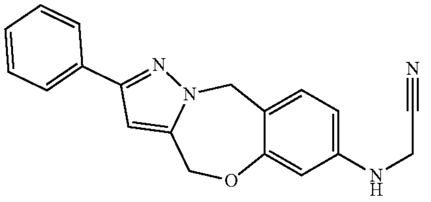

-continued
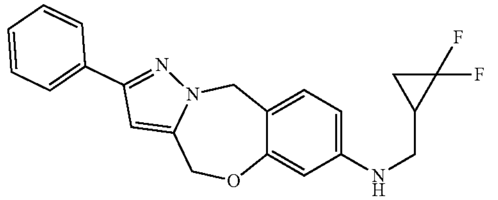
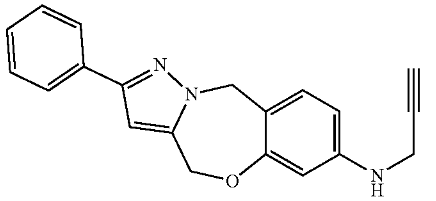
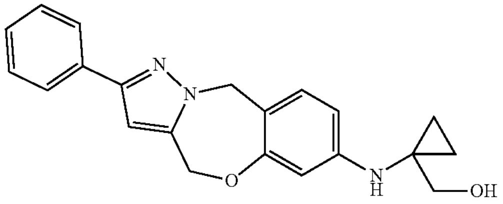
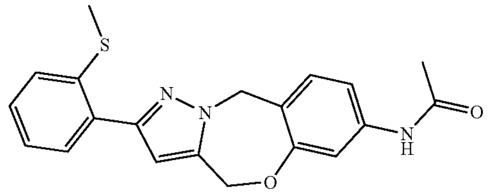
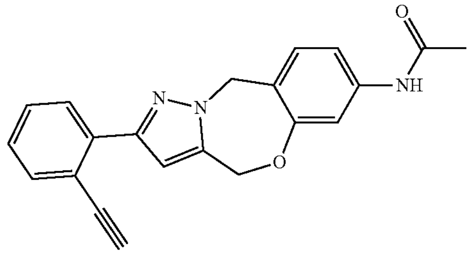
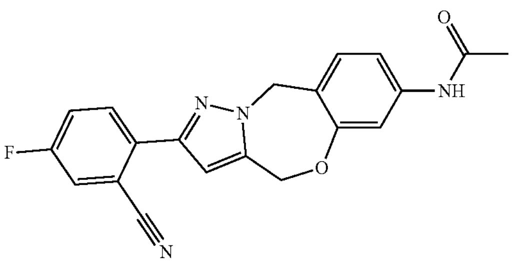
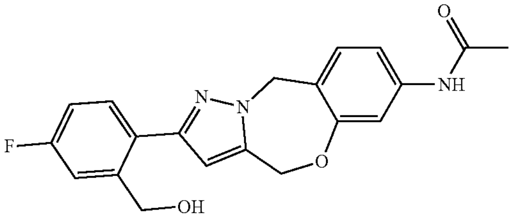
-continued
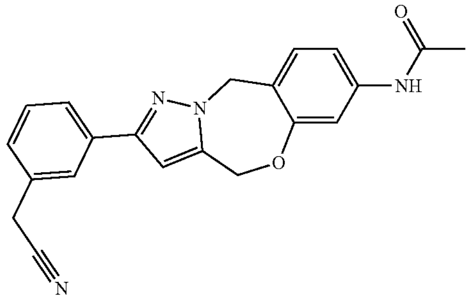
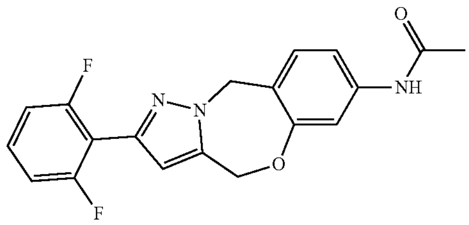
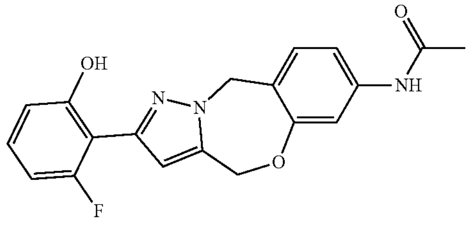
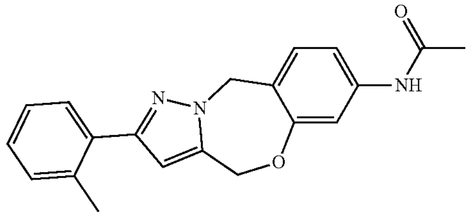
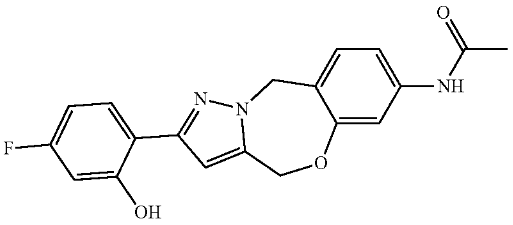
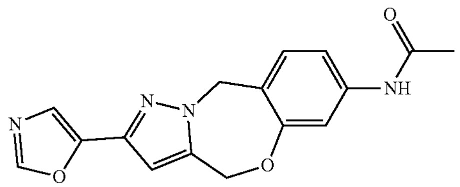
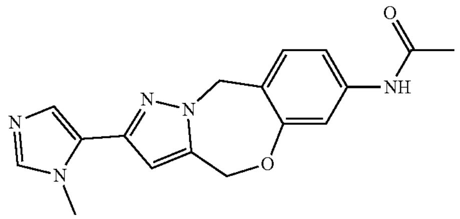

-continued
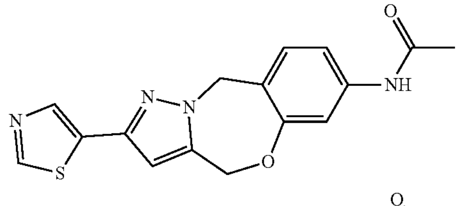
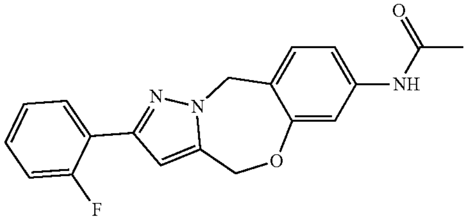
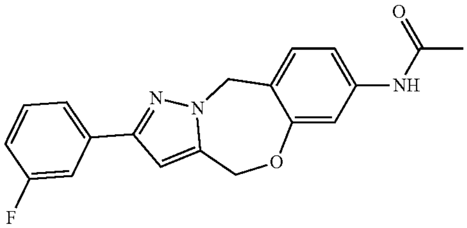
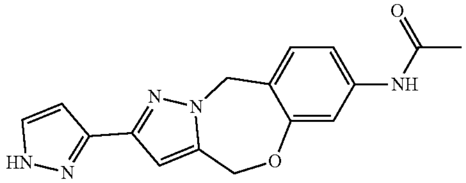
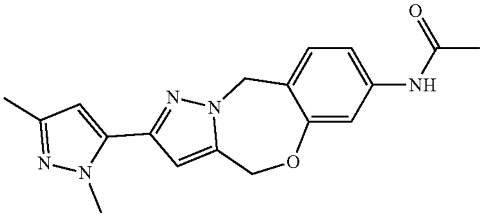
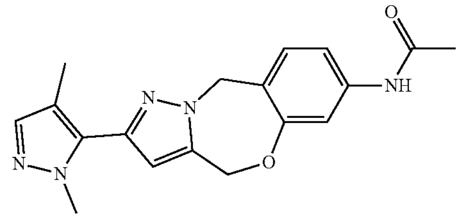
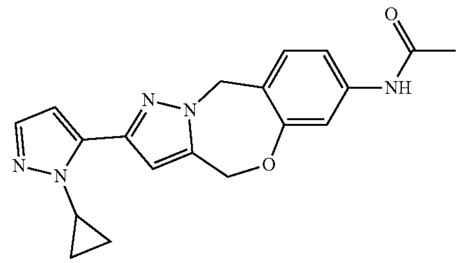
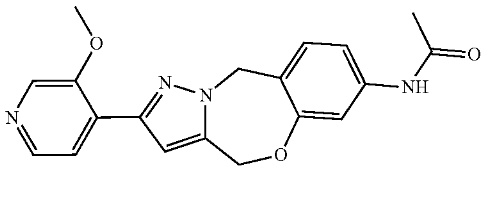
-continued
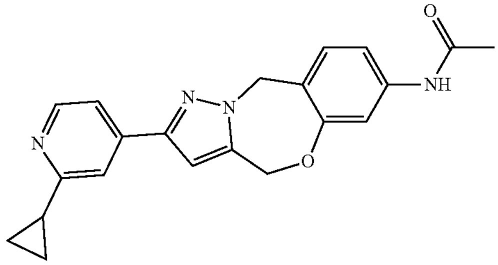
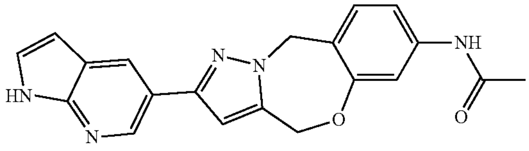
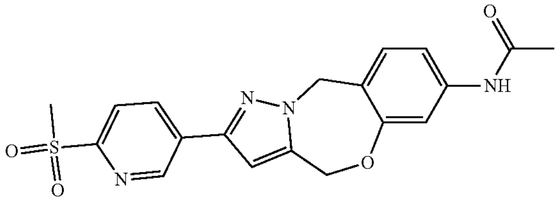
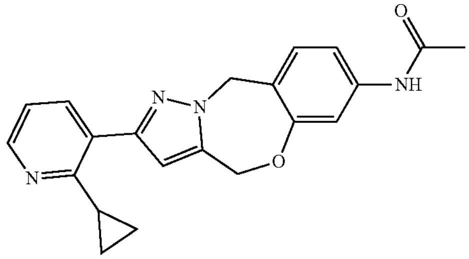
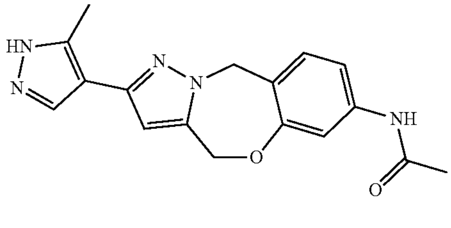
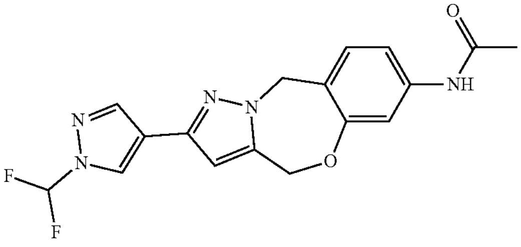
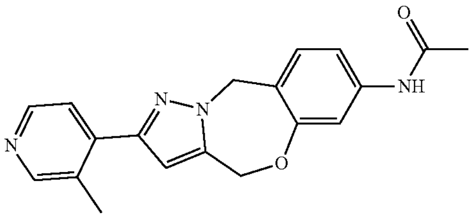

-continued
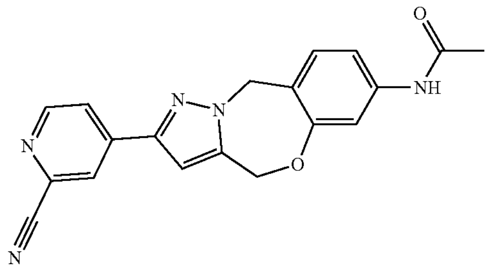
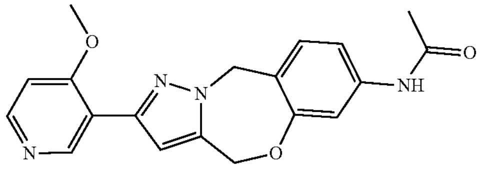
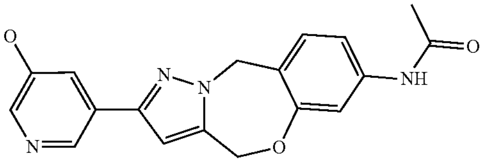
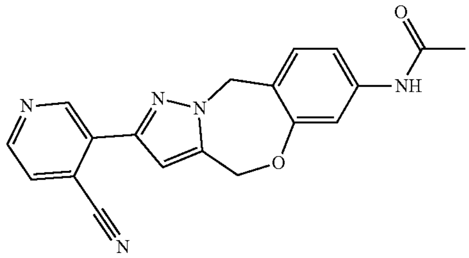
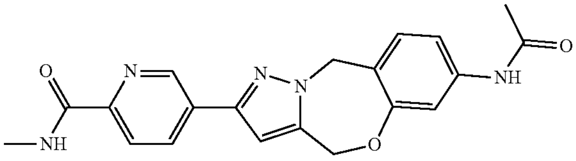
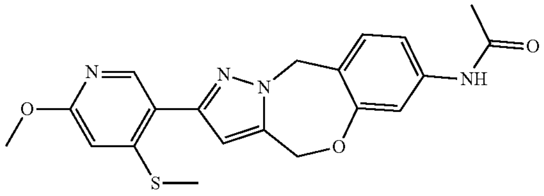
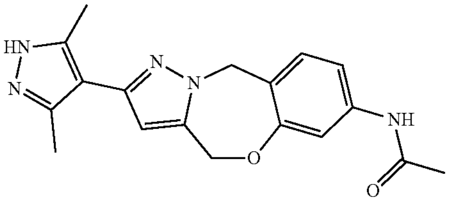
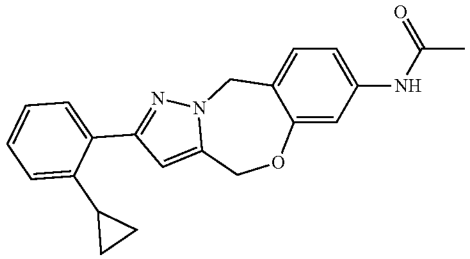
-continued
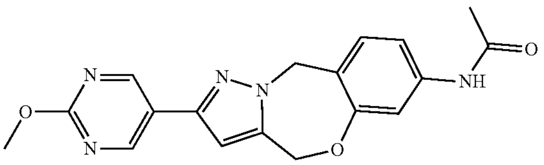
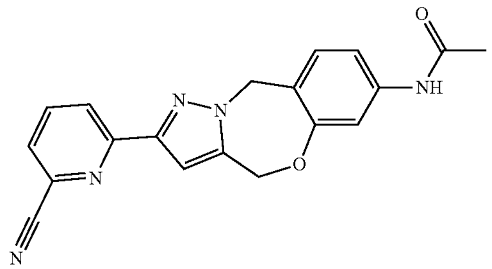
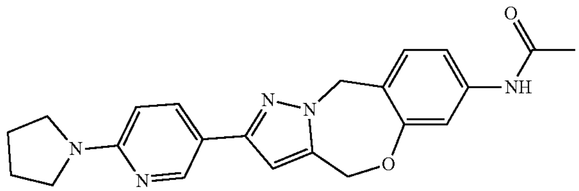
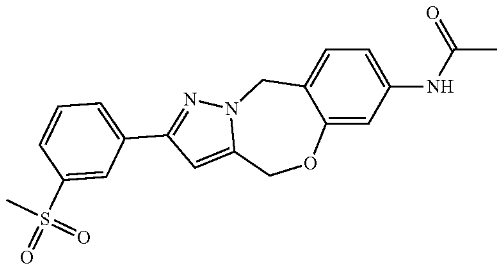
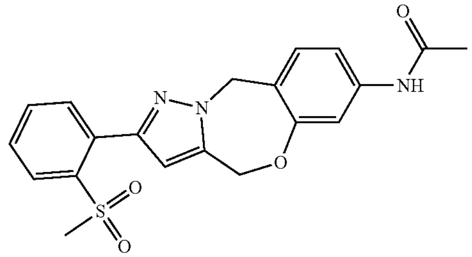
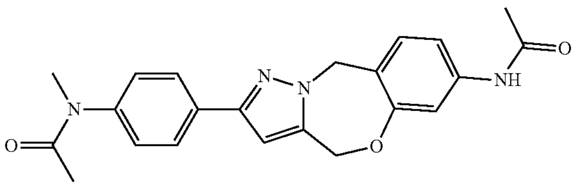
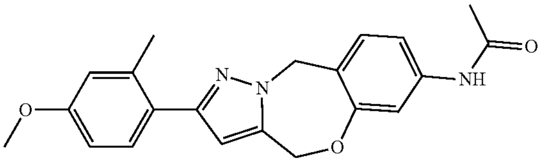
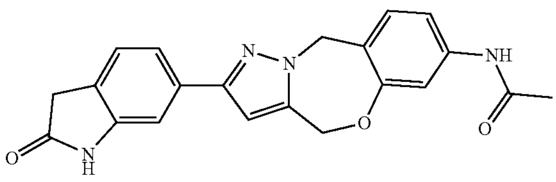

-continued
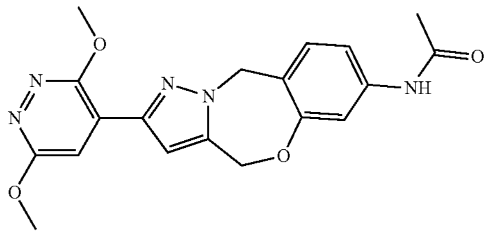
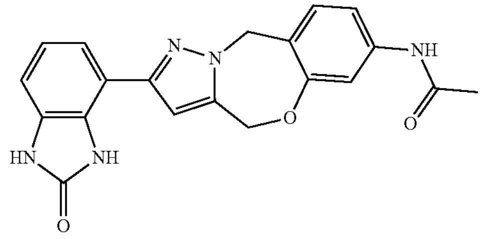
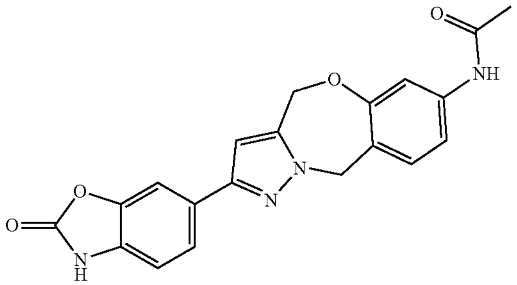
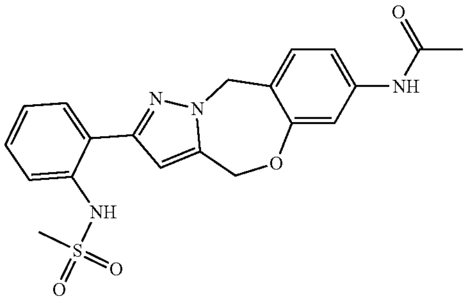
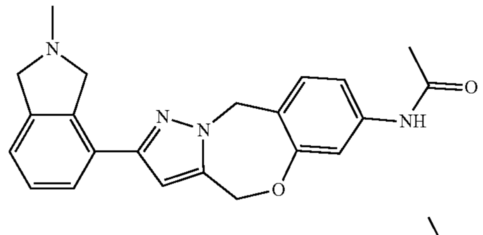
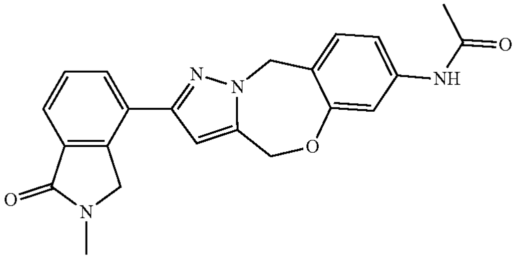
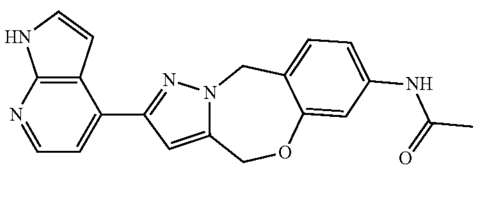
-continued
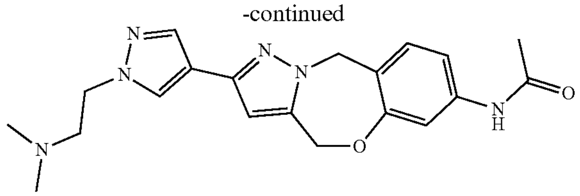
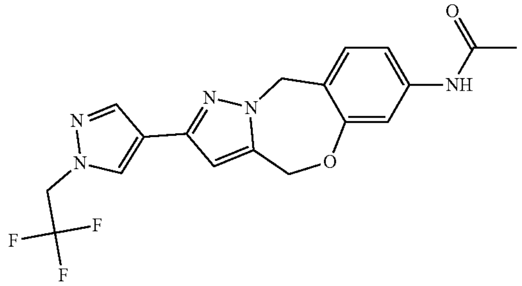
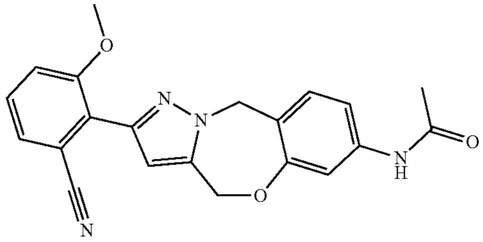
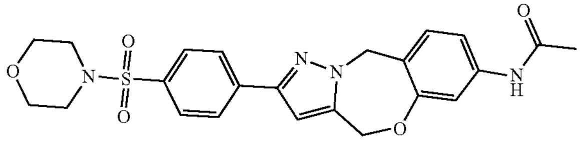
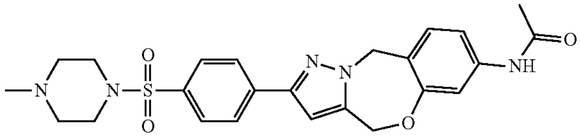
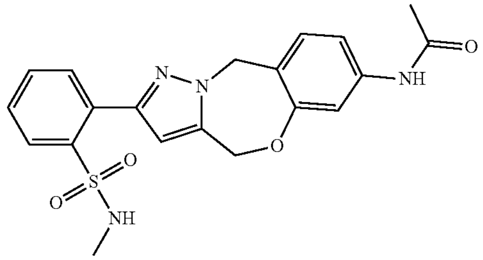
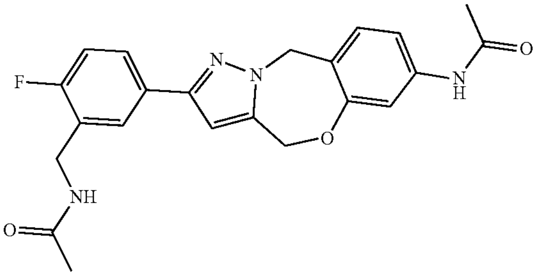
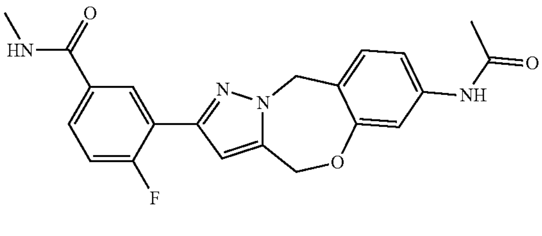

-continued
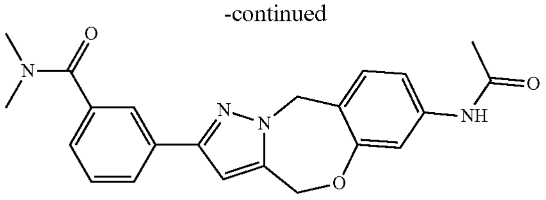
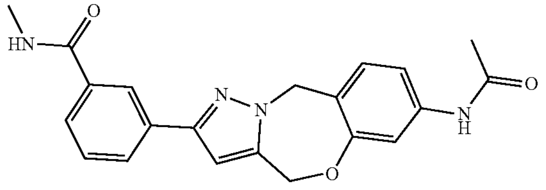
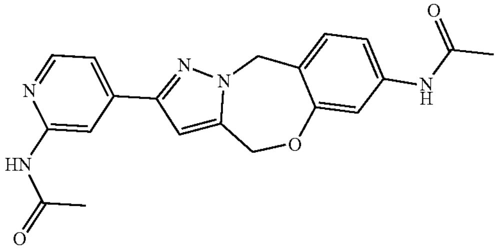
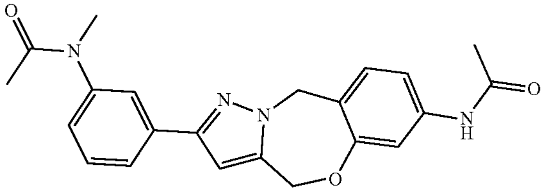
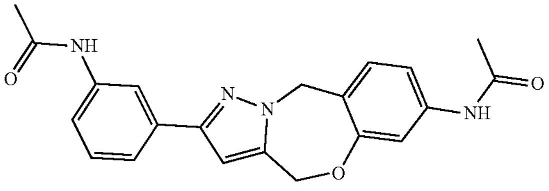
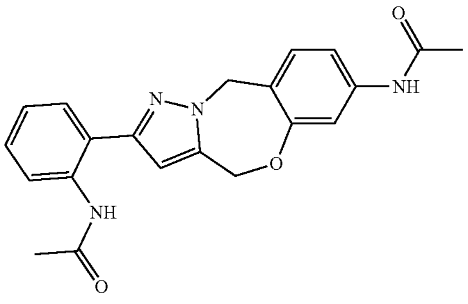
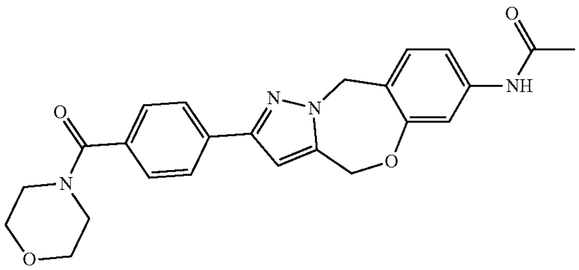
-continued
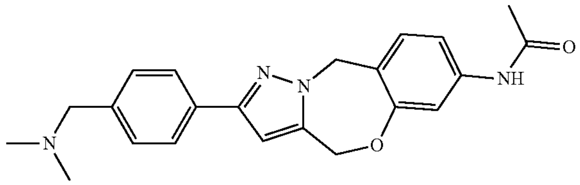
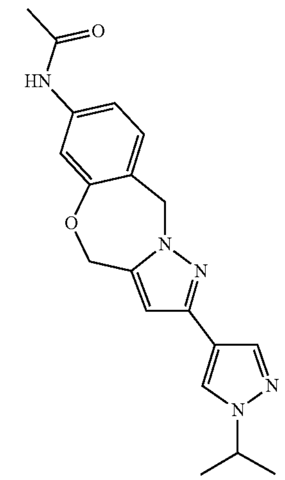
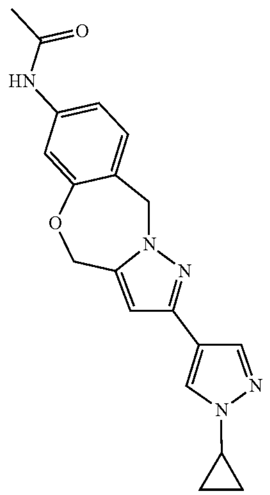
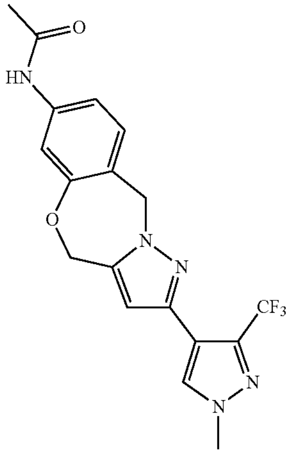
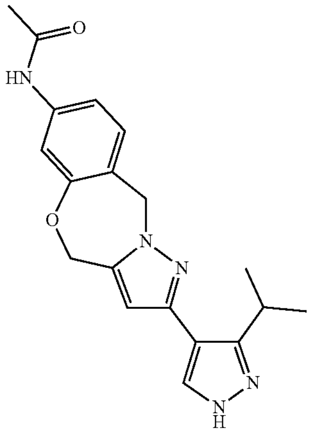

-continued
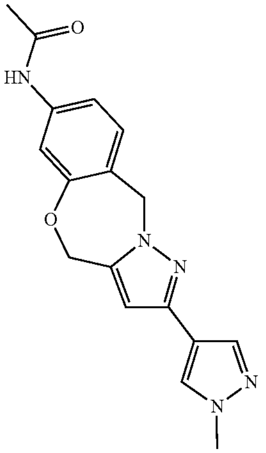
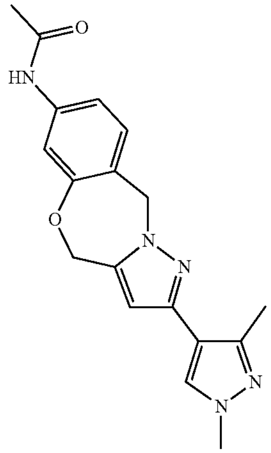
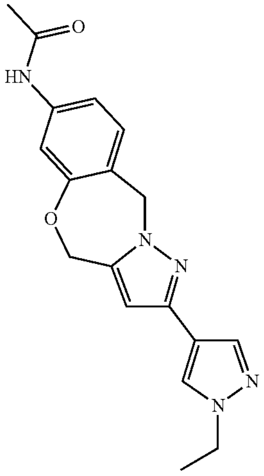
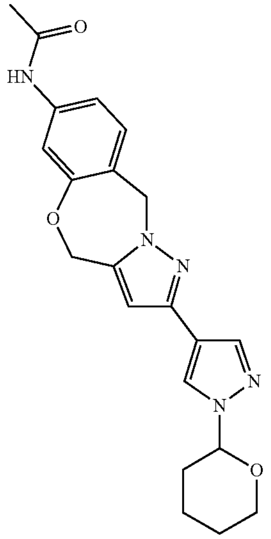
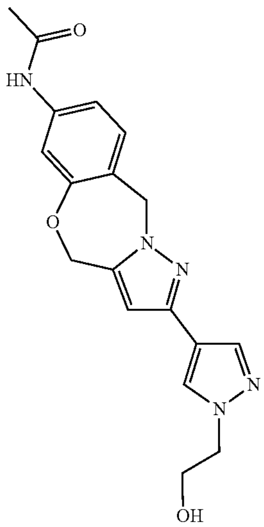
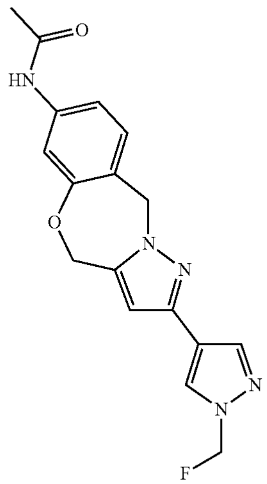
-continued
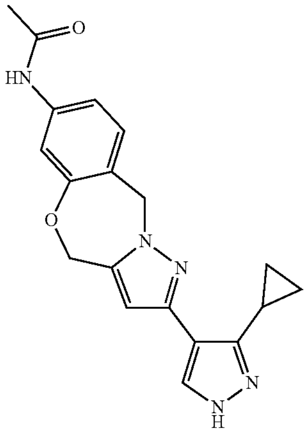
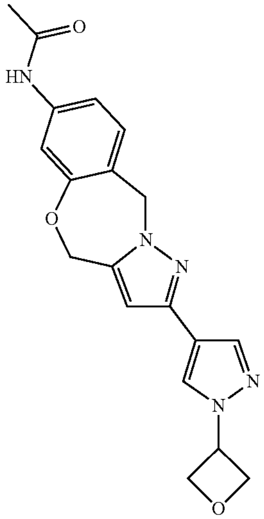
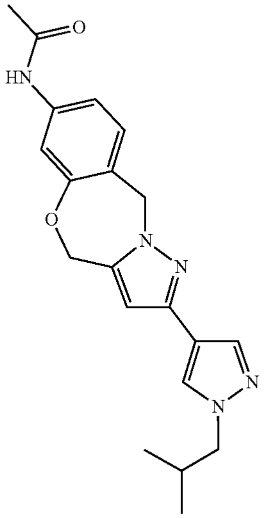
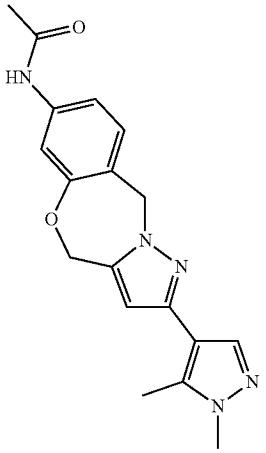
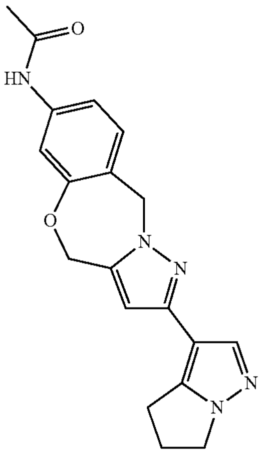
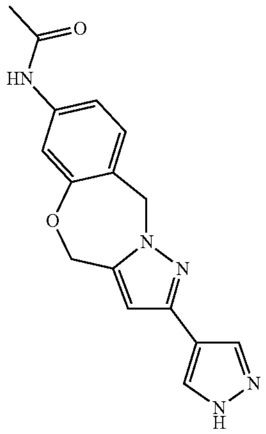
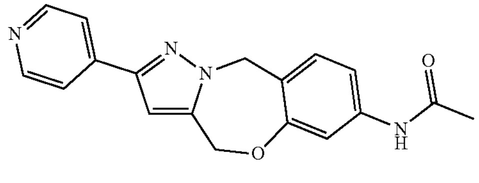

-continued

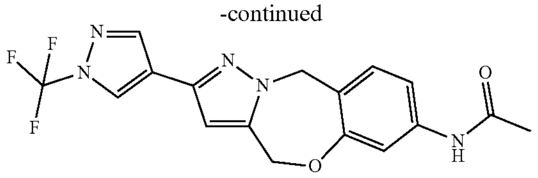

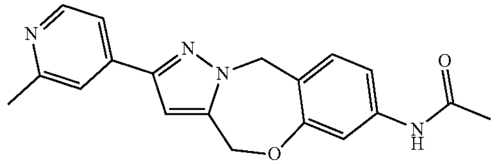

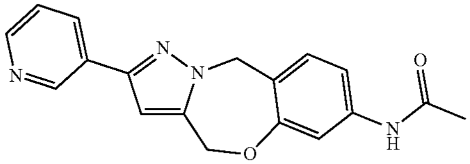

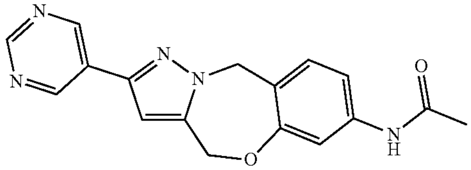

and

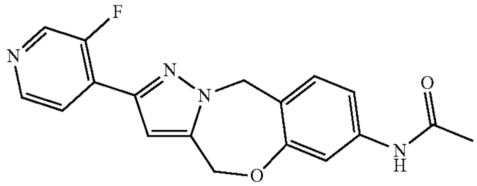

or a prodrug thereof or a pharmaceutically acceptable salt thereof.

E45. A pharmaceutical composition comprising a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 and a pharmaceutically acceptable excipient.

E46. A method for treating or preventing a disease associated with the activity of glycolytic enzyme phosphofructokinase-1 liver type in an animal, comprising administering a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to the animal.

E47. A method for treating cancer in an animal (e.g., a mammal such as a human) comprising administering a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to the animal.

E48. A method for treating diabetes in an animal (e.g., a mammal such as a human) comprising administering a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to the animal.

E49. A method for treating a caspase-associated auto-inflammatory condition in an animal, comprising administering a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to the animal.

E50. The method of E49, wherein the caspase-associated auto-inflammatory condition is sepsis or septic shock.

E51. A method for treating a disease or condition selected from the group consisting of pulmonary disease, a systemic autoimmune disease, atherosclerosis, thrombosis, multiple sclerosis, Alzheimer's disease, psoriasis, and pulmonary fibrosis in an animal, comprising administering a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to the animal.

E52. The method of claim E51, wherein the pulmonary disease is acute respiratory distress syndrome ARDS, chronic obstructive pulmonary disease COPD, or bronchiectasis.

E53. The method of E51, wherein the disease or condition is thrombosis.

E54. A method for treating a disease or condition associated with the activity of a homologous PFK enzyme, comprising administering a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to the animal.

E55. The method of E54, wherein the disease or condition is associated with the activity of PFKM (muscle-type).

E56. The method of E54, wherein the disease or condition is associated with the activity of PFKP (platelet type).

E57. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for use in medical therapy.

E58. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for the prophylactic or therapeutic treatment of a disease associated with the activity of glycolytic enzyme phosphofructokinase-1 liver type in an animal.

E59. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for the prophylactic or therapeutic treatment of cancer.

E60. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for the prophylactic or therapeutic treatment of diabetes.

E61. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for the prophylactic or therapeutic treatment of a caspase-associated auto-inflammatory condition.

E62. The compound, prodrug, or pharmaceutically acceptable salt of E61, wherein the caspase-associated auto-inflammatory condition is sepsis or septic shock.

E63. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for the prophylactic or therapeutic treatment of a disease or condition selected from the group consisting of pulmonary disease, a systemic autoimmune disease, atherosclerosis, thrombosis, multiple sclerosis, Alzheimer's disease, psoriasis, and pulmonary fibrosis.

E64. The compound, prodrug, or pharmaceutically acceptable salt of claim E63, wherein the pulmonary disease is acute respiratory distress syndrome ARDS, chronic obstructive pulmonary disease COPD, or bronchiectasis.

E65. The compound, prodrug, or pharmaceutically acceptable salt of E63, wherein the pulmonary disease is thrombosis.

E66. A compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 for the prophylactic or therapeutic treatment of a disease or condition associated with the activity of a homologous PFK enzyme.

E67. The compound, prodrug, or pharmaceutically acceptable salt of E66, wherein the disease or condition is associated with the activity of PFKM (muscle-type).

E68. The compound, prodrug, or pharmaceutically acceptable salt of E66, wherein the disease or condition is associated with the activity of PFKP (platelet type).

E69. The use of a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to prepare a medicament for treating a disease associated with the activity of glycolytic enzyme phosphofructokinase-1 liver type in an animal (e.g. a mammal such as a human).

E70. The use of a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to prepare a medicament for treating cancer in an animal (e.g. a mammal such as a human).

E71, The use of a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to prepare a medicament for treating diabetes in an animal (e.g. a mammal such as a human).

E72. The use of a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to prepare a medicament for treating a caspase-associated auto-inflammatory condition in an animal (e.g. a mammal such as a human).

E73. The use of E72, wherein the caspase-associated auto-inflammatory condition is sepsis or septic shock in an animal (e.g. a mammal such as a human).

E74. The use of a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to prepare a medicament for treating a disease or condition selected from the group consisting of pulmonary disease, a systemic autoimmune disease, atherosclerosis, thrombosis, multiple sclerosis, Alzheimer's disease, psoriasis, and pulmonary fibrosis in an animal (e.g. a mammal such as a human).

E75. The use of E74, wherein the pulmonary disease is acute respiratory distress syndrome ARDS, chronic obstructive pulmonary disease COPD, or bronchiectasis.

E76. The use of E74, wherein the disease or condition is thrombosis.

E77. The use of a compound, a prodrug, or a pharmaceutically acceptable salt of E1, E2, E3, E4, E5, E6, E7, E8, E9, E10, E11, E12, E13, E14, E15, E16, E17, E18, E19, E20, E21, E22, E23, E24, E25, E36, E27, E28, E29, E30, E31, E32, E33, E34, E35, E36, E37, E38, E39, E40, E41, E42, E43, or E44 to prepare a medicament for treating a disease or condition associated with the activity of a homologous PFK enzyme in an animal (e.g. a mammal such as a human).

E78. The use of E77, wherein the disease or condition is associated with the activity of PFKM (muscle-type).

E79. The use of E77, wherein the disease or condition is associated with the activity of PFKP (platelet type).

E80. The method of E47, the compound, prodrug, or pharmaceutically acceptable salt of E59, or the use of claim E70, wherein the cancer is selected from the group consisting of: brain, breast, lung, urinary bladder, cervical, skin, oral cavity, pharynx, colon, liver, cecum, stomach, pancreatic, prostate, oesophageal, hematologic, thyroid, uterine, and head and neck cancer.

E81. A process or a synthetic intermediate disclosed herein that is useful for preparing a compound of formula (I) or prodrug thereof, or a pharmaceutically acceptable salt thereof.

E82. An invention as described herein.

BRIEF DESCRIPTION OF THE DRAWING

FIG. 1. LDC7559 and the compound of Example 6 (NA-11) inhibit NETosis independent of GSDMD, but elicit identical phenotypes in neutrophils. LDH (A) or IL-1β (B) released from primary human monocytes. Bars show the mean±s.e.m. of monocytes from 3 donors. (C) Western blots of monocytes at 1 h after electroporation with LPS. FL, full length GSDMD. NT, N-terminal fragment of GSDMD. Results representative of 3 independent experiments. (D) Coomassie blue staining of recombinant GSDMD. Results representative of 3 independent experiments. (E) TR-FRET assay measuring Europium-labeled biotin released from liposomes exposed to caspase-4 and GSDMD. Symbols indicate the mean±s.d. of 3 independent experiments. (F-G) Percentage of polymorphonuclear leukocytes (PMNs) undergoing NETosis induced by PMA (F) or the stimuli indicated (G). Data are the mean±s.d. of cells from 3 donors. (H) ROS production by PMNs. Bars show the mean±s.e.m. of PMNs from 3 donors. P-values (Two-way ANOVA, means compared to medium alone) are shown if P<0.05. (I) Percentage of PMNs undergoing PMA-induced NETosis. The x-axis indicates when NA-11 was added relative to the addition of PMA (t=0). Bars show the mean±s.e.m. of PMNs from 3 donors. P-values (one-way ANOVA, means compared to medium alone) are shown if P<0.05.

DETAILED DESCRIPTION

In neutrophils, NADPH generated via the pentose phosphate pathway fuels NADPH oxidase NOX2 to produce reactive oxygen species for killing invading pathogens. Excessive NOX2 activity can exacerbate inflammation, as in acute respiratory distress syndrome (ARDS). Two unbiased chemical proteomic strategies were utilized to show that small molecule LDC7559 and Example 6 inhibit the NOX2-dependent oxidative burst in neutrophils by activating the glycolytic enzyme phosphofructokinase-1 liver type (PFKL) and dampening flux through the pentose phosphate pathway. Accordingly, neutrophils treated with Example 6 exhibited defects in NOX2-dependent outputs, including neutrophil cell death (NETosis) and tissue damage. A high-resolution structure of PFKL confirmed binding of Example 6 to the AMP/ADP allosteric activation site and explained why Example 6 failed to agonize phosphofructokinase-1 platelet type (PFKP) or muscle type (PFKM). Selective activation of different phosphofructokinase-1 isoforms could offer a new treatment paradigm for treating diseases such as ARDS, diabetes, and cancer.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C_5$)alkyl, ($C_2$-$C_8$)alkyl, $C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(═O)—, wherein the term alkyl has the meaning defined herein.

The term "alkanoyloxy" as used herein refers to a group (alkyl)-C(═O)—O—, wherein the term alkyl has the meaning defined herein.

As used herein, the term "heteroatom" includes oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line "∿∿" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer.

For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^{2}H$ or D). As a non-limiting example, a —$CH_3$ group may be substituted with —$CD_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Prodrugs

In addition to salt forms, the present invention provides compounds which are in a prodrug form. As used herein the term "prodrug" refers to those compounds that readily undergo chemical changes under physiological conditions to provide the compounds of formula (I). Additionally, prodrugs can be converted to the compounds of the present invention by chemical or biochemical methods in an ex vivo environment. For example, prodrugs can be slowly converted to the compounds of formula (I) when placed in a transdermal patch reservoir with a suitable enzyme or chemical reagent.

Prodrugs of the invention include compounds wherein a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984).

In one embodiment, a prodrug of a compound of formula (I) that comprises a hydroxy group (e.g., a compound of formula (I) wherein R comprises a hydroxy group) can be prepared by converting the hydroxy group to a prodrug group that increases the aqueous solubility of the compound. For example, the hydroxy group can be converted to a phosphate (—OP(=O)(OH)$_2$) or a pharmaceutically acceptable salt thereof, or the hydroxy group can be converted to a group selected from the group consisting of:

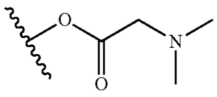
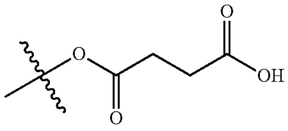
and
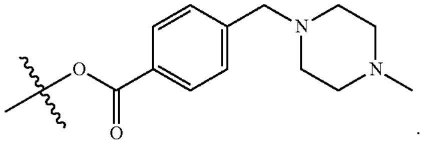
.

In another embodiment, a prodrug of a compound of formula (I) can be prepared by converting R$^b$ to a (C$_1$)alkyl group that is substituted with a group selected from the group consisting of a phosphate (—OP(=O)(OH)$_2$),

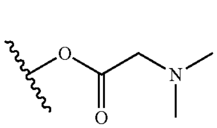
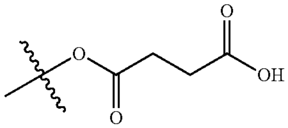
and
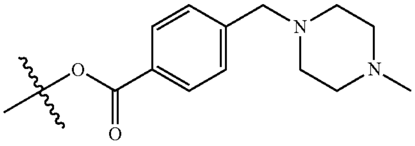

and pharmaceutically acceptable salts thereof. Such a prodrug can undergo chemical changes under physiological conditions to provide the corresponding compound of formula (I) wherein R$^b$ is H.

Non-limiting examples of a prodrug of a compound of formula (I) include the following compounds:

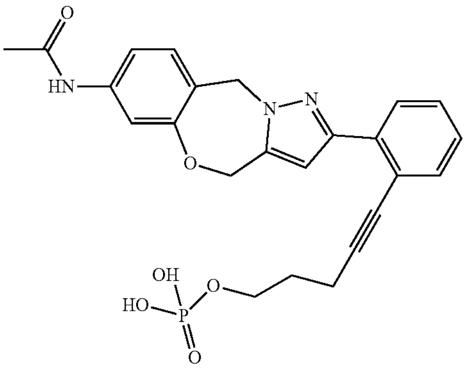

-continued

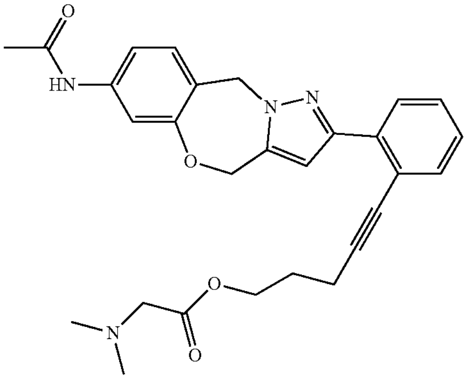

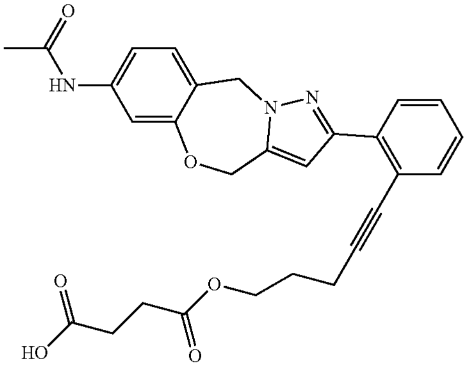

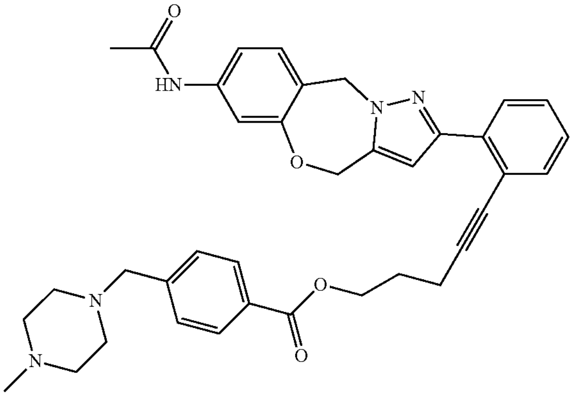

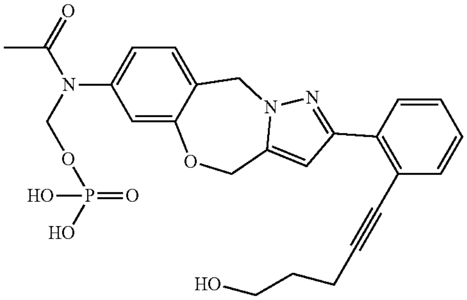

-continued

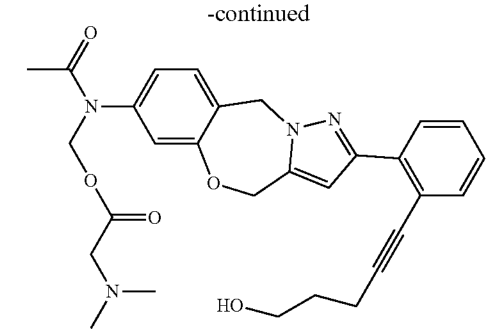

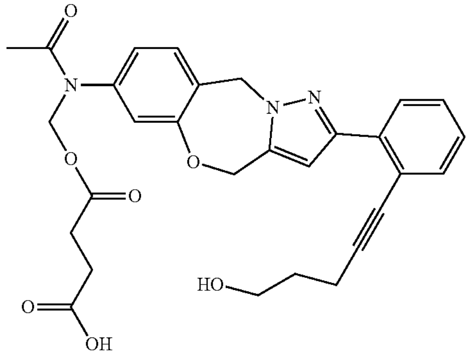

and

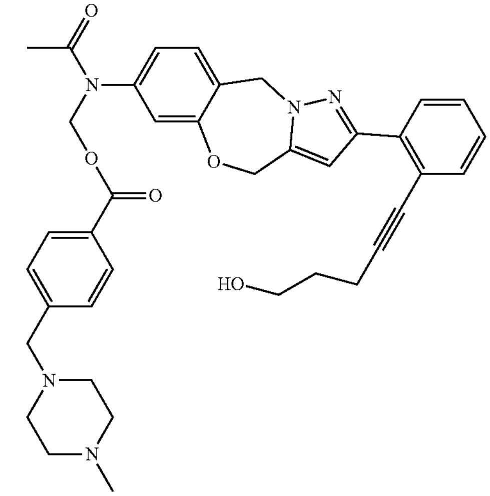

and pharmaceutically acceptable salts thereof (e.g., Na, K, and Ca salts thereof). Prodrugs of a compound of formula (I) and pharmaceutically acceptable salts thereof can be prepared from a corresponding compound of formula (I) using standard reagents and techniques.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1, -pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Processes for preparing compounds of formula (I) are provided as further embodiments of the invention. For example, compounds of formula (I) can be prepared using the reaction illustrated in Scheme 1, wherein the generic radicals have any of the values described herein.

Scheme 1

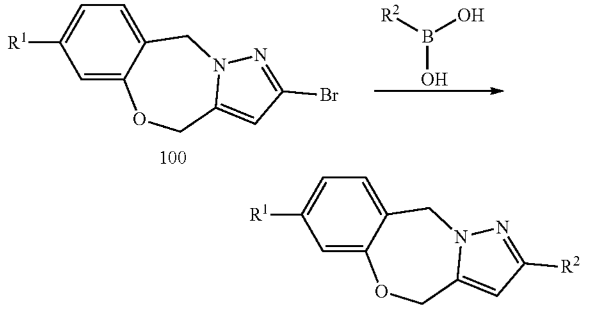

The bromo compound 100 can be coupled with $R^2B(OH)_2$ under standard coupling conditions. For example, the bromo compound can be coupled with the compound $R^2B(OH)_2$ in a suitable polar solvent (e.g. DME or dioxane) in the presence of water using a suitable catalyst (e.g. Pd(dppf)$Cl_2$).

Compounds of formula (I) can also be prepared using the reaction illustrated in Scheme 2.

Scheme 2

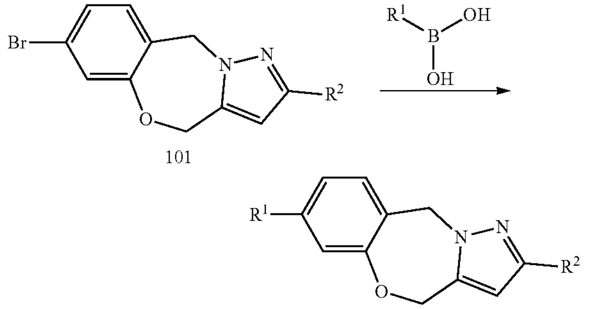

The bromo compound 101 can be coupled with $R^1B(OH)_2$ under standard coupling conditions. For example, the bromo compound can be coupled with the compound $R^1B(OH)_2$ in a suitable polar solvent (e.g. DME or dioxane) in the presence of water using a suitable catalyst (e.g. Pd(dppf) $Cl_2$).

Synthetic intermediates described herein that are useful for preparing compounds of formula (I) are provided as further embodiments of the invention. For example, the intermediate bromo compounds 100 and 101, wherein $R^1$ and $R^2$ have any of the values described herein are synthetic intermediates that can be used to prepare compounds of formula (I). Other synthetic intermediates that are useful for preparing compounds of formula (I) are described in the Examples.

In cases where compounds are sufficiently basic or acidic, a salt of a compound of formula (I) can be useful as an intermediate for isolating or purifying a compound of formula (I). Additionally, administration of a compound of formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. For intravenous injection, it may be beneficial to convert the compound of formula (I) to a prodrug having increased aqueous solubility. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

In one embodiment, a formulation suitable for intravenous administration, comprising a compound of formula (I) or a prodrug thereof, or a salt of the compound of formula (I) or a salt of the prodrug is provided.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to agonize the glycolytic enzyme phosphofructokinase-1 liver type may be determined using pharmacological models which are well known to the art, or using the assays described in the Examples below. The ability of a compound of the invention to treat cancer, diabetes, a caspase-associated auto-inflammatory condition (e.g., sepsis or septic shock), a pulmonary disease (e.g., acute respiratory distress syndrome ARDS, chronic obstructive pulmonary disease COPD, or bronchiectasis), a systemic autoimmune disease, atherosclerosis, thrombosis, multiple sclerosis, Alzheimer's disease, psoriasis, pulmonary fibrosis, or a disease or condition associated with the activity of a homologous PFK enzyme can also be determined using pharmacological models which are well known to the art.

The invention will now be illustrated by the following non-limiting Examples.

EXAMPLES

List of Abbreviations

AcOH—Acetic acid
ACN—Acetonitrile
BuLi—Butyllithium
DCM—Dichloromethane
DIAD—Diisopropyl azidocarboxylate
DME—Dimethoxyethane
EDCI—1-Ethyl-3-(3-dimethylaminopropyl)carbodiimide
EtOAc—Ethyl acetate
EtOH—Ethanol
HATU—Hexafluorophosphate azabenzotriazole tetramethyl uronium
DIPEA—N,N-diisopropylethylamine
HMPA—Hexamethylphosphoric triamide
MeOH—Methanol
MTBE—Methyl tert-butyl ether
NIS—N-Iodosuccinimide
RT—Room temperature
TBSCI—Tert-Butyldimethylsilyl chloride
TBAF—Tetra-n-butylammonium fluoride
TEA—Triethylamine
THE—Tetrahydrofurane
TLC—Thin layer chromatography
TosCl—4-toluenesulfonyl chloride

Example 1. N-(2-Phenyl-4H,10H-benzo[f]pyrazolo[5,1-c][1,4]oxazepin-7-yl)acetamide

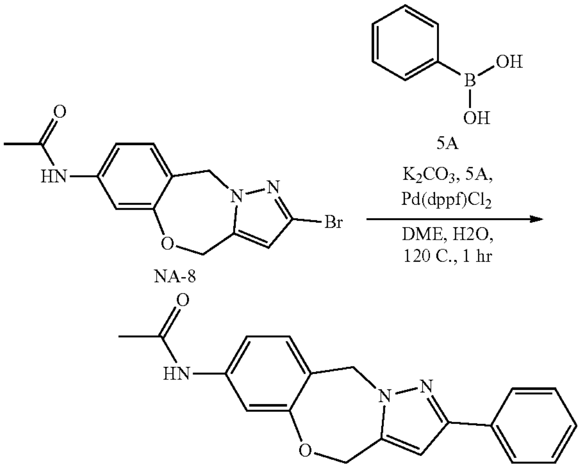

Compound NA-8 (200 mg, 621 μmol), compound 5A (98.4 mg, 807 μmol), $K_2CO_3$ (172 mg, 1.24 mmol) and $Pd(PPh_3)_4$ (143 mg, 124 μmol) were suspended in DME (4.00 mL) and $H_2O$ (2.00 mL). The mixture was heated to 120° C. for 1 hour in a microwave. TLC (petroleum ether/ethyl acetate=1/1, NA-8 $R_f$=0.35, product $R_f$=0.20) indicated compound NA-8 was consumed completely and one main spot formed. The reaction mixture was quenched by addition $H_2O$ (10.0 mL) and extracted with EtOAc (10.0 mL×3). The combined organic layers were washed with brine (10.0 mL), dried over sodium sulfate, filtered and concentrated under vacuum. The residue was purified by column chromatography ($SiO_2$, petroleum ether/ethyl acetate=10/1 to 0/1, petroleum ether/ethylacetate=1/1, product 1 $R_f$=0.2). The combined organic layers were concentrated under vacuum. The title compound (75.0 mg, 234 μmol, 37.6% yield, 99.5% purity) was obtained as a yellow solid. $^1$H NMR: DMSO 400 MHz, δ: 9.95 (s, 1H), 7.77 (d, J=7.2 Hz, 2H), 7.39 (m, J=7.6 Hz, 2H), 7.26-7.32 (m, 3H)

7.14 (d, J=8.4 Hz, 1H), 6.78 (s, 1H), 5.58 (s, 2H), 5.34 (s, 2H), 2.02 (s, 3H). LCMS: $(M+H^+)$: 320.05, calculated 319.13.

The intermediate compound NA-8 was prepared as follows.

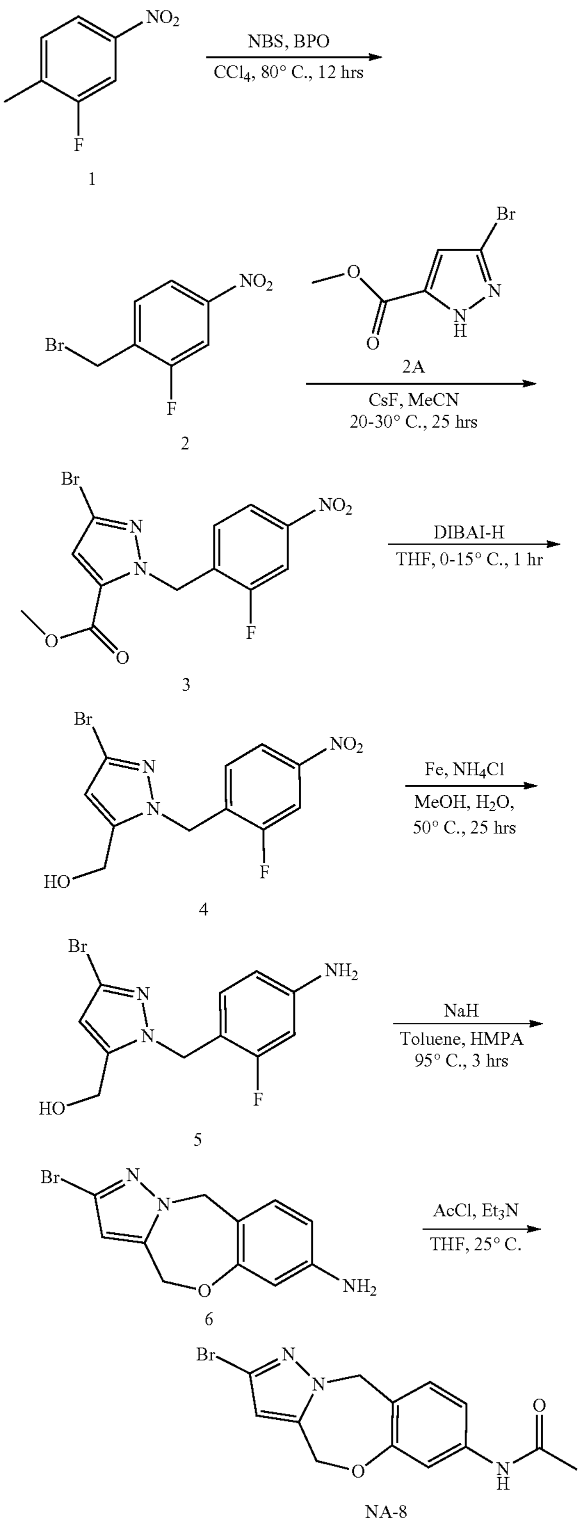

a. 1-(Bromomethyl)-2-fluoro-4-nitrobenzene (2)

To a solution of 1 (120 g, 774 mmol) in $CCl_4$ (840 mL) at 80° C. was added BPO (12.0 g, 49.5 mmol) and NBS (151 g, 851 mmol). The mixture was stirred at 80° C. for 12 hrs. TLC (petroleum ether/ethyl acetate=20/1, reactant 1 $R_f$=0.40, product $R_f$=0.30) showed the reaction was complete. The reaction mixture was cooled to RT. The residue was poured into ice-water (600 mL) and stirred for 10 min. The aqueous phase was extracted with DCM (300 mL×3). The combined organic phase was washed with brine (300 mL×1), dried with anhydrous $Na_2SO_4$, filtered and concentrated under vacuum. The residue was purified by column chromatography ($SiO_2$, petroleum ether/ethyl acetate=400/1 to 30/1) then filtered and concentrated under vacuum. Compound 2 (120 g, 513 mmol, 66.3% yield) was obtained as a yellow solid.

b. Methyl 3-bromo-1-(2-fluoro-4-nitrobenzyl)-1H-pyrazole-5-carboxylate (3)

To a solution of compound 2 (30.0 g, 146 mmol) in ACN (210 mL) was added CsF (44.5 g, 293 mmol) and compound 2A (37.7 g, 161 mmol). The mixture was stirred at 25° C. for 5 hours. TLC (petroleum ether/ethyl acetate=3/1, reactant $R_f1$=0.30, reactant $R_{f2}$=0.60, product $R_f$=0.45) showed the reaction was incomplete. The mixture concentrated under vacuum to give a crude residue. The residue was purified by column chromatography ($SiO_2$, petroleum ether/ethyl acetate=80/1 to 3/1). Compound 3 (31.0 g, 86.6 mmol, 59.1% yield) was obtained as a white solid.

c. (3-Bromo-1-(2-fluoro-4-nitrobenzyl)-1H-pyrazol-5-yl)methanol (4)

To a mixture of compound 3 (62.0 g, 173 mmol) in THF (620 mL) was added DIBAL-H (1.00 M, 346 mL) at 0° C. The mixture was stirred at 15° C. for 1 hour under $N_2$ atmosphere. TLC (Plate 1: petroleum ether/ethyl acetate=2/1, reactant 1 $R_f$=0.50, product $R_f$=0) indicated compound 3 was consumed completely and one main spot formed. The reaction mixture was quenched by addition of saturated $NH_4Cl$ solution (300 mL). The resulting mixture was dissolved in EtOAc/EtOH=1000 mL/200 mL and filtered to remove the insoluble. The filtrate was concentrated under vacuum. The residue was purified by column chromatography ($SiO_2$, petroleum ether/ethyl acetate=5/1 to 0/1, plate 2: petroleum ether/ethyl acetate=1/1, compound 4 $R_f$=0.35). The combined organic layers were concentrated under vacuum. Compound 4 (50.9 g, 154.2 mmol, 89.0% yield) was obtained as a white solid.

d. (1-(4-Amino-2-fluorobenzyl)-3-bromo-1H-pyrazol-5-yl)methanol (5)

To a solution of compound 4 (50.9 g, 154.2 mmol) in MeOH (510 mL) and $H_2O$ (51.0 mL) was added Fe (34.4 g, 617 mmol) and $NH_4Cl$ (41.2 g, 771 mmol). The mixture was stirred at 50° C. for 3 hours, then additional Fe (8.61 g, 154 mmol) and $NH_4Cl$ (16.5 g, 308 mmol) were added. The mixture was stirred at 50° C. for 22 hrs. TLC (petroleum ether/ethyl acetate=1/1, reactant 1 $R_f$=0.57, product $R_f$=0.47) indicated compound 4 was consumed completely and one main spot formed. The reaction mixture was quenched by addition saturated $NH_4Cl$ solution (200 mL), then washed with EtOAc (200 mL×3). The combined organic layers were concentrated under vacuum and the residue was extracted with DCM (200 mL×3). The combined organic layers were washed with brine (200 mL), dried over sodium sulfate, filtered and concentrated under vacuum. Compound 5 (40.3 g, 134 mmol, 87.0% yield) was obtained as a yellow solid.

e. 2-Bromo-4H,10H-benzo[f]pyrazolo[5,1-c][1,4]oxazepin-7-amine (6)

Compound 5 (23.0 g, 76.6 mmol) was dissolved in HMPA (230 mL) and added to a suspension of NaH (6.13 g, 153 mmol, 60.0% purity) in toluene (2300 mL) under $N_2$. The mixture was stirred under $N_2$ at 95° C. for 3 hours. TLC (petroleum ether/ethyl acetate=1/1, reactant 1 $R_f$=0.40, product $R_f$=0.56) indicated compound 5 was consumed completely and one main spot formed. The reaction mixture was quenched by addition $H_2O$ (1000 mL) and extracted with toluene (500 mL×3). The combined organic layers were washed with brine (500 mL), dried over sodium sulfate, filtered and concentrated under vacuum. The residue was purified by column chromatography ($SiO_2$, petroleum ether/ethyl acetate=10/1 to 0/1). The combined organic layers were concentrated under vacuum. Compound 6 (7.50 g, 26.7 mmol, 34.9% yield) was obtained as a yellow solid.

f. N-(2-Bromo-4H,10H-benzo[f]pyrazolo[5,1-c][1,4]oxazepin-7-yl)acetamide (NA-8)

Compound 6 (4.00 g, 14.3 mmol) was dissolved in THE (120 mL). $Et_3N$ (2.89 g, 28.6 mmol, 3.98 mL), then acetyl chloride (1.35 g, 17.14 mmol, 1.22 mL) were added and the mixture was stirred at 25° C. for 25 minutes. TLC (petroleum ether/ethyl acetate=1/1, compound 6 $R_f$=0.50, product 1 $R_f$=0.30) indicated compound 6 was consumed completely and one main spot formed. The reaction mixture was quenched by addition $H_2O$ (100 mL) and extracted with EtOAc (100 mL×3). The combined organic layers were washed with brine (100 mL), dried over sodium sulfate, filtered and concentrated under vacuum. The residue was purified by column chromatography ($SiO_2$, petroleum ether/ethyl acetate=10/1 to 0/1). The combined organic layers were concentrated under vacuum. Compound NA-8 (3.50 g, 10.8 mmol, 75.6% yield, 99.4% purity) was obtained as a yellow solid. $^1H$ NMR: DMSO 400 MHz, δ: 9.96 (s, 1H), 7.30 (d, J=2 Hz, 1H), 7.25 (d, J=8.4 Hz, 1H), 7.14 (d, J=8.4 Hz, 1H), 6.45 (s, 1H), 5.49 (s, 2H), 5.28 (s, 2H), 2.52-2.55 (m, 1H), 2.02 (s, 3H). LCMS: (M+H$^+$): 321.9, calculated 321.01.

Example 2. N-(2-(3-Methoxyphenyl)-4H,10H-benzo[f]pyrazolo[5,1-c][1,4]oxazepin-7-yl)acetamide

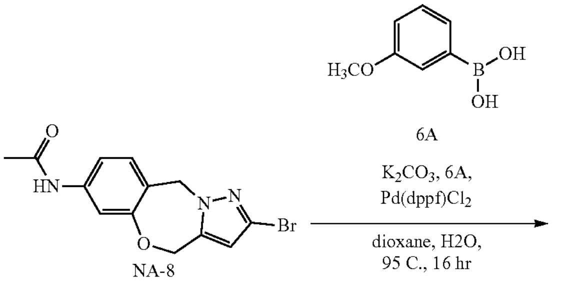

-continued

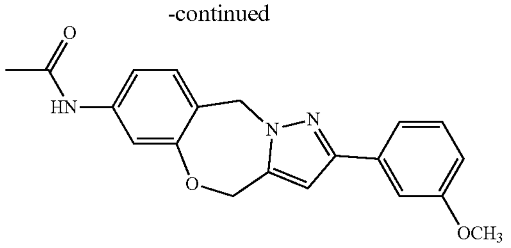

NA-8 (200 mg, 621 μmol), compound 6A (189 mg, 1.24 mmol), $Na_2CO_3$ (132 mg, 1.24 mmol) and $Pd(dppf)Cl_2$ (45.4 mg, 62.1 μmol) were suspended in $H_2O$ (2.00 mL) and dioxane (10.0 mL). The mixture was heated to 95° C. for 16 hours under $N_2$ atmosphere. TLC (petroleum ether/ethyl acetate=1/1, NA-8 $R_f$=0.30, product $R_f$=0.18) indicated NA-8 was consumed completely and one main spot formed. The reaction mixture was quenched by addition $H_2O$ (10.0 mL) and extracted with EtOAc (10.0 mL×3). The combined organic layers were washed with brine (10.0 mL), dried over sodium sulfate, filtered and concentrated under vacuum. The residue was purified by column chromatography ($SiO_2$, petroleum ether/ethyl acetate=10/1 to 0/1). The combined organic layers were concentrated under vacuum. Compound NA-6 (61.0 mg, 169 μmol, 27.2% yield, 96.7% purity) was obtained as a red brown solid. $^1H$ NMR: DMSO 400 MHz, δ: 9.96 (s, 1H), 7.24-7.35 (m, 5H), 7.13 (d, J=7.8 Hz, 1H), 6.86 (d, J=7.4 Hz, 1H), 6.79 (s, 1H), 5.57 (s, 2H), 5.34 (s, 2H), 3.78 (s, 3H), 2.01 (s, 3H). LCMS: (M+H$^+$): 350.05, calculated 349.14.

Example 3. N-(2-(4-Methoxyphenyl)-4H,10H-benzo[f]pyrazolo[5,1-c][1,4]oxazepin-7-yl)acetamide

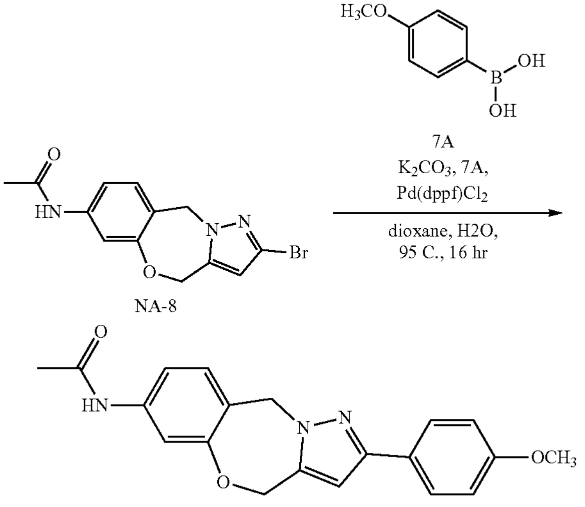

NA-8 (200 mg, 621 μmol), compound 7A (189 mg, 1.24 mmol), $Pd(dppf)Cl_2$ (45.4 mg, 62.1 μmol) and $Na_2CO_3$ (132 mg, 1.24 mmol) were suspended in $H_2O$ (2.00 mL) and dioxane (10.0 mL). The mixture was heated to 95° C. for 16 hours under $N_2$ atmosphere. TLC (petroleum ether/ethyl acetate=1/1, NA-8 $R_f$=0.30, product $R_f$=0.20) indicated NA-8 was consumed completely and one main spot formed. The reaction mixture was quenched by addition $H_2O$ (10.0 mL) and extracted with EtOAc (10.0 mL×3). The combined organic layers were washed with brine (10.0 mL), dried over sodium sulfate, filtered and concentrated under vacuum. The residue was purified by column chromatography ($SiO_2$, petroleum ether/ethyl acetate=10/1 to 0/1). The combined organic layers were concentrated under vacuum. Compound NA-7 (105 mg, 295 μmol, 47.5% yield, 98.2% purity) was obtained as a white solid. $^1H$ NMR: DMSO 400 MHz, δ: 9.96 (s, 1H), 7.69 (d, J=7.8 Hz, 2H), 7.25-7.29 (m, 2H), 7.13 (d, J=8 Hz, 1H), 6.96 (s, 1H), 6.94 (s, 1H), 6.69 (s, 1H), 5.55 (s, 2H), 5.32 (s, 2H), 3.77 (s, 3H), 3.17-3.31 (m, 3H), 2.01 (s, 3H). LCMS: ($M+H^+$): 350.05, calculated 349.14.

Example 4. N-(3-(7-acetamido-4H,10H-benzo[f]pyrazolo[5,1-c][1,4]oxazepin-2-yl)phenyl)pent-3-ynamide

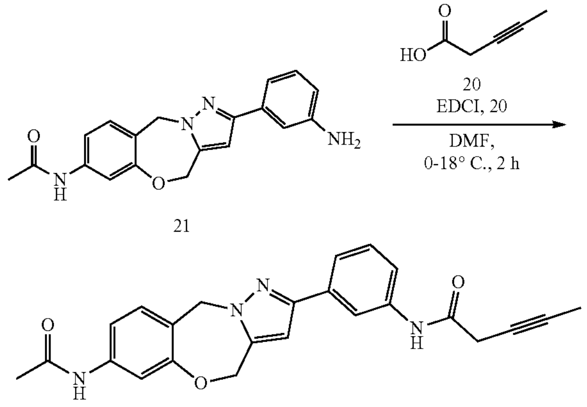

To a solution of compound 20 (117 mg, 1.20 mmol) and compound 21 (200 mg, 598 μmol, see Example 7) in DMF (10.0 mL) was added EDCl (229 mg, 1.20 mmol) at 0° C. The mixture was stirred at 18° C. for 2 hours. TLC (petroleum ether/ethyl acetate=0/1, compound 21 $R_f$=0.30, product $R_f$=0.43) and LCMS analysis indicated 21 was consumed completely and a main peak for product was detected. The reaction mixture was quenched by addition $H_2O$ (10.0 mL) and extracted with EtOAc (10.0 mL×3). The combined organic layers were filtered and concentrated under vacuum. The residue was purified by HPLC using a 5-micron Boston Prime C18 column with 150 mm×30 mm ID. The mobile phase was composed of water (with 0.05% HCl) and a gradient of ACN from 25%-50% over 10 minutes. The combined product fractions were concentrated by freeze-drying. The title compound (148 mg, 353 μmol, 59.0% yield, 98.4% purity) was obtained as a white solid. $^1H$ NMR: DMSO-d6 400 MHz, δ: 10.06 (s, 1H), 9.98 (s, 1H), 8.05 (s, 1H), 7.49 (d, J=7.45 Hz, 1H), 7.44 (d, J=7.9 Hz, 1H), 7.25-7.34 (m, 3H), 7.14 (m, J=8.10 Hz, 1H), 6.71 (s, 1H), 5.57 (s, 2H), 5.35 (s, 2H), 4.19 (s, 7H), 3.25-3.29 (m, 2H), 2.52-2.54 (m, 1H), 2.02 (s, 3H), 1.80 (m, J=2.64 Hz, 3H). LCMS: ($M+H^+$): 415.16, calculated 414.17.

The intermediate 20 was prepared as follows.

a. Pent-3-ynoic acid (20)

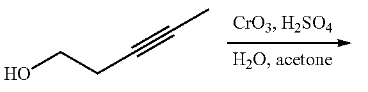

19

-continued

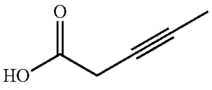

20

To a solution of compound 19 (3.80 g, 45.2 mmol) in ACETONE (38.0 mL) was added $CrO_3$ (9.03 g, 90.4 mmol), $H_2SO_4$ (31.0 g, 316 mmol) and $H_2O$ (22.8 mL). The mixture was stirred at 17° C. for 2 hours. TLC (petroleum ether/ethyl acetate=1/1, compound 19 $R_f$=0.46, product $R_f$=0.28) indicated compound 19 was consumed completely. The reaction was quenched by addition of 8.00 mL of isopropanol at 15° C. Then the suspension was filtered through a pad of Celite and the filter cake was washed with EtOAc (8.00 mL×2). The reaction mixture was poured onto ice-water (8.00 mL) and extracted with ethyl acetate (9.00 mL×3). The combined organic phase was dried with anhydrous $Na_2SO_4$, filtered and concentrated in vacuum. Compound 20 (3.05 g, 31.1 mmol, 68.8% yield) was obtained as a yellow solid.

Example 5. N-(2-(3-(5-hydroxypent-1-yn-1-yl)phenyl)-4H,10H-benzo[f]pyrazolo[5,1-c][1,4]oxazepin-7-yl)acetamide

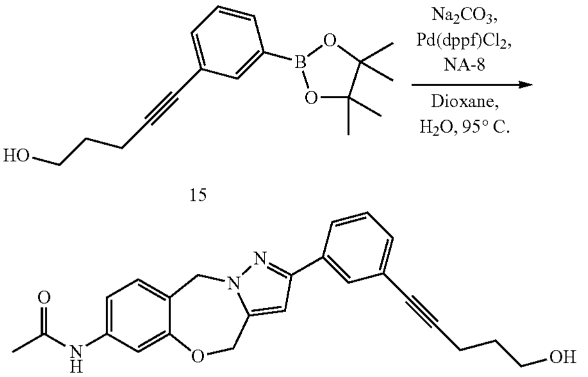

Compound 15 (200 mg, 699 μmol), NA-8 (113 mg, 349 μmol), Pd(dppf)$Cl_2$ (25.6 mg, 34.9 μmol), and $Na_2CO_3$ (74.0 mg, 699 μmol) were suspended in $H_2O$ (1.00 mL) and dioxane (5.00 mL) and heated to 95° C. for 16 hours under $N_2$ atmosphere. TLC (petroleum ether/ethyl acetate=1/1, NA-8 $R_f$=0.30, product $R_f$=0.20) and LCMS analysis indicated that the reactant 15 was consumed completely and one main spot formed. The reaction mixture was quenched by addition $H_2O$ (20.0 mL) and extracted with EtOAc (20.0 mL×3). The combined organic layers were washed with brine (10.0 mL), dried over sodium sulfate, filtered and concentrated under vacuum. The residue was purified by HPLC using a 10-micron Kromasil C18 column 100 mm×40 mm. The mobile phase was composed of water (0.1% TFA) and ACN, gradient of ACN from 32%-54% over 10 minutes. The collected fractions were concentrated by freeze-drying. The product was dissolved in a solution of aqueous HCl (0.5%, 10.0 mL) and MeCN (2.00 mL), then the liquor was concentrated again by freeze-drying. The title compound (67.8 mg, 158 μmol, 45.2% yield, 93.7% purity) was obtained as a white solid. $^1H$ NMR: $CDCl_3$ 400 MHz, δ: 7.84 (s, 1H), 7.77 (d, J=6.4 Hz, 1H), 7.48 (s, 1H), 7.31-7.37 (m, 2H), 7.21-7.25 (m, 1H), 7.18 (s, 1H), 3.86 (m, J=6.2 Hz, 2H), 2.57 (m, J=7.1 Hz, 2H), 2.19 (s, 3H), 1.85-1.93 (m, 3H), 1.27 (s, 3H). LCMS: $(M+H^+)$: 402.15, calculated 401.17.

The intermediate compound 15 was prepared as follows.

a. 5-(3-Bromophenyl)pent-4-yn-1-ol (14)

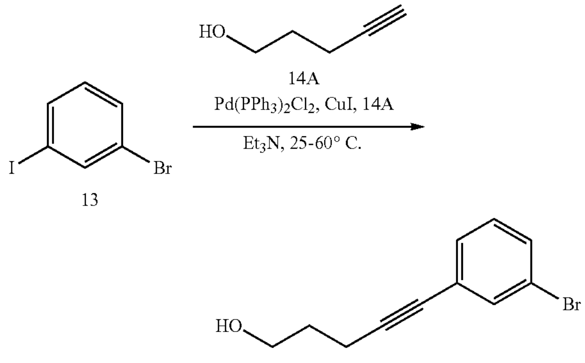

13

14

A mixture of compound 13 (2.50 g, 8.84 mmol, 1.13 mL), CuI (101 mg, 530 μmol), $Pd(PPh_3)_2Cl_2$ (186 mg, 265 μmol) in $Et_3N$ (20.0 mL) was stirred under $N_2$ at 25° C. for 30 minutes. Compound 14A (892 mg, 10.6 mmol) was added and the mixture was stirred at 60° C. for 2 hours under Ar atmosphere. TLC (petroleum ether/ethyl acetate=5/1, compound 13 $R_f$=0.70, product $R_f$=0.20) indicated compound 13 was consumed completely and one main spot formed. The reaction mixture was quenched by addition $H_2O$ (20.0 mL) and extracted with EtOAc (20.0 mL×3). The combined organic layers were washed with brine (20.0 mL), dried over sodium sulfate, filtered and concentrated under vacuum. The residue was purified by column chromatography ($SiO_2$, petroleum ether/ethyl acetate=50/1 to 0/1). The combined organic layers were concentrated under vacuum. Compound 14 (2.00 g, 8.36 mmol, 94.6% yield) was obtained as a brown solid.

b. 5-(3-(4,4,5,5-Tetramethyl-1,3,2-dioxaborolan-2-yl)phenyl)pent-4-yn-1-ol (15)

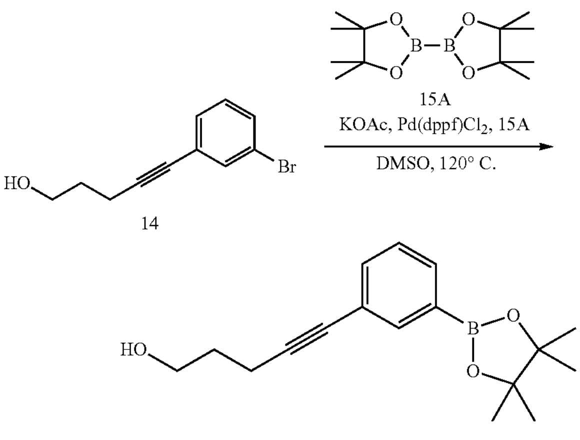

14

15

A mixture of compound 14 (1.00 g, 4.18 mmol), KOAc (821 mg, 8.36 mmol) and compound 15A (1.27 g, 5.02 mmol) in DMSO (10.0 mL) was degassed and purged with $N_2$ for 3 times. Then $Pd(dppf)Cl_2$ (306 mg, 418 μmol) was added and the mixture was stirred at 120° C. for 18 hours under $N_2$ atmosphere. TLC (petroleum ether/ethyl acetate=2/1, compound 14 $R_f$=0.35, product $R_f$=0.3) and HPLC analysis indicated that the reactant 14 was consumed completely and one main spot formed. The reaction mixture was quenched by addition $H_2O$ (50.0 mL) and extracted with EtOAc (50.0 mL×3). The combined organic layers were washed with brine (30 mL), dried over sodium sulfate, filtered and concentrated under vacuum. The residue was purified by column chromatography ($SiO_2$, petroleum ether/ethyl acetate=8/1 to 0/1). The combined organic layers were concentrated under vacuum. Compound 15 (800 mg, 2.80 mmol, 66.8% yield) was obtained as a yellow oil.

Example 6. N-(2-(2-(5-hydroxypent-1-yn-1-yl)phenyl)-4H,10H-benzo[f]pyrazolo[5,1-c][1,4]oxazepin-7-yl)acetamide

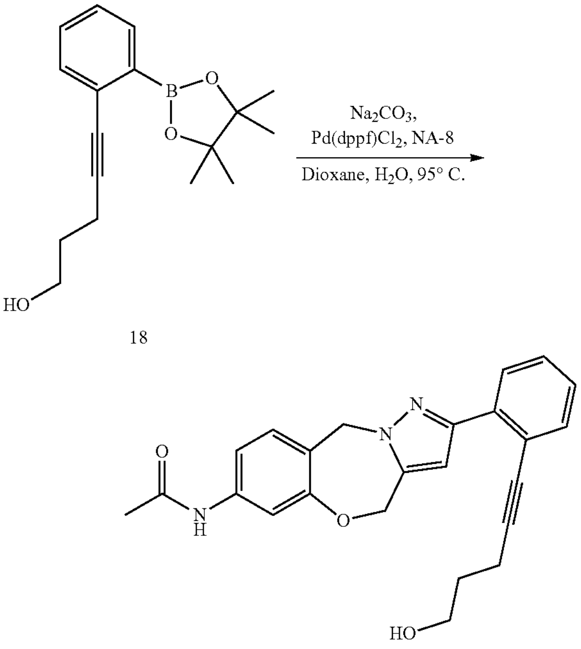

18

Compound NA-8 (113 mg, 349 μmol), compound 18 (200 mg, 699 μmol), $Pd(dppf)Cl_2$ (25.6 mg, 34.9 μmol) and $Na_2CO_3$ (74.1 mg, 699 μmol) were suspended in $H_2O$ (1.00 mL) and dioxane (5.00 mL) and heated to 95° C. for 16 hours under $N_2$ atmosphere. TLC (petroleum ether/ethyl acetate=1/1, compound 18 $R_f$=0.30, product $R_f$=0.20) and LCMS analysis indicated that NA-8 was consumed completely and one main spot formed. The reaction mixture was quenched by addition $H_2O$ (10.0 mL) and extracted with EtOAc (10.0 mL×3). The combined organic layers were washed with brine (10.0 mL), dried over sodium sulfate, filtered and concentrated under vacuum. The residue was purified by HPLC using a 10-micron Kromasil C18 column 100 mm×40 mm. The mobile phase was composed of water (0.1% TFA) and ACN, gradient of ACN from 32%-54% over 10 minutes. The collected fractions were concentrated by freeze-drying. The product was dissolved in a solution of aqueous HCl (0.5%, 10.0 mL) and MeCN (2.00 mL), then the liquor was concentrated again by freeze-drying. The title compound (36.5 mg, 87.9 μmol, 25.1% yield, 96.6% purity) was obtained as a white solid. $^1H$ NMR: $CDCl_3$ 400 MHz, δ: 7.82 (d, J=7.82 Hz, 1H), 7.46-7.51 (m, 2H), 7.29-7.43 (m, 3H), 7.21-7.25 (m, 1H), 7.10 (d, J=8.80 Hz, 1H), 6.87 (s, 1H), 5.67 (s, 2H), 5.30 (s, 2H), 3.77 (m, J=5.9 Hz, 2H), 2.57 (m, J=6.8 Hz, 2H), 2.18 (s, 3H), 1.84 (m, J=6.4 Hz, 2H), 1.26 (s, 2H). LCMS: $(M+H^+)$: 402.1, calculated 401.17.

The intermediate compound 18 was prepared as follows.

a. 5-(2-Bromophenyl)pent-4-yn-1-ol (17)

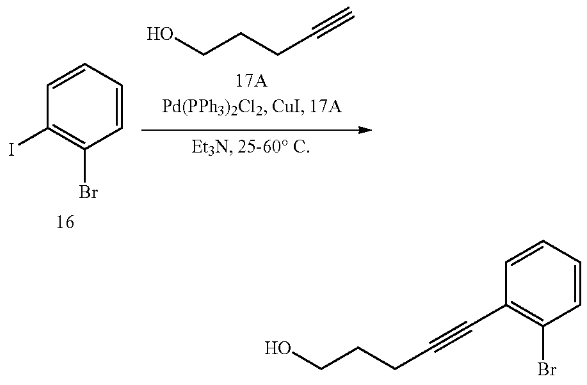

16

17

A mixture of compound 16 (2.50 g, 8.84 mmol, 1.14 mL), CuI (100 mg, 530 μmol) and $Pd(PPh_3)_2Cl_2$ (186 mg, 265 μmol) in $Et_3N$ (20.0 mL) was stirred under $N_2$ at 25° C. for 30 minutes. Then compound 17A (892 mg, 10.6 mmol) was added and the mixture was stirred at 60° C. for 3 hours under Ar atmosphere. TLC (petroleum ether/ethyl acetate=5/1, compound 16 $R_f$=0.7, product $R_f$=0.2) indicated compound 16 was consumed completely and one main spot formed. The reaction mixture was quenched by addition $H_2O$ (20.0 mL) and extracted with EtOAc (20.0 mL×3). The combined organic layers were washed with brine (20.0 mL), dried over sodium sulfate, filtered and concentrated under vacuum. The residue was purified by column chromatography ($SiO_2$, petroleum ether/ethyl acetate=10/1 to 0/1). The combined organic layers were concentrated under vacuum. Compound 17 (1.71 g, 7.15 mmol, 80.9% yield) was obtained as a white solid.

b. 5-(2-(4,4,5,5-Tetramethyl-1,3,2-dioxaborolan-2-yl)phenyl)pent-4-yn-1-ol (18)

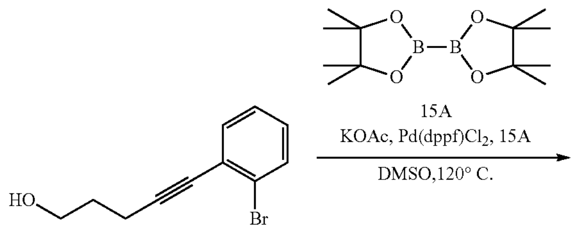

17

-continued

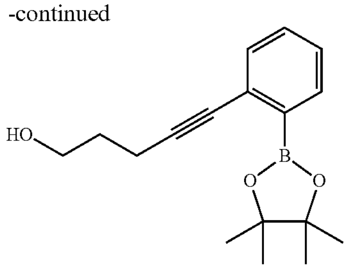

18

A mixture of compound 17 (1.00 g, 4.18 mmol), KOAc (821 mg, 8.36 mmol), and compound 15A (1.27 g, 5.02 mmol) in DMSO (10.0 mL) was degassed and purged with $N_2$ for 3 times, then $Pd(dppf)Cl_2$ (306 mg, 418 μmol) was added and the mixture was stirred at 120° C. for 18 hours under $N_2$ atmosphere. TLC (petroleum ether/ethyl acetate=2/1, compound 17 $R_f$=0.35, product $R_f$=0.3) and HPLC analysis indicated that compound 17 was consumed completely and one main spot formed. The reaction mixture was quenched by addition $H_2O$ (50.0 mL) and extracted with EtOAc (50.0 mL×3). The combined organic layers were washed with brine (30.0 mL), dried over sodium sulfate, filtered and concentrated under vacuum. The residue was purified by column chromatography ($SiO_2$, petroleum ether/ethyl acetate=8/1 to 0/1). The combined organic layers were concentrated under vacuum. Compound 18 (750 mg, 2.62 mmol, 62.7% yield) was obtained as a yellow oil.

Example 7. N-(2-(3-Aminophenyl)-4H,10H-benzo[f]pyrazolo[5,1-c][1,4]oxazepin-7-yl)acetamide

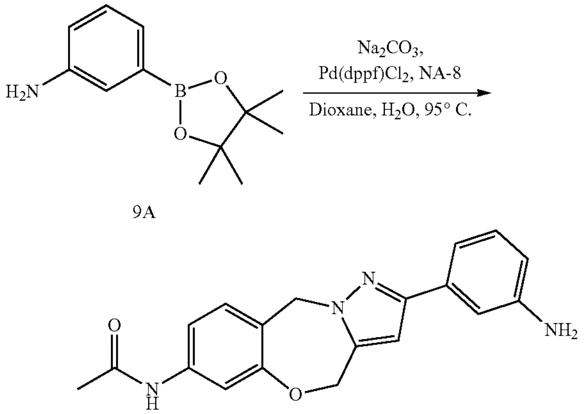

9A

Compound NA-8 (500 mg, 1.55 mmol), compound 9A (425 mg, 3.10 mmol), $Pd(dppf)Cl_2$ (114 mg, 155 μmol) and $Na_2CO_3$ (329 mg, 3.10 mmol) were suspended in $H_2O$ (5.00 mL) and dioxane (25.0 mL) and heated to 95° C. for 16 hours under $N_2$ atmosphere. TLC (petroleum ether/ethyl acetate=1/1, NA-8 $R_f$=0.30, product $R_f$=0.25) indicated NA-8 was consumed completely and one main spot formed. The reaction mixture was quenched by addition $H_2O$ (20.0 mL) and extracted with EtOAc (20.0 mL×3). The combined organic layers were washed with brine (10.0 mL), dried over sodium sulfate, filtered and concentrated under vacuum. The residue was purified by column chromatography ($SiO_2$, petroleum ether/ethyl acetate=20/1 to 0/1). The combined organic layers were concentrated under vacuum. The title compound (250 mg, 748 μmol, 48.2% yield) was obtained as a yellow solid.

Example 8. N-(2-(2-Methoxyphenyl)-4H,10H-benzo[f]pyrazolo[5,1-c][1,4]oxazepin-7-yl)pent-3-ynamide

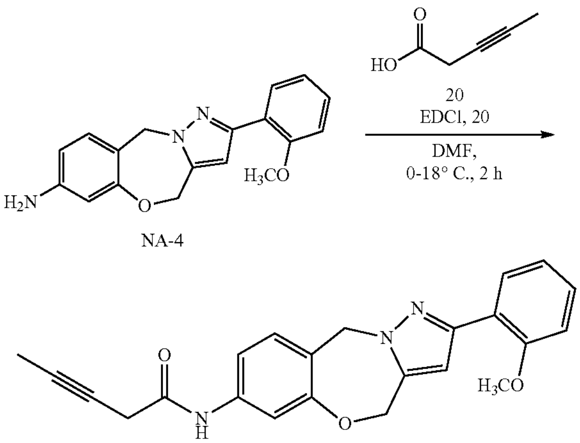

NA-4

To a solution of NA-4 (300 mg, 976 μmol) and compound 20 (192 mg, 1.95 mmol) in DMF (10.0 mL) was added EDCI (374 mg, 1.95 mmol) at 0° C. The mixture was stirred at 18° C. for 2 hours. TLC (petroleum ether/ethyl acetate=1/1, NA-4 $R_f$=0.35, product $R_f$=0.45) and LCMS analysis indicated NA-4 was consumed completely and a main peak for product was detected. The reaction mixture was quenched by addition $H_2O$ (10.0 mL) and extracted with EtOAc (10.0 mL×3). The combined organic layers were filtered and concentrated under vacuum. The residue was purified by HPLC using a 5-micron Boston Prime C18 column with 150 mm×30 mm ID. The mobile phase was composed of water (with 0.05% HCl) and a gradient of ACN from 35%-60% over 10 minutes. The combined product fractions were concentrated by freeze-drying. The title compound (73.6 mg, 187 μmol, 19.1% yield, 98.3% purity) was obtained as a white solid. $^1$H NMR: $CDCl_3$ 400 MHz, δ: 8.36 (s, 1H), 8.17 (d, J=7.0 Hz, 1H), 7.79 (s, 1H), 7.44 (m, J=7.9 Hz, 2H), 7.00-7.08 (m, 2H), 6.98-7.16 (m, 1H), 6.81 (s, 1H), 6.11 (s, 2H), 5.35 (s, 2H), 3.98 (s, 3H), 3.34 (d, J=2.19 Hz, 2H), 1.95 (m, J=2.41 Hz, 3H). LCMS: (M+H$^+$): 388.15, calculated 387.16.

The intermediate compound NA-4 was prepared as follows.

a. 2-(2-Methoxyphenyl)-4H,10H-benzo[f]pyrazolo[5,1-c][1,4]oxazepin-7-amine (NA-4)

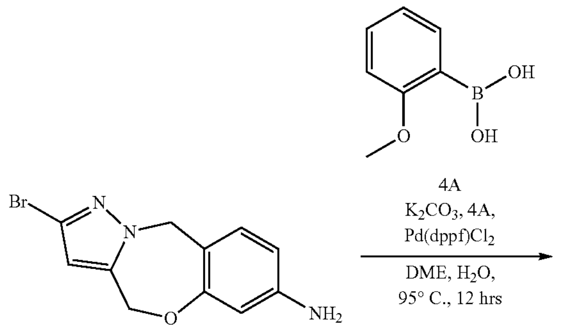

6

-continued

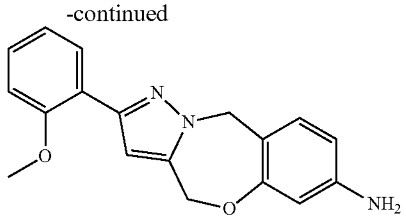

NA-4

A mixture of compound 6 (4.00 g, 14.3 mmol), compound 4A (2.60 g, 17.1 mmol), Pd(dppf)$Cl_2$ (2.09 g, 2.86 mmol) and $K_2CO_3$ (3.95 g, 28.6 mmol) in DME (40.0 mL) and $H_2O$ (4.00 mL) was degassed and purged with $N_2$ for 3 times. The mixture was stirred at 95° C. for 12 hrs under $N_2$ atmosphere. TLC (petroleum ether/ethyl acetate=1/1, compound 6 $R_f$=0.43, product $R_f$=0.24) showed the reaction was complete. The mixture was poured into $H_2O$ (100 mL) and extracted with EtOAc (50.0 mL×3). The combined organic layers were washed with brine (20.0 mL), dried over $Na_2SO_4$, filtered and concentrated under vacuum. The residue was purified by column chromatography ($SiO_2$, petroleum ether/ethyl acetate=10/1 to 0/1). Compound NA-4 (3.00 g, 9.63 mmol, 67.4% yield, 98.6% purity) was obtained as a yellow solid. $^1$H NMR: DMSO 400 MHz, δ: 7.84 (m, J=7.62 Hz, 1H), 7.28 (m, J=8.4 Hz, 1H), 7.07 (m, J=7.82 Hz, 1H), 6.94-7.00 (m, 2H), 6.72 (s, 1H), 6.21 (m, J=8.12 Hz, 1H), 6.16 (m, J=2.4 Hz, 1H), 5.40 (s, 2H), 5.24 (s, 2H), 5.15 (s, 2H), 3.84 (s, 3H), 3.32 (s, 2H). LCMS: (M+H$^+$): 308.05, calculated 307.13.

Example 9. N-(2-(4-Amino-2-(5-hydroxypent-1-yn-1-yl)phenyl)-4H,10H-benzo[f]pyrazolo[5,1-c][1,4]oxazepin-7-yl)acetamide

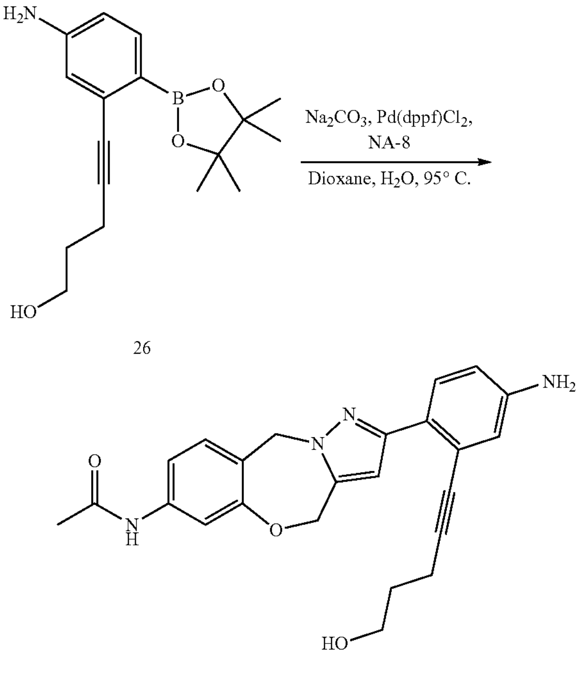

26

A mixture of compound 26 (467 mg, 1.55 mmol), compound NA-8 (250 mg, 776 μmol) and $Na_2CO_3$ (165 mg, 1.55 mmol) in $H_2O$ (2.50 mL) and dioxane (12.5 mL) was degassed and purged with $N_2$ for 3 times, then Pd(dppf)$Cl_2$ (56.8 mg, 77.6 μmol) was added and the mixture was stirred at 90° C. for 9 hours under $N_2$ atmosphere. TLC (ethyl acetate, starting material: $R_f$=0.7, product: $R_f$=0.3) and LCMS analysis indicated compound 26 was consumed completely and ~22.4% of desired product was detected. The reaction mixture was poured into water (10.0 mL) and extracted with ethyl acetate (15.0 mL×3), dried over $Na_2SO_4$, filtered and concentrated under vacuum. The crude product was purified by column chromatography ($SiO_2$, petroleum ether/ethyl acetate=30/1 to 1/3). Compound 27 (100 mg, 19.3% yield) was obtained as a brown solid.

The intermediate 26 was prepared as follows.

a. 1-Bromo-2-iodo-4-nitrobenzene (23)

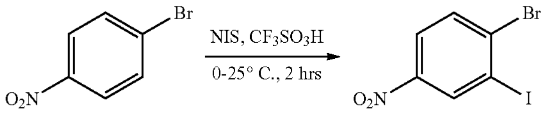

22 23

To a solution of compound 22 (10.0 g, 49.5 mmol) in $CF_3SO_3H$ (22.0 mL) was added portion-wise NIS (11.1 g, 49.5 mmol) at 0° C. After addition, the mixture was stirred at 25° C. for 2 hours. TLC (petroleum ether, starting material: $R_f$=0.5, product: $R_f$=0.45) indicated compound 22 was consumed completely. The reaction mixture was quenched with ice-water (20.0 mL) and extracted with DCM (25.0 mL×3). The combined organic extracts were washed with aqueous 10% sodium sulfite solution (20.0 mL) and water (10.0 mL), dried over $Na_2SO_4$, and evaporated under reduced pressure to give compound 23 (11.5 g, 70.9% yield) as a brown solid, which was used into the next step without further purification.

b. 4-Bromo-3-iodoaniline (24)

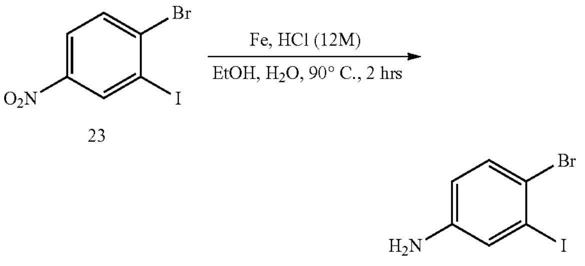

23

24

To a solution of compound 23 (11.6 g, 35.4 mmol) in EtOH (15.0 mL) and $H_2O$ (15.0 mL) was added drop-wise HCl (12 M, 4.42 mL) and Fe (5.93 g, 106 mmol) at 90° C. The resulting mixture was stirred at 90° C. for 2 hours. TLC (petroleum ether/ethyl acetate=3/1, starting material: $R_f$=0.5, product: $R_f$=0.3) indicated compound 23 was consumed completely.

The residue was poured into water (10.0 mL). The aqueous phase was extracted with ethyl acetate (30.0 mL×3). The combined organic phase was dried with anhydrous $Na_2SO_4$, filtered and concentrated under vacuum to give compound 24 (10.5 g, 99.6% yield) as a brown oil, which was used into the next step without further purification.

c. 5-(5-Amino-2-bromophenyl)pent-4-yn-1-ol (25)

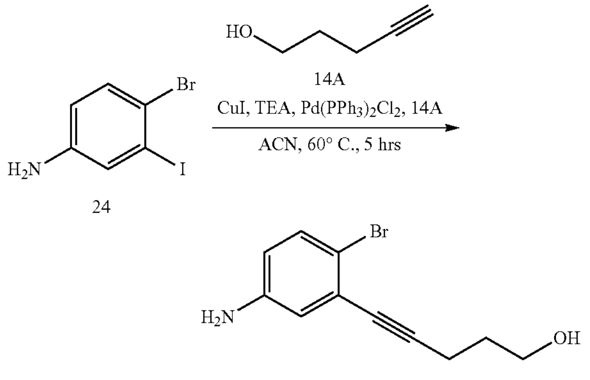

14A

24

25

To a solution of compound 24 (5.50 g, 18.5 mmol) in ACN (20.0 mL) was added compound 14A (1.86 g, 22.2 mmol) and TEA (3.74 g, 36.9 mmol, 5.14 mL). The mixture was degassed with Ar, then CuI (70.3 mg, 369 μmol) and Pd$(PPh_3)_2Cl_2$ (259 mg, 369 umol) were added. The reaction was heated at 60° C. for 5 hrs. TLC (petroleum ether/ethyl acetate=3/1, starting material: $R_f$=0.3, product: $R_f$=0.2) indicated compound 24 was consumed completely.

The reaction mixture was concentrated under reduced pressure to remove ACN. The residue was diluted with $H_2O$ (10.0 mL) and extracted with EtOAc (10.0 mL×3), and dried over $Na_2SO_4$, filtered and concentrated under vacuum. The residue was purified by column chromatography ($SiO_2$, petroleum ether/ethyl acetate=10/1 to 2/1). Compound 25 (3.40 g, 72.5% yield) was obtained as a brown solid.

d. 5-(5-Amino-2-(4,4,5,5-tetramethyl-1,3,2-dioxaborolan-2-yl)phenyl)pent-4-yn-1-ol (26)

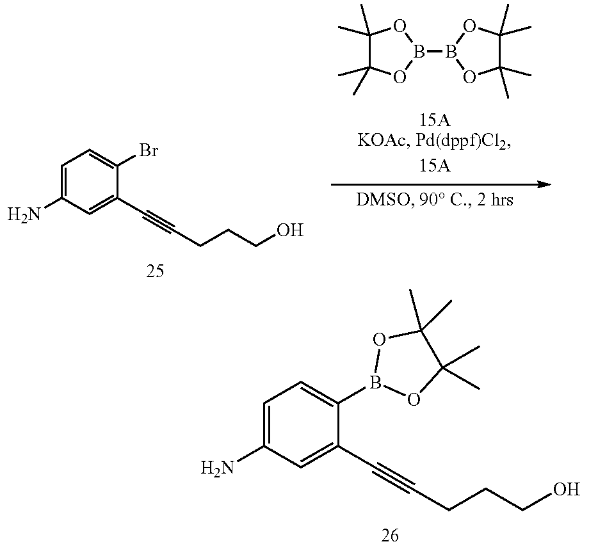

15A

25

26

A mixture of compound 25 (4.40 g, 17.3 mmol), compound 15A (8.79 g, 34.6 mmol) and KOAc (5.10 g, 51.9 mmol) in DMSO (25.0 mL) was degassed and purged with $N_2$ for 3 times. Pd(dppf)$Cl_2$·$CH_2Cl_2$ (1.41 g, 1.73 mmol) was added and then the mixture was stirred at 90° C. for 2 hours under $N_2$ atmosphere. TLC (petroleum ether/ethyl acetate=1/1, starting material: $R_f$=0.4, product: $R_f$=0.45) indicated compound 25 was consumed completely. LCMS analysis showed compound 25 was consumed completely and ~21.6% of desired mass was detected.

The residue was diluted with $H_2O$ (20.0 mL) and extracted with EtOAc (20.0 mL×3), and dried over $Na_2SO_4$, filtered and concentrated under vacuum. The residue was purified by column chromatography ($SiO_2$, petroleum ether/ethyl acetate=10/1 to 1/1) to give compound 26 (660 mg, 12.7% yield) as a brown oil. $^1$H NMR: $CDCl_3$-400 MHz, δ: 7.50 (d, J=8.0 Hz, 1H), 6.65 (d, J=2.4 Hz, 1H), 6.50 (dd, J=8.0, 2.4 Hz, 1H), 4.05 (q, J=7.2 Hz, 1H), 3.80 (t, J=6.0 Hz, 2H), 2.50 (t, J=6.4 Hz, 2H), 1.97 (s, 1H), 1.79 (q, J=6.4 Hz, 3H), 1.47 (s, 3H), 1.26 (s, 12H).

Example 10. N-(2-(4-hydroxy-2-(5-hydroxypent-1-yn-1-yl)phenyl)-4H,10H-benzo[f]pyrazolo[5,1-c][1,4]oxazepin-7-yl)acetamide

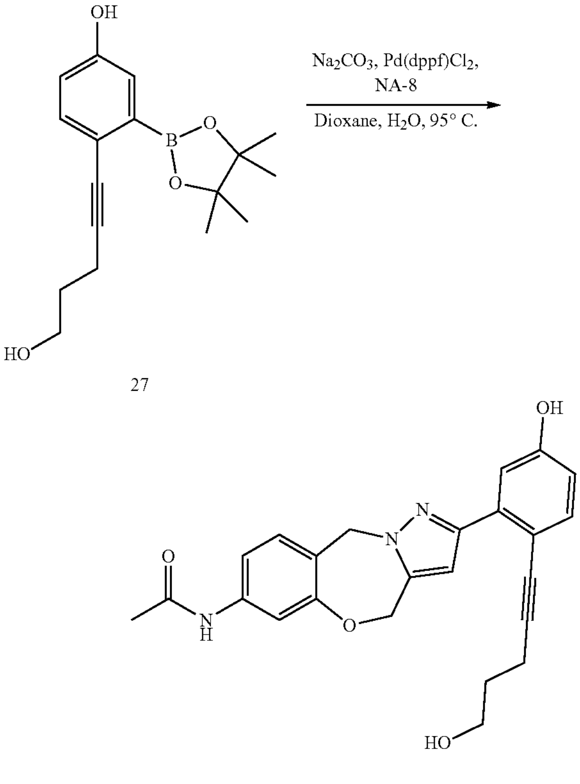

27

To a solution of 3-(5-Hydroxypent-1-yn-1-yl)-4-(4,4,5,5-tetramethyl-1,3,2-dioxaborolan-2-yl)phenol (703 mg, 2.33 mmol) in dioxane (25.0 mL) and $H_2O$ (5.00 mL) was added compound NA-8 (500 mg, 1.55 mmol), $Na_2CO_3$ (329 mg, 3.10 mmol) and Pd(dppf)$Cl_2$ (114 mg, 155 μmol) at 25° C. the reaction mixture was degassed and purged with $N_2$ for 3 times, and then the mixture was stirred at 90° C. for 12 hours under $N_2$ atmosphere. LCMS analysis showed compound 27 was consumed completely and one main peak of the desired product was detected. The reaction mixture was diluted with $H_2O$ (7.00 mL) and extracted with EtOAc (5.00 mL×3). The combined organic layers were washed with brine (5.00 mL×2). The combined organic layers were dried over $Na_2SO_4$, filtered and concentrated under vacuum. The residue was purified by column chromatography ($SiO_2$, petroleum ether/ethyl acetate=5/1 to 0/1). The title compound (160 mg, 24.6% yield) was obtained as a light yellow solid.

The intermediate 3-(5-hydroxypent-1-yn-1-yl)-4-(4,4,5,5-tetramethyl-1,3,2-dioxaborolan-2-yl)phenol was prepared as follows.

a. 4-Bromo-3-iodophenol

To a solution of 2-iodophenol (20.0 g, 90.9 mmol) was added $Br_2$ (18.2 g, 114 mmol, 5.86 mL) in AcOH (120 mL) at 15° C. The mixture was stirred at 25° C. for 2 hours. HPLC analysis indicated compound 24 was consumed completely. The reaction mixture was stirred at 25° C. and a saturated solution of $Na_2S_2O_3$ (100 mL) was added, then it was neutralized with $NaHCO_3$ (40.0 mL) and the layers were separated. The aqueous layer was extracted with DCM (100 mL×2). The combined organic layers were washed with water, dried over $Na_2SO_4$ and concentrated under vacuum. The residue was purified by column chromatography ($SiO_2$, petroleum ether/ethyl acetate=10/1 to 1/1). 4-Bromo-3-iodophenol (23.0 g, 84.6% yield) was obtained as a white solid. $^1$H NMR: $CDCl_3$-400 MHz, δ: 7.42 (d, J=8.8 Hz, 1H), 7.37 (t, J=2.8 Hz, 1H), 6.73-6.70 (m, 1H).

b. 4-Bromo-3-(5-hydroxypent-1-yn-1-yl)phenol

To a solution of compound 4-bromo-3-iodophenol (23.0 g, 77.0 mmol) in ACN (115 mL) was added compound 5-hydroxypentyne (9.06 g, 108 mmol) and TEA (15.6 g, 154 mmol, 21.4 mL). The mixture was degassed with $N_2$, then $Pd(PPh_3)_2Cl_2$ (1.08 g, 1.54 mmol) and CuI (586 mg, 3.08 mmol) were added. The reaction was heated at 70° C. for 2 hours. TLC (ethyl acetate, product: $R_f$=0.39) indicated the 4-bromo-3-iodophenol was consumed completely and one new spot formed. The reaction mixture was diluted with $H_2O$ (70.0 mL) and extracted with ethyl acetate (25.0 mL×3). The combined organic layers were washed with brine (20.0 mL×2), dried over $Na_2SO_4$, filtered and concentrated under vacuum. The residue was purified by column chromatography ($SiO_2$, petroleum ether/ethyl acetate=5/1 to 0/1). 4-Bromo-3-(5-hydroxypent-1-yn-1-yl)phenol (16.0 g, 81.5% yield) was obtained as a white solid. $^1$H NMR: $CDCl_3$-400 MHz, δ: 7.35 (d, J=8.8 Hz, 1H), 6.9 (d, J=2.8 Hz, 1H), 6.67-6.64 (m, 1H), 3.89 (t, J=6.4 Hz, 2H), 2.59 (t, J=6.8 Hz, 2H), 1.93-1.86 (m, 2H).

c. 3-(5-Hydroxypent-1-yn-1-yl)-4-(4,4,5,5-tetramethyl-1,3,2-dioxaborolan-2-yl)phenol To a solution of 4-bromo-3-(5-hydroxypent-1-yn-1-yl)phenol (16.0 g, 62.7 mmol) in DMSO (160 mL) was added compound 15A (31.9 g, 125 mmol), Pd(dppf)$Cl_2$·$CH_2Cl_2$ (5.12 g, 6.27 mmol) and KOAc (18.5 g, 188 mmol) at 25° C. The reaction mixture was degassed and purged with $N_2$ for 3 times, and then the mixture was stirred at 90° C. for 2 hours under $N_2$ atmosphere. LCMS analysis showed the 4-bromo-3-(5-hydroxypent-1-yn-1-yl)phenol was consumed completely and one peak of the desired product was detected. The reaction mixture was diluted with $H_2O$ (70.0 mL) and extracted with ethyl acetate (25.0 mL×3). The combined organic layers were washed with brine (20.0 mL×2), dried over $Na_2SO_4$, filtered and concentrated under vacuum. The residue was purified by column chromatography ($SiO_2$, petroleum ether/ethyl acetate=10/1 to 0/1). 3-(5-Hydroxypent-1-yn-1-yl)-4-(4,4,5,5-tetramethyl-1,3,2-dioxaborolan-2-yl)phenol (10.4 g, 49.8% yield, 90.8% purity) was obtained as a brown oil. $^1$H NMR: DMSO-$d_6$400 MHz, δ: 7.45 (d, J=8.0 Hz, 1H), 6.74-6.68 (m, 2H), 3.58-3.54 (m, 2H), 2.43 (t, J=6.8 Hz, 2H), 1.73-1.65 (m, 2H), 1.08 (s, 12H). LCMS: (M+H$^+$): 303.1, Calculated 302.17.

Example 12. 2-(4-(2-phenyl-4H,10H-benzo[f]pyrazolo[5,1-c][1,4]oxazepin-7-yl)-1H-pyrazol-1-yl) acetonitrile

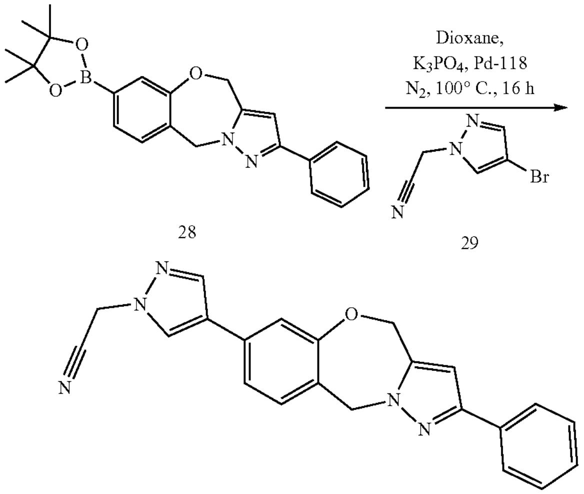

28

29

To a vial containing a solution of 28 (0.350 mmol, 1.00 eq), 29 (0.525 mmol, 1.50 eq) in Dioxane (3.0 mL) was added $K_3PO_4$ (2.0 M, 350 ul) and Pd-118 (0.018 mmol, 0.05 eq). The mixture was degassed and purged with $N_2$, and then the mixture was stirred at 100° C. for 16 hrs under $N_2$ atmosphere. The reaction mixture was concentrated under reduced pressure to remove Dioxane. Added 1.0 mL water to the reaction mixture and extracted with EtOAc (3 mL*3). Collected organic layer and removed the solvent by Speed-vac to give residues. Purified the residue by prep-HPLC (Xtimate C18 150*25 mm*5 um columns under formic acid conditions (B)) to give desired product Example 12 as white solid. $^1$H NMR (400 MHz, DMSO-d6) δ 8.28 (s, 1H), 8.06 (s, 1H), 7.75-7.80 (m, 2H), 7.37-7.42 (m, 3H), 7.26-7.32 (m, 1H), 7.18-7.25 (m, 2H), 6.80 (s, 1H), 5.65 (s, 2H), 5.49 (s, 2H), 5.39 (s, 2H). LCMS: (M+H$^+$): 368, Calculated 367.

This general procedure was used to make Examples 11-17. Condition A=prep-HPLC under basic conditions; Condition B=prep-HPLC under formic acid; Condition C=prep-TLC.

| Structure | MS [M + H]$^+$ | $^1$HNMR | Condition | Example |
|---|---|---|---|---|
| 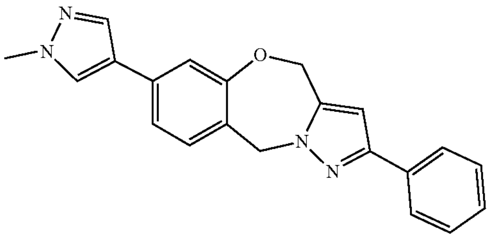 [SMILES: Cn1cc(-c2ccc3c(c2)OCc2cc(-c4ccccc4)nn2C3)cn1] | 343 | | B | 11 |
| 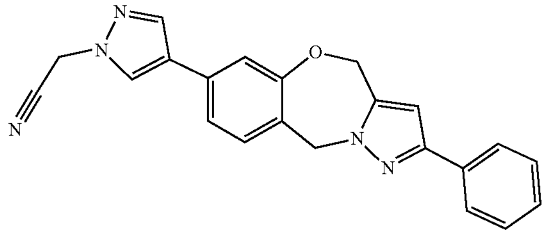 [SMILES: N#CCn1cc(-c2ccc3c(c2)OCc2cc(-c4ccccc4)nn2C3)cn1] | 368 | $^1$H NMR (400 MHz, DMSO-d6) δ 8.28 (s, 1H), 8.06 (s, 1H), 7.75-7.80 (m, 2H), 7.37-7.42 (m, 3H), 7.26-7.32 (m, 1H), 7.18-7.25 (m, 2H), 6.80 (s, 1H), 5.65 (s, 2H), 5.49 (s, 2H), 5.39 (s, 2H) | B | 12 |
| 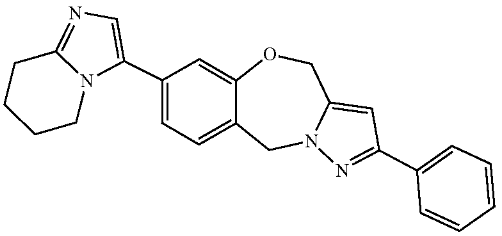 [SMILES: c1ccc(-c2cc3n(n2)Cc2ccc(-c4cnc5n4CCCC5)cc2OC3)cc1] | 383 | | B | 13 |

-continued
| Structure | MS [M + H]+ | 1HNMR | Condition | Example |
|---|---|---|---|---|
| 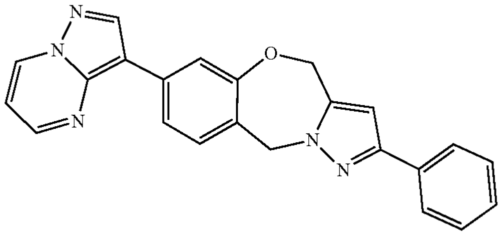 [SMILES: c1ccc(-c2cc3n(n2)Cc2ccc(-c4cnn5cccnc45)cc2OC3)cc1] | 380 | | B | 14 |
| 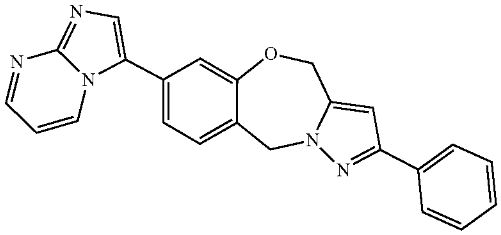 [SMILES: c1ccc(-c2cc3n(n2)Cc2ccc(-c4cnc5ncccn45)cc2OC3)cc1] | 380 | | B | 15 |
| 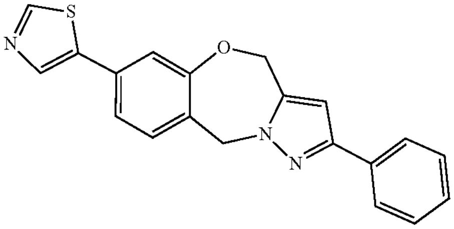 [SMILES: c1ccc(-c2cc3n(n2)Cc2ccc(-c4cncs4)cc2OC3)cc1] | 346 | $^1$H NMR (400 MHz, DMSO-d6) δ 9.08 (s, 1H), 8.31-8.36 (m, 1H), 7.75-7.81 (m, 2H), 7.47 (d, J = 7.95 Hz, 1H), 7.36-7.43 (m, 2H), 7.25-7.34 (m, 3H), 6.82 (s, 1H), 5.70 (s, 2H), 5.43 (s, 2H), 2.07 (s, 1H) | B | 16 |
| 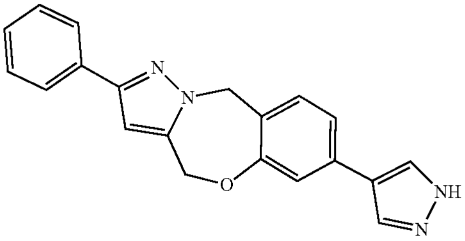 [SMILES: c1ccc(-c2cc3n(n2)Cc2ccc(-c4cn[nH]c4)cc2OC3)cc1] | 329 | | B | 17 |
a. Synthesis of 7-bromo-2-phenyl-4H,10H-benzo[f]pyrazolo[5,1-c][1,4]oxazepane (34)
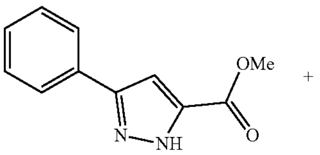
30
+
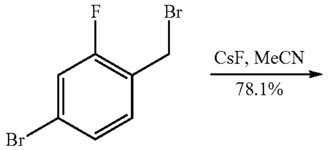
31
-continued
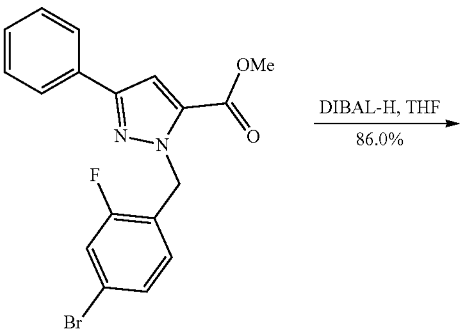
32

-continued

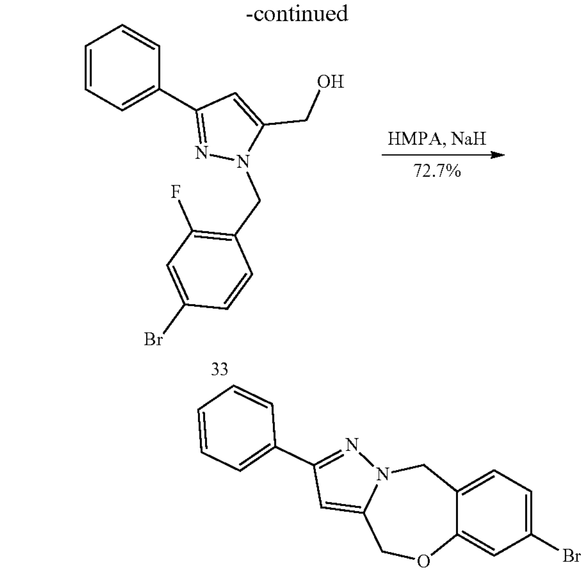

33

34 b. Methyl 1-(4-bromo-2-fluorobenzyl)-3-phenyl-1H-pyrazole-5-carboxylate (32)

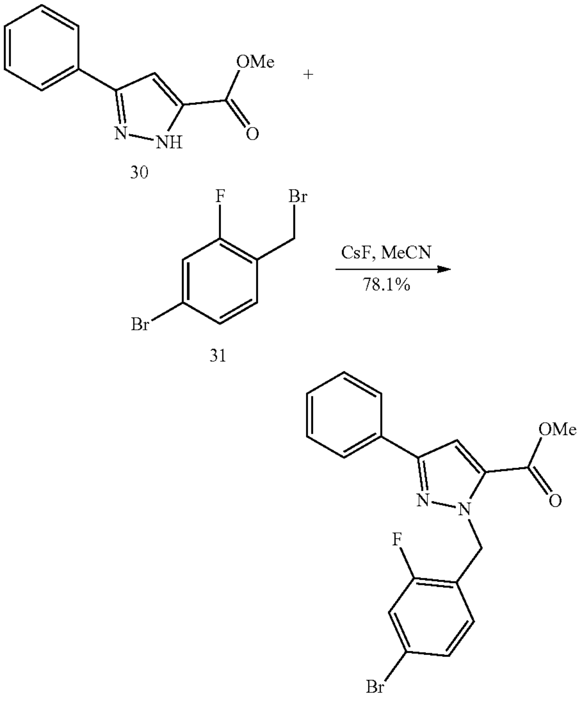

30

31

32

To a solution of Compound 30 (36.1 g, 134.8 mmol) in ACN (300 mL) was added CsF (41.0 g, 269.8 mmol) and Compound 31 (30.0 g, 148.4 mmol). The mixture was stirred at 25° C. for 5 hrs. TLC (petroleum ether/ethyl acetate=3/1) showed the reaction was incomplete. Filtered to give the solid, which was added into water (200 mL), extracted with EtOAc (300 mL×3), washed with brine (200 mL×3), dried over anhydrous $Na_2SO_4$, filtered and concentrated under reduced pressure to give Compound 32 (41.0 g, 78.1% yield) as a white solid. 1H NMR (300 MHz, $CDCl_3$): δ 7.86-7.84 (m, 2H), 7.59 (dd, J=9.9, 2.1 Hz, 1H), 7.48-7.35 (m, 5H), 6.94 (t, J=8.1 Hz, 1H), 3.84 (s, 3H). LCMS: 389.0, 391.0 ($[M+H]^+$).

c. (1-(4-bromo-2-fluorobenzyl)-3-phenyl-1H-pyrazol-5-yl)methanol (33)

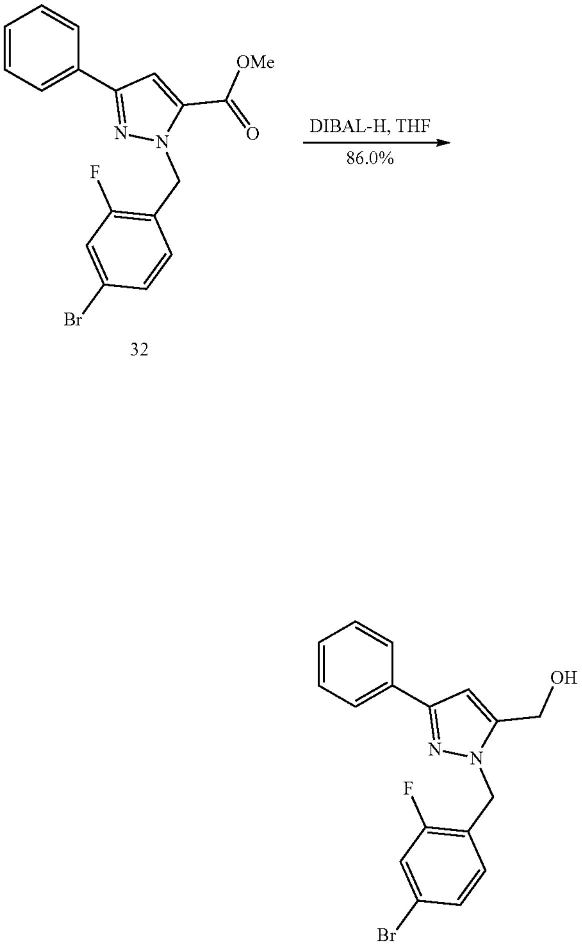

32

33

To a mixture of the Compound 32 (10.0 g, 25.7 mmol) in THE (100 mL) was added DIBAL-H (1.5 M, 34.0 mL) at 0° C. The mixture was stirred at 15° C. for 1 hr under $N_2$ atmosphere. TLC (petroleum ether/ethyl acetate=5/1) indicated Compound 32 was consumed completely. The reaction mixture was quenched by addition of Potassium Sodium tartrate solution (30 mL). Extracted with EtOAc (100 mL×3), washed with brine (30 mL×3), dried over anhydrous $Na_2SO_4$, filtered and concentrated under reduced pressure and recrystallized in MTBE to give Compound 33 (8.0 g, 86.0% yield) as a white solid. $^1H$ NMR (300 MHz, DMSO-$d_6$): δ 7.76-7.74 (m, 2H), 7.59 (dd, J=9.6, 1.8 Hz, 1H), 7.40-7.35 (m, 3H), 7.31-7.25 (m, 1H), 6.99 (t, J=8.1 Hz, 1H), 5.44-5.40 (m, 3H), 4.53 (d, J=5.4 Hz, 2H). LCMS: 361.0, 363.0 ($[M+H]^+$).

d. 7-bromo-2-phenyl-4H,10H-benzo[f]pyrazolo[5,1-c][1,4]oxazepane (34)

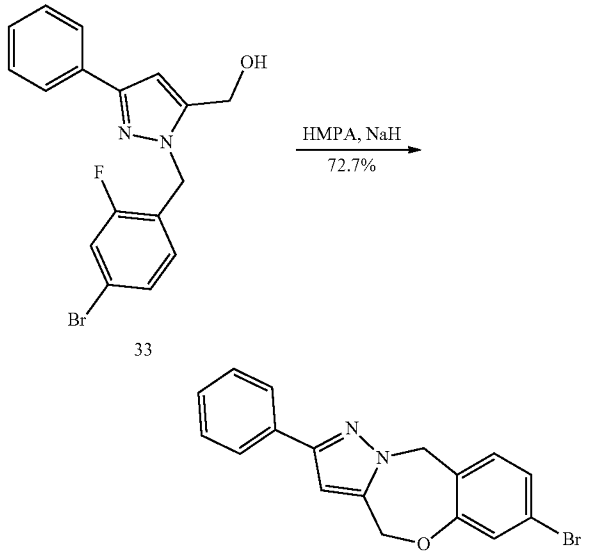

33

34

To the solution of suspending NaH (5.7 g, 60%, 141.7 mmol) in PhMe (1.2 L), Compound 33 (23.3 g, 64.5 mmol) and HMPA (230 mL), the resulting solution was heated to 95° C. and kept the temperature for overnight, after monitored by LCMS showed A4 was consumed completely, the mixture was cooled to room temperature and quenched with water (250 mL), extracted with EtOAc (300 mL×3), washed with water (50 mL), brine (50 mL×4), dried over $Na_2SO_4$, concentrated to dryness, the residue was re-crystalled in EtOAc to give Compound 34 (16.0, 72.7%) as an off-white solid. $^1$H NMR (400 MHz, DMSO-$d_6$): δ 7.84-7.76 (m, 2H), 7.41-7.36 (m, 3H), 7.32-7.28 (m, 1H), 7.20-7.14 (m, 2H), 6.82 (s, 1H), 5.67 (s, 2H), 5.41 (s, 2H). LCMS: 341.0, 343.1 ([M+H]$^+$).

Example 21. N-cyclopentyl-2-phenyl-4H,10H-benzo[f]pyrazolo[5,1-c][1,4]oxazepin-7-amine

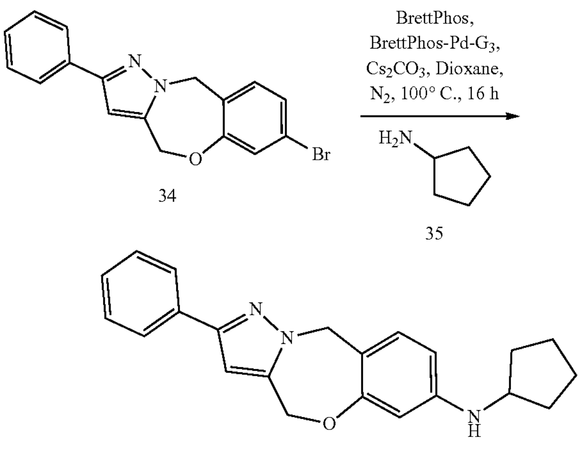

34

35

Example 21

Aliphatic Amines:

To a vial containing a solution of Compound 34 (34.12 mg, 0.100 mmol, 1.0 eq) and Compound 35 (1.0 eq, 0.150 mmol) in 1,4-Dioxane (1.00 mL) was added $Cs_2CO_3$ (97.5 mg, 0.300 mmol), BrettPhos (2.68 mg, 0.01 mmol) and BrettPhos-Pd G3 (4.53 mg, 0.01 mmol) at the protection of $N_2$. The vail was capped and the mixture was stirred at 100° C. for 16 hrs. The mixture was concentrated by vaccum. Diluted the residue with 1.0 mL of $H_2O$, and extracted with EtOAc (1.50*3 mL). The organic layer was collected and concentrated by vaccum. The residue was purified by pre-HPLC to give desired product Example 21 (27.3 mg, 79%) as a white solid. $^1$H NMR (400 MHz, DMSO-d6): 7.73-7.79 (m, 2H), 7.35-7.41 (m, 2H), 7.25-7.30 (m, 1H), 7.03 (d, J=8.44 Hz, 1H), 6.71 (s, 1H), 6.22 (dd, J=2.26, 8.25 Hz, 1H), 6.13 (d, J=2.20 Hz, 1H), 5.68 (d, J=6.60 Hz, 1H), 5.41 (s, 2H), 5.26 (s, 2H), 3.63 (sxt, J=6.21 Hz, 1H), 1.82-1.92 (m, 2H), 1.58-1.68 (m, 2H), 1.49-1.55 (m, 2H), 1.33-1.43 (m, 2H). LCMS: 346 ([M+H]$^+$). This general procedure was used to make Examples 21, 23, 26, 29, 30, 37-42. Condition A=prep-HPLC under basic conditions; Condition B=prep-HPLC under formic acid; Condition C=prep-TLC.

Example 28: N-(5-chloro-1H-pyrazol-4-yl)-2-phenyl-4H,10H-benzo[f]pyrazolo[5,1-c][1,4]oxazepin-7-amine

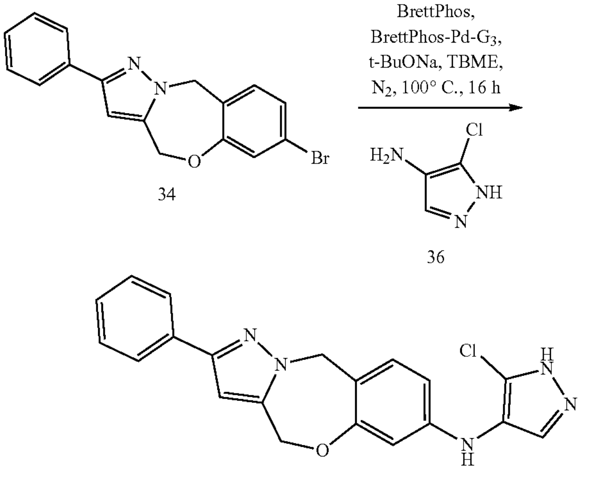

34

36

Example 28

Aniline/Amino-Heterocycles

To a vial containing a solution of Compound 34 (34.12 mg, 0.100 mmol, 1.0 eq) and Compound 36 (1.0 eq, 0.150 mmol) in tert-Butyl methyl ether (1.00 mL) and was added t-BuONa (19.6 mg, 0.200 mmol) and BrettPhos (2.68 mg, 0.010 mmol) and BrettPhos-Pd G3 (4.53 mg, 0.010 mmol) at the protection of $N_2$. The vail was capped and the mixture was heated marcowave at 150° C. for 5 hrs. Check by LCMS, the reactions gave desired product. The mixture was concentrated by vaccum. Diluted the residue with 1.0 mL of $H_2O$, and extracted with EtOAc (1.50*3 mL). The organic layer was collected and concentrated by vaccum. The residue was purified by pre-HPLC to give desired product Example 28 (11.6 mg, 31%) as a white solid. $^1$H NMR (400 MHz, DMSO-d6): (br s, 1H), 7.82 (d, J=1.59 Hz, 1H), 7.73-7.79 (m, 2H), 7.34-7.41 (m, 3H), 7.25-7.31 (m, 1H), 7.10 (d, J=8.31 Hz, 1H), 6.73 (s, 1H), 6.29 (dd, J=2.32, 8.31 Hz, 1H), 6.16 (d, J=2.32 Hz, 1H), 5.46 (s, 2H), 5.27 (s, 2H). LCMS: 378 ($[M+H]^+$).
This general procedure was used to make Examples 18-20, 22, 24, 25, 27, 28, 31-36. Condition A=prep-HPLC under basic conditions; Condition B=prep-HPLC under formic acid; Condition C=prep-TLC.
| Compound | MS $[M + H]^+$ | $^1$HNMR | Condition | Example |
|---|---|---|---|---|
| 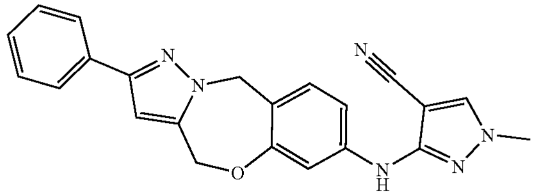 [SMILES: Cn1cc(C#N)c(Nc2ccc3c(c2)OCc2cc(-c4ccccc4)nn2C3)n1] | 383 | | B | 18 |
| 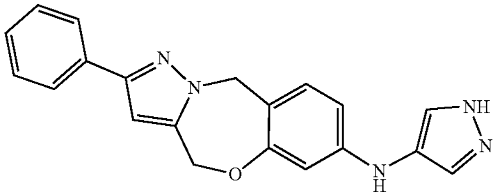 [SMILES: c1ccc(-c2cc3n(n2)Cc2ccc(Nc4cn[nH]c4)cc2OC3)cc1] | 344 | | A | 19 |
| 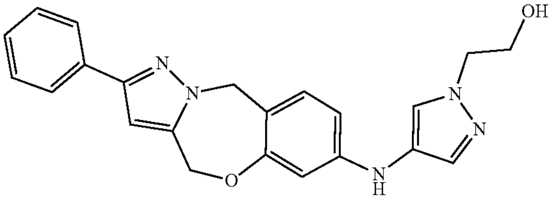 [SMILES: OCCn1cc(Nc2ccc3c(c2)OCc2cc(-c4ccccc4)nn2C3)cn1] | 388 | | A | 20 |
| 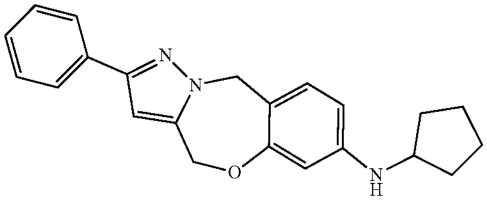 [SMILES: c1ccc(-c2cc3n(n2)Cc2ccc(NC4CCCC4)cc2OC3)cc1] | 346 | 1H NMR (400 MHz, DMSO-d6) Shift 7.73-7.79 (m, 2H), 7.35-7.41 (m, 2H), 7.25-7.30 (m, 1H), 7.03 (d, J = 8.44 Hz, 1H), 6.71 (s, 1H), 6.22 (dd, J = 2.26, 8.25 Hz, 1H), 6.13 (d, J = 2.20 Hz, 1H), 5.68 (d, J = 6.60 Hz, 1H), 5.41 (s, 2H), 5.26 (s, 2H), 3.63 (sxt, J = 6.21 Hz, 1H), 1.82-1.92 (m, 2H), 1.58-1.68 (m, 2H), 1.49-1.55 (m, 2H), 1.33-1.43 (m, 2H) | A | 21 |
| 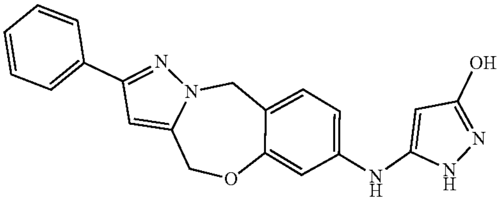 [SMILES: Oc1cc(Nc2ccc3c(c2)OCc2cc(-c4ccccc4)nn2C3)[nH]n1] | 360 | | B | 22 |

-continued
| Compound | MS [M + H]+ | 1HNMR | Condition | Example |
|---|---|---|---|---|
| 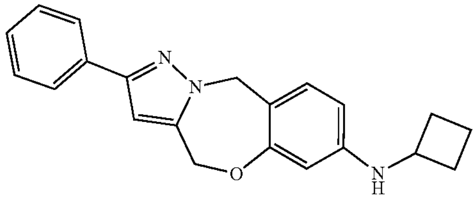 [SMILES: c1ccc(-c2cc3n(n2)Cc2ccc(NC4CCC4)cc2OC3)cc1] | 332 | | A | 23 |
| 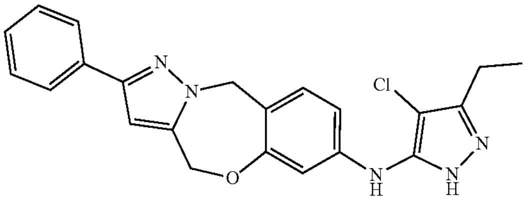 [SMILES: CCc1n[nH]c(Nc2ccc3c(c2)OCc2cc(-c4ccccc4)nn2C3)c1Cl] | 406 | | A | 24 |
| 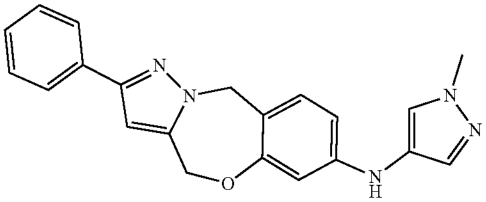 [SMILES: Cn1cc(Nc2ccc3c(c2)OCc2cc(-c4ccccc4)nn2C3)cn1] | 358 | | A | 25 |
| 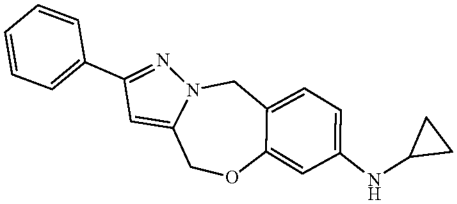 [SMILES: c1ccc(-c2cc3n(n2)Cc2ccc(NC4CC4)cc2OC3)cc1] | 318 | | A | 26 |
| 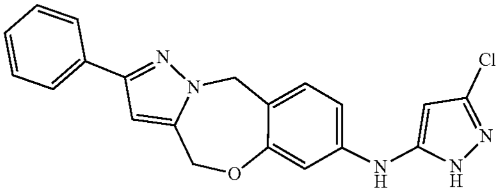 [SMILES: Clc1cc(Nc2ccc3c(c2)OCc2cc(-c4ccccc4)nn2C3)[nH]n1] | 378 | | A | 27 |
| 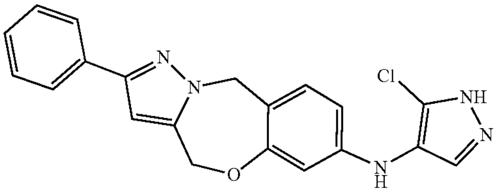 [SMILES: Clc1[nH]ncc1Nc1ccc2c(c1)OCc1cc(-c3ccccc3)nn1C2] | 378 | 1H NMR (400 MHz, DMSO-d6) Shift 12.95 (br s, 1H), 7.82 (d, J = 1.59 Hz, 1H), 7.73-7.79 (m, 2H), 7.34-7.41 (m, 3H), 7.25-7.31 (m, 1H), 7.10 (d, J = 8.31 Hz, 1H), 6.73 (s, 1H), 6.29 (dd, J = 2.32, 8.31 Hz, 1H), 6.16 (d, J = 2.32 Hz, 1H), 5.46 (s, 2H), 5.27 (s, 2H) | A | 28 |

-continued
| Compound | MS [M + H]+ | 1HNMR | Condition | Example |
|---|---|---|---|---|
| 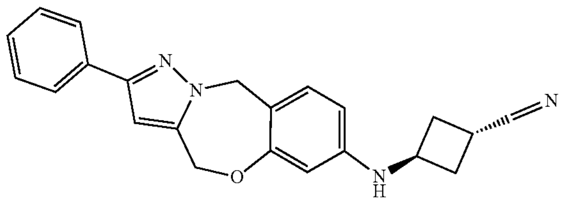 | 357 | | A | 29 |
| 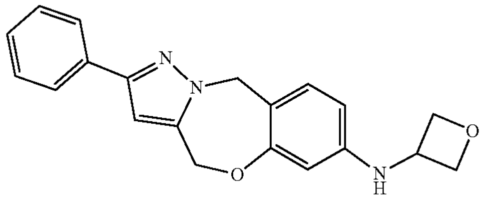 [SMILES: c1ccc(-c2cc3n(n2)Cc2ccc(NC4COC4)cc2OC3)cc1] | 334 | | B | 30 |
| 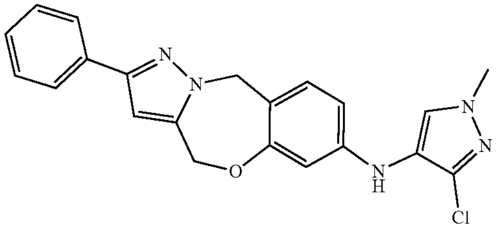 [SMILES: Cn1cc(Nc2ccc3c(c2)OCc2cc(-c4ccccc4)nn2C3)c(Cl)n1] | 392 | 1H NMR (400 MHz, DMSO-d6) Shift 8.07 (s, 1H), 7.83 (s, 1H), 7.75-7.79 (m, 2H), 7.39 (t, J = 7.58 Hz, 2H), 7.26-7.31 (m, 1H), 7.16 (d, J = 8.44 Hz, 1H), 7.02 (d, J = 2.20 Hz, 1H), 6.94 (dd, J = 2.26, 8.38 Hz, 1H), 6.75 (s, 1H), 5.50 (s, 2H), 5.37 (s, 1H), 5.31 (s, 2H), 3.74 (s, 3H), 2.07 (s, 1H) | A | 31 |
| 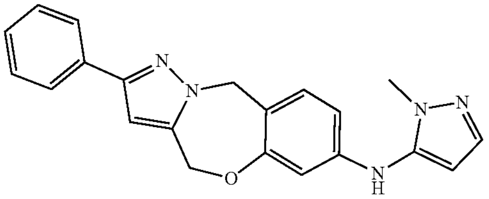 [SMILES: Cn1nccc1Nc1ccc2c(c1)OCc1cc(-c3ccccc3)nn1C2] | 358 | | A | 32 |
| 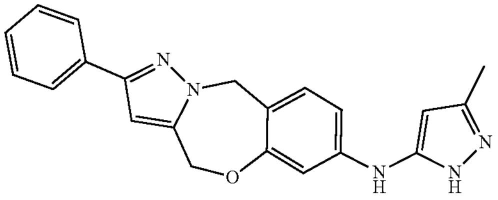 [SMILES: Cc1cc(Nc2ccc3c(c2)OCc2cc(-c4ccccc4)nn2C3)[nH]n1] | 358 | | A | 33 |
| 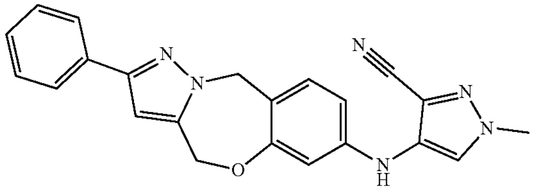 [SMILES: Cn1cc(Nc2ccc3c(c2)OCc2cc(-c4ccccc4)nn2C3)c(C#N)n1] | 383 | | A | 34 |

-continued
| Compound | MS [M + H]+ $^1$HNMR | Condition | Example |
| --- | --- | --- | --- |
| 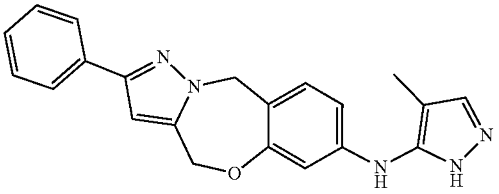 [SMILES: Cc1cn[nH]c1Nc1ccc2c(c1)OCc1cc(-c3ccccc3)nn1C2] | 358 | A | 35 |
| 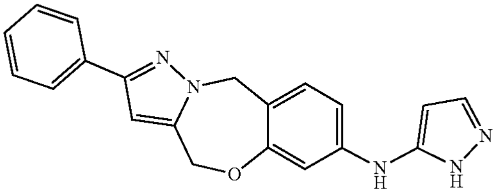 | 344 | A | 36 |
| 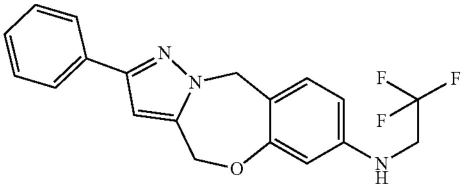 [SMILES: FC(F)(F)CNc1ccc2c(c1)OCc1cc(-c3ccccc3)nn1C2] | 360 | A | 37 |
| 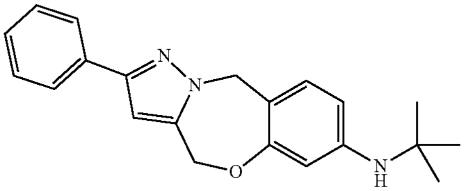 [SMILES: CC(C)(C)Nc1ccc2c(c1)OCc1cc(-c3ccccc3)nn1C2] | 334 | A | 38 |
| 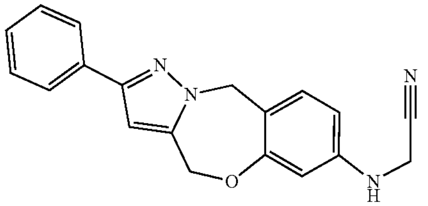 [SMILES: N#CCNc1ccc2c(c1)OCc1cc(-c3ccccc3)nn1C2] | 317 | B | 39 |
| 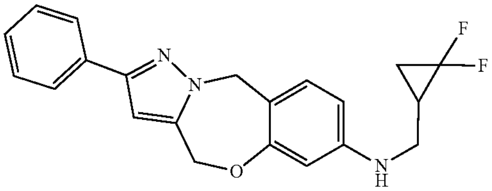 [SMILES: FC1(F)CC1CNc1ccc2c(c1)OCc1cc(-c3ccccc3)nn1C2] | 368 | A | 40 |
| 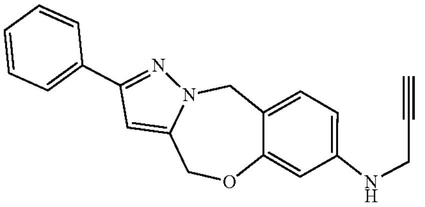 | 316 | B | 41 |

-continued

| Compound | MS [M + H]+ ¹HNMR | Condition | Example |
| --- | --- | --- | --- |
| 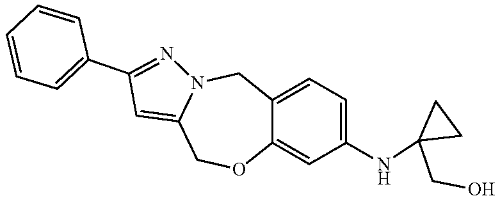 [SMILES: OCC1(Nc2ccc3c(c2)OCc2cc(-c4ccccc4)nn2C3)CC1] | 348 | A | 42 |

Example 67. N-(2-(1-(difluoromethyl)-1H-pyrazol-4-yl)-4H,10H-benzo[f]pyrazolo[5,1-c][1,4]oxazepin-7-yl)acetamide

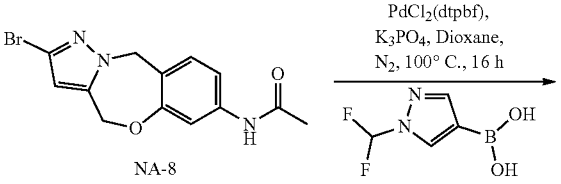

NA-8

37

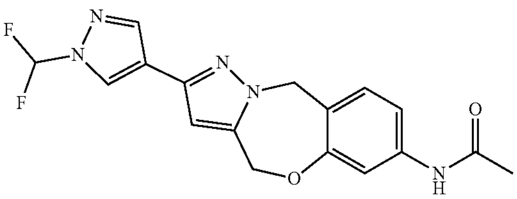

Example 67

To a vial containing a solution of NA-8 (0.120 mmol, 1.00 eq), Compound 37 (0.180 mmol, 1.50 eq) in Dioxane (1.0 mL) was added $K_3PO_4$ (2 M, 120 uL) and $PdCl_2$(dtbpf) (0.006 mmol, 0.05 eq). The mixture was degassed and purged with $N_2$, and then the mixture was stirred at 100° C. for 16 hrs under $N_2$ atmosphere. The reaction mixture was concentrated under reduced pressure to remove Dioxane. Added 1.0 mL water to the reaction mixture and extracted with EtOAc (1.0 mL*2). Collected organic layer and removed the solvent by Speedvac to give residues. Purified the residue by prep-HPLC to give Example 67 (14.1 mg, 33%) as a white solid. $^1$H NMR (400 MHz, DMSO-d6) δ 9.96 (s, 1H), 8.52 (s, 1H), 8.07 (s, 1H), 7.65-7.98 (m, 1H), 7.23-7.30 (m, 2H), 7.13 (dd, J=1.69, 8.32 Hz, 1H), 6.62 (s, 1H), 5.54 (s, 2H), 5.33 (s, 2H), 2.01 (s, 3H). LCMS: 360 ([M+H]$^+$).

This general procedure was used to make Examples 43-45, 47-50, 42-56, 58-62, 64-72, 74, 76-83, 85, 89-90, 92-96, 100, 103, 106-107. Condition A=prep-HPLC under basic conditions; Condition B=prep-HPLC under formic acid; Condition C=prep-TLC.

Example 46. N-(2-(4-fluoro-2-(hydroxymethyl)phenyl)-4H,10H-benzo[f]pyrazolo[5,1-c][1,4]oxazepin-7-yl)acetamide

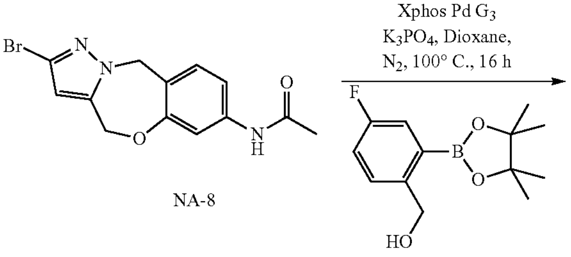

NA-8

38

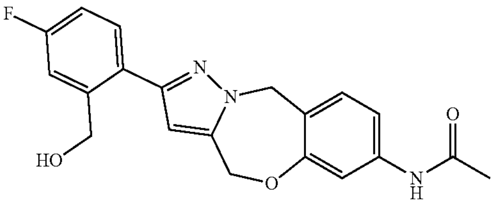

Example 46

To a vial containing a solution of NA-8 (0.120 mmol, 1.00 eq), Compound 38 (0.180 mmol, 1.50 eq) in Dioxane (1.0 mL) was added $K_3PO_4$ (2 M, 120 uL) and Xphos Pd G3 (0.006 mmol, 0.05 eq). The mixture was degassed and purged with $N_2$, and then the mixture was stirred at 100° C. for 16 hrs under $N_2$ atmosphere. The reaction mixture was concentrated under reduced pressure to remove Dioxane. Added 1.0 mL water to the reaction mixture and extracted with EtOAc (1.0 mL*2). Collected organic layer and removed the solvent by Speedvac to give residues. Purified the residue by prep-HPLC to give Example 46 (26.4 mg, 60%) as a white solid. $^1$H NMR (400 MHz, DMSO-d6) δ 9.97 (s, 1H), 7.59 (dd, J=5.94, 8.57 Hz, 1H), 7.33-7.40 (m, 1H), 7.25-7.32 (m, 2H), 7.04-7.18 (m, 2H), 6.65 (s, 1H), 5.58 (s, 2H), 5.31-5.39 (m, 3H), 4.68 (d, J=5.75 Hz, 2H), 2.02 (s, 3H). LCMS: 368 ([M+H]$^+$). This general procedure was used to make Examples 46, 51, 57, 63, 73, 75, 84, 86-88, 91, 97-99, 101-102, 104-105. Condition A=prep-HPLC under basic conditions; Condition B=prep-HPLC under formic acid; Condition C=prep-TLC.

Example 125. N-(2-(1-(trifluoromethyl)-1H-pyrazol-4-yl)-4H,10H-benzo[f]pyrazolo[5,1-c][1,4]oxazepin-7-yl)acetamide

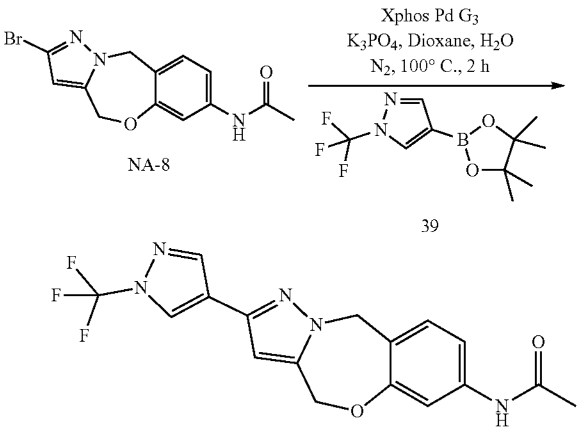

NA-8

39

Example 125

To a vial containing a solution of NA-8 (0.30 mmol, 1.00 eq), Compound 39 (0.30 mmol, 1.0 eq) in Dioxane (0.15 M) and water (0.15 M) was added $K_3PO_4$ (3 mmol, 10 eq) and Xphos Pd G3 (0.015 mmol, 0.05 eq). The mixture was degassed and purged with $N_2$, and then the mixture was stirred at 100° C. for 16 hrs under $N_2$ atmosphere. The reaction mixture was diluted with water to precipitate the product after filtration. The crude was purified by prep-HPLC to give Example 125 (59.6 mg, 530%) as a white solid. $^1$H NMR (400 MHUz, DMSO-d6) δ 9.95 (s, 1H), 8.79 (s, 1H), 8.24 (t, J=0.9 Hz, 1H), 7.31-7.23 (m, 2H), 7.13 (dd, J=8.3, 2.1 Hz, 1H), 6.66 (s, 1H), 5.55 (s, 2H), 5.35 (s, 2H), 2.02 (s, 3H). LCMS: 378.1 ([M+H]$^+$). This general procedure was used to make Examples 108-129. Condition A=prep-HPLC under basic conditions; Condition B=prep-HPLC under formic acid; Condition C=prep-TLC.

| Structure | MS [M + H]$^+$ | $^1$HNMR | Condition | Example |
|---|---|---|---|---|
| 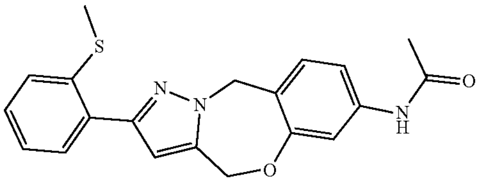 [SMILES: CSc1ccccc1-c1cc2n(n1)Cc1ccc(NC(C)=O)cc1OC2] | 366 | | C | 43 |
| 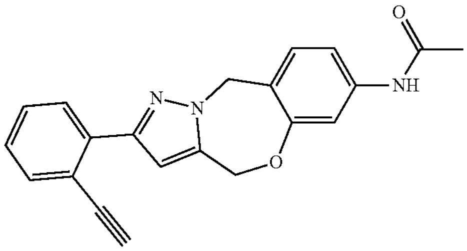 [SMILES: C#Cc1ccccc1-c1cc2n(n1)Cc1ccc(NC(C)=O)cc1OC2] | 344 | | A | 44 |
| 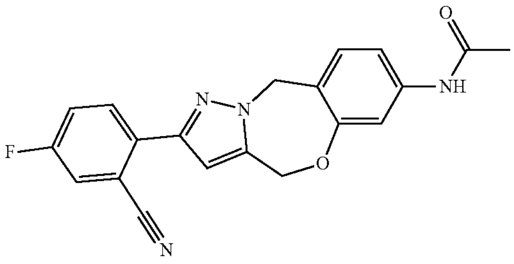 [SMILES: CC(=O)Nc1ccc2c(c1)OCc1cc(-c3ccc(F)cc3C#N)nn1C2] | 363 | | A | 45 |
| 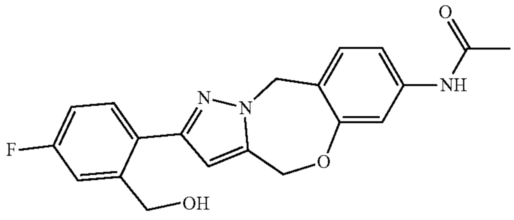 [SMILES: CC(=O)Nc1ccc2c(c1)OCc1cc(-c3ccc(F)cc3CO)nn1C2] | 368 | $^1$H NMR (400 MHz, DMSO-d6) δ 9.97 (s, 1H), 7.59 (dd, J = 5.94, 8.57 Hz, 1H), 7.33-7.40 (m, 1H), 7.25-7.32 (m, 2H), 7.04-7.18 (m, 2H), 6.65 (s, 1H), 5.58 (s, 2H), 5.31-5.39 (m, 3H), 4.68 (d, J = 5.75 | A | 46 |

-continued
| Structure | MS [M + H]+ | ¹HNMR | Condition | Example |
|---|---|---|---|---|
| | | Hz, 2H), 2.02 (s, 3H) | | |
| 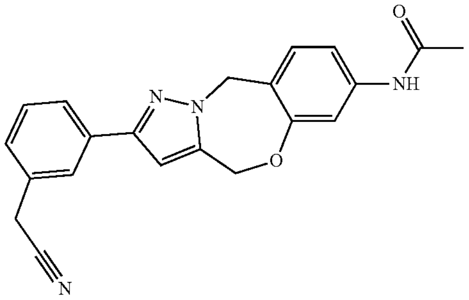 [SMILES: CC(=O)Nc1ccc2c(c1)OCc1cc(-c3cccc(CC#N)c3)nn1C2] | 359 | | A | 47 |
| 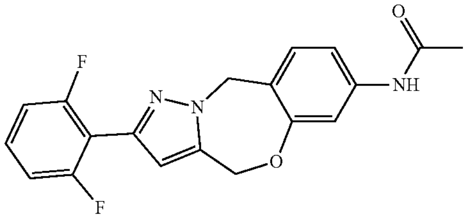 [SMILES: CC(=O)Nc1ccc2c(c1)OCc1cc(-c3c(F)cccc3F)nn1C2] | 356 | | A | 48 |
| 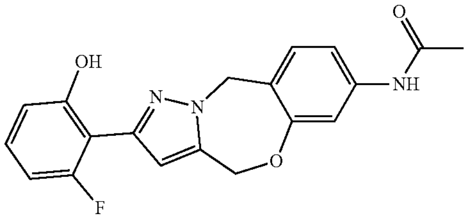 [SMILES: CC(=O)Nc1ccc2c(c1)OCc1cc(-c3c(O)cccc3F)nn1C2] | 354 | | A | 49 |
| 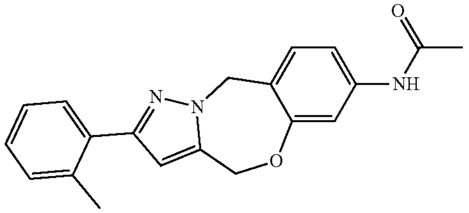 [SMILES: CC(=O)Nc1ccc2c(c1)OCc1cc(-c3ccccc3C)nn1C2] | 334 | | B | 50 |
| 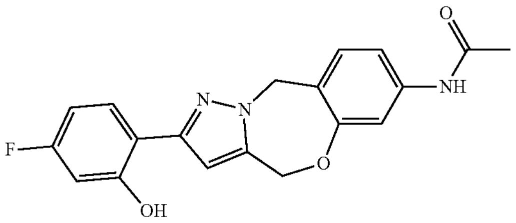 [SMILES: CC(=O)Nc1ccc2c(c1)OCc1cc(-c3ccc(F)cc3O)nn1C2] | 354 | | A | 51 |
| 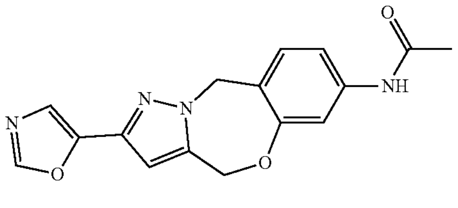 [SMILES: CC(=O)Nc1ccc2c(c1)OCc1cc(-c3cnco3)nn1C2] | 311 | | A | 52 |

-continued
| Structure | MS [M + H]+ | ¹HNMR | Condition | Example |
|---|---|---|---|---|
| 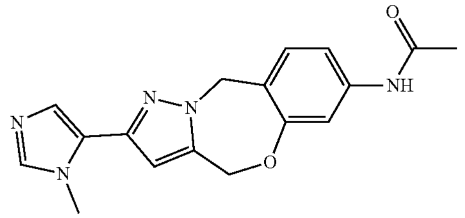 [SMILES: CC(=O)Nc1ccc2c(c1)OCc1cc(-c3cncn3C)nn1C2] | 324 | | C | 53 |
| 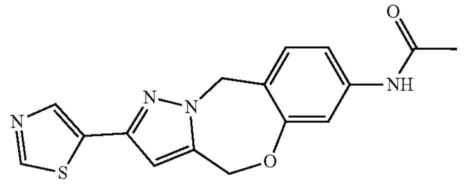 [SMILES: CC(=O)Nc1ccc2c(c1)OCc1cc(-c3cncs3)nn1C2] | 327 | | A | 54 |
| 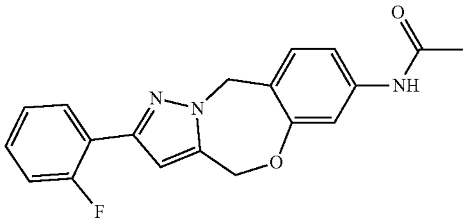 [SMILES: CC(=O)Nc1ccc2c(c1)OCc1cc(-c3ccccc3F)nn1C2] | 338 | | A | 55 |
| 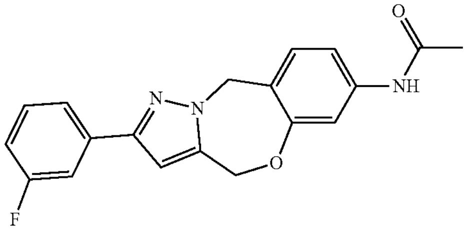 [SMILES: CC(=O)Nc1ccc2c(c1)OCc1cc(-c3cccc(F)c3)nn1C2] | 338 | | C | 56 |
| 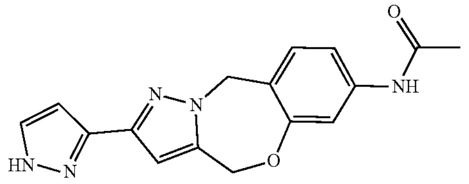 [SMILES: CC(=O)Nc1ccc2c(c1)OCc1cc(-c3cc[nH]n3)nn1C2] | 310 | | A | 57 |
| 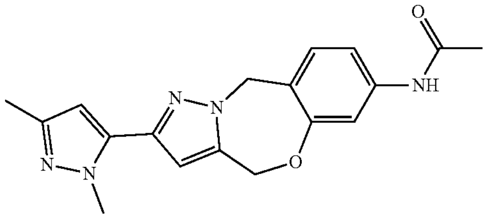 [SMILES: CC(=O)Nc1ccc2c(c1)OCc1cc(-c3cc(C)nn3C)nn1C2] | 338 | | A | 58 |
| 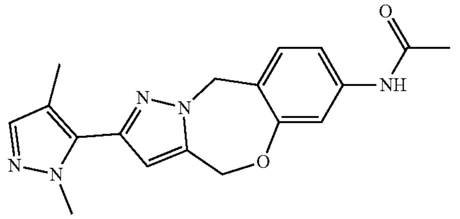 [SMILES: CC(=O)Nc1ccc2c(c1)OCc1cc(-c3c(C)cnn3C)nn1C2] | 338 | | A | 59 |

-continued
| Structure | MS [M + H]+ ¹HNMR | Condition | Example |
| --- | --- | --- | --- |
| 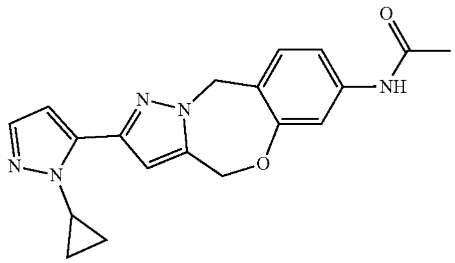 [SMILES: CC(=O)Nc1ccc2c(c1)OCc1cc(-c3ccnn3C3CC3)nn1C2] | 350 | A | 60 |
| 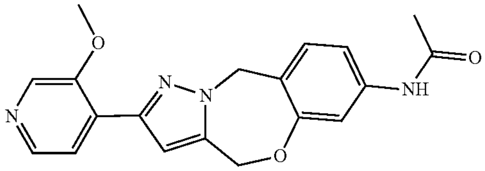 [SMILES: COc1cnccc1-c1cc2n(n1)Cc1ccc(NC(C)=O)cc1OC2] | 351 | A | 61 |
| 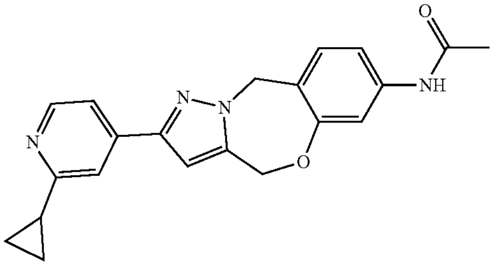 [SMILES: CC(=O)Nc1ccc2c(c1)OCc1cc(-c3ccnc(C4CC4)c3)nn1C2] | 361 | A | 62 |
| 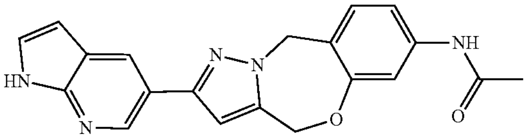 [SMILES: CC(=O)Nc1ccc2c(c1)OCc1cc(-c3cnc4[nH]ccc4c3)nn1C2] | 360 | A | 63 |
| 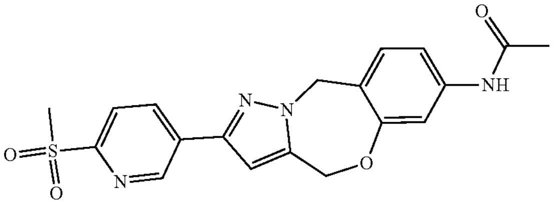 [SMILES: CC(=O)Nc1ccc2c(c1)OCc1cc(-c3ccc(S(C)(=O)=O)nc3)nn1C2] | 399 | A | 64 |
| 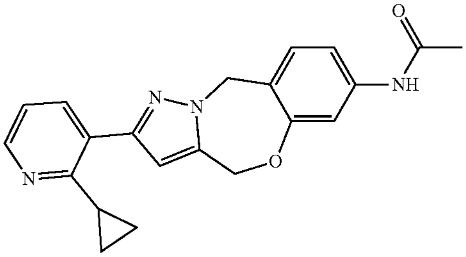 [SMILES: CC(=O)Nc1ccc2c(c1)OCc1cc(-c3cccnc3C3CC3)nn1C2] | 361 | A | 65 |
| 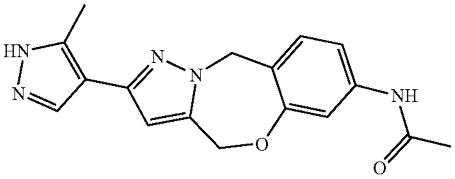 [SMILES: CC(=O)Nc1ccc2c(c1)OCc1cc(-c3cn[nH]c3C)nn1C2] | 324 | A | 66 |

-continued
| Structure | MS [M + H]+ | 1HNMR | Condition | Example |
|---|---|---|---|---|
| 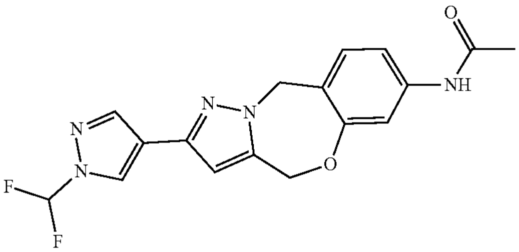 [SMILES: CC(=O)Nc1ccc2c(c1)OCc1cc(-c3cnn(C(F)F)c3)nn1C2] | 360 | 1H NMR (400 MHz, DMSO-d6) δ 9.96 (s, 1H), 8.52 (s, 1H), 8.07 (s, 1H), 7.65-7.98 (m, 1H), 7.23-7.30 (m, 2H), 7.13 (dd, J = 1.69, 8.32 Hz, 1H), 6.62 (s, 1H), 5.54 (s, 2H), 5.33 (s, 2H), 2.01 (s, 3H) | A | 67 |
| 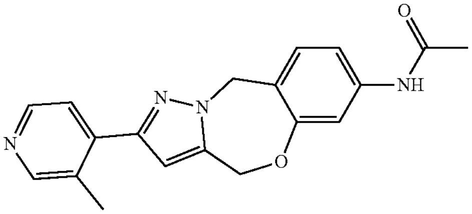 [SMILES: CC(=O)Nc1ccc2c(c1)OCc1cc(-c3ccncc3C)nn1C2] | 335 | | A | 68 |
| 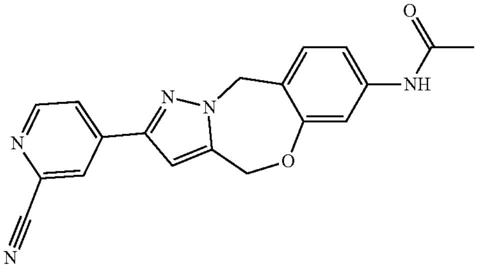 [SMILES: CC(=O)Nc1ccc2c(c1)OCc1cc(-c3ccnc(C#N)c3)nn1C2] | 346 | | A | 69 |
| 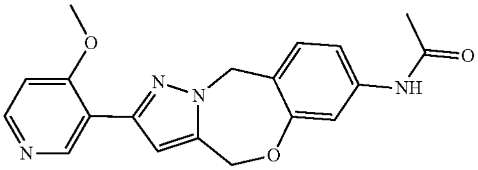 [SMILES: COc1ccncc1-c1cc2n(n1)Cc1ccc(NC(C)=O)cc1OC2] | 351 | | A | 70 |
| 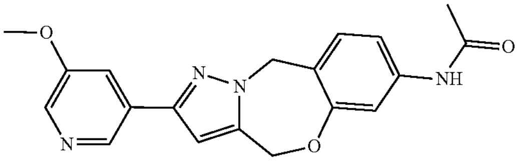 [SMILES: COc1cncc(-c2cc3n(n2)Cc2ccc(NC(C)=O)cc2OC3)c1] | 351 | | A | 71 |
| 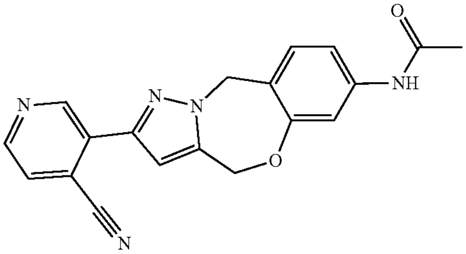 [SMILES: CC(=O)Nc1ccc2c(c1)OCc1cc(-c3cnccc3C#N)nn1C2] | 346 | | A | 72 |
| 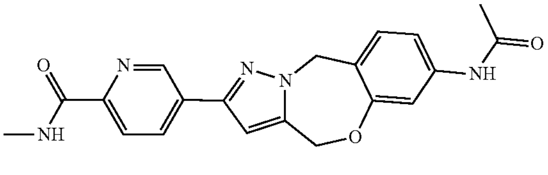 [SMILES: CNC(=O)c1ccc(-c2cc3n(n2)Cc2ccc(NC(C)=O)cc2OC3)cn1] | 378 | | A | 73 |

-continued
| Structure | MS [M + H]+ | 1HNMR | Condition | Example |
|---|---|---|---|---|
| 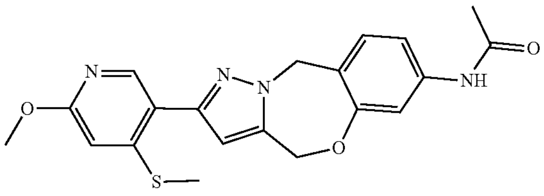 [SMILES: COc1cc(SC)c(-c2cc3n(n2)Cc2ccc(NC(C)=O)cc2OC3)cn1] | 397 | | A | 74 |
| 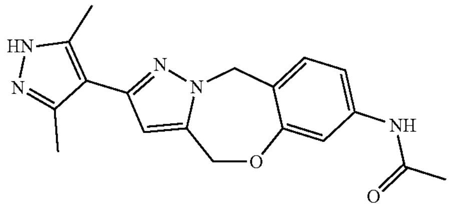 [SMILES: CC(=O)Nc1ccc2c(c1)OCc1cc(-c3c(C)n[nH]c3C)nn1C2] | 338 | | A | 75 |
| 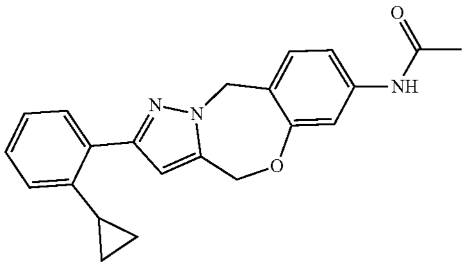 [SMILES: CC(=O)Nc1ccc2c(c1)OCc1cc(-c3ccccc3C3CC3)nn1C2] | 360 | | A | 76 |
| 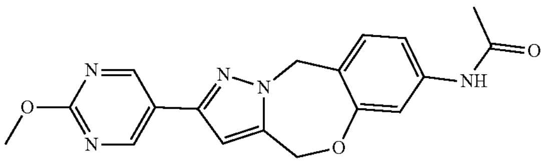 [SMILES: COc1ncc(-c2cc3n(n2)Cc2ccc(NC(C)=O)cc2OC3)cn1] | 352 | | A | 77 |
| 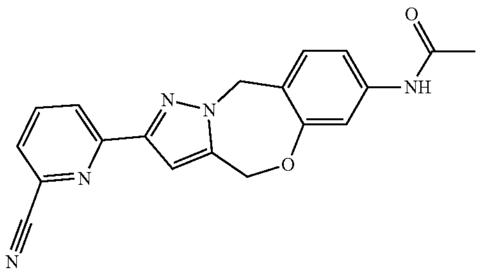 [SMILES: CC(=O)Nc1ccc2c(c1)OCc1cc(-c3cccc(C#N)n3)nn1C2] | 346 | $^1$H NMR (400 MHz, DMSO-d6) δ 9.97 (s, 1H), 8.19 (d, J = 7.38 Hz, 1H), 8.07 (t, J = 7.88 Hz, 1H), 7.93 (d, J = 7.63 Hz, 1H), 7.23-7.33 (m, 2H), 7.15 (br d, J = 8.13 Hz, 1H), 6.97 (s, 1H), 5.64 (s, 2H), 5.38 (s, 2H), 2.02 (s, 3H), 1.23 (s, 1H), 1.12-1.17 (m, 1H) | A | 78 |
| 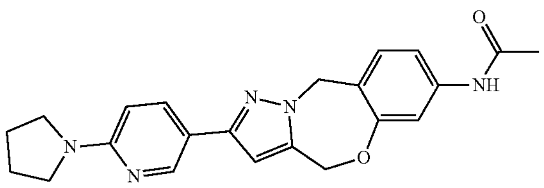 [SMILES: CC(=O)Nc1ccc2c(c1)OCc1cc(-c3ccc(N4CCCC4)nc3)nn1C2] | 390 | | A | 79 |

-continued
| Structure | MS [M + H]+ | ¹HNMR | Condition | Example |
|---|---|---|---|---|
| 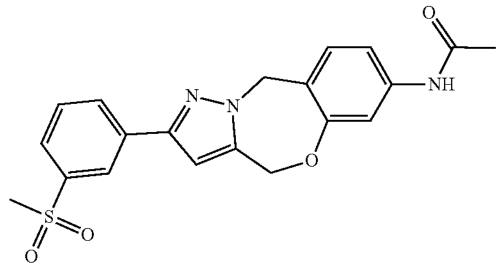 [SMILES: CC(=O)Nc1ccc2c(c1)OCc1cc(-c3cccc(S(C)(=O)=O)c3)nn1C2] | 398 | | C | 80 |
| 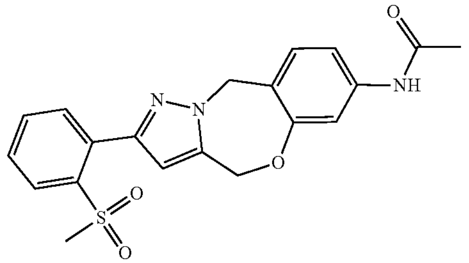 [SMILES: CC(=O)Nc1ccc2c(c1)OCc1cc(-c3ccccc3S(C)(=O)=O)nn1C2] | 398 | | A | 81 |
| 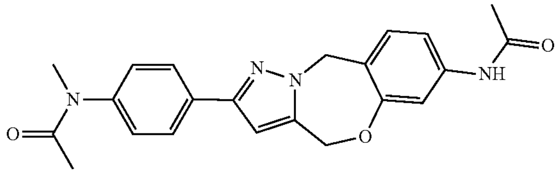 [SMILES: CC(=O)Nc1ccc2c(c1)OCc1cc(-c3ccc(N(C)C(C)=O)cc3)nn1C2] | 391 | ¹H NMR (400 MHz, DMSO-d6) δ 9.96 (s, 1H), 7.82 (br d, J = 8.13 Hz, 2H), 7.34 (br d, J = 8.25 Hz, 2H), 7.26-7.31 (m, 2H), 7.14 (dd, J = 2.06, 8.32 Hz, 1H), 6.82 (s, 1H), 5.59 (s, 2H), 5.35 (s, 2H), 3.16 (br s, 3H), 2.02 (s, 3H), 1.69-1.91 (m, 3H) | A | 82 |
| 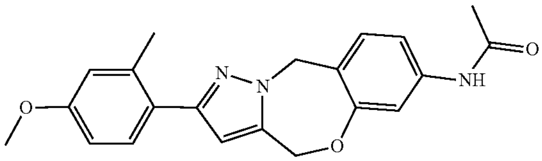 [SMILES: COc1ccc(-c2cc3n(n2)Cc2ccc(NC(C)=O)cc2OC3)c(C)c1] | 364 | | A | 83 |
| 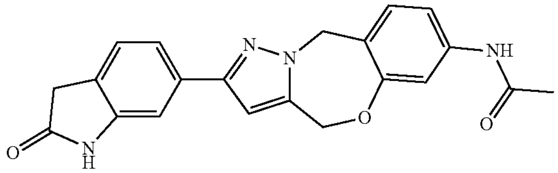 [SMILES: CC(=O)Nc1ccc2c(c1)OCc1cc(-c3ccc4c(c3)NC(=O)C4)nn1C2] | 375 | | A | 84 |
| 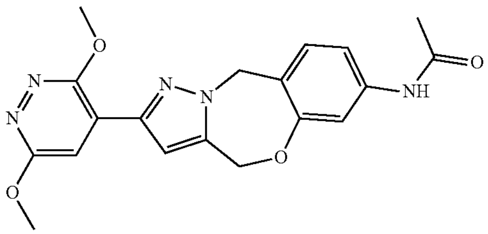 [SMILES: COc1cc(-c2cc3n(n2)Cc2ccc(NC(C)=O)cc2OC3)c(OC)nn1] | 382 | | A | 85 |

-continued
| Structure | MS [M + H]+ | 1HNMR | Condition | Example |
|---|---|---|---|---|
| 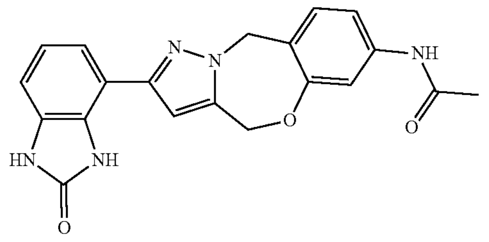 [SMILES: CC(=O)Nc1ccc2c(c1)OCc1cc(-c3cccc4[nH]c(=O)[nH]c34)nn1C2] | 376 | | A | 86 |
| 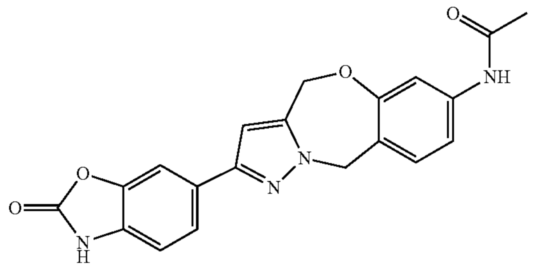 [SMILES: CC(=O)Nc1ccc2c(c1)OCc1cc(-c3ccc4[nH]c(=O)oc4c3)nn1C2] | 377 | | A | 87 |
| 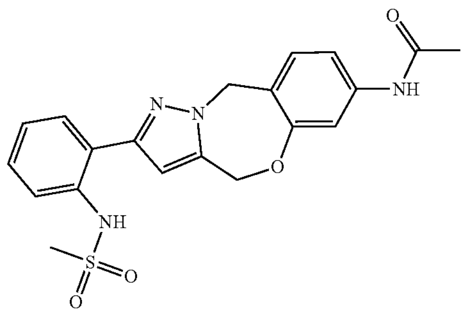 [SMILES: CC(=O)Nc1ccc2c(c1)OCc1cc(-c3ccccc3NS(C)(=O)=O)nn1C2] | 413 | $^1$H NMR (400 MHz, DMSO-d6) δ 10.55 (br s, 1H), 10.00 (s, 1H), 7.79 (dd, J = 1.38, 7.88 Hz, 1H), 7.54 (dd, J = 0.81, 8.19 Hz, 1H), 7.31-7.38 (m, 3H), 7.12-7.23 (m, 2H), 6.96 (s, 1H), 5.60 (s, 2H), 5.38 (s, 2H), 3.05 (s, 3H), 2.02 (s, 3H) | A | 88 |
| 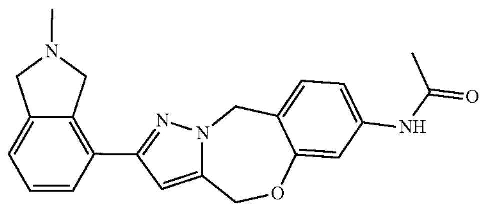 [SMILES: CC(=O)Nc1ccc2c(c1)OCc1cc(-c3cccc4c3CN(C)C4)nn1C2] | 375 | | A | 89 |
| 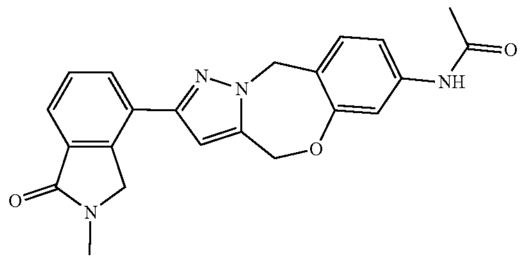 [SMILES: CC(=O)Nc1ccc2c(c1)OCc1cc(-c3cccc4c3CN(C)C4=O)nn1C2] | 389 | | A | 90 |
| 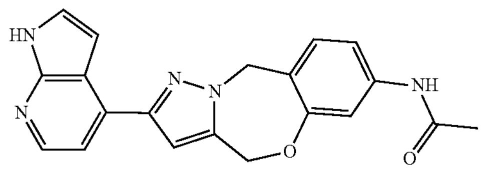 [SMILES: CC(=O)Nc1ccc2c(c1)OCc1cc(-c3ccnc4[nH]ccc34)nn1C2] | 360 | | A | 91 |

-continued
| Structure | MS [M + H]+ 1HNMR | Condition | Example |
|---|---|---|---|
| 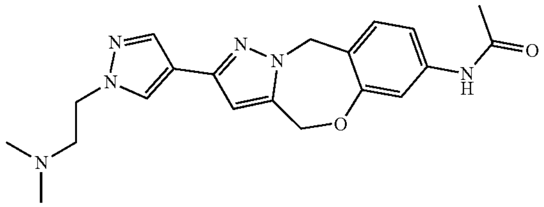 [SMILES: CC(=O)Nc1ccc2c(c1)OCc1cc(-c3cnn(CCN(C)C)c3)nn1C2] | 381 | A | 92 |
| 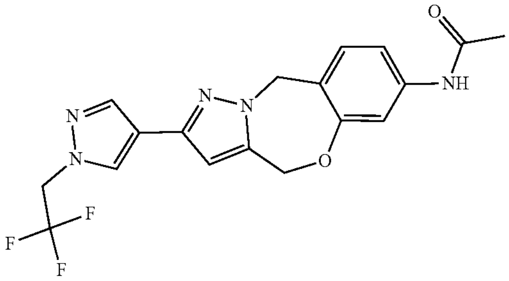 [SMILES: CC(=O)Nc1ccc2c(c1)OCc1cc(-c3cnn(CC(F)(F)F)c3)nn1C2] | 392 | A | 93 |
| 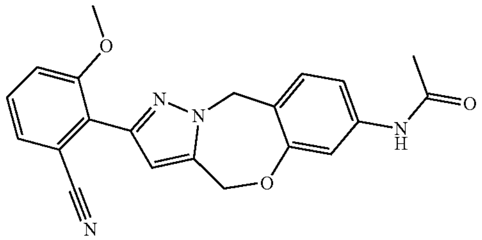 [SMILES: COc1cccc(C#N)c1-c1cc2n(n1)Cc1ccc(NC(C)=O)cc1OC2] | 375 | A | 94 |
| 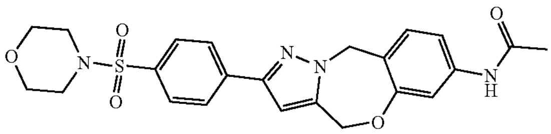 [SMILES: CC(=O)Nc1ccc2c(c1)OCc1cc(-c3ccc(S(=O)(=O)N4CCOCC4)cc3)nn1C2] | 469 | A | 95 |
| 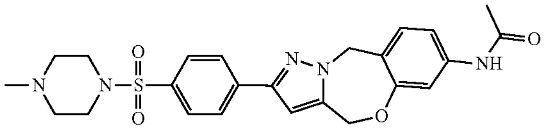 [SMILES: CC(=O)Nc1ccc2c(c1)OCc1cc(-c3ccc(S(=O)(=O)N4CCN(C)CC4)cc3)nn1C2] | 482 | C | 96 |
| 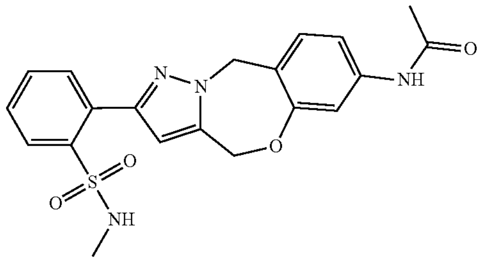 [SMILES: CNS(=O)(=O)c1ccccc1-c1cc2n(n1)Cc1ccc(NC(C)=O)cc1OC2] | 413 | A | 97 |
| 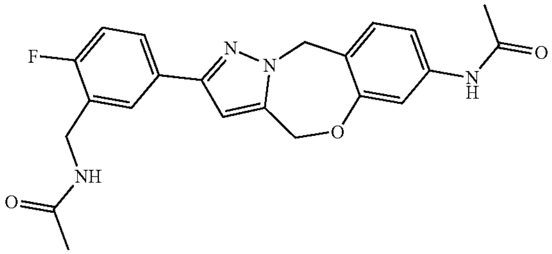 [SMILES: CC(=O)NCc1cc(-c2cc3n(n2)Cc2ccc(NC(C)=O)cc2OC3)ccc1F] | 409 | A | 98 |

-continued
| Structure | MS [M + H]+ | 1HNMR | Condition | Example |
|---|---|---|---|---|
| 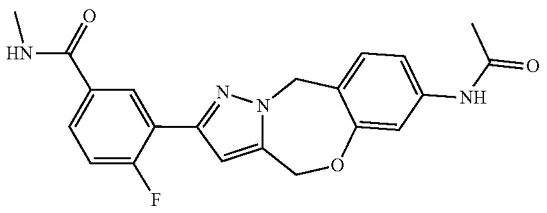 [SMILES: CNC(=O)c1ccc(F)c(-c2cc3n(n2)Cc2ccc(NC(C)=O)cc2OC3)c1] | 395 | | A | 99 |
| 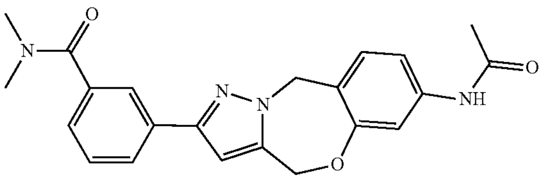 [SMILES: CC(=O)Nc1ccc2c(c1)OCc1cc(-c3cccc(C(=O)N(C)C)c3)nn1C2] | 391 | $^{1}$H NMR (400 MHz, DMSO-d6) δ 9.96 (s, 1H), 7.83 (d, J = 7.88 Hz, 1H), 7.77 (s, 1H), 7.45 (t, J = 7.69 Hz, 1H), 7.24-7.33 (m, 3H), 7.14 (dd, J = 1.94, 8.32 Hz, 1H), 6.85 (s, 1H), 5.59 (s, 2H), 5.35 (s, 2H), 2.86-3.05 (m, 6H), 2.02 (s, 3H) | A | 100 |
| 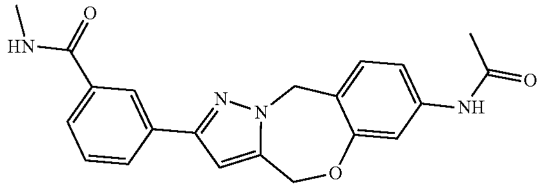 [SMILES: CNC(=O)c1cccc(-c2cc3n(n2)Cc2ccc(NC(C)=O)cc2OC3)c1] | 377 | | A | 101 |
| 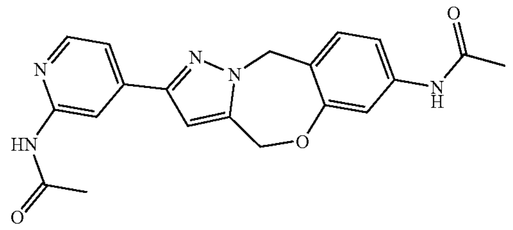 [SMILES: CC(=O)Nc1ccc2c(c1)OCc1cc(-c3ccnc(NC(C)=O)c3)nn1C2] | 378 | | A | 102 |
| 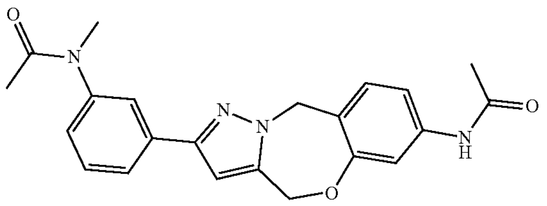 [SMILES: CC(=O)Nc1ccc2c(c1)OCc1cc(-c3cccc(N(C)C(C)=O)c3)nn1C2] | 391 | | A | 103 |
| 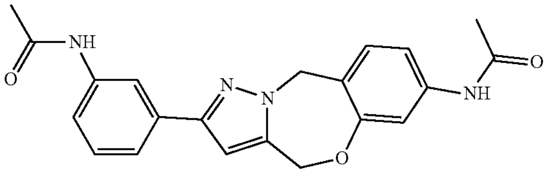 [SMILES: CC(=O)Nc1cccc(-c2cc3n(n2)Cc2ccc(NC(C)=O)cc2OC3)c1] | 377 | | A | 104 |

-continued
| Structure | MS [M + H]+ | 1HNMR | Condition | Example |
|---|---|---|---|---|
| 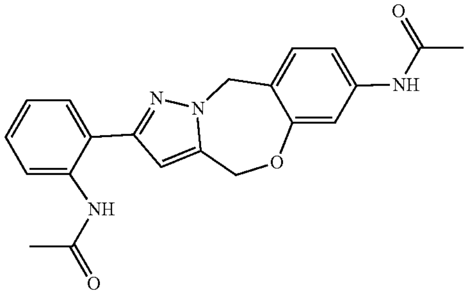 [SMILES: CC(=O)Nc1ccc2c(c1)OCc1cc(-c3ccccc3NC(C)=O)nn1C2] | 377 | | A | 105 |
| 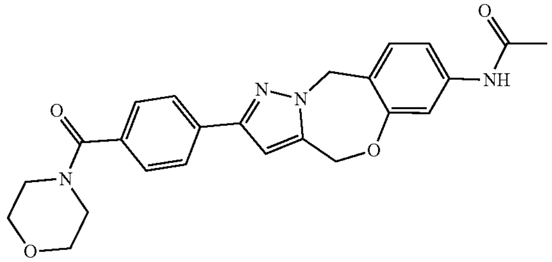 [SMILES: CC(=O)Nc1ccc2c(c1)OCc1cc(-c3ccc(C(=O)N4CCOCC4)cc3)nn1C2] | 433 | | A | 106 |
| 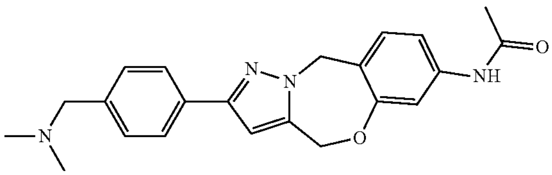 [SMILES: CC(=O)Nc1ccc2c(c1)OCc1cc(-c3ccc(CN(C)C)cc3)nn1C2] | 377 | | A | 107 |
| 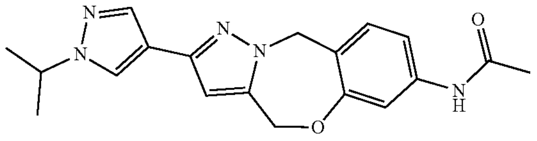 [SMILES: CC(=O)Nc1ccc2c(c1)OCc1cc(-c3cnn(C(C)C)c3)nn1C2] | 352.1 | 1H NMR (400 MHz, DMSO) δ 9.94 (s, 1H), 8.02 (d, J = 0.7 Hz, 1H), 7.67 (d, J = 0.8 Hz, 1H), 7.30-7.21 (m, 2H), 7.12 (dd, J = 8.3, 2.1 Hz, 1H), 6.46 (s, 1H), 5.49 (s, 2H), 5.30 (s, 2H), 4.49 (hept, J = 6.7 Hz, 1H), 2.01 (s, 3H), 1.42 (d, J = 6.7 Hz, 6H). | A | 108 |
| 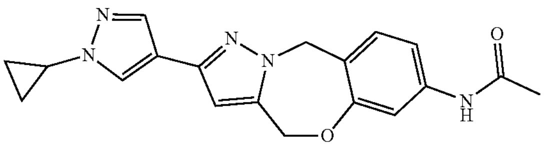 [SMILES: CC(=O)Nc1ccc2c(c1)OCc1cc(-c3cnn(C4CC4)c3)nn1C2] | 350.1 | 1H NMR (400 MHz, DMSO) δ 9.94 (s, 1H), 8.03 (s, 1H), 7.66 (s, 1H), 7.29-7.21 (m, 2H), 7.12 (dd, J = 8.4, 2.1 Hz, 1H), 6.46 (s, 1H), 5.49 (s, 2H), 5.30 (s, 2H), 3.72 (tt, J = 7.4, 3.9 Hz, 1H), 2.01 (s, 3H), 1.09-0.91 (m, 4H). | A | 109 |
| 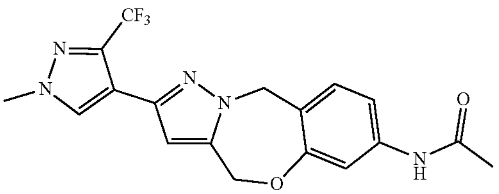 [SMILES: CC(=O)Nc1ccc2c(c1)OCc1cc(-c3cn(C)nc3C(F)(F)F)nn1C2] | 392.1 | 1H NMR (400 MHz, DMSO) δ 9.95 (s, 1H), 8.19 (d, J = 1.4 Hz, 1H), 7.27 (dd, J = 5.3, 3.1 Hz, 2H), 7.14 (dd, J = 8.3, 2.1 Hz, 1H), 6.44 (s, 1H), 5.53 (s, 2H), 5.34 (s, 2H), 3.93 | A | 110 |

-continued

| Structure | MS [M + H]$^+$ | $^1$HNMR | Condition | Example |
|---|---|---|---|---|
| | | (s, 3H), 2.02 (s, 3H). | | |
| 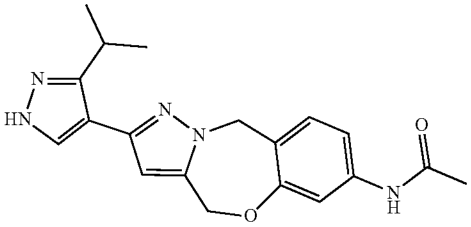 [SMILES: CC(=O)Nc1ccc2c(c1)OCc1cc(-c3c[nH]nc3C(C)C)nn1C2] | 352.1 | 1H NMR (400 MHz, DMSO) δ 12.61 (s, 1H), 12.44 (s, 0H), 9.94 (s, 1H), 7.59 (s, 1H), 7.30-7.24 (m, 2H), 7.12 (dd, J = 8.4, 2.1 Hz, 1H), 6.43 (s, 1H), 5.51 (s, 2H), 5.30 (s, 2H), 3.54 (s, 1H), 2.02 (s, 3H), 1.24 (d, J = 6.9 Hz, 6H). (mixture of tautomers observed) | A | 111 |
| 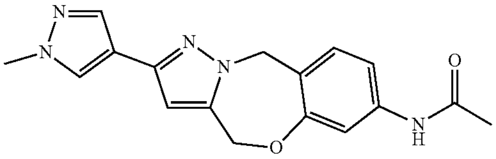 [SMILES: CC(=O)Nc1ccc2c(c1)OCc1cc(-c3cnn(C)c3)nn1C2] | 324.1 | 1H NMR (400 MHz, DMSO) δ 9.94 (s, 1H), 7.95 (s, 1H), 7.66 (d, J = 0.8 Hz, 1H), 7.30-7.21 (m, 2H), 7.12 (dd, J = 8.3, 2.1 Hz, 1H), 6.45 (s, 1H), 5.49 (s, 2H), 5.30 (s, 2H), 3.84 (s, 3H), 2.01 (s, 3H) | B | 112 |
| 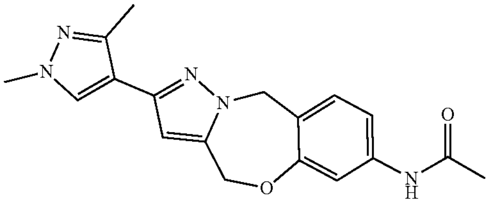 [SMILES: CC(=O)Nc1ccc2c(c1)OCc1cc(-c3cn(C)nc3C)nn1C2] | 338.1 | 1H NMR (400 MHz, DMSO) δ 9.94 (s, 1H), 7.84 (s, 1H), 7.30-7.23 (m, 2H), 7.12 (dd, J = 8.3, 2.1 Hz, 1H), 6.41 (s, 1H), 5.50 (s, 2H), 5.30 (s, 2H), 3.75 (s, 3H), 2.31 (s, 3H), 2.02 (s, 3H). | B | 113 |
| 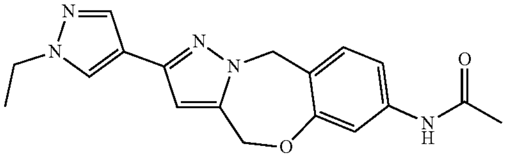 [SMILES: CCn1cc(-c2cc3n(n2)Cc2ccc(NC(C)=O)cc2OC3)cn1] | 338.1 | 1H NMR (400 MHz, DMSO) δ 9.94 (s, 1H), 7.99 (d, J = 0.8 Hz, 1H), 7.68 (d, J = 0.8 Hz, 1H), 7.30-7.21 (m, 2H), 7.12 (dd, J = 8.3, 2.1 Hz, 1H), 6.45 (s, 1H), 5.49 (s, 2H), 5.30 (s, 2H), 4.13 (q, J = 7.3 Hz, 2H), 2.01 (s, 3H), 1.38 (t, J = 7.3 Hz, 3H) | B | 114 |
| 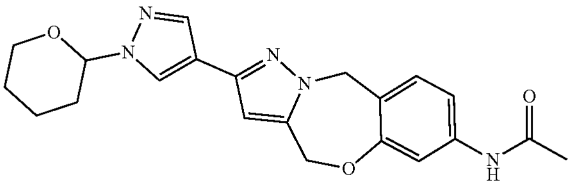 [SMILES: CC(=O)Nc1ccc2c(c1)OCc1cc(-c3cnn(C4CCCCO4)c3)nn1C2] | 394.1 | 1H NMR (400 MHz, DMSO) δ 9.94 (s, 1H), 8.14 (d, J = 0.7 Hz, 1H), 7.75 (d, J = 0.7 Hz, 1H), 7.33-7.21 (m, 2H), 7.12 (dd, J = 8.3, 2.1 Hz, 1H), 6.51 (s, 1H), 5.50 (s, 2H), 5.39 (dd, J = 9.9, 2.4 Hz, 1H), 5.31 (s, 2H), 3.97-3.88 (m, 1H), 3.63 (ddd, J = 13.8, 7.2, 5.1 Hz, 1H), 2.17-2.03 | B | 115 |

-continued
| Structure | MS $[M + H]^+$ | $^1$HNMR | Condition | Example |
|---|---|---|---|---|
| | | (m, 1H), 2.01 (s, 3H), 1.93 (s, 2H), 1.98-1.87 (m, 0H), 1.66 (ddt, J = 19.0, 13.8, 6.1 Hz, 1H), 1.54 (dq, J = 9.8, 4.6 Hz, 2H). | | |
| 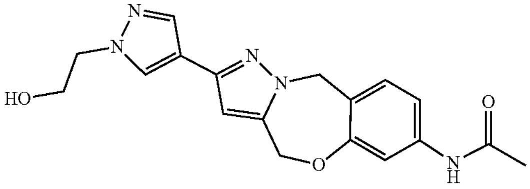 [SMILES: CC(=O)Nc1ccc2c(c1)OCc1cc(-c3cnn(CCO)c3)nn1C2] | 354.1 | 1H NMR (400 MHz, DMSO) δ 9.94 (s, 1H), 7.96 (d, J = 0.8 Hz, 1H), 7.69 (d, J = 0.8 Hz, 1H), 7.30-7.21 (m, 2H), 7.12 (dd, J = 8.3, 2.1 Hz, 1H), 6.46 (s, 1H), 5.50 (s, 2H), 5.30 (s, 2H), 4.89 (t, J = 5.3 Hz, 1H), 4.14 (t, J = 5.7 Hz, 2H), 3.73 (q, J = 5.6 Hz, 2H), 2.01 (s, 3H). | B | 116 |
| 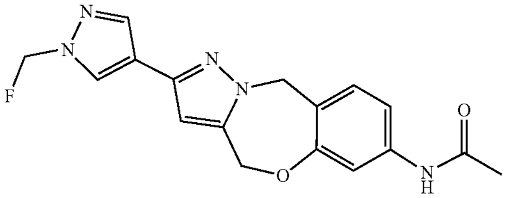 [SMILES: CC(=O)Nc1ccc2c(c1)OCc1cc(-c3cnn(CF)c3)nn1C2] | 342.1 | 1H NMR (400 MHz, DMSO) δ 9.94 (s, 1H), 8.33 (s, 1H), 7.95 (d, J = 1.7 Hz, 1H), 7.31-7.21 (m, 2H), 7.13 (dd, J = 8.3, 2.2 Hz, 1H), 6.55 (s, 1H), 6.21 (s, 1H), 6.08 (s, 1H), 5.53 (s, 2H), 5.32 (s, 2H), 2.02 (s, 3H). | A | 117 |
| 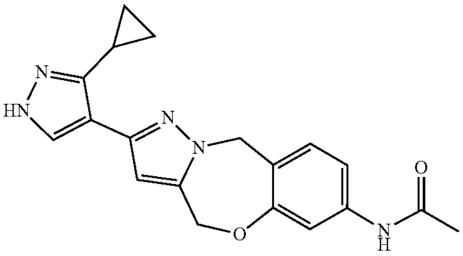 [SMILES: CC(=O)Nc1ccc2c(c1)OCc1cc(-c3c[nH]nc3C3CC3)nn1C2] | 350.1 | 1H NMR (400 MHz, DMSO) δ 12.40 (s, 0H), 12.36 (s, 1H), 9.94 (s, 1H), 7.60 (s, 0H), 7.30-7.23 (m, 2H), 7.12 (dd, J = 8.3, 2.1 Hz, 1H), 6.52 (s, 1H), 5.51 (s, 2H), 5.32 (s, 2H), 2.31 (d, J = 6.6 Hz, 1H), 2.02 (s, 3H), 0.96 (d, J = 8.3 Hz, 1H), 0.85-0.78 (m, 3H). | B | 118 |
| 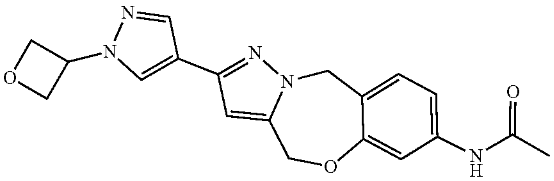 [SMILES: CC(=O)Nc1ccc2c(c1)OCc1cc(-c3cnn(C4COC4)c3)nn1C2] | 366.1 | 1H NMR (400 MHz, DMSO) δ 9.94 (s, 1H), 8.16 (s, 1H), 7.84 (s, 1H), 7.30-7.22 (m, 2H), 7.12 (dd, J = 8.3, 2.1 Hz, 1H), 6.49 (s, 1H), 5.58 (p, J = 7.0 Hz, 1H), 5.51 (s, 2H), 5.31 (s, 2H), 4.96-4.86 (m, 4H), 2.01 (s, 3H). | B | 119 |

-continued

| Structure | MS [M + H]+ | 1HNMR | Condition | Example |
|---|---|---|---|---|
| 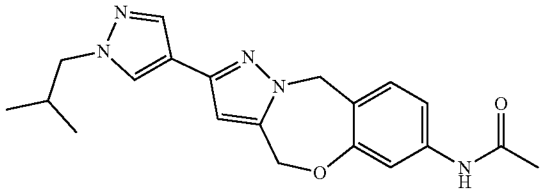 [SMILES: CC(=O)Nc1ccc2c(c1)OCc1cc(-c3cnn(CC(C)C)c3)nn1C2] | 366.1 | 1H NMR (400 MHz, DMSO) δ 9.94 (s, 1H), 7.96 (d, J = 0.8 Hz, 1H), 7.69 (d, J = 0.8 Hz, 1H), 7.30-7.21 (m, 2H), 7.12 (dd, J = 8.3, 2.1 Hz, 1H), 6.46 (s, 1H), 5.49 (s, 2H), 5.30 (s, 2H), 3.91 (d, J = 7.2 Hz, 2H), 2.11 (hept, J = 6.8 Hz, 1H), 2.01 (s, 3H), 0.83 (d, J = 6.7 Hz, 6H). | A | 120 |
| 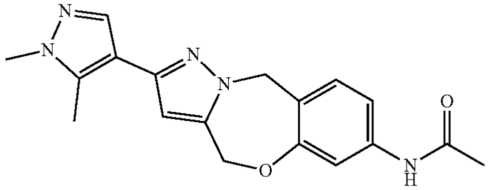 [SMILES: CC(=O)Nc1ccc2c(c1)OCc1cc(-c3cnn(C)c3C)nn1C2] | 338.1 | 1H NMR (400 MHz, DMSO) δ 9.94 (s, 1H), 7.56 (s, 1H), 7.30-7.23 (m, 2H), 7.13 (dd, J = 8.3, 2.1 Hz, 1H), 6.45 (s, 1H), 5.51 (s, 2H), 5.31 (s, 2H), 3.74 (s, 3H), 2.44 (s, 3H), 2.02 (s, 3H). | A | 121 |
| 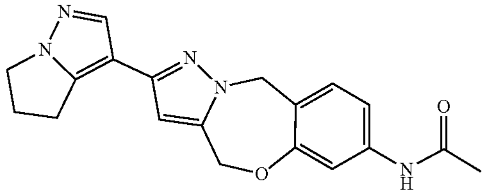 [SMILES: CC(=O)Nc1ccc2c(c1)OCc1cc(-c3cnn4c3CCC4)nn1C2] | 350.1 | 1H NMR (400 MHz, DMSO) δ 9.95 (s, 1H), 7.68 (s, 1H), 7.30-7.22 (m, 2H), 7.12 (dd, J = 8.3, 2.1 Hz, 1H), 6.39 (s, 1H), 5.49 (s, 2H), 5.30 (s, 2H), 4.07 (t, J = 7.2 Hz, 2H), 2.99-2.91 (m, 2H), 2.64-2.50 (m, 2H), 2.01 (s, 3H). | A | 122 |
| 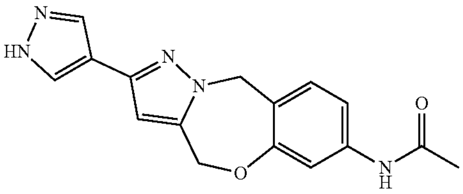 [SMILES: CC(=O)Nc1ccc2c(c1)OCc1cc(-c3cn[nH]c3)nn1C2] | 324.1 | 1H NMR (400 MHz, DMSO) δ 9.94 (s, 1H), 7.95 (s, 1H), 7.67 (d, J = 0.8 Hz, 1H), 7.30-7.21 (m, 2H), 7.12 (dd, J = 8.3, 2.1 Hz, 1H), 6.45 (s, 1H), 5.49 (s, 2H), 5.30 (s, 2H), 3.84 (s, 3H), 2.01 (s, 3H). | A | 123 |
| 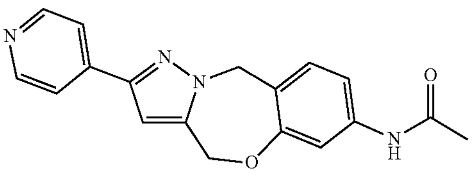 [SMILES: CC(=O)Nc1ccc2c(c1)OCc1cc(-c3ccncc3)nn1C2] | 321.1 | 1H NMR (400 MHz, DMSO) δ 9.97 (s, 1H), 8.60-8.54 (m, 2H), 8.24 (s, 1H), 7.76-7.70 (m, 2H), 7.32-7.26 (m, 2H), 7.14 (dd, J = 8.4, 2.1 Hz, 1H), 6.97 (s, 1H), 5.62 (s, 2H), 5.37 (s, 2H), 2.02 (s, 3H). | A | 124 |
| 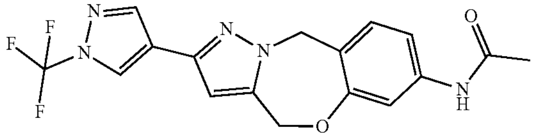 [SMILES: CC(=O)Nc1ccc2c(c1)OCc1cc(-c3cnn(C(F)(F)F)c3)nn1C2] | 378.1 | 1H NMR (400 MHz, DMSO) δ 9.95 (s, 1H), 8.79 (s, 1H), 8.24 (t, J = 0.9 Hz, 1H), 7.31-7.23 (m, 2H), 7.13 (dd, J = 8.3, 2.1 | B | 125 |

-continued

| Structure | MS $[M + H]^+$ | $^1$HNMR | Condition | Example |
|---|---|---|---|---|
| | | Hz, 1H), 6.66 (s, 1H), 5.55 (s, 2H), 5.35 (s, 2H), 2.02 (s, 3H). | | |
| 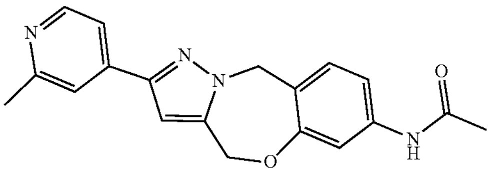 [SMILES: CC(=O)Nc1ccc2c(c1)OCc1cc(-c3ccnc(C)c3)nn1C2] | 335.1 | 1H NMR (400 MHz, DMSO) δ 9.96 (s, 1H), 8.43 (d, J = 5.2 Hz, 1H), 7.61 (s, 1H), 7.52 (dd, J = 5.3, 1.6 Hz, 1H), 7.32-7.25 (m, 2H), 7.14 (dd, J = 8.3, 2.1 Hz, 1H), 6.94 (s, 1H), 5.61 (s, 2H), 5.37 (s, 2H), 2.49 (s, 3H), 2.02 (s, 3H). | B | 126 |
| 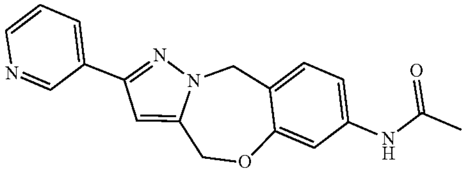 [SMILES: CC(=O)Nc1ccc2c(c1)OCc1cc(-c3cccnc3)nn1C2] | 321.1 | | A | 127 |
| 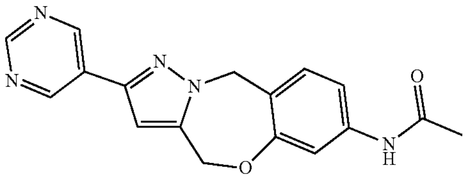 [SMILES: CC(=O)Nc1ccc2c(c1)OCc1cc(-c3cncnc3)nn1C2] | 322.1 | 1H NMR (400 MHz, DMSO) δ 9.96 (s, 1H), 9.17 (s, 2H), 9.12 (s, 1H), 7.33-7.26 (m, 2H), 7.14 (dd, J = 8.3, 2.1 Hz, 1H), 7.00 (s, 1H), 5.64 (s, 2H), 5.39 (s, 2H), 2.02 (s, 3H). | A | 128 |
| 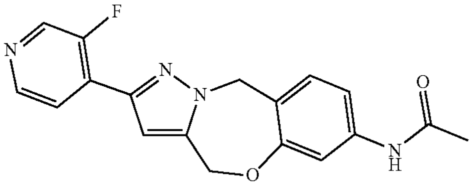 [SMILES: CC(=O)Nc1ccc2c(c1)OCc1cc(-c3ccncc3F)nn1C2] | 339.1 | 1H NMR (400 MHz, DMSO) δ 9.95 (s, 1H), 8.63 (s, 1H), 8.44 (s, 1H), 7.90 (dd, J = 6.7, 5.0 Hz, 1H), 7.34-7.22 (m, 2H), 7.14 (td, J = 8.5, 2.1 Hz, 1H), 6.89 (d, J = 3.7 Hz, 1H), 5.66 (s, 2H), 5.40 (s, 2H), 2.02 (d, J = 2.6 Hz, 3H). | B | 129 |

Assay Example 1. LDC7559 does not Inhibit GSDMD

LDC7559 was reported to block the pore-forming activity of GSDMD (Sollberger et al., 2018). The ability to inhibit GSDMD-dependent pyroptosis in primary human monocytes and human monocytic THP-1 cells was tested (FIG. 1A-C). Using lactate dehydrogenase (LDH) release to monitor cell death, LDC7559 did not alter GSDMD-dependent pyroptosis induced by nigericin, cytoplasmic LPS, or cytoplasmic poly(deoxyadenosine-deoxythymidine) [poly(dA-dT)](FIG. 1A). The GSDMD-dependent release of interleukin-1β (IL-1β) from monocytes in response to nigericin or poly(dA-dT) also occurred normally in the presence of LDC7559 (FIG. 1*i*). Western blotting confirmed that LDC7559 did not prevent LPS-induced cleavage of GSDMD (FIG. 1C). Accordingly, LDC7559 did not inhibit cleavage of recombinant GSDMD by caspase-4 (FIG. 1D). Nor did it prevent the GSDMD pore-forming fragment from permeabilizing liposomes (FIG. 1E). In contrast, inhibition of GSDMD with disulfiram (Hu et al., 2020) prevented liposome permeabilization (FIG. 1E). It was determined that LDC7559 does not inhibit GSDMD.

Assay Example 2. Quantification of NETosis Using SYTOX Green

Semi-automated analysis of both phase and fluorescence images of SYTOX Green-stained neutrophils used a MATLAB algorithm. Total cells were counted by scoring phase standard deviation and radial symmetry. NETosis was classified in cells by measuring the DNA area in the fluorescence image and comparing with a select internal training set for each experiment. Unstimulated cells and PMA-stimulated, pyocyanin-inhibited cells served as negative controls. PMA-stimulated cells served as a positive control. NET-forming cells are presented as a percentage of total cells. Data for representative compounds of the invention is provided in the following Table.
| Example | Compound | IC50 (μM) |
|---|---|---|
| 1 | 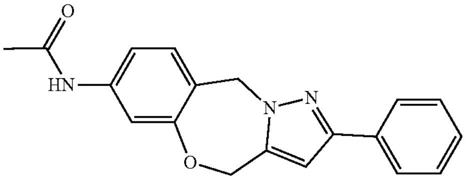 [SMILES: CC(=O)Nc1ccc2c(c1)OCc1cc(-c3ccccc3)nn1C2] | 0.19 ± 0.03 |
| 2 | 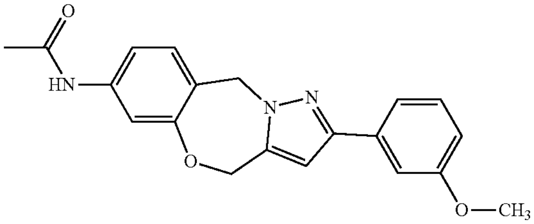 [SMILES: COc1cccc(-c2cc3n(n2)Cc2ccc(NC(C)=O)cc2OC3)c1] | 0.9 ± 0.2 |
| 3 | 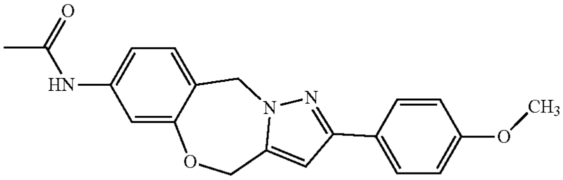 [SMILES: COc1ccc(-c2cc3n(n2)Cc2ccc(NC(C)=O)cc2OC3)cc1] | 0.52 ± 0.06 |
| 4 | 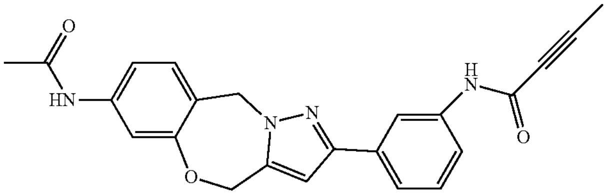 [SMILES: CC#CC(=O)Nc1cccc(-c2cc3n(n2)Cc2ccc(NC(C)=O)cc2OC3)c1] | 0.8 ± 0.02 |
| 5 | 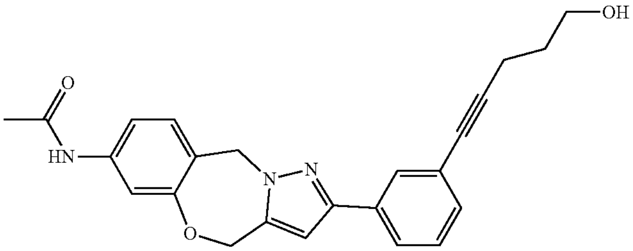 [SMILES: CC(=O)Nc1ccc2c(c1)OCc1cc(-c3cccc(C#CCCCO)c3)nn1C2] | 3 ± 1 |
| 6 | 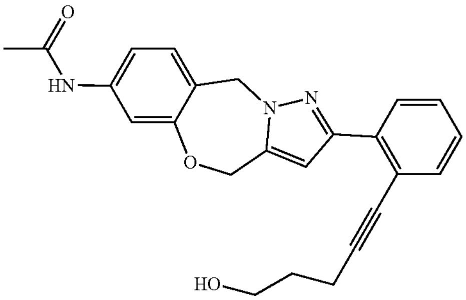 [SMILES: CC(=O)Nc1ccc2c(c1)OCc1cc(-c3ccccc3C#CCCCO)nn1C2] | 0.004 ± 0.0005 |
Semi-automated analysis of both phase and fluorescence images of SYTOX Green-stained neutrophils used a MATLAB algorithm. Total cells were counted by scoring phase standard deviation and radial symmetry. NETosis was classified in cells by measuring the DNA area in the fluorescence image and comparing with a select internal training set for each experiment. Unstimulated cells and PMA-stimulated, pyocyanin-inhibited cells served as negative controls. PMA-stimulated cells served as a positive control. NET-forming cells are presented as a percentage of total cells. Data at 5 uM concentration is provided in the following table.

| Example | Compound | 5 uM (% NETosis) |
|---|---|---|
| 1 | 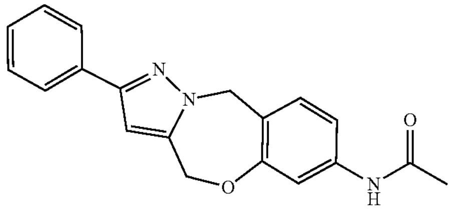 [SMILES: CC(=O)Nc1ccc2c(c1)OCc1cc(-c3ccccc3)nn1C2] | 37.78 |
| 6 | 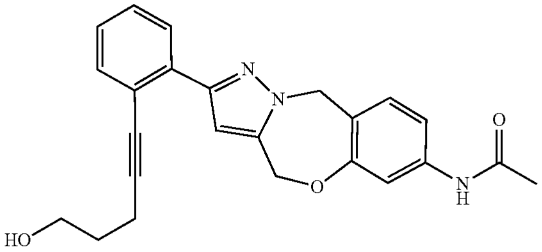 [SMILES: CC(=O)Nc1ccc2c(c1)OCc1cc(-c3ccccc3C#CCCCO)nn1C2] | 58.67 |
| 11 | 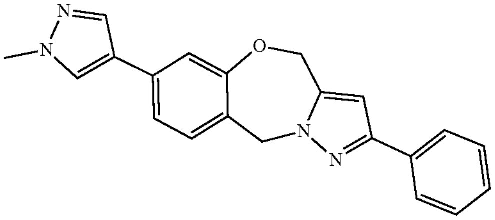 [SMILES: Cn1cc(-c2ccc3c(c2)OCc2cc(-c4ccccc4)nn2C3)cn1] | 80.81 |
| 12 | 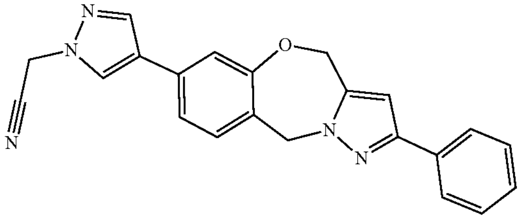 [SMILES: N#CCn1cc(-c2ccc3c(c2)OCc2cc(-c4ccccc4)nn2C3)cn1] | 81.41 |
| 13 | 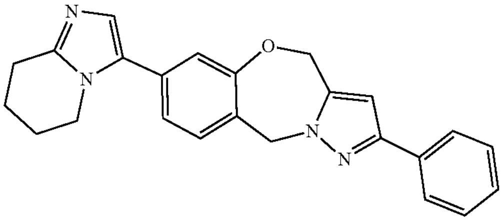 [SMILES: c1ccc(-c2cc3n(n2)Cc2ccc(-c4cnc5n4CCCC5)cc2OC3)cc1] | 80.46 |
| 14 | 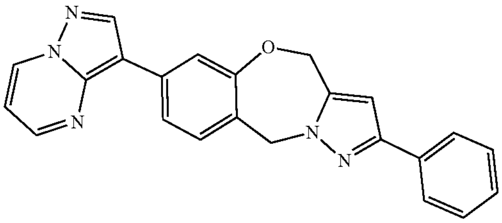 [SMILES: c1ccc(-c2cc3n(n2)Cc2ccc(-c4cnn5cccnc45)cc2OC3)cc1] | 83.04 |

-continued
| Example | Compound | 5 uM (% NETosis) |
|---|---|---|
| 15 | 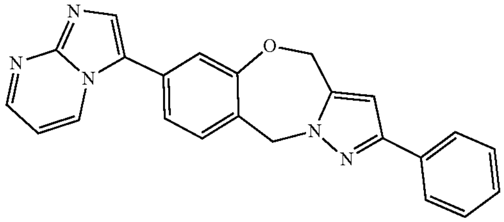 [SMILES: c1ccc(-c2cc3n(n2)Cc2ccc(-c4cnc5ncccn45)cc2OC3)cc1] | 77.26 |
| 16 | 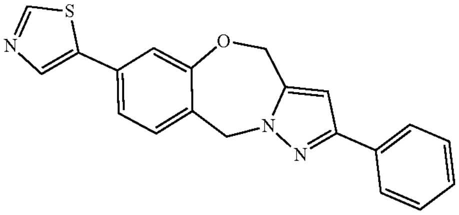 [SMILES: c1ccc(-c2cc3n(n2)Cc2ccc(-c4cncs4)cc2OC3)cc1] | 80.91 |
| 17 | 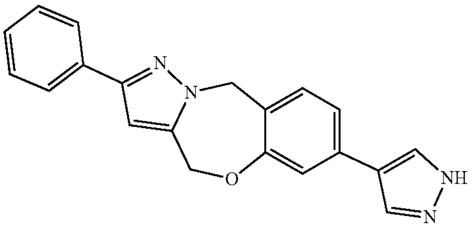 [SMILES: c1ccc(-c2cc3n(n2)Cc2ccc(-c4cn[nH]c4)cc2OC3)cc1] | 76.49 |
| 18 | 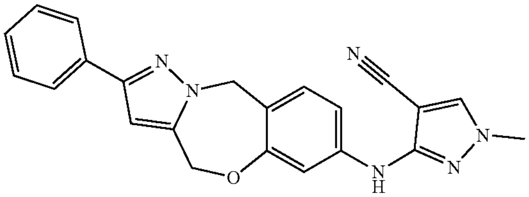 [SMILES: Cn1cc(C#N)c(Nc2ccc3c(c2)OCc2cc(-c4ccccc4)nn2C3)n1] | 79.81 |
| 19 | 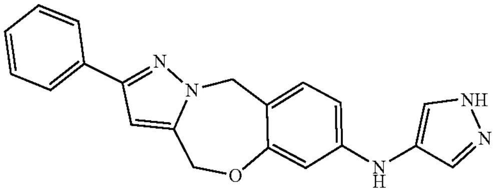 [SMILES: c1ccc(-c2cc3n(n2)Cc2ccc(Nc4cn[nH]c4)cc2OC3)cc1] | 62.75 |
| 20 | 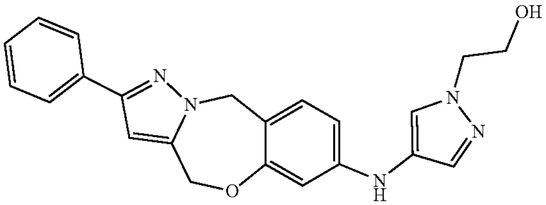 [SMILES: OCCn1cc(Nc2ccc3c(c2)OCc2cc(-c4ccccc4)nn2C3)cn1] | 77.97 |
| 21 | 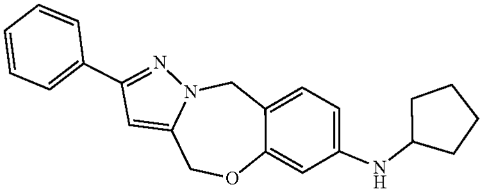 [SMILES: c1ccc(-c2cc3n(n2)Cc2ccc(NC4CCCC4)cc2OC3)cc1] | 86.47 |

-continued
| Example | Compound | 5 uM (% NETosis) |
| --- | --- | --- |
| 22 | 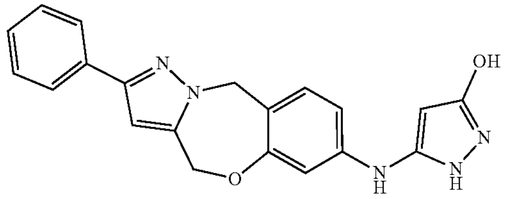 [SMILES: Oc1cc(Nc2ccc3c(c2)OCc2cc(-c4ccccc4)nn2C3)[nH]n1] | 79.55 |
| 23 | 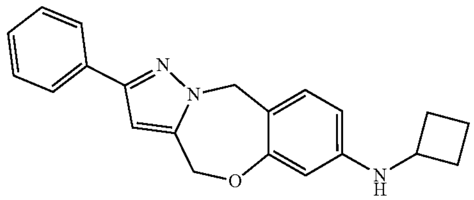 [SMILES: c1ccc(-c2cc3n(n2)Cc2ccc(NC4CCC4)cc2OC3)cc1] | 86.22 |
| 24 | 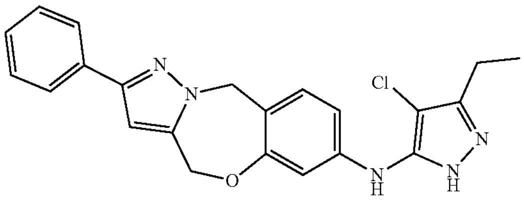 [SMILES: CCc1n[nH]c(Nc2ccc3c(c2)OCc2cc(-c4ccccc4)nn2C3)c1Cl] | 81.55 |
| 25 | 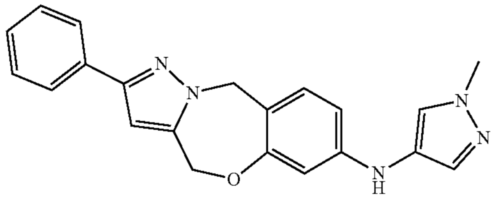 [SMILES: Cn1cc(Nc2ccc3c(c2)OCc2cc(-c4ccccc4)nn2C3)cn1] | 78.63 |
| 26 | 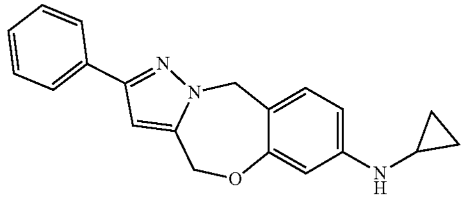 [SMILES: c1ccc(-c2cc3n(n2)Cc2ccc(NC4CC4)cc2OC3)cc1] | 78.70 |
| 27 | 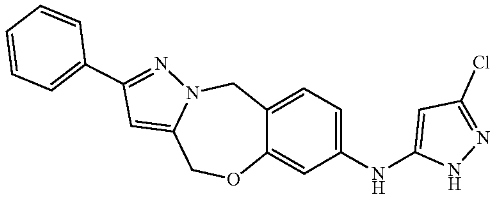 [SMILES: Clc1cc(Nc2ccc3c(c2)OCc2cc(-c4ccccc4)nn2C3)[nH]n1] | 54.56 |
| 28 | 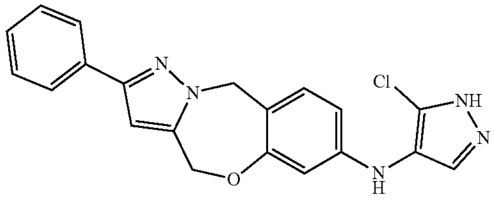 [SMILES: Clc1[nH]ncc1Nc1ccc2c(c1)OCc1cc(-c3ccccc3)nn1C2] | 44.49 |

-continued
| Example | Compound | 5 uM (% NETosis) |
| --- | --- | --- |
| 29 | 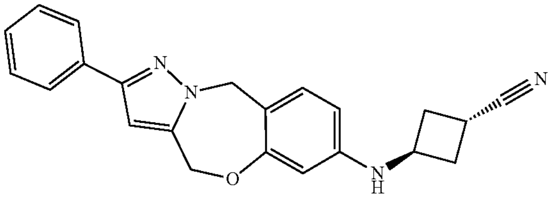 [SMILES: N#C[C@H]1C[C@H](Nc2ccc3c(c2)OCc2cc(-c4ccccc4)nn2C3)C1] | 87.44 |
| 30 | 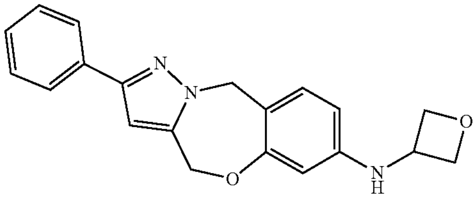 [SMILES: c1ccc(-c2cc3n(n2)Cc2ccc(NC4COC4)cc2OC3)cc1] | 84.70 |
| 31 | 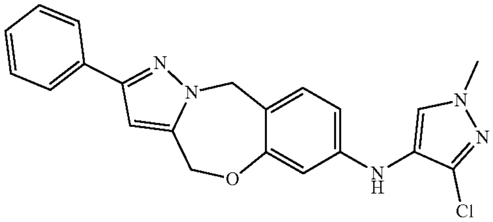 [SMILES: Cn1cc(Nc2ccc3c(c2)OCc2cc(-c4ccccc4)nn2C3)c(Cl)n1] | 85.26 |
| 32 | 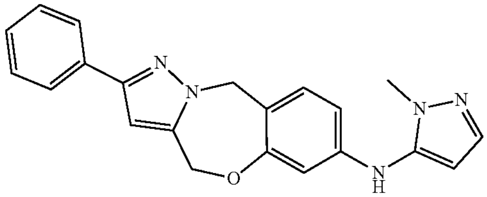 [SMILES: Cn1nccc1Nc1ccc2c(c1)OCc1cc(-c3ccccc3)nn1C2] | 76.40 |
| 33 | 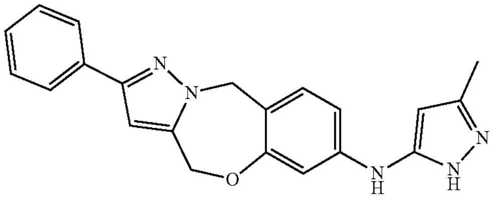 [SMILES: Cc1cc(Nc2ccc3c(c2)OCc2cc(-c4ccccc4)nn2C3)[nH]n1] | 69.42 |
| 34 | 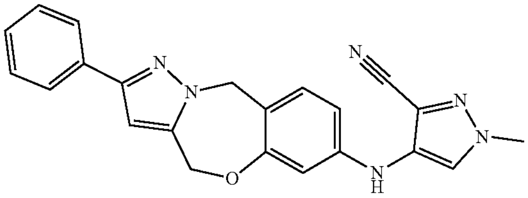 [SMILES: Cn1cc(Nc2ccc3c(c2)OCc2cc(-c4ccccc4)nn2C3)c(C#N)n1] | 80.80 |
| 35 | 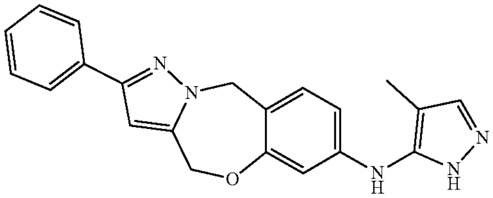 [SMILES: Cc1cn[nH]c1Nc1ccc2c(c1)OCc1cc(-c3ccccc3)nn1C2] | 73.98 |

-continued
| Example | Compound | 5 uM (% NETosis) |
| --- | --- | --- |
| 36 | 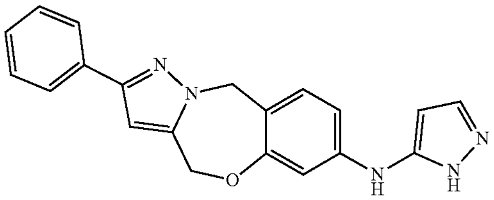 [SMILES: c1ccc(-c2cc3n(n2)Cc2ccc(Nc4ccn[nH]4)cc2OC3)cc1] | 46.06 |
| 37 | 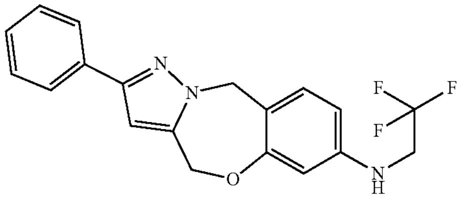 [SMILES: FC(F)(F)CNc1ccc2c(c1)OCc1cc(-c3ccccc3)nn1C2] | 83.25 |
| 38 | 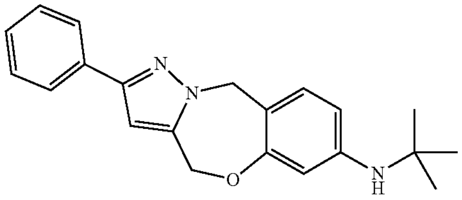 [SMILES: CC(C)(C)Nc1ccc2c(c1)OCc1cc(-c3ccccc3)nn1C2] | 81.48 |
| 39 | 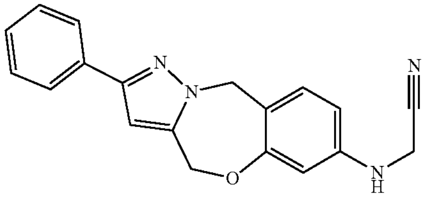 [SMILES: N#CCNc1ccc2c(c1)OCc1cc(-c3ccccc3)nn1C2] | 52.08 |
| 40 | 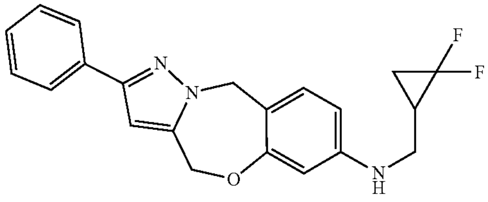 [SMILES: FC1(F)CC1CNc1ccc2c(c1)OCc1cc(-c3ccccc3)nn1C2] | 71.44 |
| 41 | 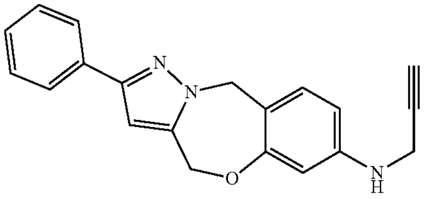 [SMILES: C#CCNc1ccc2c(c1)OCc1cc(-c3ccccc3)nn1C2] | 73.65 |
| 42 | 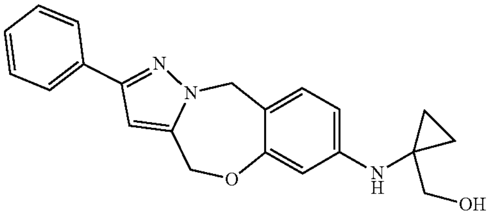 [SMILES: OCC1(Nc2ccc3c(c2)OCc2cc(-c4ccccc4)nn2C3)CC1] | 82.57 |

-continued
| Example | Compound | 5 uM (% NETosis) |
| --- | --- | --- |
| 43 | 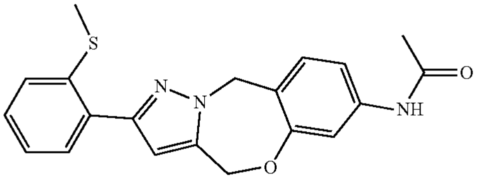 [SMILES: CSc1ccccc1-c1cc2n(n1)Cc1ccc(NC(C)=O)cc1OC2] | 49.48 |
| 44 | 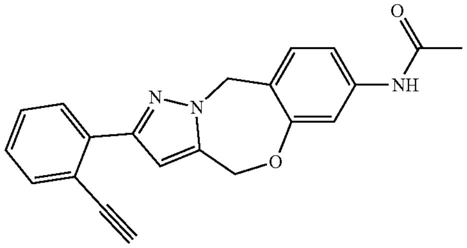 [SMILES: C#Cc1ccccc1-c1cc2n(n1)Cc1ccc(NC(C)=O)cc1OC2] | 83.27 |
| 45 | 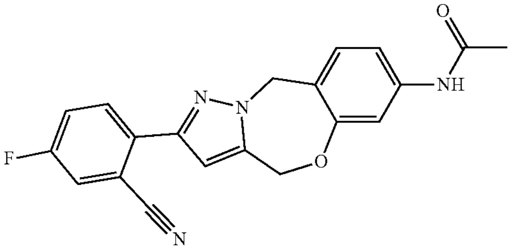 [SMILES: CC(=O)Nc1ccc2c(c1)OCc1cc(-c3ccc(F)cc3C#N)nn1C2] | 56.95 |
| 46 | 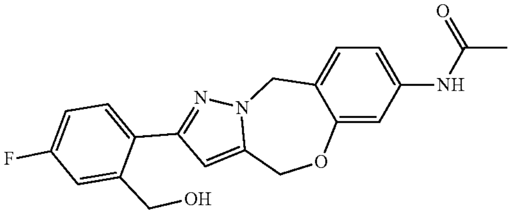 [SMILES: CC(=O)Nc1ccc2c(c1)OCc1cc(-c3ccc(F)cc3CO)nn1C2] | 51.25 |
| 47 | 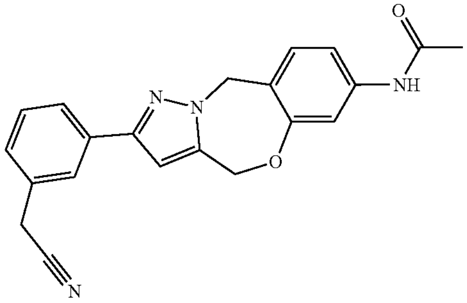 [SMILES: CC(=O)Nc1ccc2c(c1)OCc1cc(-c3cccc(CC#N)c3)nn1C2] | 62.82 |
| 48 | 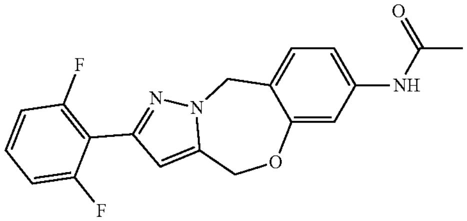 [SMILES: CC(=O)Nc1ccc2c(c1)OCc1cc(-c3c(F)cccc3F)nn1C2] | 42.40 |

-continued
| Example | Compound | 5 uM (% NETosis) |
| --- | --- | --- |
| 49 | 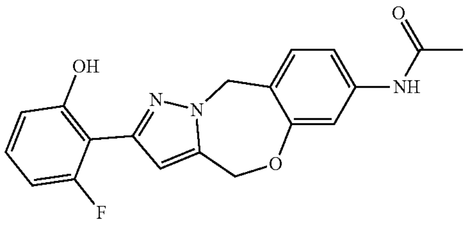 [SMILES: CC(=O)Nc1ccc2c(c1)OCc1cc(-c3c(O)cccc3F)nn1C2] | 42.24 |
| 50 | 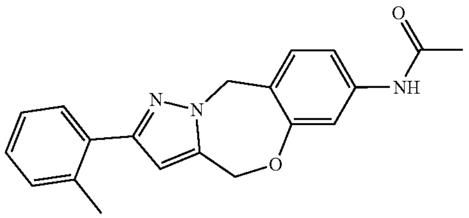 [SMILES: CC(=O)Nc1ccc2c(c1)OCc1cc(-c3ccccc3C)nn1C2] | 72.49 |
| 51 | 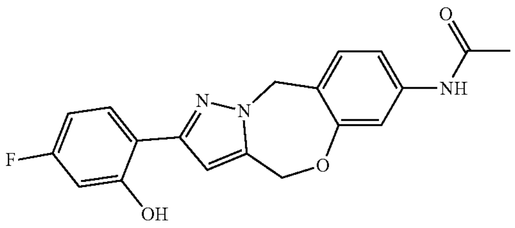 [SMILES: CC(=O)Nc1ccc2c(c1)OCc1cc(-c3ccc(F)cc3O)nn1C2] | 57.20 |
| 52 | 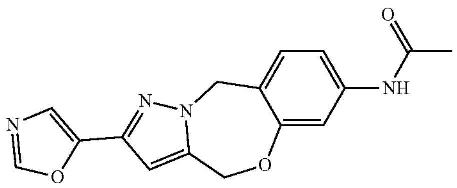 | 66.03 |
| 53 | 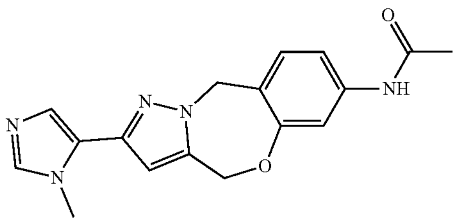 [SMILES: CC(=O)Nc1ccc2c(c1)OCc1cc(-c3cncn3C)nn1C2] | 57.77 |
| 54 | 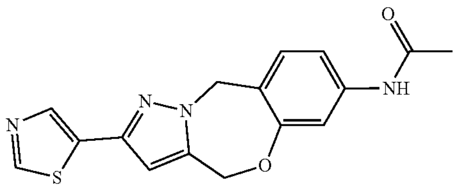 [SMILES: CC(=O)Nc1ccc2c(c1)OCc1cc(-c3cncs3)nn1C2] | 37.45 |
| 55 | 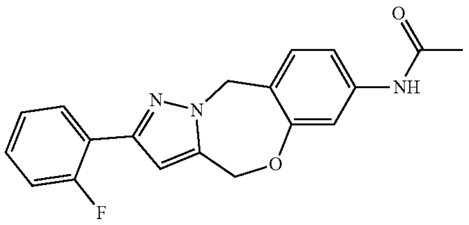 [SMILES: CC(=O)Nc1ccc2c(c1)OCc1cc(-c3ccccc3F)nn1C2] | 36.33 |

-continued
| Example | Compound | 5 uM (% NETosis) |
|---|---|---|
| 56 | 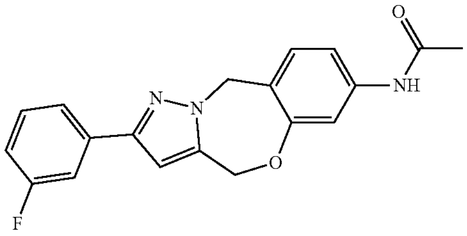 [SMILES: CC(=O)Nc1ccc2c(c1)OCc1cc(-c3cccc(F)c3)nn1C2] | 35.77 |
| 57 | 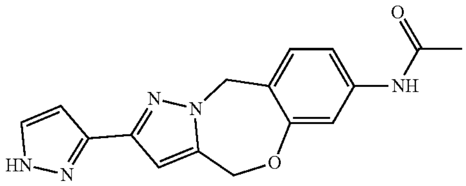 [SMILES: CC(=O)Nc1ccc2c(c1)OCc1cc(-c3cc[nH]n3)nn1C2] | 87.44 |
| 58 | 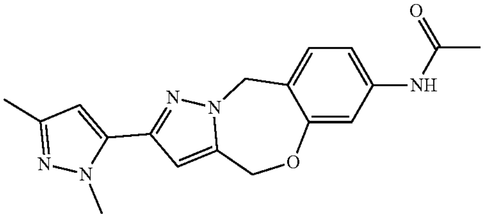 [SMILES: CC(=O)Nc1ccc2c(c1)OCc1cc(-c3cc(C)nn3C)nn1C2] | 53.96 |
| 59 | 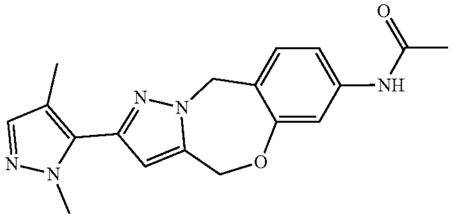 [SMILES: CC(=O)Nc1ccc2c(c1)OCc1cc(-c3c(C)cnn3C)nn1C2] | 66.88 |
| 60 | 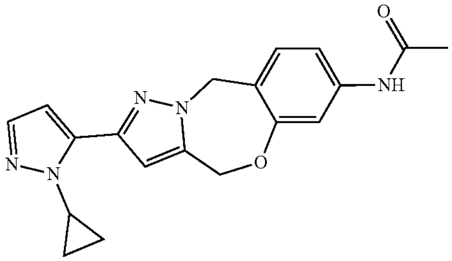 [SMILES: CC(=O)Nc1ccc2c(c1)OCc1cc(-c3ccnn3C3CC3)nn1C2] | 63.78 |
| 61 | 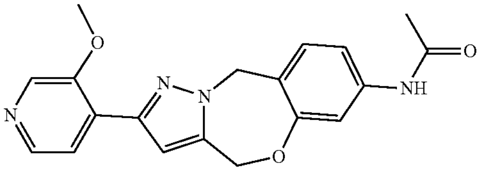 [SMILES: COc1cnccc1-c1cc2n(n1)Cc1ccc(NC(C)=O)cc1OC2] | 78.57 |

-continued
| Example | Compound | 5 uM (% NETosis) |
|---|---|---|
| 62 | 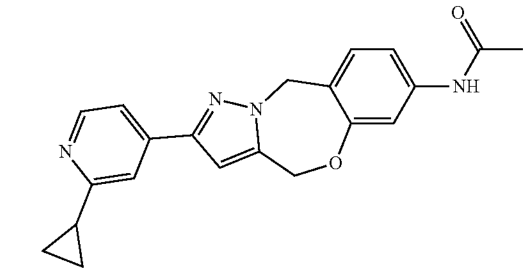 [SMILES: CC(=O)Nc1ccc2c(c1)OCc1cc(-c3ccnc(C4CC4)c3)nn1C2] | 41.23 |
| 63 | 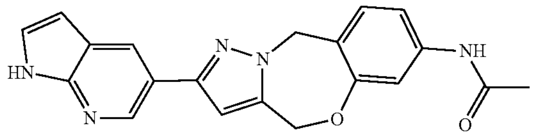 [SMILES: CC(=O)Nc1ccc2c(c1)OCc1cc(-c3cnc4[nH]ccc4c3)nn1C2] | 80.04 |
| 64 | 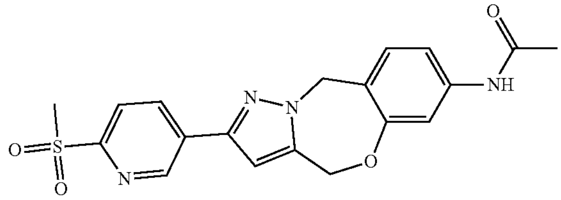 [SMILES: CC(=O)Nc1ccc2c(c1)OCc1cc(-c3ccc(S(C)(=O)=O)nc3)nn1C2] | 75.82 |
| 65 | 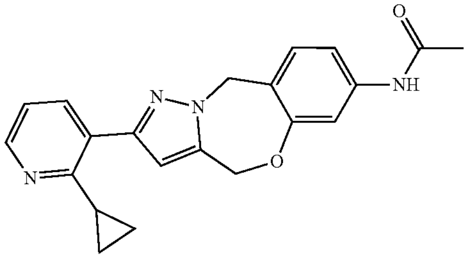 [SMILES: CC(=O)Nc1ccc2c(c1)OCc1cc(-c3cccnc3C3CC3)nn1C2] | 83.56 |
| 66 | 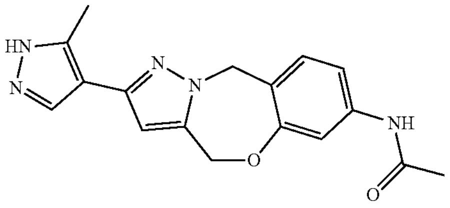 [SMILES: CC(=O)Nc1ccc2c(c1)OCc1cc(-c3cn[nH]c3C)nn1C2] | 84.91 |
| 67 | 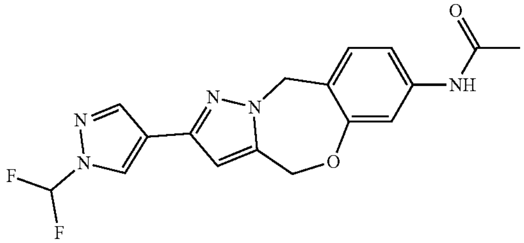 [SMILES: CC(=O)Nc1ccc2c(c1)OCc1cc(-c3cnn(C(F)F)c3)nn1C2] | 39.88 |

-continued
| Example | Compound | 5 uM (% NETosis) |
|---|---|---|
| 68 | 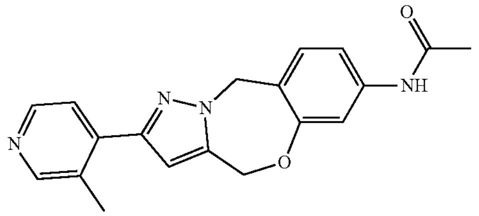 [SMILES: CC(=O)Nc1ccc2c(c1)OCc1cc(-c3ccncc3C)nn1C2] | 43.49 |
| 69 | 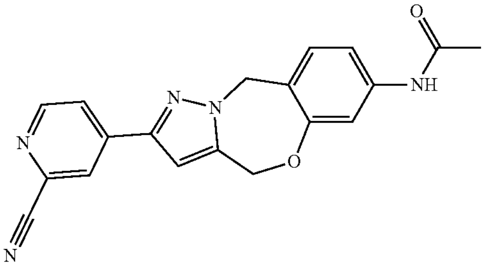 [SMILES: CC(=O)Nc1ccc2c(c1)OCc1cc(-c3ccnc(C#N)c3)nn1C2] | 66.18 |
| 70 | 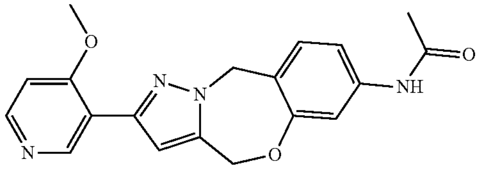 [SMILES: COc1ccncc1-c1cc2n(n1)Cc1ccc(NC(C)=O)cc1OC2] | 78.10 |
| 71 | 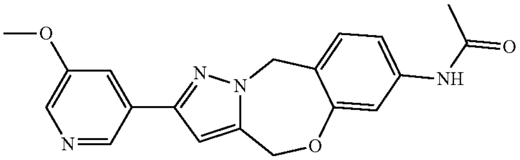 [SMILES: COc1cncc(-c2cc3n(n2)Cc2ccc(NC(C)=O)cc2OC3)c1] | 69.95 |
| 72 | 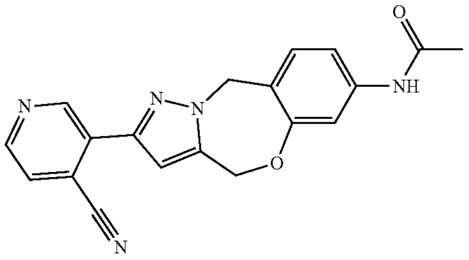 [SMILES: CC(=O)Nc1ccc2c(c1)OCc1cc(-c3cnccc3C#N)nn1C2] | 80.10 |
| 73 | 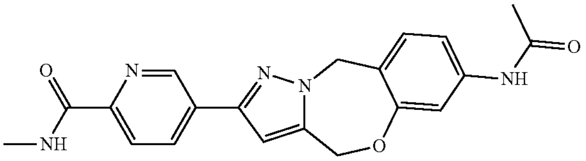 [SMILES: CNC(=O)c1ccc(-c2cc3n(n2)Cc2ccc(NC(C)=O)cc2OC3)cn1] | 82.63 |
| 75 | 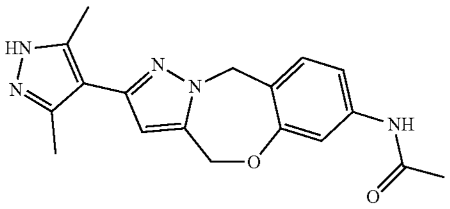 [SMILES: CC(=O)Nc1ccc2c(c1)OCc1cc(-c3c(C)n[nH]c3C)nn1C2] | 85.26 |

-continued
| Example | Compound | 5 uM (% NETosis) |
|---|---|---|
| 76 | 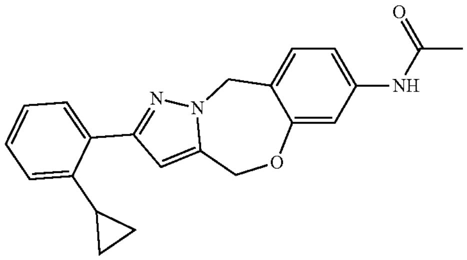 [SMILES: CC(=O)Nc1ccc2c(c1)OCc1cc(-c3ccccc3C3CC3)nn1C2] | 63.32 |
| 77 | 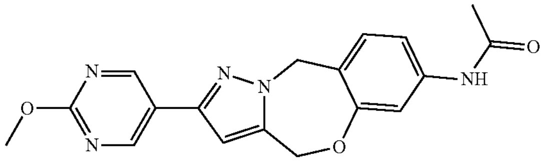 [SMILES: COc1ncc(-c2cc3n(n2)Cc2ccc(NC(C)=O)cc2OC3)cn1] | 86.51 |
| 78 | 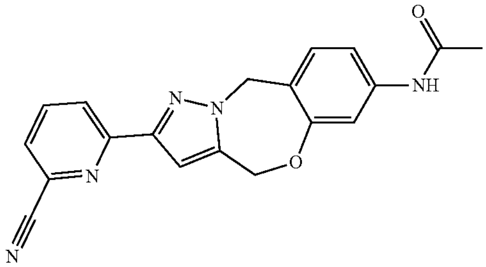 [SMILES: CC(=O)Nc1ccc2c(c1)OCc1cc(-c3cccc(C#N)n3)nn1C2] | 58.91 |
| 79 | 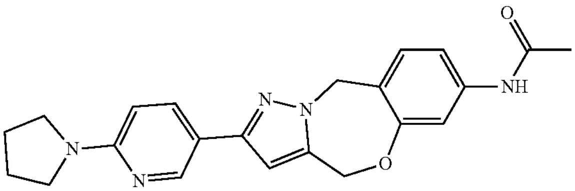 [SMILES: CC(=O)Nc1ccc2c(c1)OCc1cc(-c3ccc(N4CCCC4)nc3)nn1C2] | 83.33 |
| 80 | 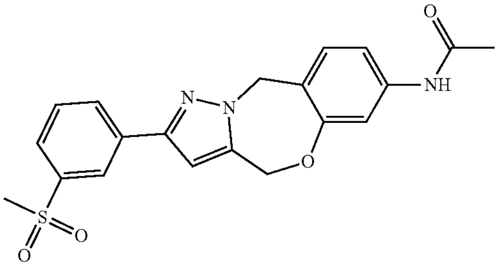 [SMILES: CC(=O)Nc1ccc2c(c1)OCc1cc(-c3cccc(S(C)(=O)=O)c3)nn1C2] | 46.95 |
| 81 | 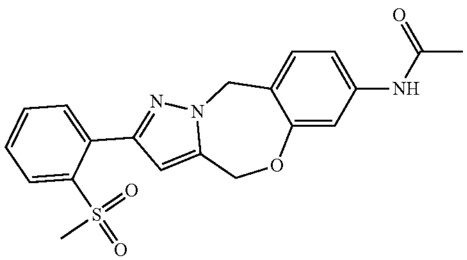 [SMILES: CC(=O)Nc1ccc2c(c1)OCc1cc(-c3ccccc3S(C)(=O)=O)nn1C2] | 84.34 |

-continued
| Example | Compound | 5 uM (% NETosis) |
|---|---|---|
| 82 | 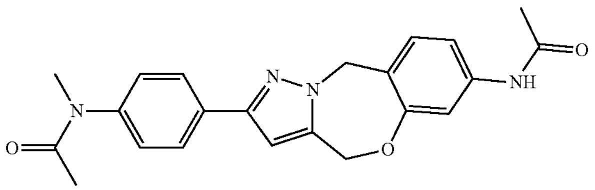 [SMILES: CC(=O)Nc1ccc2c(c1)OCc1cc(-c3ccc(N(C)C(C)=O)cc3)nn1C2] | 77.67 |
| 83 | 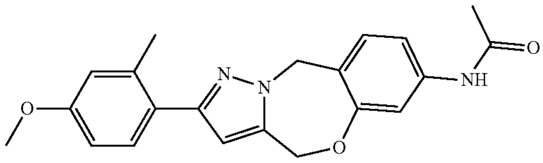 [SMILES: COc1ccc(-c2cc3n(n2)Cc2ccc(NC(C)=O)cc2OC3)c(C)c1] | 51.91 |
| 84 | 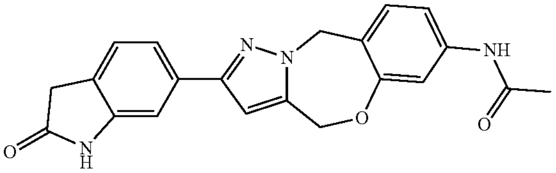 [SMILES: CC(=O)Nc1ccc2c(c1)OCc1cc(-c3ccc4c(c3)NC(=O)C4)nn1C2] | 42.93 |
| 85 | 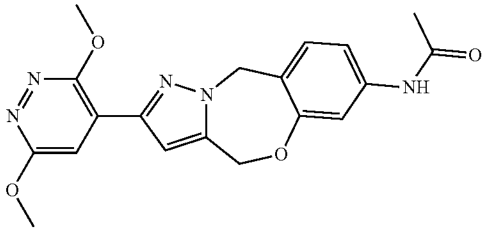 [SMILES: COc1cc(-c2cc3n(n2)Cc2ccc(NC(C)=O)cc2OC3)c(OC)nn1] | 74.51 |
| 86 | 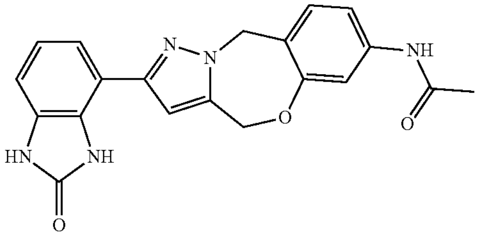 [SMILES: CC(=O)Nc1ccc2c(c1)OCc1cc(-c3cccc4[nH]c(=O)[nH]c34)nn1C2] | 84.35 |
| 87 | 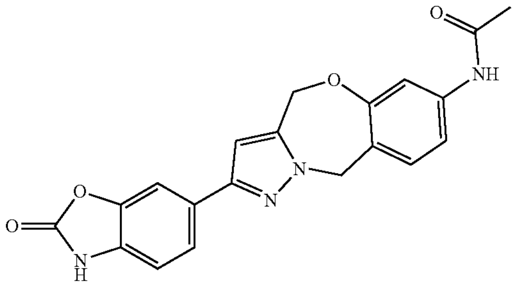 [SMILES: CC(=O)Nc1ccc2c(c1)OCc1cc(-c3ccc4[nH]c(=O)oc4c3)nn1C2] | 78.92 |

-continued
| Example | Compound | 5 uM (% NETosis) |
|---|---|---|
| 88 | 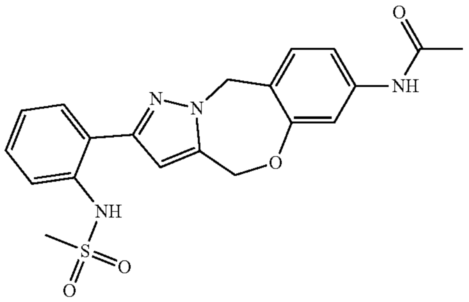 [SMILES: CC(=O)Nc1ccc2c(c1)OCc1cc(-c3ccccc3NS(C)(=O)=O)nn1C2] | 71.64 |
| 89 | 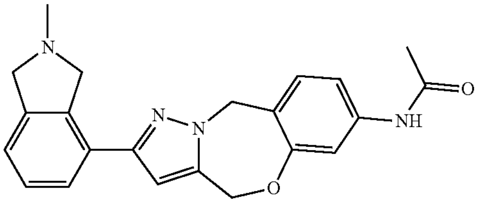 [SMILES: CC(=O)Nc1ccc2c(c1)OCc1cc(-c3cccc4c3CN(C)C4)nn1C2] | 84.44 |
| 90 | 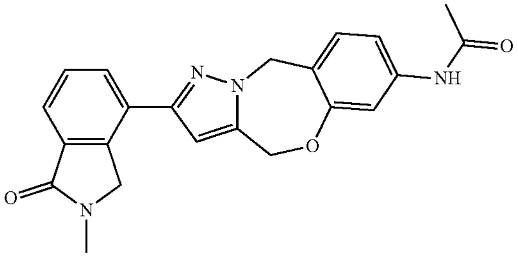 [SMILES: CC(=O)Nc1ccc2c(c1)OCc1cc(-c3cccc4c3CN(C)C4=O)nn1C2] | 78.83 |
| 91 | 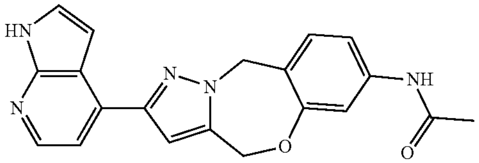 [SMILES: CC(=O)Nc1ccc2c(c1)OCc1cc(-c3ccnc4[nH]ccc34)nn1C2] | 77.13 |
| 92 | 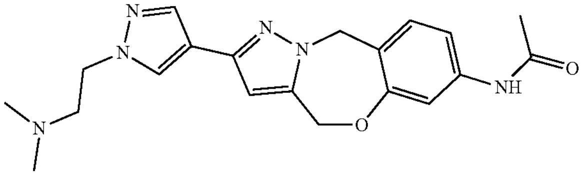 [SMILES: CC(=O)Nc1ccc2c(c1)OCc1cc(-c3cnn(CCN(C)C)c3)nn1C2] | 81.09 |
| 93 | 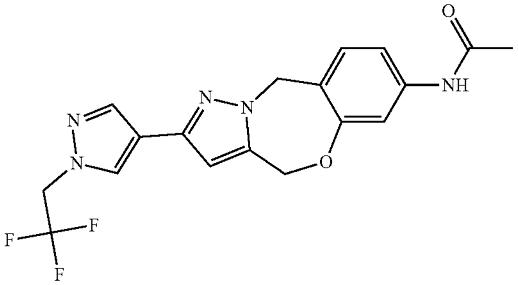 [SMILES: CC(=O)Nc1ccc2c(c1)OCc1cc(-c3cnn(CC(F)(F)F)c3)nn1C2] | 73.17 |

-continued
| Example | Compound | 5 uM (% NETosis) |
|---|---|---|
| 94 | 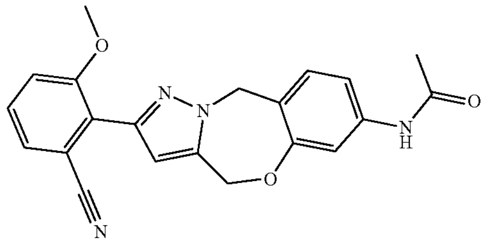 [SMILES: COc1cccc(C#N)c1-c1cc2n(n1)Cc1ccc(NC(C)=O)cc1OC2] | 90.90 |
| 95 | 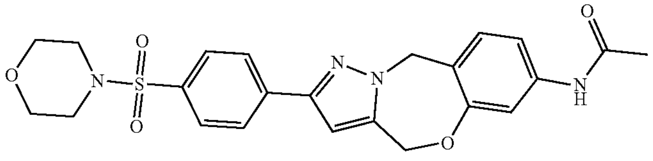 [SMILES: CC(=O)Nc1ccc2c(c1)OCc1cc(-c3ccc(S(=O)(=O)N4CCOCC4)cc3)nn1C2] | 85.90 |
| 96 | 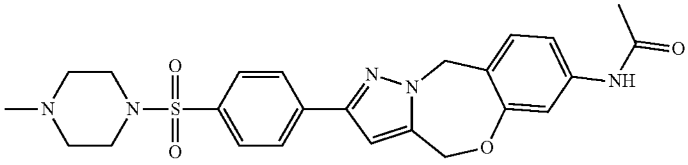 [SMILES: CC(=O)Nc1ccc2c(c1)OCc1cc(-c3ccc(S(=O)(=O)N4CCN(C)CC4)cc3)nn1C2] | 82.37 |
| 97 | 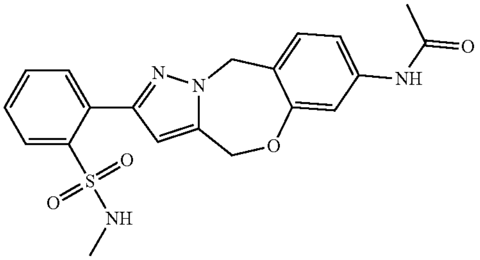 [SMILES: CNS(=O)(=O)c1ccccc1-c1cc2n(n1)Cc1ccc(NC(C)=O)cc1OC2] | 81.93 |
| 98 | 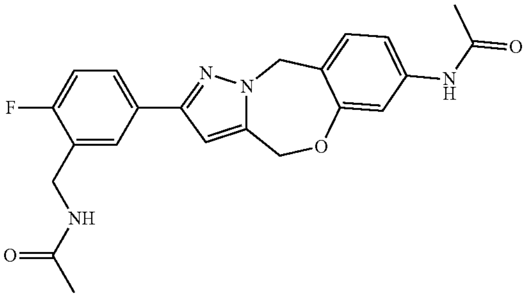 [SMILES: CC(=O)NCc1cc(-c2cc3n(n2)Cc2ccc(NC(C)=O)cc2OC3)ccc1F] | 48.65 |
| 99 | 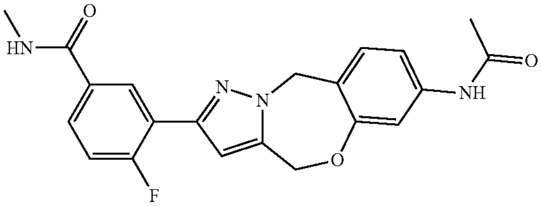 [SMILES: CNC(=O)c1ccc(F)c(-c2cc3n(n2)Cc2ccc(NC(C)=O)cc2OC3)c1] | 84.59 |
| 100 | 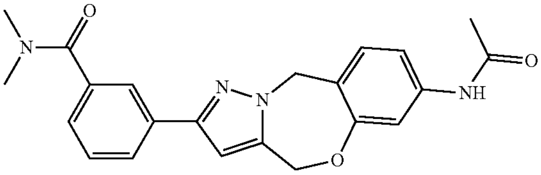 [SMILES: CC(=O)Nc1ccc2c(c1)OCc1cc(-c3cccc(C(=O)N(C)C)c3)nn1C2] | 85.05 |

-continued
| Example | Compound | 5 uM (% NETosis) |
| --- | --- | --- |
| 101 | 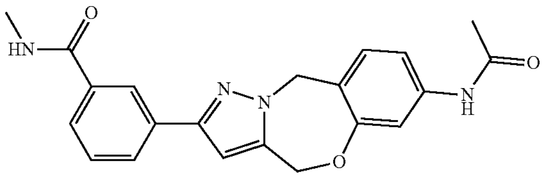 [SMILES: CNC(=O)c1cccc(-c2cc3n(n2)Cc2ccc(NC(C)=O)cc2OC3)c1] | 85.18 |
| 102 | 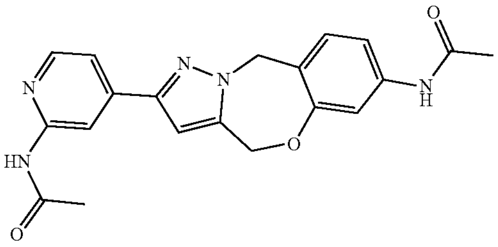 [SMILES: CC(=O)Nc1ccc2c(c1)OCc1cc(-c3ccnc(NC(C)=O)c3)nn1C2] | 85.50 |
| 103 | 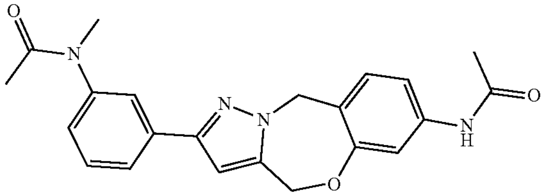 [SMILES: CC(=O)Nc1ccc2c(c1)OCc1cc(-c3cccc(N(C)C(C)=O)c3)nn1C2] | 75.39 |
| 104 | 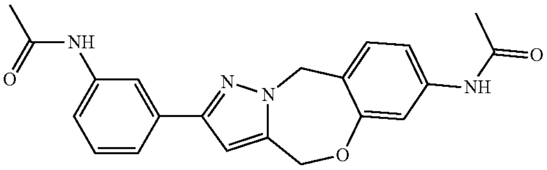 [SMILES: CC(=O)Nc1cccc(-c2cc3n(n2)Cc2ccc(NC(C)=O)cc2OC3)c1] | 26.79 |
| 105 | 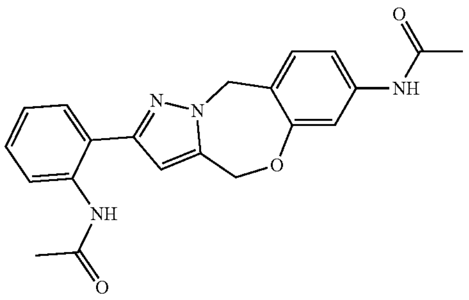 [SMILES: CC(=O)Nc1ccc2c(c1)OCc1cc(-c3ccccc3NC(C)=O)nn1C2] | 70.78 |
| 106 | 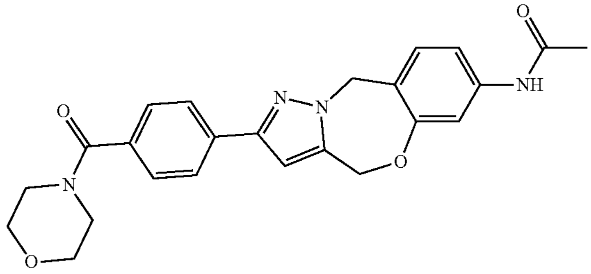 [SMILES: CC(=O)Nc1ccc2c(c1)OCc1cc(-c3ccc(C(=O)N4CCOCC4)cc3)nn1C2] | 86.21 |

-continued

| Example | Compound | 5 uM (% NETosis) |
|---|---|---|
| 107 | 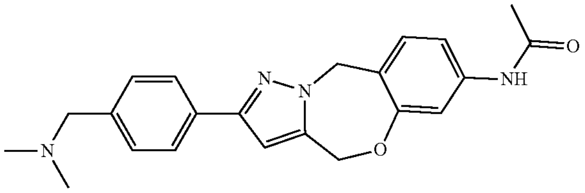 [SMILES: CC(=O)Nc1ccc2c(c1)OCc1cc(-c3ccc(CN(C)C)cc3)nn1C2] | 85.67 |
| NA | Untreated | 14.54 |
| NA | Vehicle | 79.66 |
| NA | Apocynin (100 uM) | 29.06 |

The activity of the compounds and salts can also be evaluated in biochemical assays measuring PFKL, PFKM and PFKP activity.

Assay Example 3. ROS Detection Assay

ROS were measured in neutrophils using the ROS-Glo bioluminescent assay (Promega) for the direct detection of $H_2O_2$. Neutrophils were isolated from fresh human blood using a biphasic Histopaque gradient as described here. Cells (100 uL per well) were plated in 96-well plates at a density of 200,000 cells/mL in high glucose DMEM medium. Cells were preincubated with either DMSO vehicle or compounds (10-point dilution curve starting at 2 uM with 3-fold serial dilution) for 30 min, and then stimulated with 50 nM PMA for 30 min. Luminescence, after the addition of $H_2O_2$ substrate solution for 20 min, and then ROS-Glo detection solution for 20 min, was recorded on a luminescence plate reader. The fifty percent inhibitory concentration ($IC_{50}$) was determined with GraphPad Prism by plotting the assay output (RLU) versus the logarithm of the compound concentration using a non-linear sigmoid with variable slope algorithm with the default curve-fitting parameters in the Prism software.

| Example | Compound | ROS $IC_{50}$ (uM) |
|---|---|---|
| 1 | 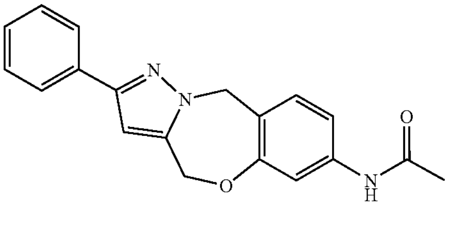 [SMILES: CC(=O)Nc1ccc2c(c1)OCc1cc(-c3ccccc3)nn1C2] | 0.093 |
| 6 | 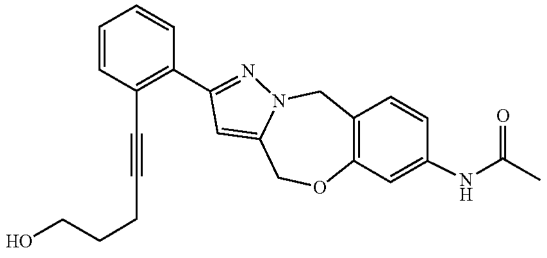 [SMILES: CC(=O)Nc1ccc2c(c1)OCc1cc(-c3ccccc3C#CCCCO)nn1C2] | 0.026 |
| 19 | 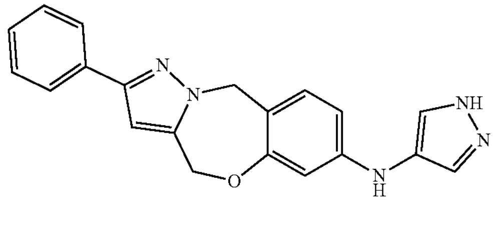 [SMILES: c1ccc(-c2cc3n(n2)Cc2ccc(Nc4cn[nH]c4)cc2OC3)cc1] | >20 |

-continued
| Example | Compound | ROS $IC_{50}$ (uM) |
|---|---|---|
| 33 | 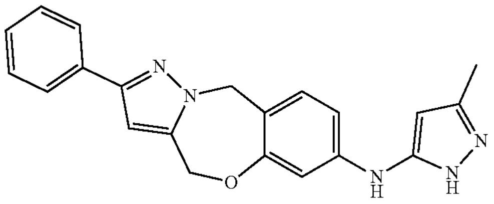 [SMILES: Cc1cc(Nc2ccc3c(c2)OCc2cc(-c4ccccc4)nn2C3)[nH]n1] | >20 |
| 36 | 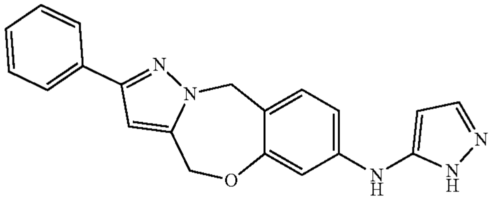 [SMILES: c1ccc(-c2cc3n(n2)Cc2ccc(Nc4ccn[nH]4)cc2OC3)cc1] | 1.4 |
| 39 | 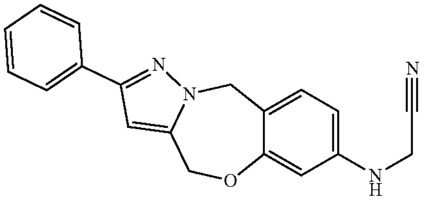 [SMILES: N#CCNc1ccc2c(c1)OCc1cc(-c3ccccc3)nn1C2] | 0.51 |
| 54 | 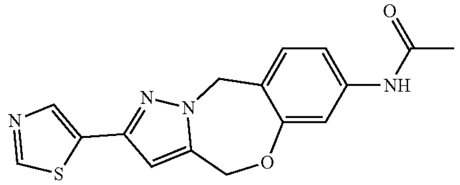 [SMILES: CC(=O)Nc1ccc2c(c1)OCc1cc(-c3cncs3)nn1C2] | >20 |
| 55 | 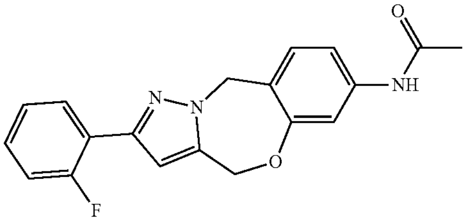 [SMILES: CC(=O)Nc1ccc2c(c1)OCc1cc(-c3ccccc3F)nn1C2] | 0.046 |
| 58 | 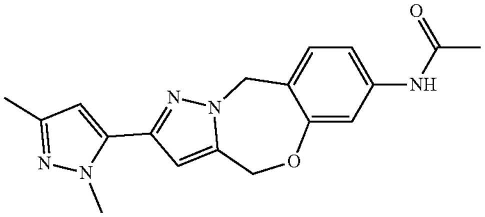 [SMILES: CC(=O)Nc1ccc2c(c1)OCc1cc(-c3cc(C)nn3C)nn1C2] | 2.44 |
| 67 | 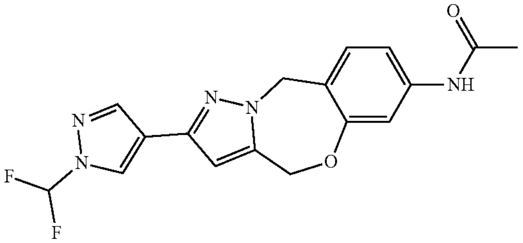 [SMILES: CC(=O)Nc1ccc2c(c1)OCc1cc(-c3cnn(C(F)F)c3)nn1C2] | 0.192 |

-continued
| Example | Compound | ROS $IC_{50}$ (uM) |
|---|---|---|
| 68 | 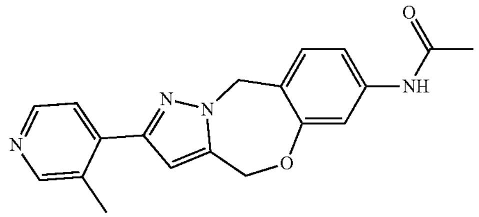 [SMILES: CC(=O)Nc1ccc2c(c1)OCc1cc(-c3ccncc3C)nn1C2] | 0.233 |
| 108 | 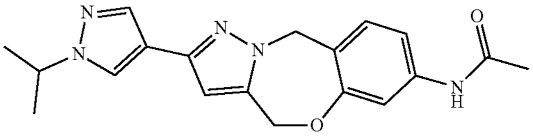 [SMILES: CC(=O)Nc1ccc2c(c1)OCc1cc(-c3cnn(C(C)C)c3)nn1C2] | 0.285 |
| 109 | 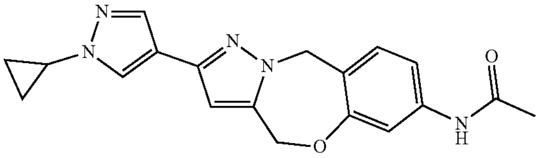 [SMILES: CC(=O)Nc1ccc2c(c1)OCc1cc(-c3cnn(C4CC4)c3)nn1C2] | 0.480 |
| 110 | 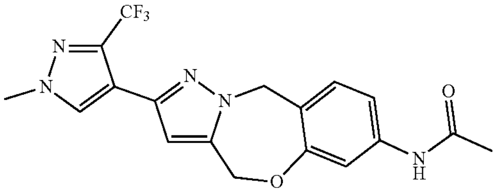 [SMILES: CC(=O)Nc1ccc2c(c1)OCc1cc(-c3cn(C)nc3C(F)(F)F)nn1C2] | 1.584 |
| 111 | 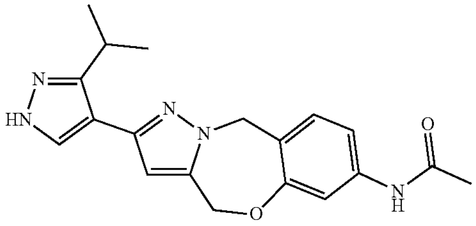 [SMILES: CC(=O)Nc1ccc2c(c1)OCc1cc(-c3c[nH]nc3C(C)C)nn1C2] | 2.098 |
| 112 | 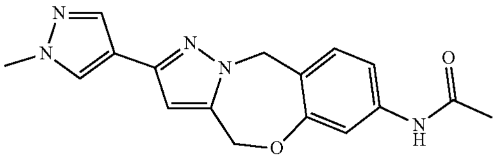 [SMILES: CC(=O)Nc1ccc2c(c1)OCc1cc(-c3cnn(C)c3)nn1C2] | 3.05 |
| 113 | 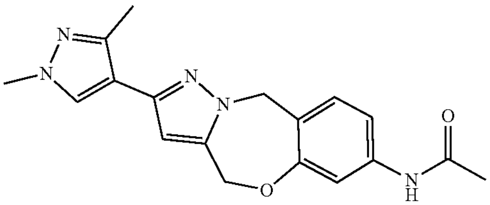 [SMILES: CC(=O)Nc1ccc2c(c1)OCc1cc(-c3cn(C)nc3C)nn1C2] | 1.46 |
| 114 | 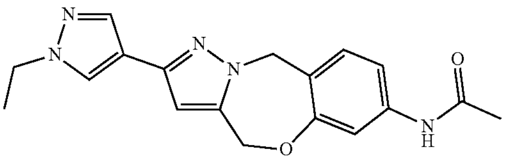 [SMILES: CCn1cc(-c2cc3n(n2)Cc2ccc(NC(C)=O)cc2OC3)cn1] | 0.405 |

-continued
| Example | Compound | ROS $IC_{50}$ (uM) |
|---|---|---|
| 115 | 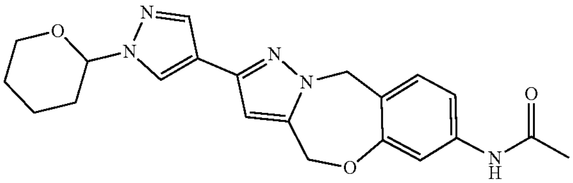 [SMILES: CC(=O)Nc1ccc2c(c1)OCc1cc(-c3cnn(C4CCCCO4)c3)nn1C2] | 7.751 |
| 117 | 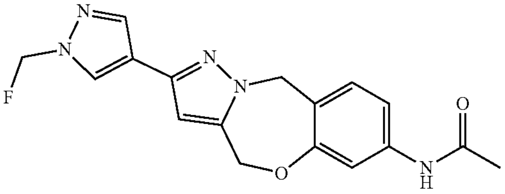 [SMILES: CC(=O)Nc1ccc2c(c1)OCc1cc(-c3cnn(CF)c3)nn1C2] | 0.204 |
| 118 | 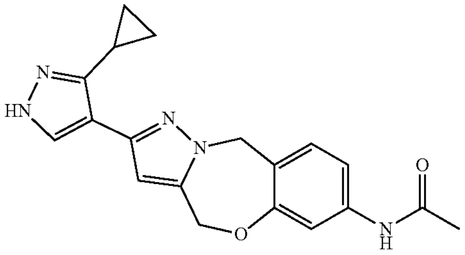 [SMILES: CC(=O)Nc1ccc2c(c1)OCc1cc(-c3c[nH]nc3C3CC3)nn1C2] | >20 |
| 119 | 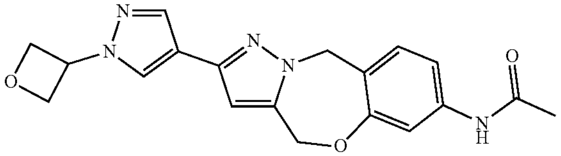 [SMILES: CC(=O)Nc1ccc2c(c1)OCc1cc(-c3cnn(C4COC4)c3)nn1C2] | 0.714 |
| 120 | 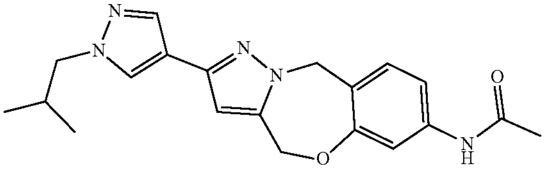 [SMILES: CC(=O)Nc1ccc2c(c1)OCc1cc(-c3cnn(CC(C)C)c3)nn1C2] | 0.346 |
| 121 | 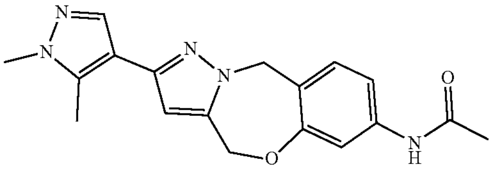 [SMILES: CC(=O)Nc1ccc2c(c1)OCc1cc(-c3cnn(C)c3C)nn1C2] | 0.836 |
| 122 | 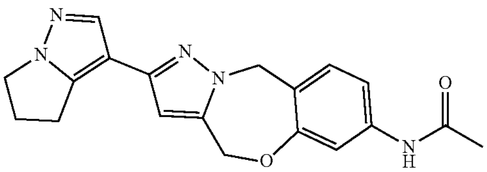 [SMILES: CC(=O)Nc1ccc2c(c1)OCc1cc(-c3cnn4c3CCC4)nn1C2] | 1.201 |
| 123 | 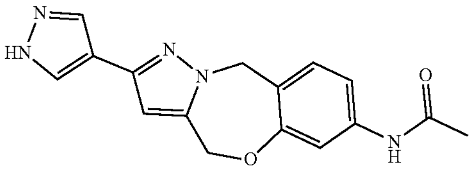 [SMILES: CC(=O)Nc1ccc2c(c1)OCc1cc(-c3cn[nH]c3)nn1C2] | 0.787 |

-continued

| Example | Compound | ROS $IC_{50}$ (uM) |
| --- | --- | --- |
| 124 | 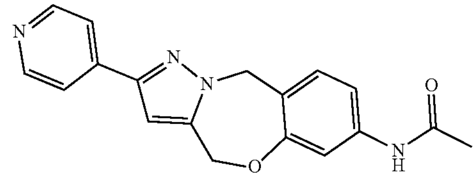 [SMILES: CC(=O)Nc1ccc2c(c1)OCc1cc(-c3ccncc3)nn1C2] | 0.410 |
| 125 | 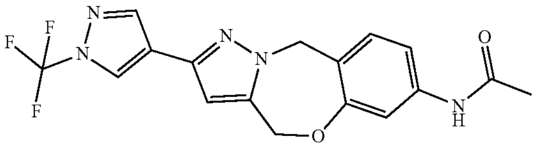 [SMILES: CC(=O)Nc1ccc2c(c1)OCc1cc(-c3cnn(C(F)(F)F)c3)nn1C2] | 0.056 |
| 126 | 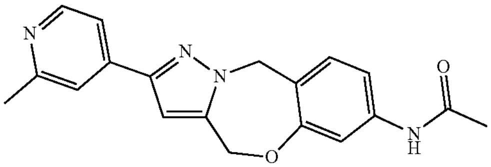 [SMILES: CC(=O)Nc1ccc2c(c1)OCc1cc(-c3ccnc(C)c3)nn1C2] | 0.529 |
| 127 | 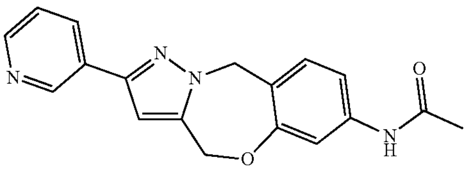 [SMILES: CC(=O)Nc1ccc2c(c1)OCc1cc(-c3cccnc3)nn1C2] | 1.362 |
| 128 | 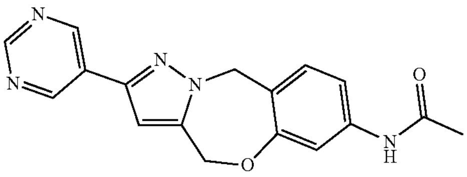 [SMILES: CC(=O)Nc1ccc2c(c1)OCc1cc(-c3cncnc3)nn1C2] | 3.095 |
| 129 | 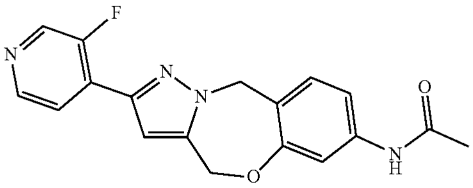 [SMILES: CC(=O)Nc1ccc2c(c1)OCc1cc(-c3ccncc3F)nn1C2] | 0.903 |

Formulation Example. The following illustrate representative pharmaceutical dosage forms, containing a compound of formula (I) ('Compound X'), for therapeutic or prophylactic use in humans.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

-continued

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |

-continued

| | |
|---|---|
| Pregelatinized starch | 120.0 |
| Magnesium stearate | 3.0 |
| | 600.0 |
| (iv) Injection 1 (1 mg/ml) | mg/ml |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | mg/ml |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Preparative Example 1 N-(2-(2-methoxyphenyl)-4H,10H-benzo[f]pyrazolo[5,1-c][1,4]oxazepin-7-yl) acetamide (LDC7559)

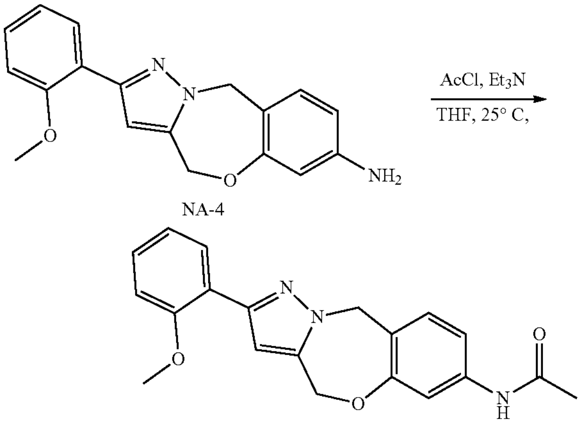

NA-4

LDC7559

Compound NA-4 (200 mg, 651 μmol) was dissolved in THE (6.00 mL). $Et_3N$ (132 mg, 1.30 mmol), then Acetyl chloride (61.3 mg, 781 μmol) were added and the mixture was stirred at 18° C. for 25 min. TLC (petroleum ether/ethyl acetate=1/1, NA-4 $R_f$=0.50, product $R_f$=0.30) indicated NA-4 was consumed completely and one main spot formed. The reaction mixture was quenched by addition $H_2O$ (15.0 mL) and extracted with EtOAc (15.0 mL×3). The combined organic layers were washed with brine (10.0 mL), dried over sodium sulfate, filtered and concentrated under vacuum. The residue was purified by column chromatography ($SiO_2$, petroleum ether/ethyl acetate=50/1 to 0/1). The combined organic layers were concentrated under vacuum. The residue was purified by HPLC using a Waters Xbridge 150 mm×25 mm and 5 μm particle size. The mobile phase was composed of 10 mM $NH_4HCO_3$ (aq) and ACN, gradient of ACN from 25%-55% over 20 minutes. The collected fractions were concentrated by freeze-drying to yield compound LDC7559 (188 mg, 532 μmol, 81.7% yield, 98.8% purity) as a white powder. $^1H$ NMR: $CDCl_3$ 400 MHz, δ: 7.87 (d, J=7.45 Hz, 1H), 7.27-7.37 (m, 3H), 7.14-7.20 (m, 1H), 6.94-7.11 (m, 3H), 6.69 (s, 1H), 5.51 (s, 2H), 5.27 (s, 2H), 3.89 (s, 3H), 2.16 (s, 3H), 1.91-2.05 (m, 2H). LCMS: ($M+H^+$): 350.05, calculated 349.14.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating a symptom of a disease associated with the activity of glycolytic enzyme phosphofructokinase-1 liver type in an animal, comprising administering to the animal a compound of formula (I):

(I)

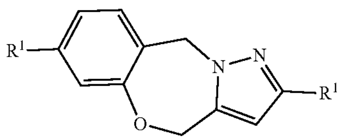

or a prodrug thereof, or a pharmaceutically acceptable salt thereof, wherein:

$R^1$ is —$NR^aR^b$ or a 5-10 membered heteroaryl that is optionally substituted with one or more groups $R^c$;

$R^2$ is a 6-10 membered aryl that is optionally substituted with one or more groups $R^r$; or $R^2$ is a 5-10 membered heteroaryl that is that is optionally substituted with one or more groups $R^s$; or $R^2$ is a 3-10 membered heterocycle that is that is optionally substituted with one or more groups $R^2$;

$R^a$ is ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkanoyl, ($C_3$-$C_6$)cycloalkyl ($C_1$-$C_6$)alkyl, ($C_2$-$C_6$)alkynylcarbonyl, 3-6 membered heterocycle, or a 5-6 membered heteroaryl that is optionally substituted with one or more groups $R^f$; wherein each ($C_1$-$C_6$)alkyl, ($C_3$-$C_6$)cycloalkyl, ($C_2$-$C_6$) alkenyl, ($C_2$-$C_6$)alkynyl, ($C_1$-$C_6$)alkanoyl, ($C_3$-$C_6$)cycloalkyl($C_1$-$C_6$)alkyl, ($C_2$-$C_6$)alkynylcarbonyl, and 3-6 membered heterocycle is optionally substituted with one or more groups independently selected from the group consisting of halo, hydroxy, cyano, ($C_2$-$C_6$) alkenyl, ($C_2$-$C_6$)alkynyl, C(═O)$NR'''R''$, and ($C_1$-$C_6$) alkyl that is optionally substituted with one or more groups independently selected form the group consisting of halo, hydroxy, cyano, —$NR'''R''$, and —C(═O) $NR'''R''$;

$R^b$ is H or ($C_1$-$C_6$)alkyl;

each $R^c$ is independently selected from the group consisting of cyano, —$NR^dR^e$, —C(═O)$NR^dR^e$, ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkoxy, and ($C_1$-$C_6$)alkanoyl, wherein each ($C_1$-$C_6$)alkyl, ($C_3$-$C_6$)cycloalkyl, ($C_3$-$C_6$)cycloalkyl ($C_1$-$C_6$)alkyl, ($C_1$-$C_6$)alkoxy and ($C_1$-$C_6$)alkanoyl is optionally substituted with one or more groups independently selected from the group consisting of halo, hydroxy, carboxy, and cyano;

$R^d$ and $R^e$ are each independently selected from the group consisting of H and ($C_1$-$C_6$)alkyl; or $R^d$ and $R^e$ taken together with the nitrogen to which they are attached form a 3-6 membered heterocyclic ring that is optionally substituted with one or more groups independently selected from the group consisting of halo and ($C_1$-$C_6$) alkyl;

each $R^f$ is independently selected from the group consisting of halo, hydroxy, cyano, —$NR^gR^h$, —C(═O)$N^gR^h$, and ($C_1$-$C_6$)alkyl that is optionally substituted with one or more groups independently selected from the group consisting of halo, hydroxy, carboxy, —$NR^gR^h$, —C(═O)$NR^gR^h$, and cyano;

$R^g$ and $R^h$ are each independently selected from the group consisting of H and ($C_1$-$C_6$)alkyl; or $R^g$ and $R^h$ taken together with the nitrogen to which they are attached form a 3-6 membered heterocyclic ring that is optionally substituted with one or more groups independently selected from the group consisting of halo and ($C_1$-$C_6$) alkyl;

$R^m$ is H or ($C_1$-$C_6$)alkyl that is optionally substituted with one or more groups independently selected from the group consisting of halo, hydroxy, carboxy, cyano, and oxo;

$R^n$ is H or ($C_1$-$C_6$)alkyl that is optionally substituted with one or more groups independently selected from the group consisting of halo, hydroxy, carboxy, cyano, and oxo;

each $R^r$ is independently selected from the group consisting of halo, hydroxy, cyano, —$NR^tR^u$, —C(═O)$NR^tR^u$, —$S(O)_2NR^tR^u$, ($C_1$-$C_6$)alkyl, ($C_3$-$C_6$)cycloalkyl, ($C_1$-$C_6$)alkoxy, ($C_1$-$C_6$)alkylthio, —N(H)$S(O)_2R^x$, —$S(O)_2R^x$, ($C_2$-$C_6$)alkenyl, and ($C_2$-$C_6$)alkynyl, wherein each ($C_1$-$C_6$)alkyl, ($C_3$-$C_6$)cycloalkyl, ($C_1$-$C_6$) alkoxy, ($C_1$-$C_6$)alkylthio, ($C_2$-$C_6$)alkenyl, and ($C_2$-$C_6$) alkynyl is optionally substituted with one or more groups independently selected from the group consisting of halo, hydroxy, carboxy, —$NR^tR^u$, —C(═O) $NR^tR^u$, —$S(O)_2NR^tR^u$, —$S(O)_2R^x$, and cyano;

each $R^s$ is independently selected from the group consisting of halo, cyano, —$NR^vR^w$, —C(═O)$NR^vR^w$, —$S(O)_2NR^vR^w$, ($C_1$-$C_6$)alkyl, ($C_3$-$C_6$)cycloalkyl, ($C_1$-$C_6$)alkoxy, ($C_1$-$C_6$)alkanoyl, ($C_1$-$C_6$)alkylthio, 3-6 membered heterocycle, and —$S(O)_2R^y$, wherein each ($C_1$-$C_6$)alkyl, ($C_3$-$C_6$)cycloalkyl, ($C_1$-$C_6$)alkoxy, ($C_1$-$C_6$)alkanoyl, 3-6 membered heterocycle, and ($C_1$-$C_6$)alkylthio, is optionally substituted with one or more groups independently selected from the group consisting of halo, hydroxy, carboxy, —$NR^tR^u$, —C(═O) $NR^tR^u$, $S(O)_2NR^vR^w$, —$S(O)_2R^y$, and cyano;

$R^t$ and $R^u$ are each independently selected from the group consisting of H, ($C_1$-$C_6$)alkyl, ($C_1$-$C_6$)alkanoyl, and ($C_2$-$C_6$)alkynylcarbonyl; or $R^t$ and $R^u$ taken together with the nitrogen to which they are attached form a 3-6 membered heterocyclic ring that is optionally substituted with one or more groups independently selected from the group consisting of halo and ($C_1$-$C_6$)alkyl;

$R^v$ and $R^w$ are each independently selected from the group consisting of H, ($C_1$-$C_6$)alkyl, and ($C_1$-$C_6$)alkanoyl; or $R^v$ and $R^w$ taken together with the nitrogen to which they are attached form a 3-6 membered heterocyclic ring that is optionally substituted with one or more groups independently selected from the group consisting of halo and ($C_1$-$C_6$)alkyl;

$R^x$ is H or ($C_1$-$C_6$)alkyl that is optionally substituted with one or more groups independently selected from the group consisting of halo, hydroxy, carboxy, cyano, and oxo;

$R^y$ is H or ($C_1$-$C_6$)alkyl that is optionally substituted with one or more groups independently selected from the group consisting of halo, hydroxy, carboxy, cyano, and oxo; and each $R^z$ is independently selected from the group consisting of oxo, halo, hydroxy, and ($C_1$-$C_6$)alkyl that is optionally substituted with one or more groups independently selected from the group consisting of halo, hydroxy, carboxy, —$NR^tR^u$, —C(═O)$NR^tR^u$, $S(O)_2$ $NR^vR^w$, —$S(O)_2R^y$, cyano, and oxo;

provided the compound is not:

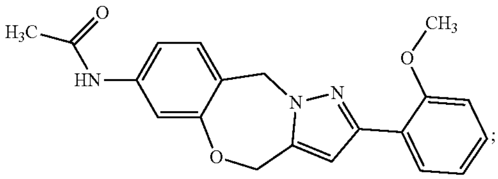 [SMILES: COc1ccccc1-c1cc2n(n1)Cc1ccc(NC(C)=O)cc1OC2]

;

wherein the disease associated with the activity of glycolytic enzyme phosphofructokinase-1 liver type is cancer, diabetes, a caspase-associated auto-inflammatory condition, pulmonary disease, a systemic autoimmune disease, atherosclerosis, thrombosis, multiple sclerosis, Alzheimer's disease, psoriasis, or pulmonary fibrosis.

2. The method of claim 1, wherein:

$R^1$ is —$NR^aR^b$ or a 5-10 membered heteroaryl that is optionally substituted with one or more groups $R^c$;

$R^2$ is a phenyl that is optionally substituted with one or more groups $R^r$; or $R^2$ is a 5-9 membered heteroaryl that is that is optionally substituted with one or more groups $R^s$; or $R^2$ is a 9-membered heterocycle that is that is optionally substituted with one or more groups $R^2$;

$R^a$ is ($C_1$-$C_6$)alkyl, ($C_3$-$C_6$)cycloalkyl, ($C_2$-$C_6$)alkynyl, ($C_1$-$C_6$)alkanoyl, ($C_2$-$C_6$)alkynylcarbonyl, 3-6 membered heterocycle, or a 5-membered heteroaryl that is optionally substituted with one or more groups $R^f$; wherein each ($C_1$-$C_6$)alkyl and ($C_3$-$C_6$)cycloalkyl is optionally substituted with one or more groups independently selected from the group consisting of halo, cyano, ($C_2$-$C_6$)alkynyl, C(═O)$NR^mR^n$, and ($C_1$-$C_6$) alkyl that is optionally substituted with one or more hydroxy;

$R^b$ is H or ($C_1$-$C_6$)alkyl;

each $R^c$ is independently selected from the group consisting of cyano, —$NR^dR^e$, and ($C_1$-$C_6$)alkyl that is optionally substituted with one or more cyano;

$R^d$ and $R^e$ are each H;

each $R^f$ is independently selected from the group consisting of halo, hydroxy, cyano, —C(═O)$NR^gR^h$, and ($C_1$-$C_6$)alkyl that is optionally substituted with one or more groups independently selected from the group consisting of halo, hydroxy and carboxy;

$R^d$ and $R^e$ are each H;

$R^m$ is H;

$R^n$ is H;

each $R^r$ is independently selected from the group consisting of halo, hydroxy, cyano, —NR$^t$R$^u$, —C(═O)NR$^t$R$^u$, —S(O)$_2$NR$^t$R$^u$, ($C_1$-$C_6$)alkyl, ($C_3$-$C_6$)cycloalkyl, ($C_1$-$C_6$)alkoxy, ($C_1$-$C_6$)alkylthio, —N(H)S(O)$_2$R$^x$, —S(O)$_2$R$^x$, and ($C_2$-$C_6$)alkynyl, wherein each ($C_1$-$C_6$)alkyl and ($C_2$-$C_6$)alkynyl, is optionally substituted with one or more groups independently selected from the group consisting of hydroxy, —NR$^t$R$^u$, —C(═O)NR$^t$R$^u$, and cyano;

each R$^g$ is independently selected from the group consisting of halo, cyano, —NR$^v$R$^w$, —C(═O)NR$^v$R$^w$, ($C_1$-$C_6$)alkyl, ($C_3$-$C_6$)cycloalkyl, ($C_1$-$C_6$)alkoxy, ($C_1$-$C_6$)alkanoyl, ($C_1$-$C_6$)alkylthio, 3-6 membered heterocycle, and —S(O)$_2$R$^y$, wherein each ($C_1$-$C_6$)alkyl is optionally substituted with one or more groups independently selected from the group consisting of halo and —NR$^t$R$^u$;

R$^t$ and R$^u$ are each independently selected from the group consisting of H, ($C_1$-$C_6$)alkyl, ($C_1$-$C_6$)alkanoyl, and ($C_2$-$C_6$)alkynylcarbonyl; or R$^t$ and R$^u$ taken together with the nitrogen to which they are attached form a 3-6 membered heterocyclic ring that is optionally substituted with one or more groups independently selected from the group consisting of halo and ($C_1$-$C_6$)alkyl;

R$^v$ and R$^w$ are each independently selected from the group consisting of H, ($C_1$-$C_6$)alkyl, and ($C_1$-$C_6$)alkanoyl;

R$^x$ is ($C_1$-$C_6$)alkyl;

R$^y$ is ($C_1$-$C_6$)alkyl; and each R$^z$ is independently selected from the group consisting of oxo and ($C_1$-$C_6$)alkyl;

or a prodrug thereof, or a pharmaceutically acceptable salt thereof.

3. The method of claim 1, wherein R$^1$ is —NR$^a$R$^b$.

4. The method of claim 1, wherein R$^a$ is acetyl.

5. The method of claim 1, wherein R$^a$ is selected from the group consisting of

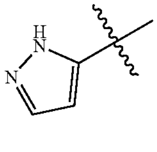
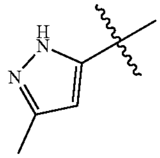
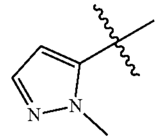
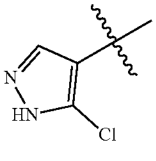
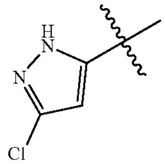
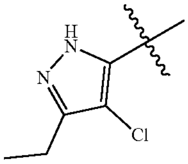
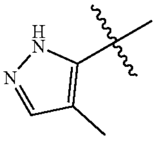
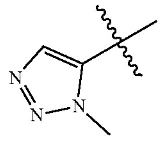
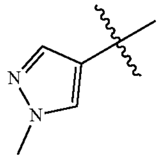
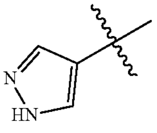
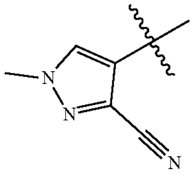
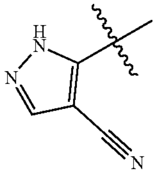

-continued

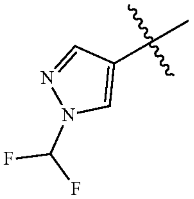
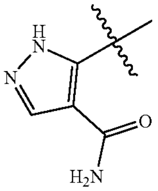
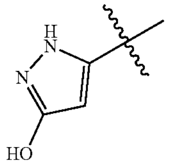
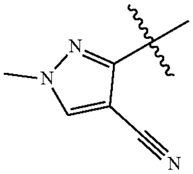
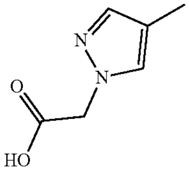
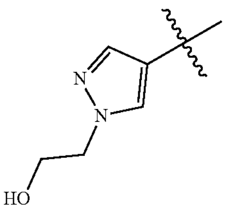
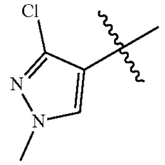
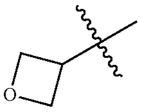
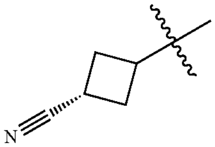
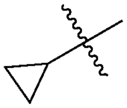
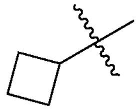
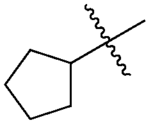
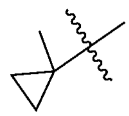
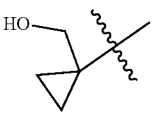
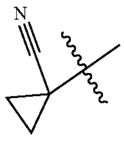
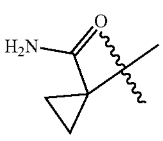
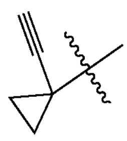
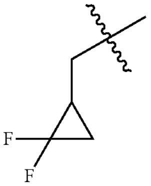
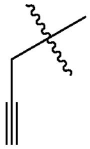
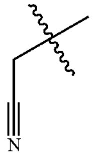
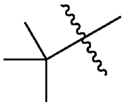

and

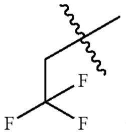

.

6. The method of claim 1, wherein R$^1$ is a 5-membered heteroaryl that is optionally substituted with one or more groups R$^c$.

7. The method of claim 1, wherein R$^1$ is selected from the group consisting of:

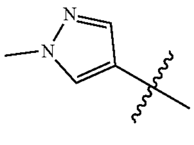
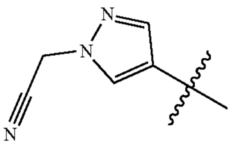

-continued
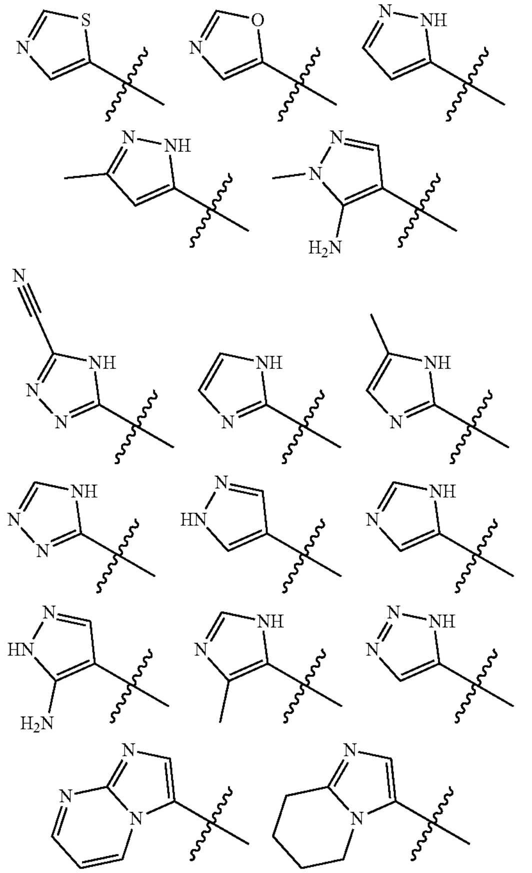
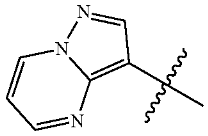
and
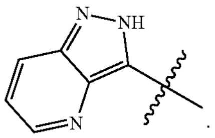
.
8. The method of claim 1, wherein $R^2$ is a 5-9 membered heteroaryl that is that is optionally substituted with one or more groups $R^s$.
9. The method of claim 1, wherein $R^2$ is selected from the group consisting of
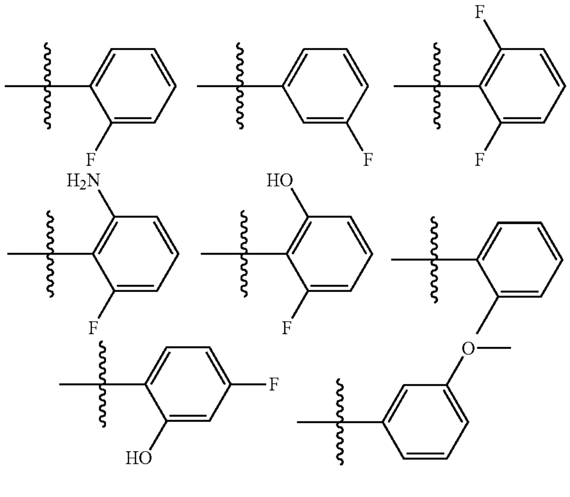
-continued
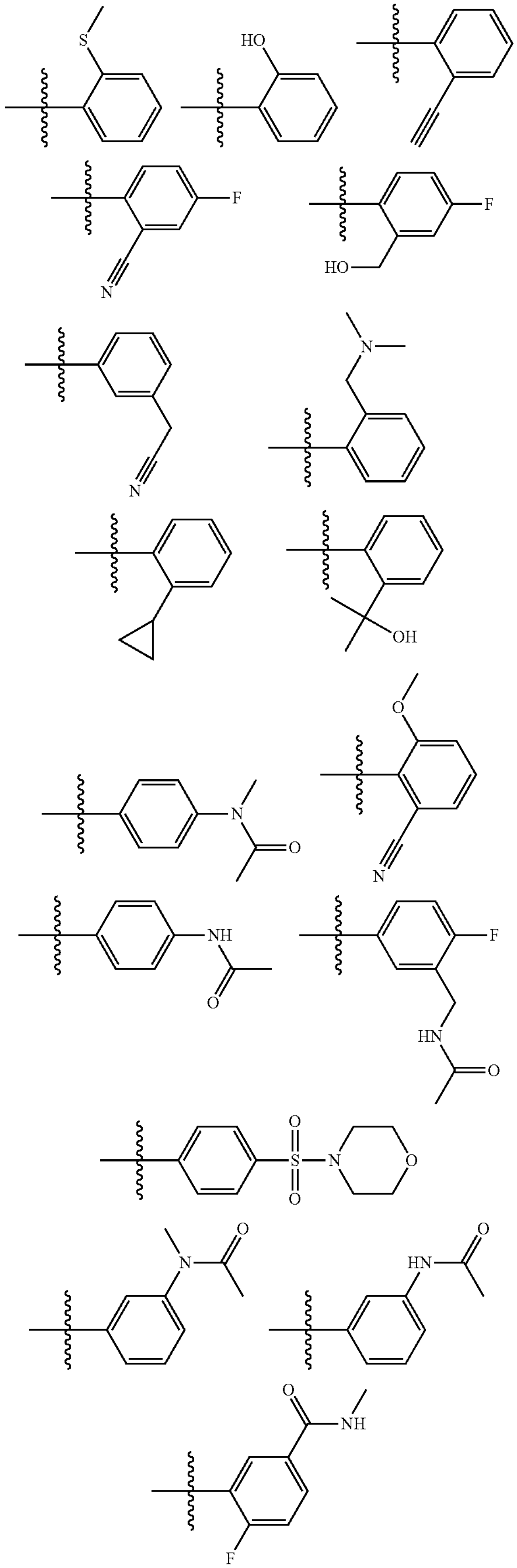

-continued

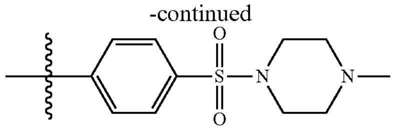

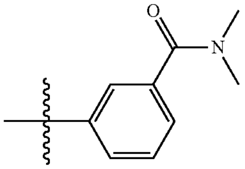

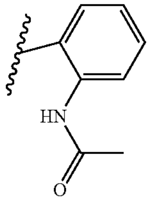

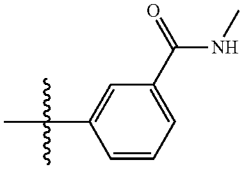

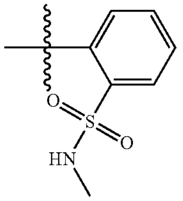

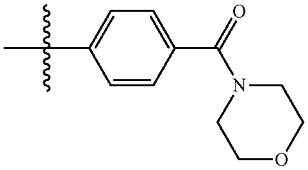

and

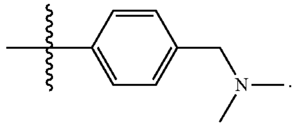

10. The method of claim 1, wherein $R^2$ is:

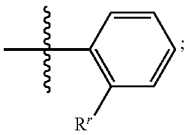

$R^r$ $(C_2$-$C_6)$alkynyl that is substituted with hydroxy.

11. The method of claim 1, wherein $R^2$ is selected from the group consisting of:

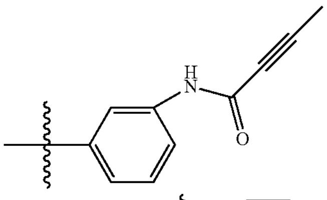

and

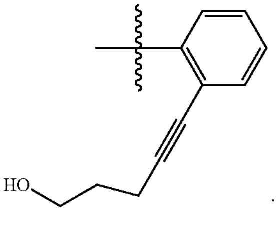

.

12. The method of claim 1, wherein the compound, prodrug, or pharmaceutically acceptable salt is selected from the group consisting of:

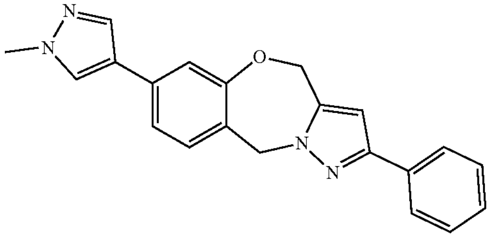

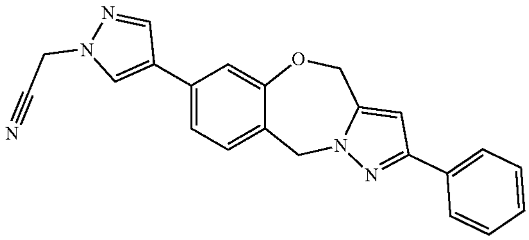

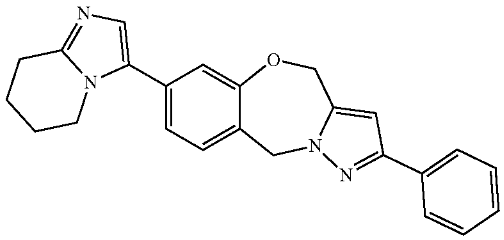

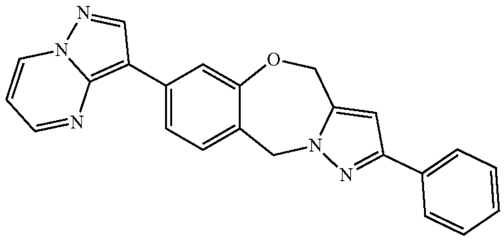

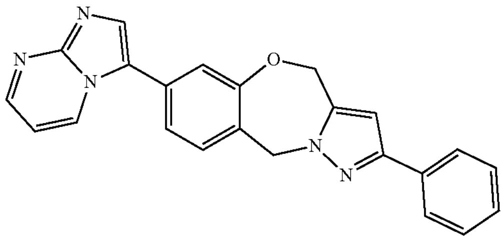

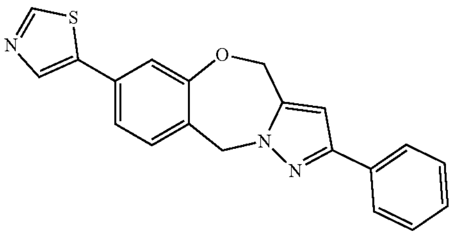

and

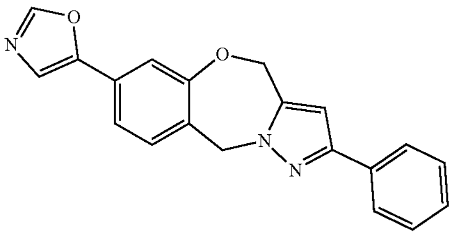

and prodrugs and pharmaceutically acceptable salts thereof.

13. The method of claim 1, wherein the prodrug is a compound of formula (I) that comprises a hydroxy group that has been converted to a prodrug group that increases the aqueous solubility of the compound; or a pharmaceutically acceptable salt thereof.

14. The method of claim 13, wherein the hydroxy group has been converted to a prodrug group selected from the group consisting of: a phosphate,

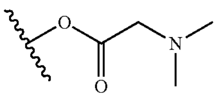

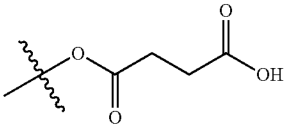

and

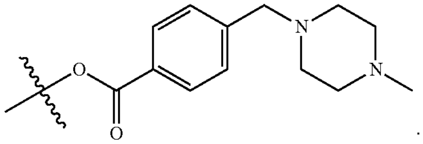

.

15. The method of claim 1, wherein the prodrug or pharmaceutically acceptable salt is selected from the group consisting of:

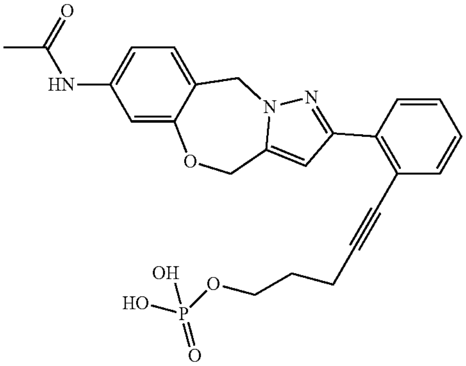

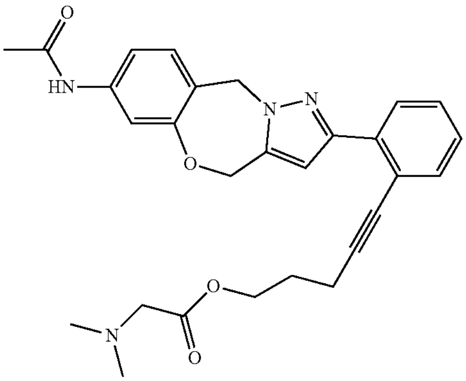

-continued

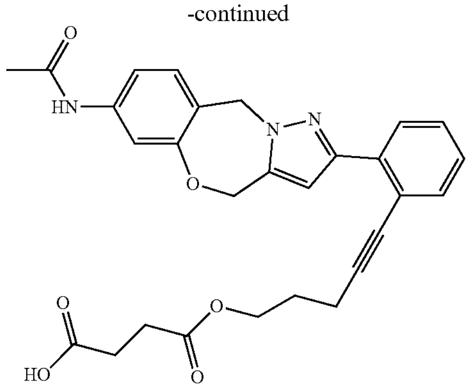

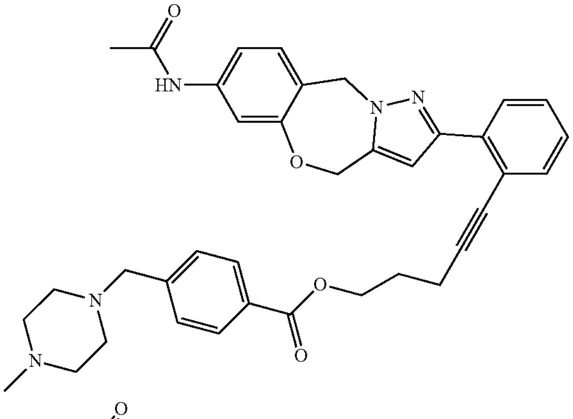

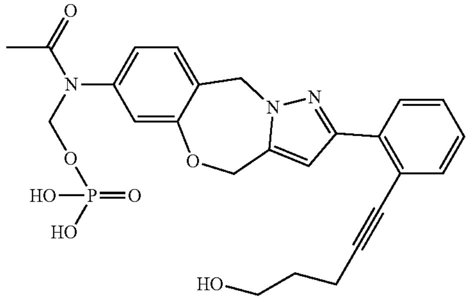

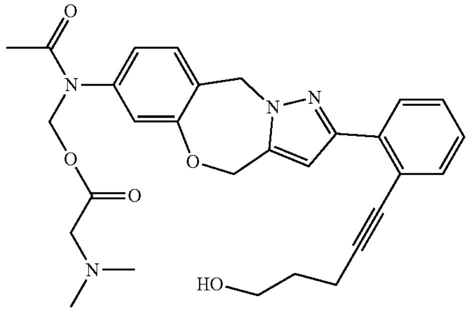

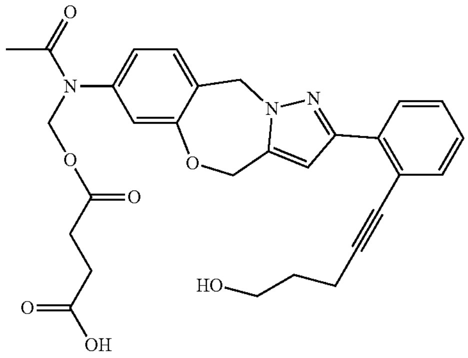

and

-continued
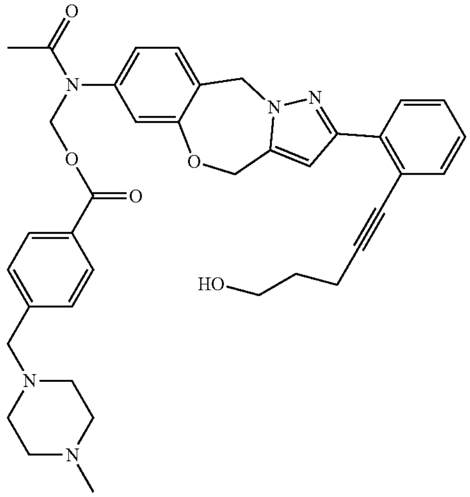
and pharmaceutically acceptable salts thereof.
16. A method for treating a symptom of a disease associated with the activity of glycolytic enzyme phosphofructokinase-1 liver type in an animal, comprising administering to the animal a compound selected from the group consisting of:
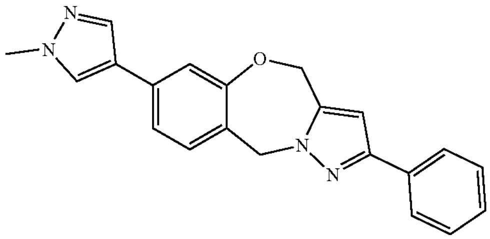
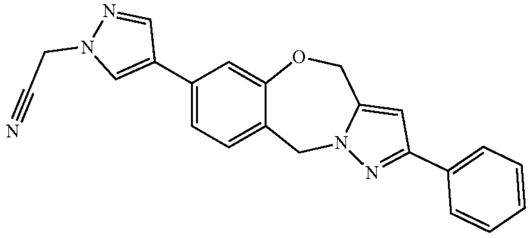
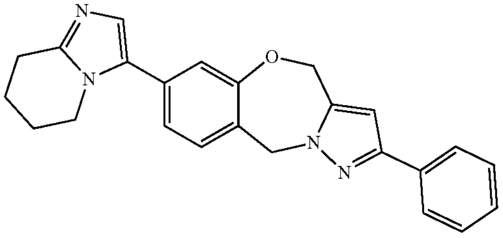
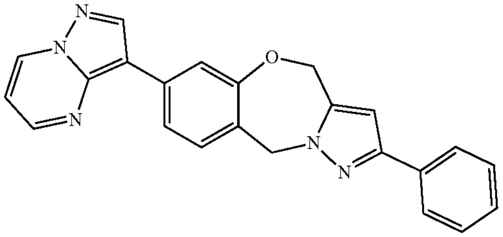
-continued
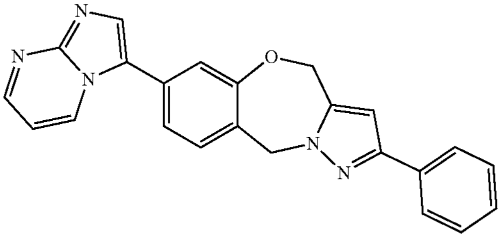
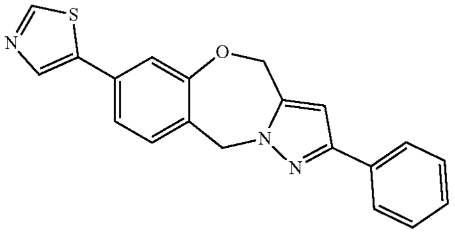
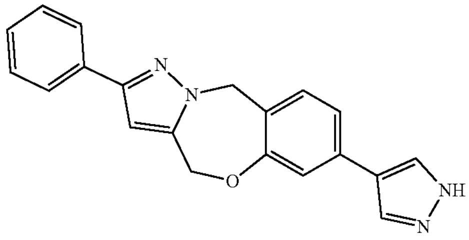
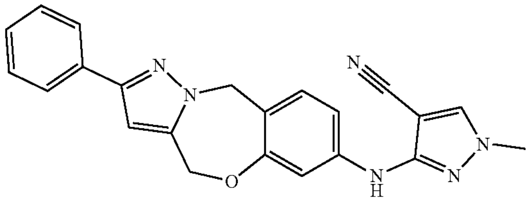
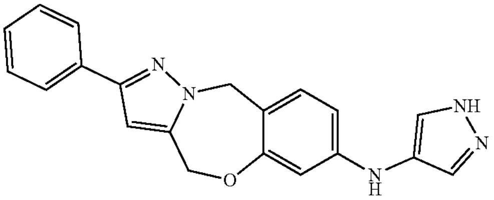
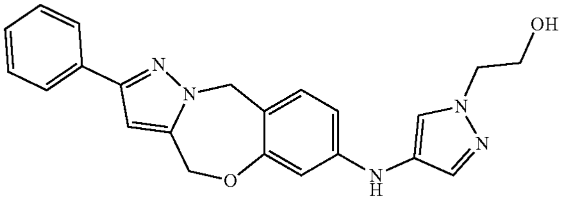
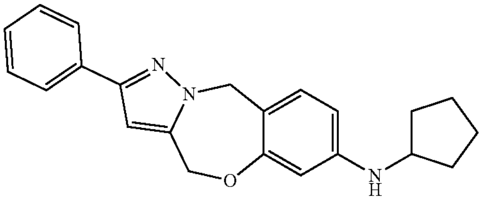
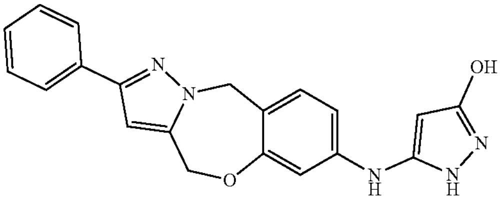

-continued
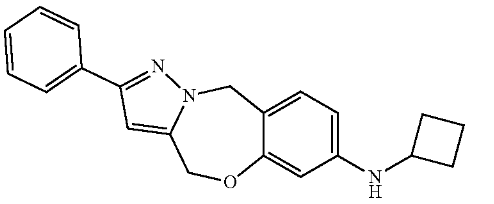
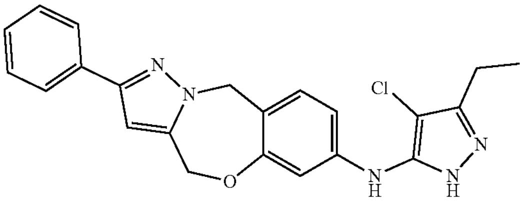
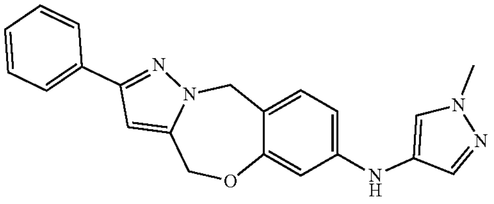
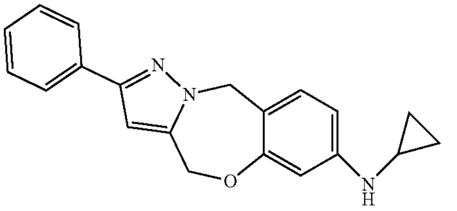
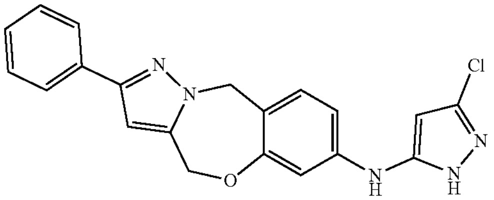
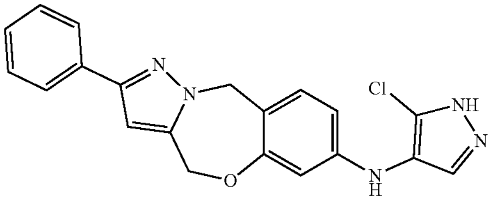
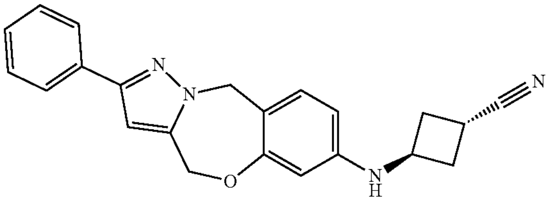
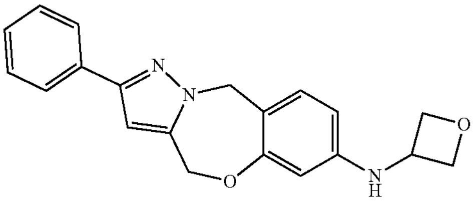
-continued
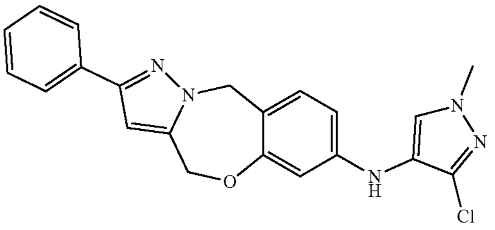
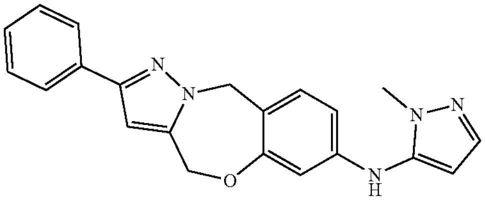
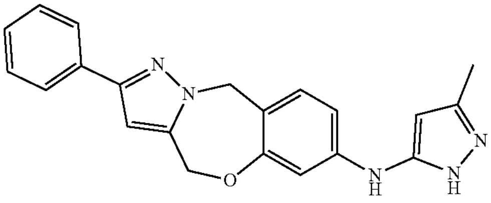
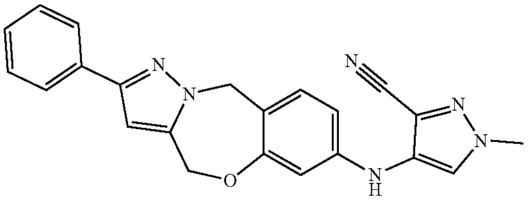
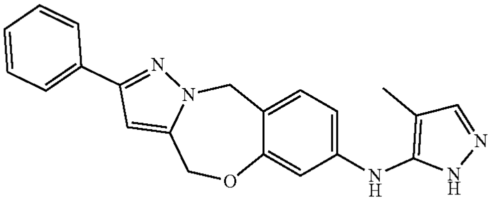
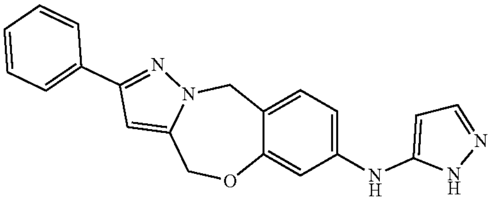
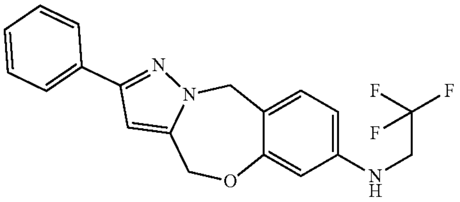
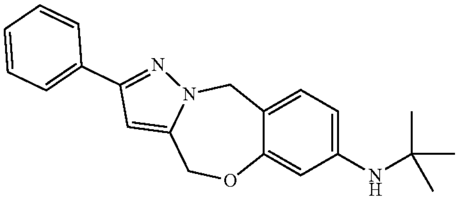

-continued
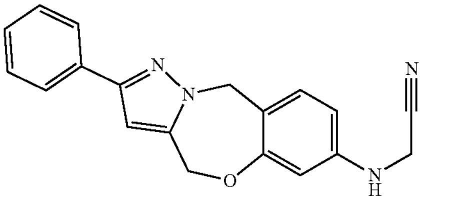
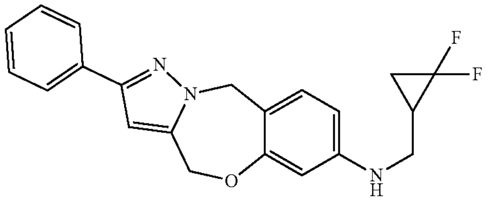
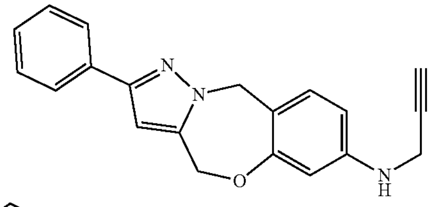
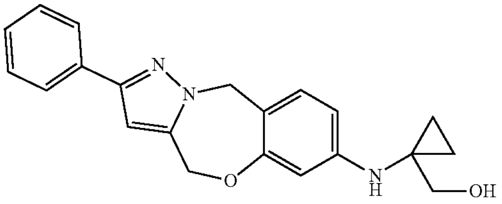
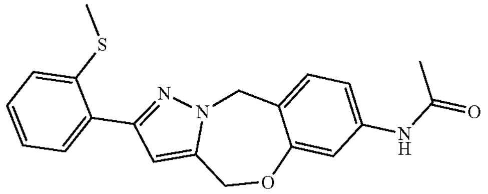
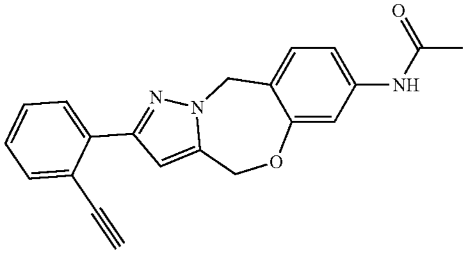
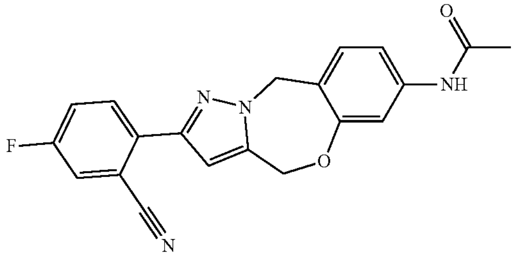
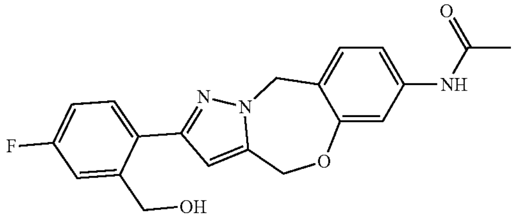
-continued
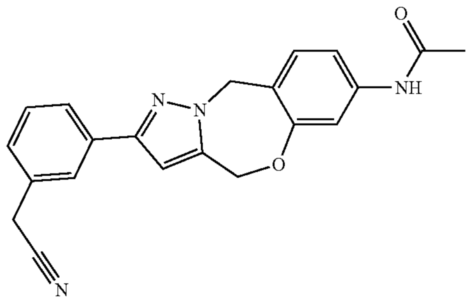
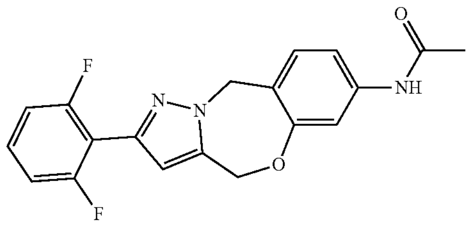
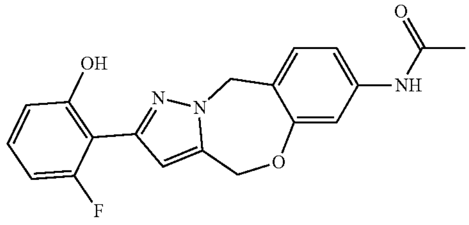
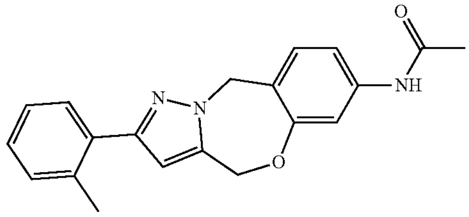
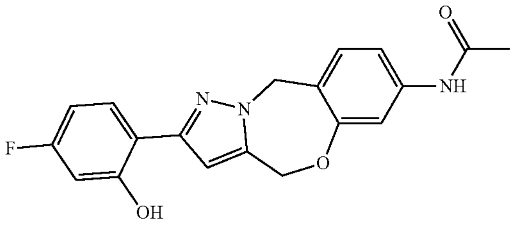
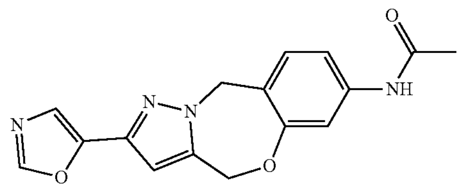
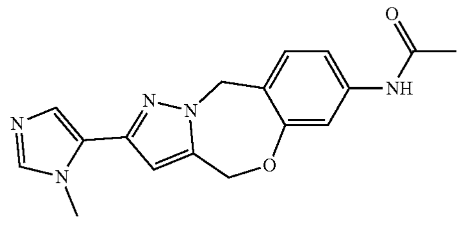

-continued
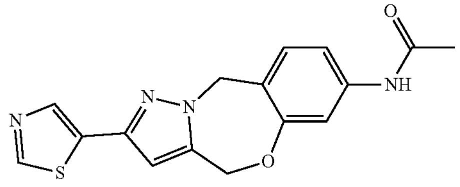
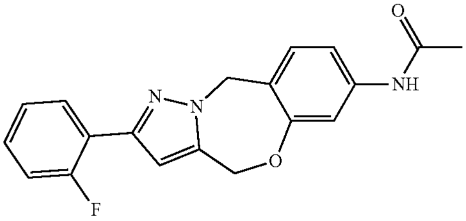
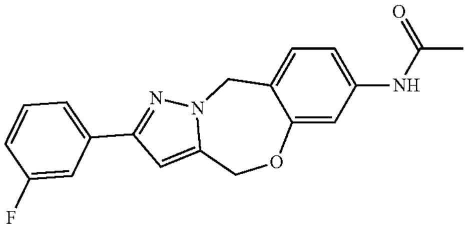
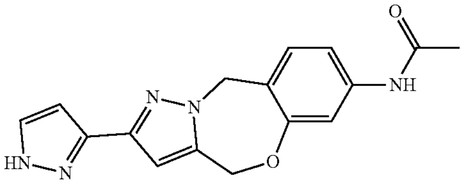
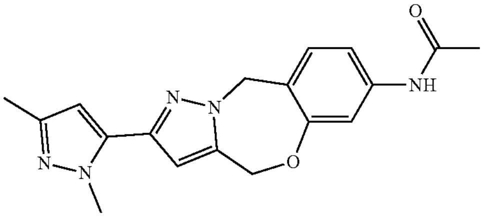
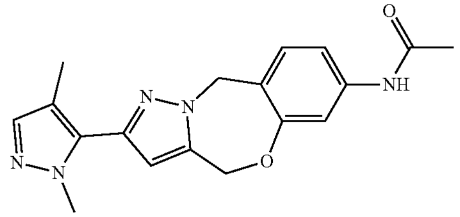
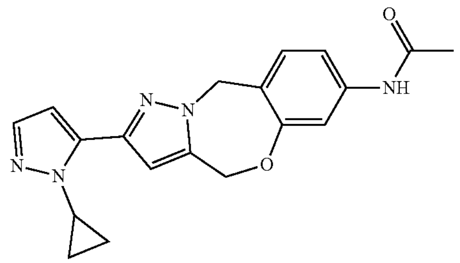
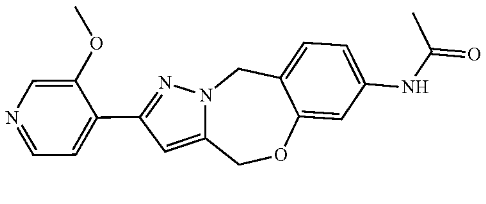
-continued
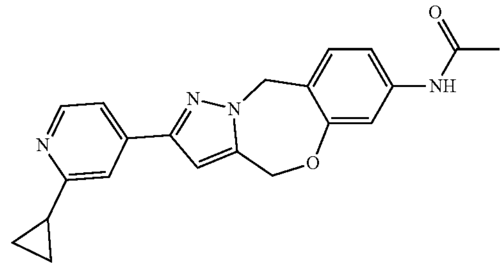
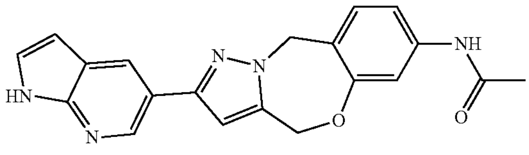
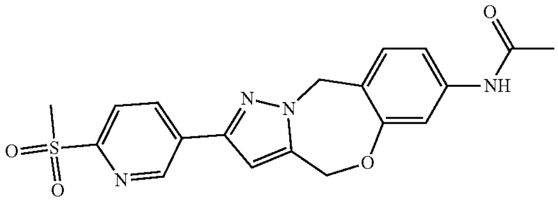
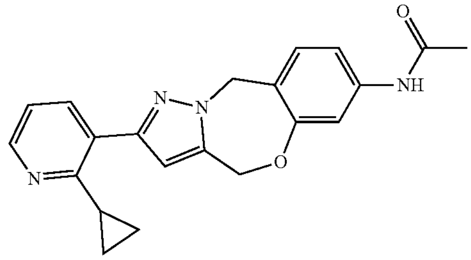
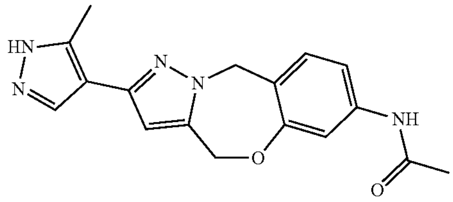
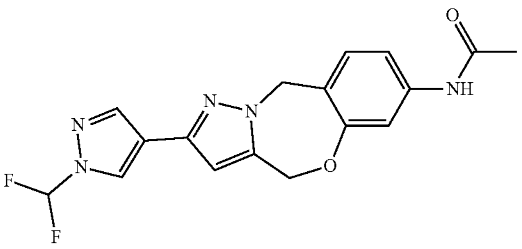
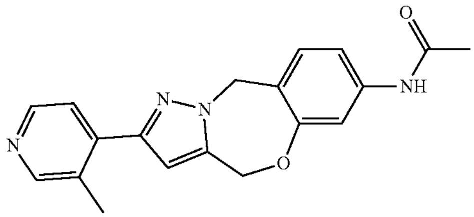

-continued
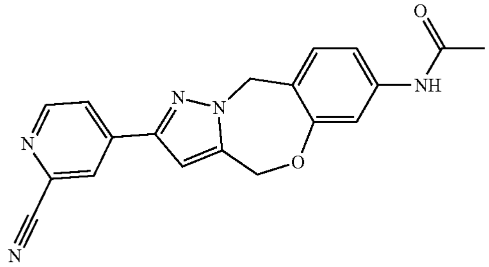
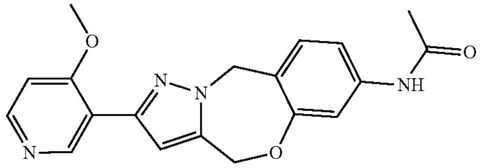
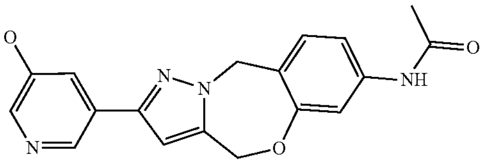
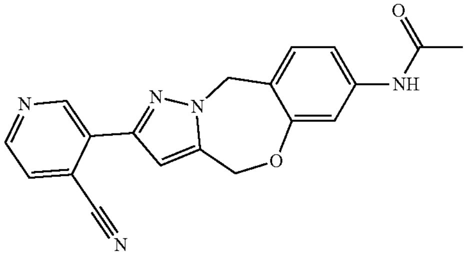
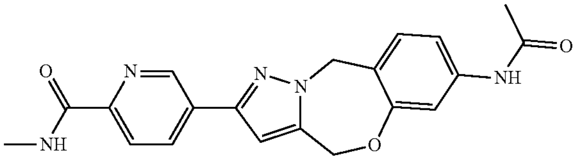
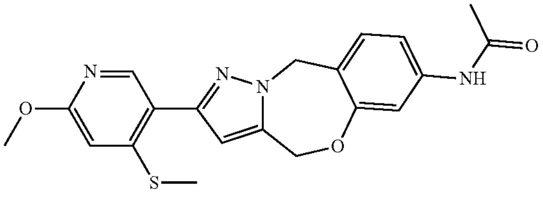
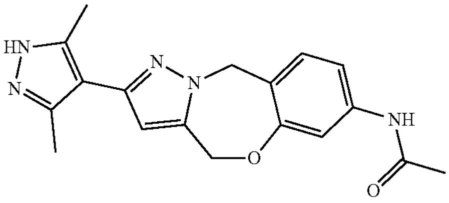
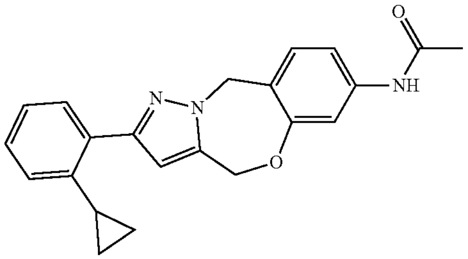
-continued
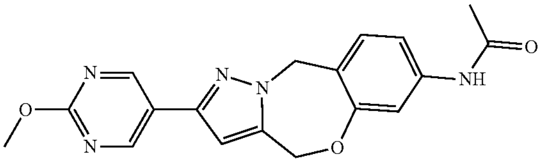
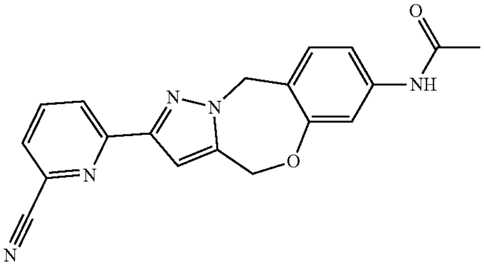
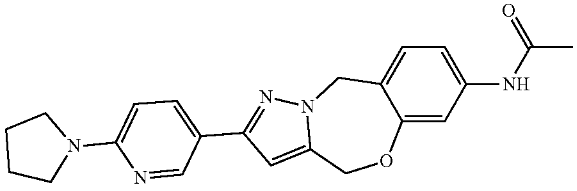
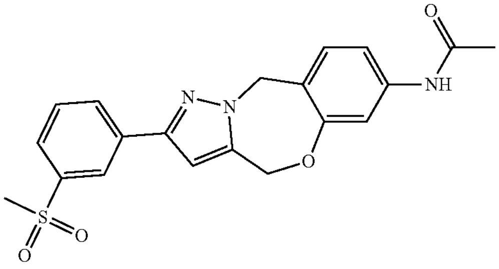
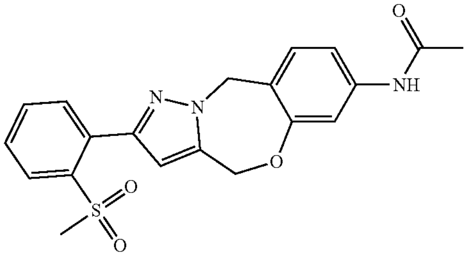
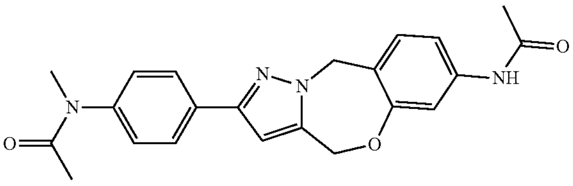
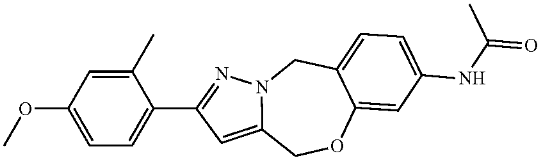
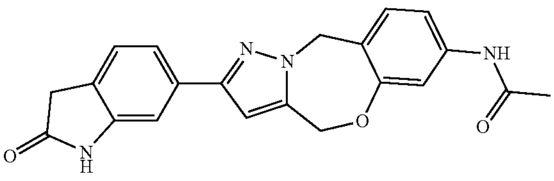

-continued
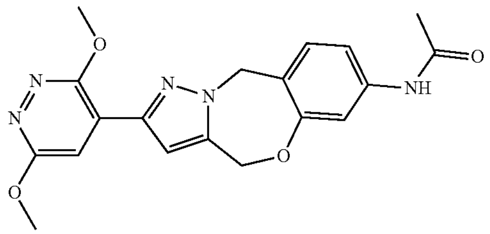
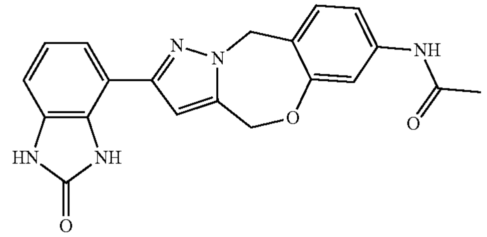
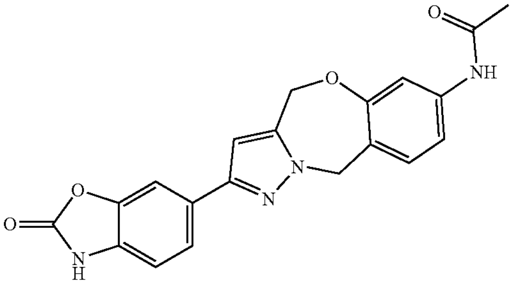
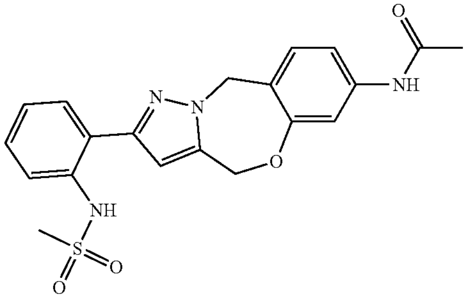
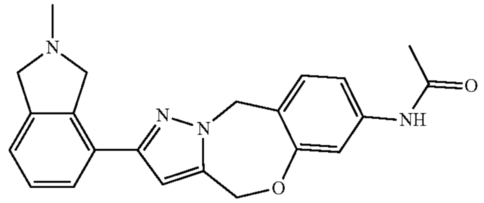
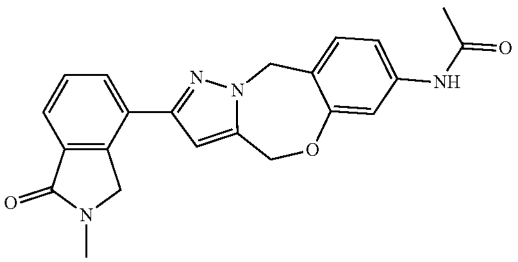
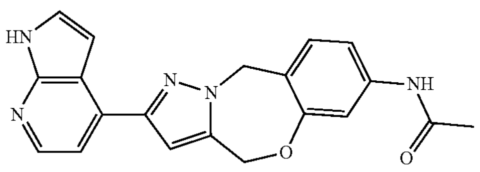
-continued
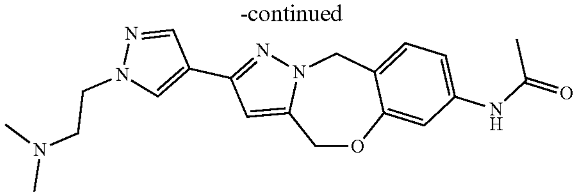
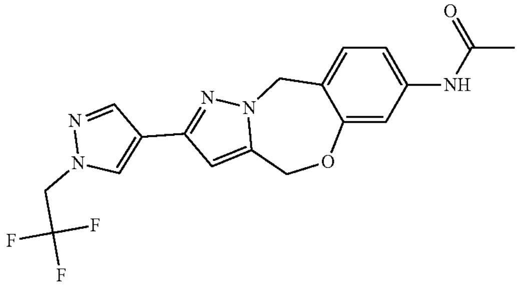
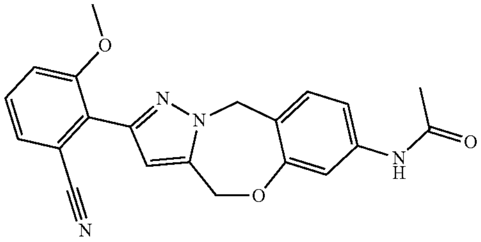
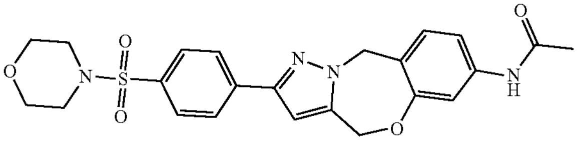
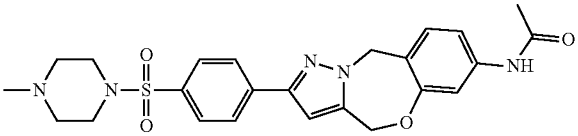
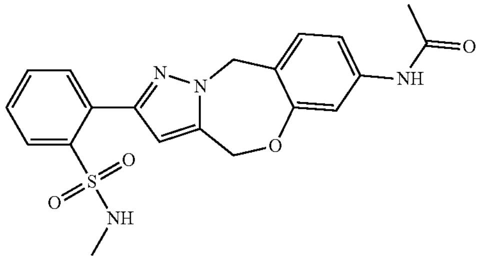
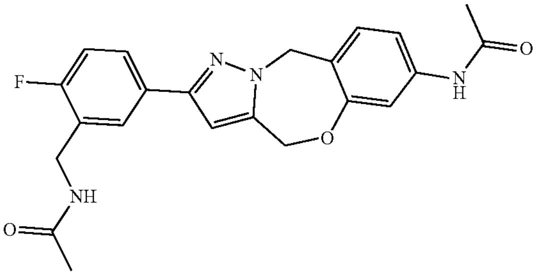
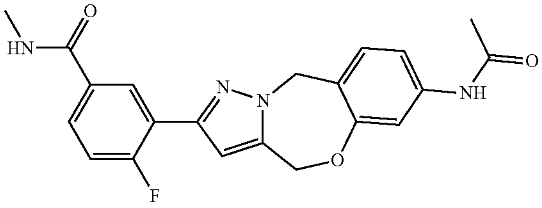

-continued
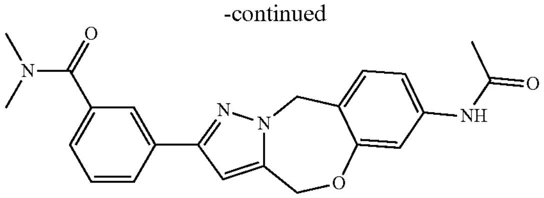
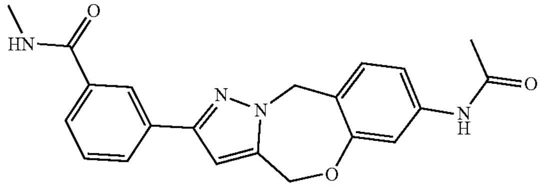
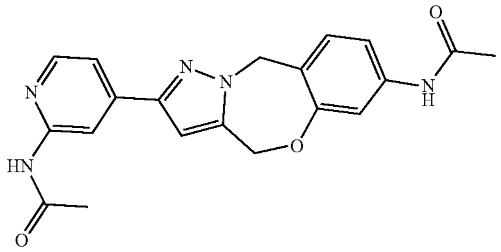
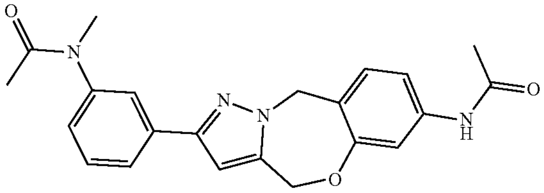
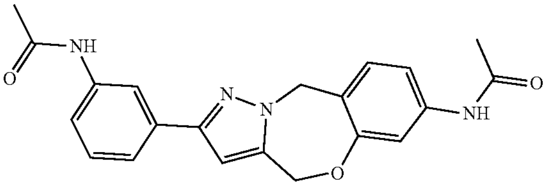
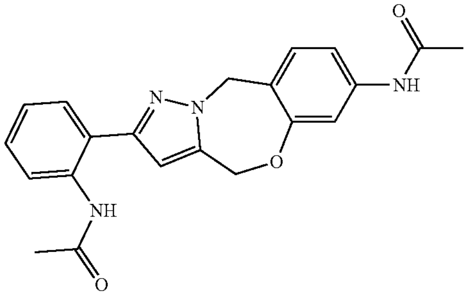
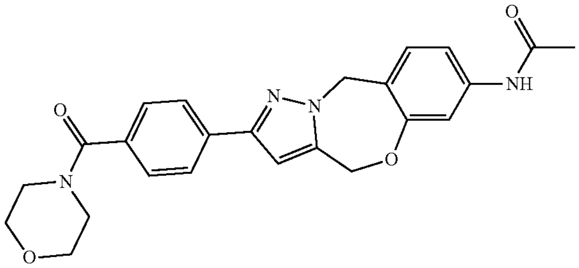
-continued
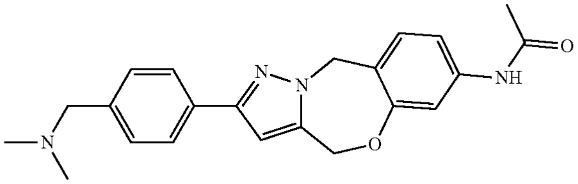
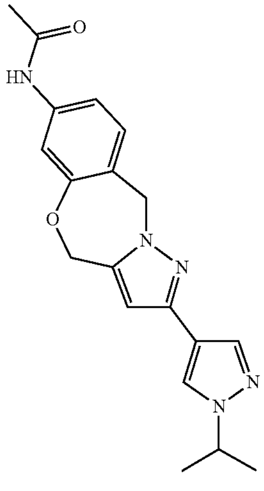
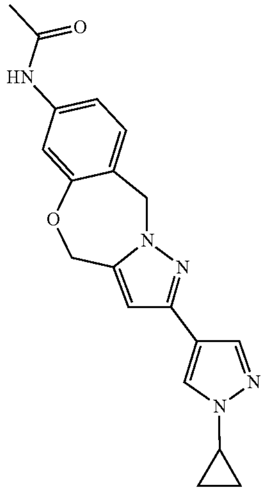
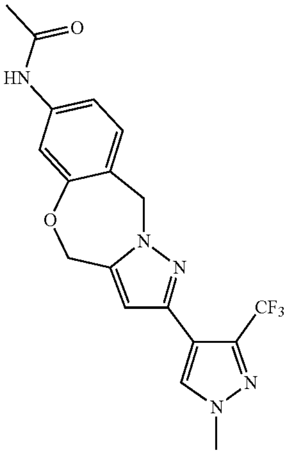
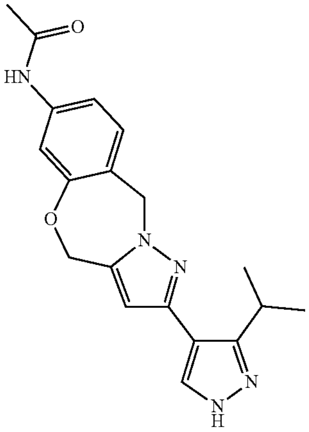

-continued
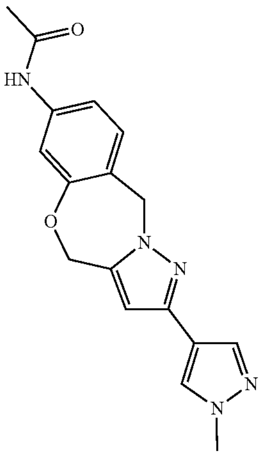
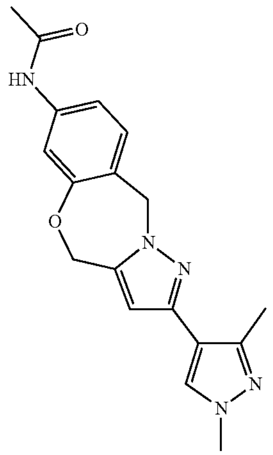
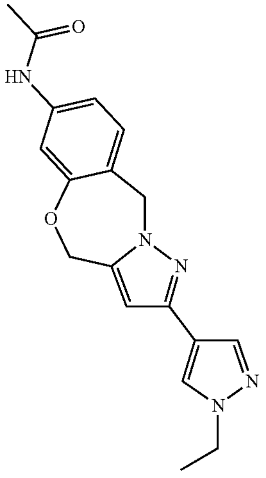
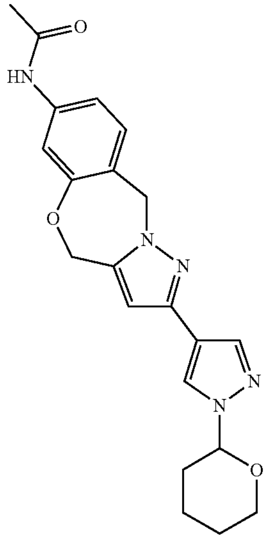
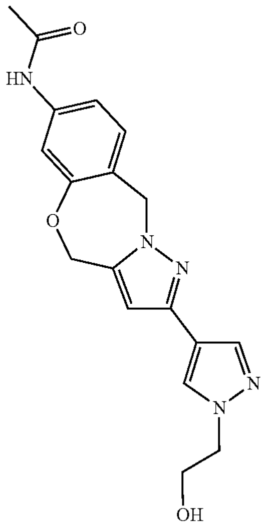
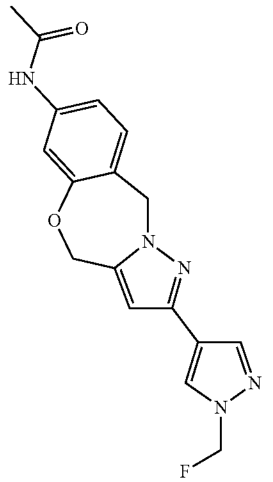
-continued
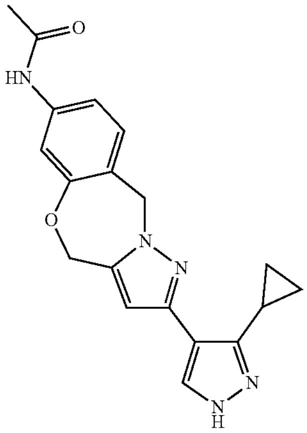
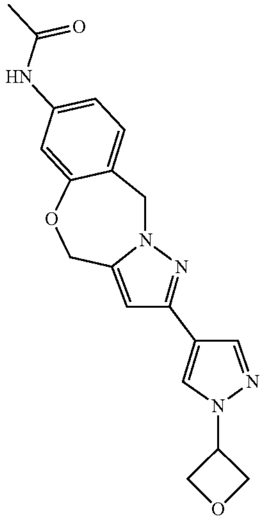
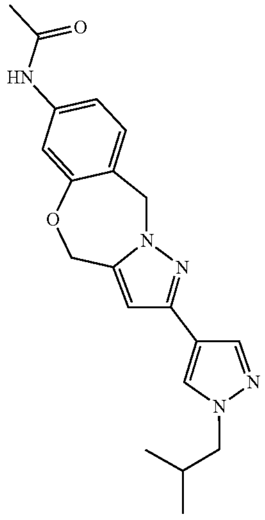
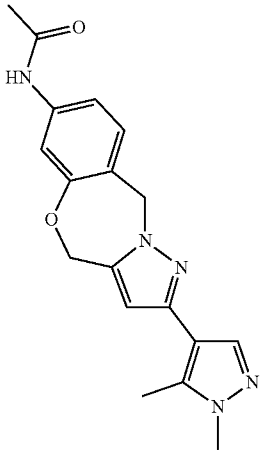
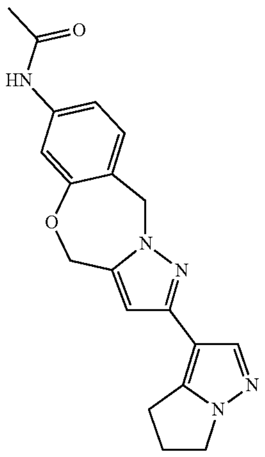
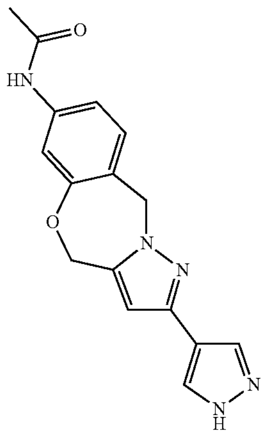
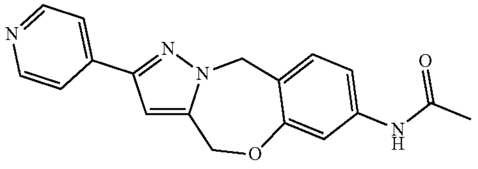

-continued

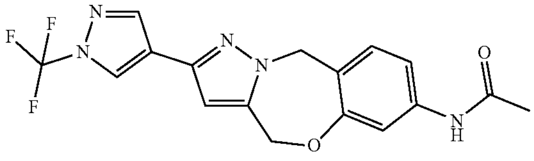

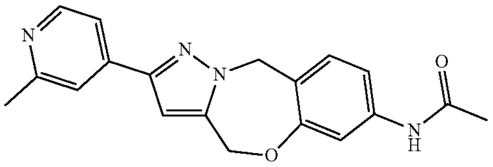

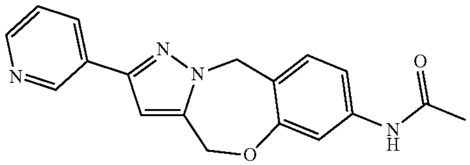

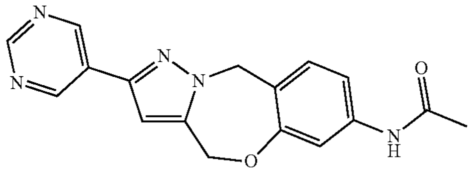

and

-continued

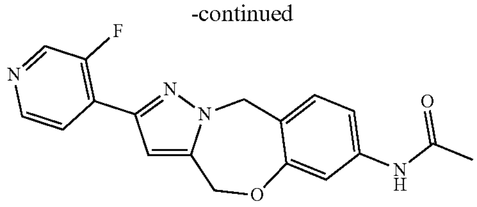

or a pharmaceutically acceptable salt thereof, wherein the disease associated with the activity of glycolytic enzyme phosphofructokinase-1 liver type is cancer, diabetes, a caspase-associated auto-inflammatory condition, pulmonary disease, a systemic autoimmune disease, atherosclerosis, thrombosis, multiple sclerosis, Alzheimer's disease, psoriasis, or pulmonary fibrosis.

17. The method of claim 1, wherein the caspase-associated auto-inflammatory condition is sepsis or septic shock.

18. The method of claim 1, wherein the pulmonary disease is acute respiratory distress syndrome ARDS, chronic obstructive pulmonary disease COPD, or bronchiectasis.

19. The method of claim 1, wherein the disease or condition is thrombosis.

20. The method of claim 1, wherein the cancer is selected from the group consisting of brain, breast, lung, urinary bladder, cervical, skin, oral cavity, pharynx, colon, liver, cecum, stomach, pancreatic, prostate, oesophageal, hematologic, thyroid, uterine, and head and neck cancer.

* * * * *